US009850530B2

(12) United States Patent
Park et al.

(10) Patent No.: US 9,850,530 B2
(45) Date of Patent: *Dec. 26, 2017

(54) AUTOMATIC REAL-TIME PCR SYSTEM FOR THE VARIOUS ANALYSIS OF BIOLOGICAL SAMPLE

(75) Inventors: Han Oh Park, Daejeon (KR); Kwon Sic Kim, Daejeon (KR); Yang Won Lee, Daejeon (KR); Jin Il Lee, Uiwang-si (KR); Byung Rae Jeong, Daejeon (KR); Jong Hoon Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 82 days.

This patent is subject to a terminal disclaimer.

(21) Appl. No.: 13/881,900

(22) PCT Filed: Oct. 27, 2011

(86) PCT No.: PCT/KR2011/008100
§ 371 (c)(1),
(2), (4) Date: Apr. 26, 2013

(87) PCT Pub. No.: WO2012/057548
PCT Pub. Date: May 3, 2012

(65) Prior Publication Data
US 2013/0230860 A1 Sep. 5, 2013

(30) Foreign Application Priority Data
Oct. 27, 2010 (KR) ........................ 10-2010-0105630

(51) Int. Cl.
*C12Q 1/68* (2006.01)
*B01L 3/02* (2006.01)
*C12Q 1/02* (2006.01)
*G01N 35/02* (2006.01)
*B01L 7/00* (2006.01)
*G01N 35/00* (2006.01)
*G01N 35/04* (2006.01)

(52) U.S. Cl.
CPC ............ *C12Q 1/686* (2013.01); *B01L 3/0227* (2013.01); *B01L 3/0234* (2013.01); *C12Q 1/02* (2013.01); *C12Q 1/6844* (2013.01); *G01N 35/028* (2013.01); *B01L 7/52* (2013.01); *B01L 2300/0829* (2013.01); *B01L 2300/1805* (2013.01); *B01L 2400/0478* (2013.01); *G01N 35/0098* (2013.01); *G01N 2035/0425* (2013.01); *G01N 2035/0465* (2013.01)

(58) Field of Classification Search
None
See application file for complete search history.

(56) References Cited

U.S. PATENT DOCUMENTS

| 6,846,680 B2 * | 1/2005 | Friswell ................ B01L 3/0279 422/501 |
|---|---|---|
| 2005/0233314 A1 | 10/2005 | Juang et al. |
| 2008/0233586 A1 | 9/2008 | Turner |
| 2010/0216194 A1 | 8/2010 | Bergtsson et al. |
| 2010/0243019 A1 | 9/2010 | Larsson |
| 2011/0009608 A1 * | 1/2011 | Kim et al. ................ 536/25.41 |

FOREIGN PATENT DOCUMENTS

| JP | 2002-031642 A | 1/2002 |
|---|---|---|
| JP | 2006-068669 A | 3/2006 |
| KR | 10-2010-0102560 | 9/2010 |
| KR | 10-2010-0102560 A | 9/2010 |
| WO | 2009-054780 A1 | 4/2009 |
| WO | WO 2009125971 A3 * | 12/2009 |
| WO | 2010-104345 A2 | 9/2010 |

OTHER PUBLICATIONS

Examination Report issued by Intellectual Property India for Patent Application No. 683/MUMNP/2013, dated Oct. 10, 2017.

* cited by examiner

*Primary Examiner* — Prabha Chunduru
(74) *Attorney, Agent, or Firm* — Kile Park Reed & Houtteman PLLC

(57) ABSTRACT

The present invention relates to an automatic real-time quantitative amplification system which can perform analysis of various biological samples, and more particularly to an automatic real-time quantitative amplification system in which a plurality of decks for respectively accommodating biological samples are put in a deck storing/transferring device, whereby it is possible to automatically analyze an amount or existence of a target substance containing a target nucleic acid in the biologic sample, such as a particular gene, a particular, a particular pathogenic bacterium and a particular protein, by amplifying the target nucleic acid purified by some processes of purification, purification after culture, or purification after reaction of the target substance contained in the biological sample and then checking an amount of the amplified target nucleic acid.

32 Claims, 40 Drawing Sheets

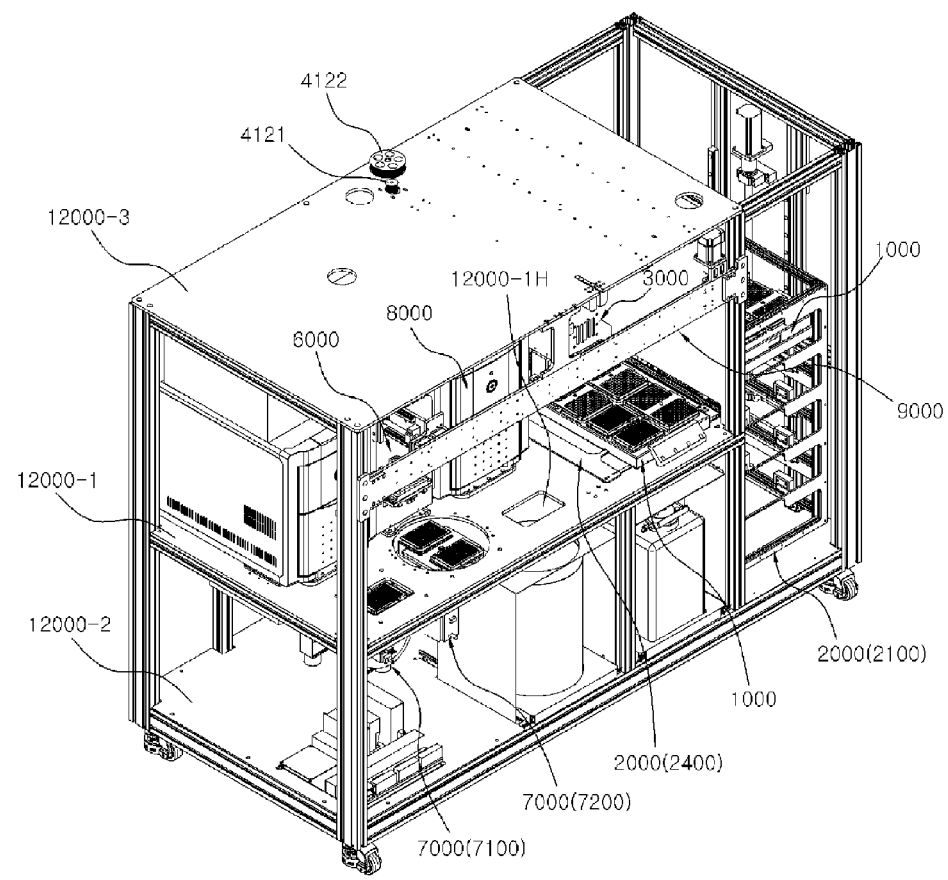
[Fig. 1]

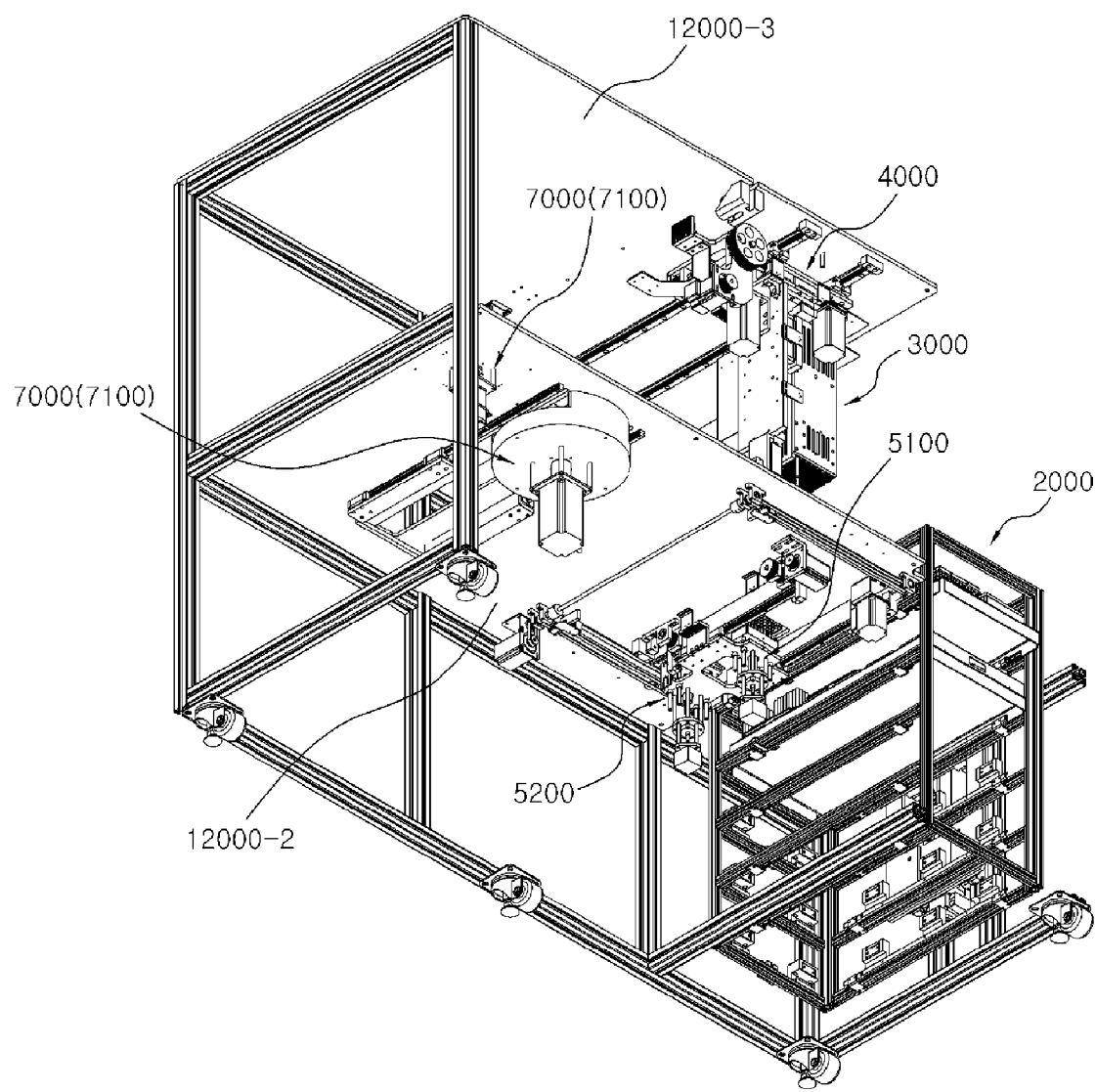
[Fig. 2]

[Fig. 3]
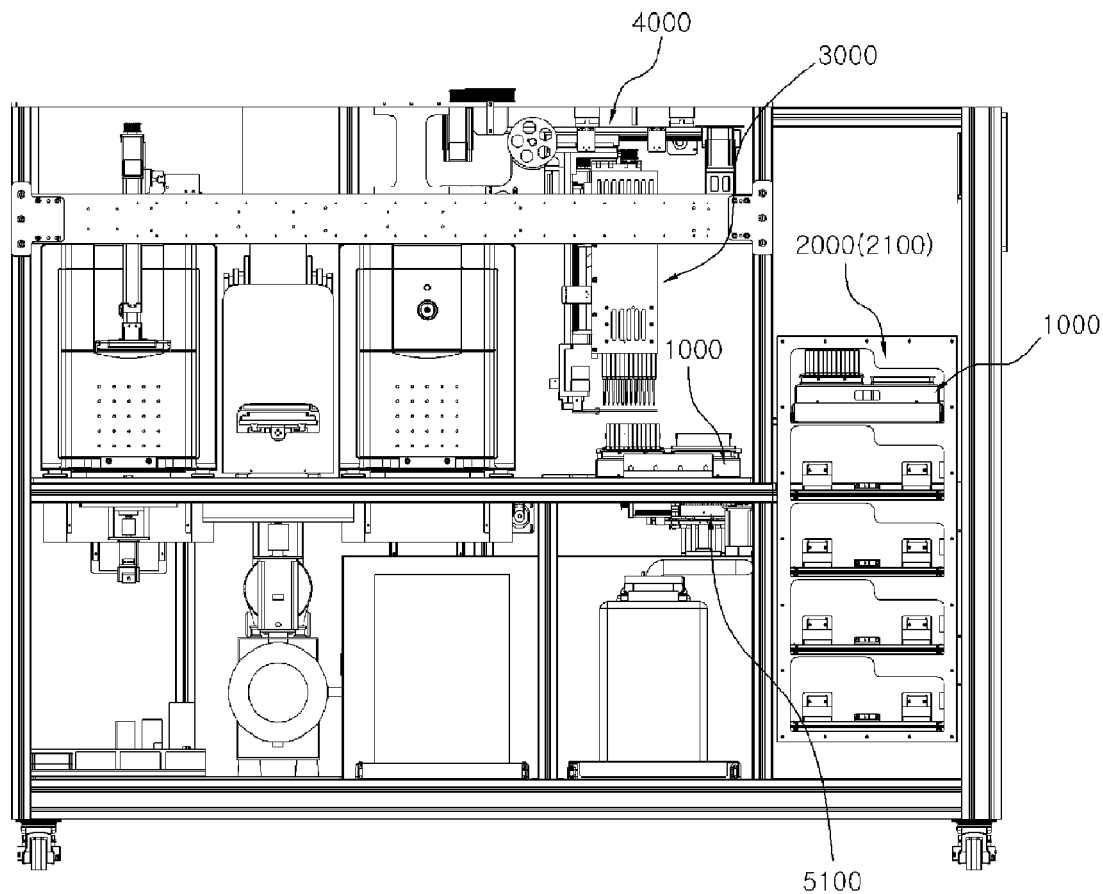
[Fig. 4]
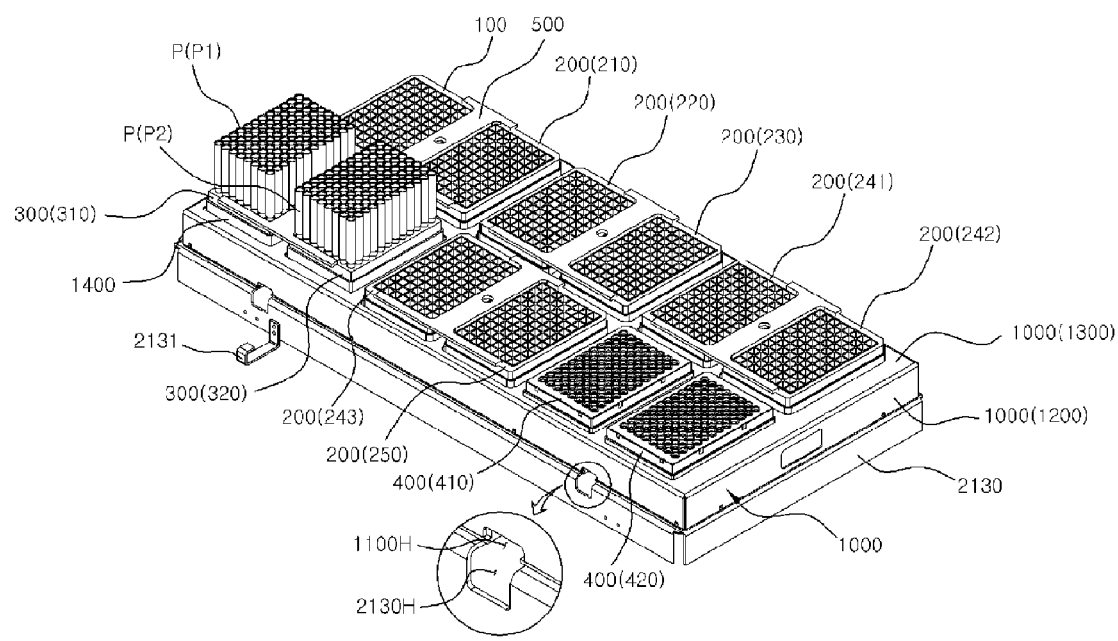

[Fig. 5]
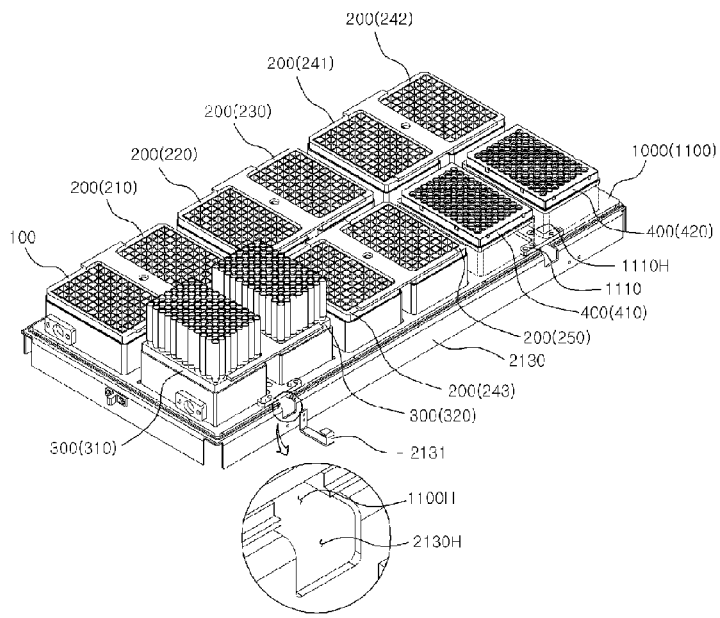
[Fig. 6]
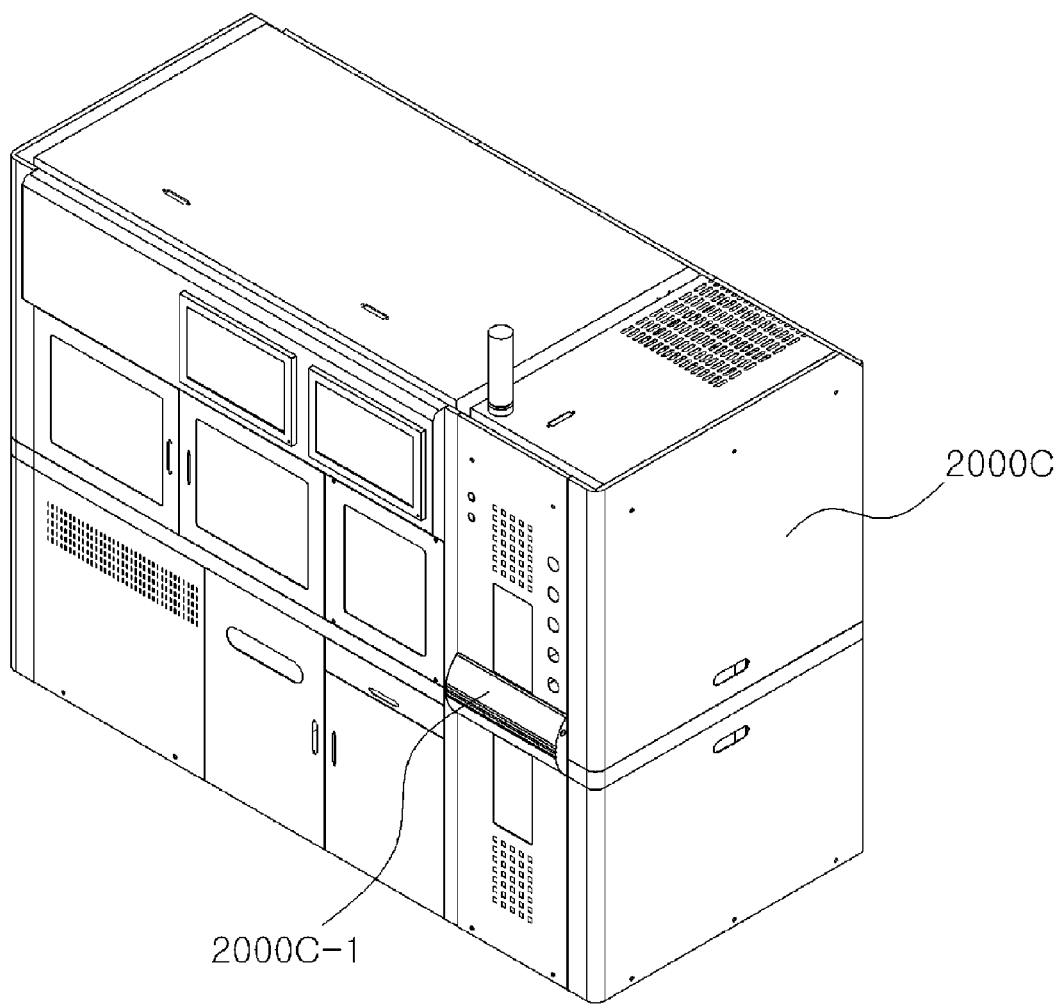

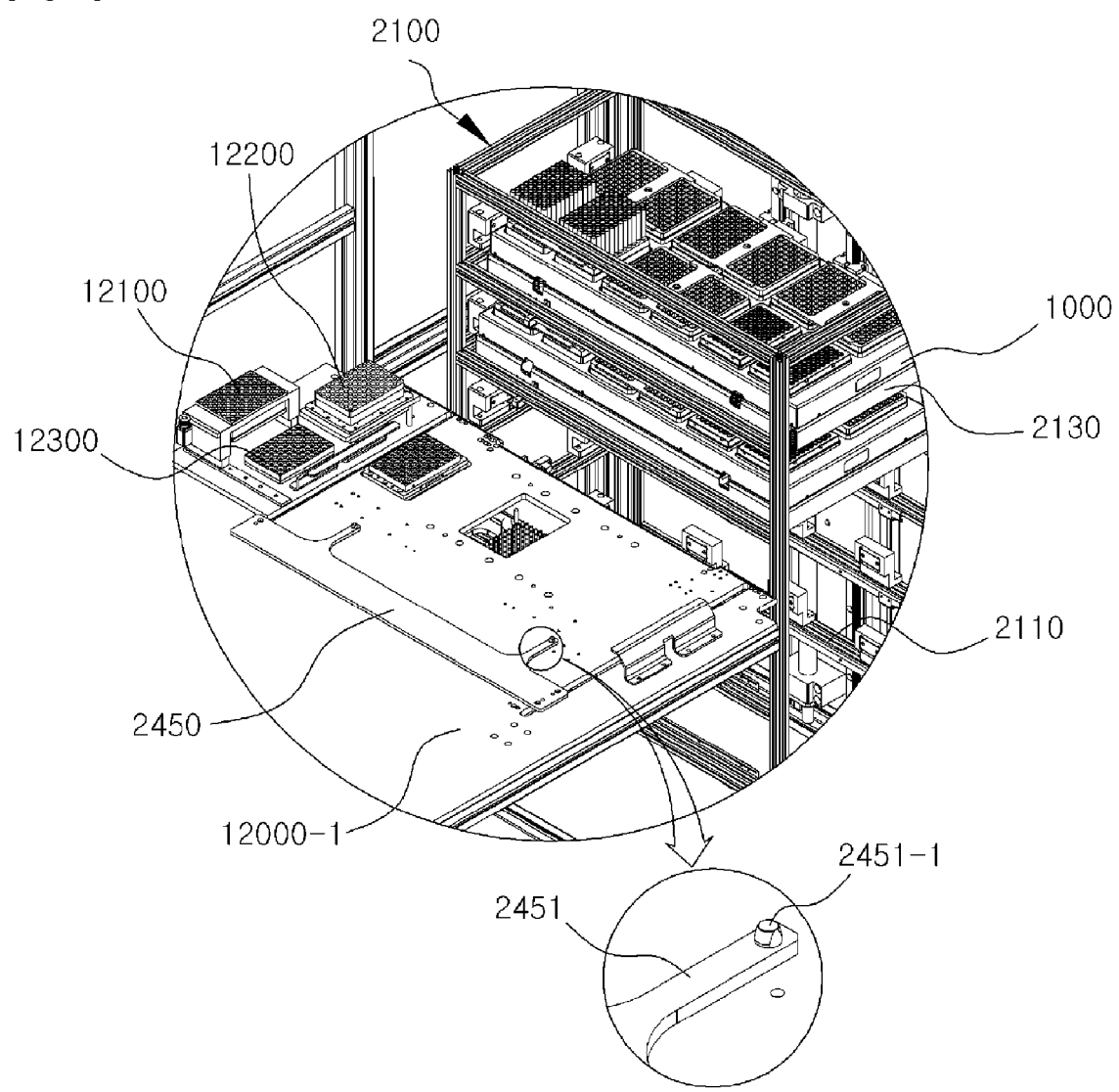
[Fig. 7]

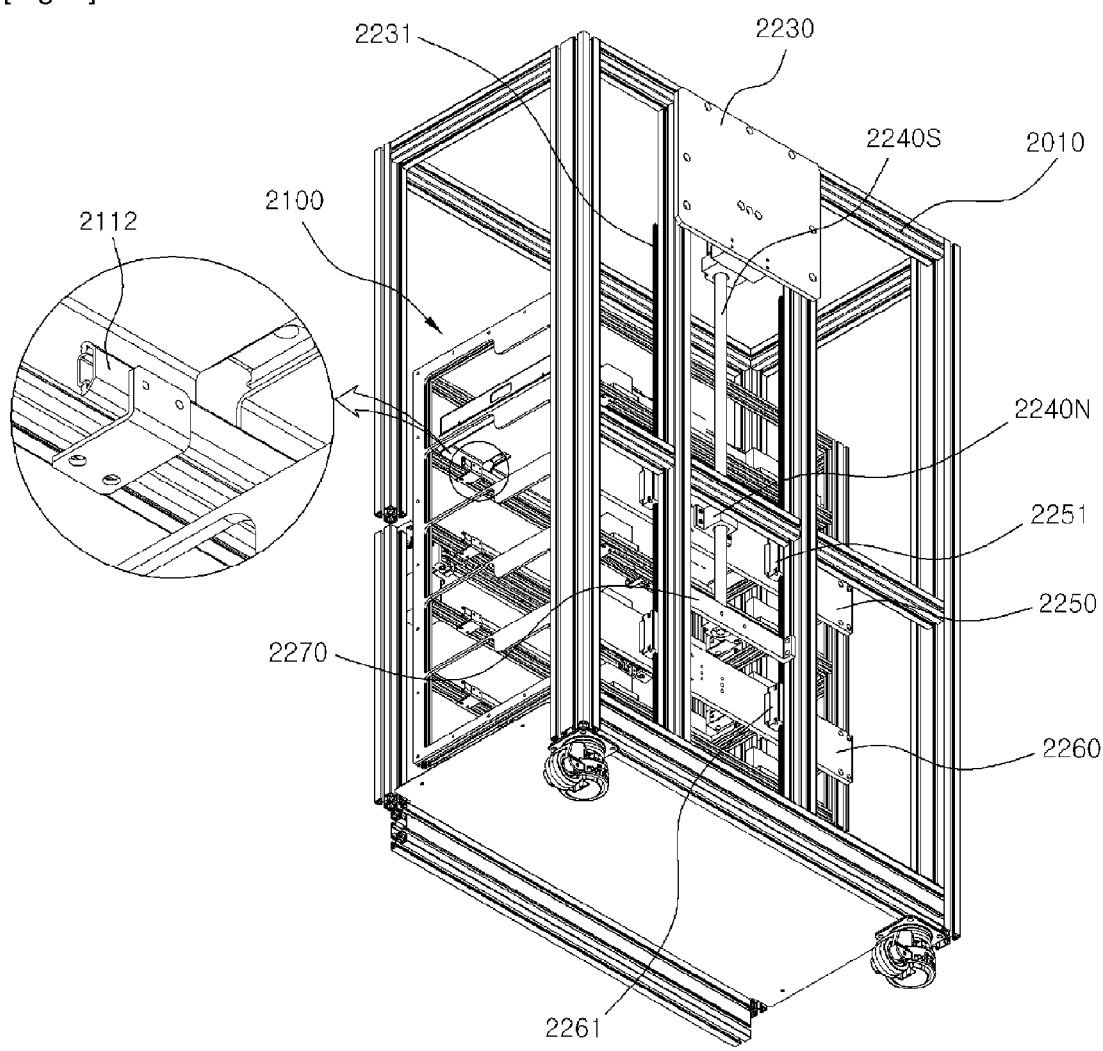
[Fig. 8]

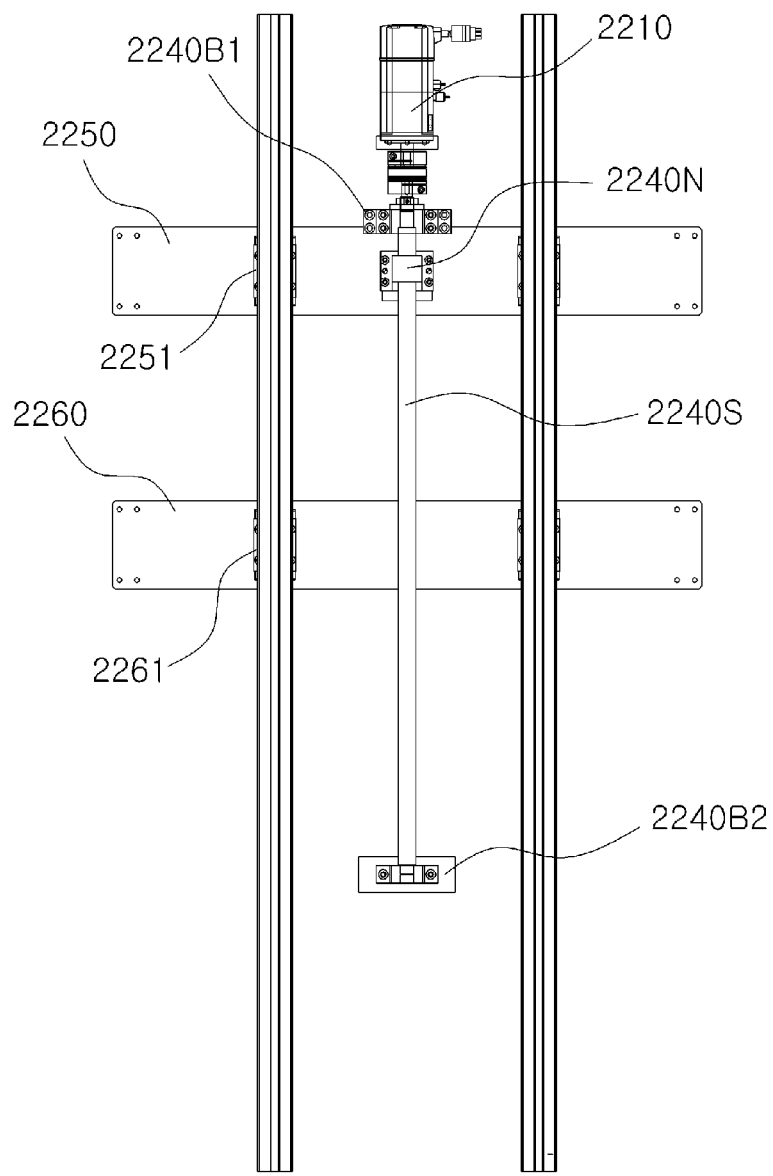

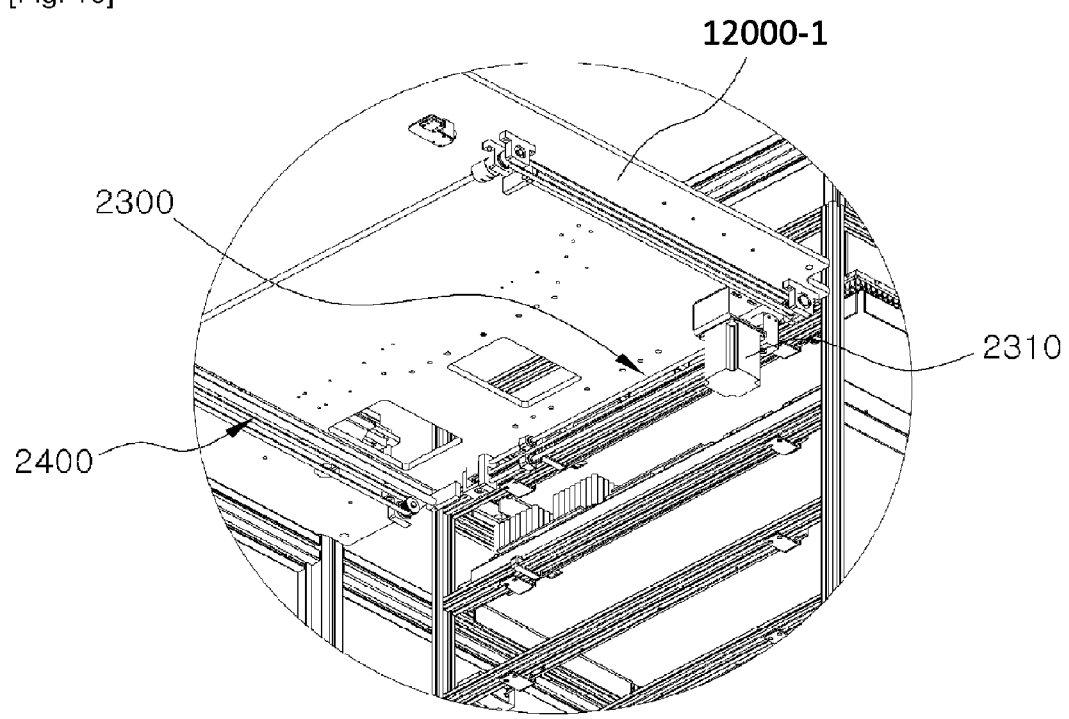
[Fig. 10]

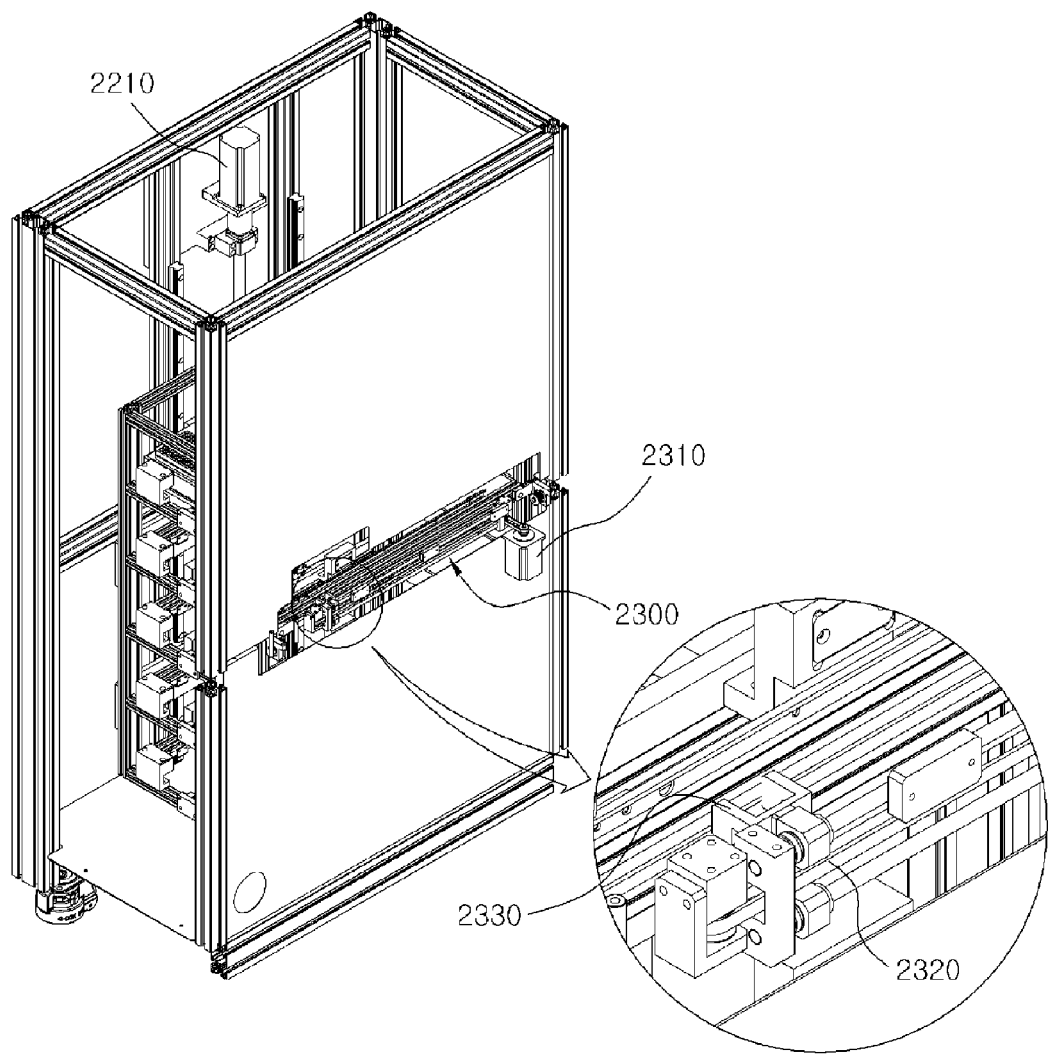
[Fig. 11]

[Fig. 12]
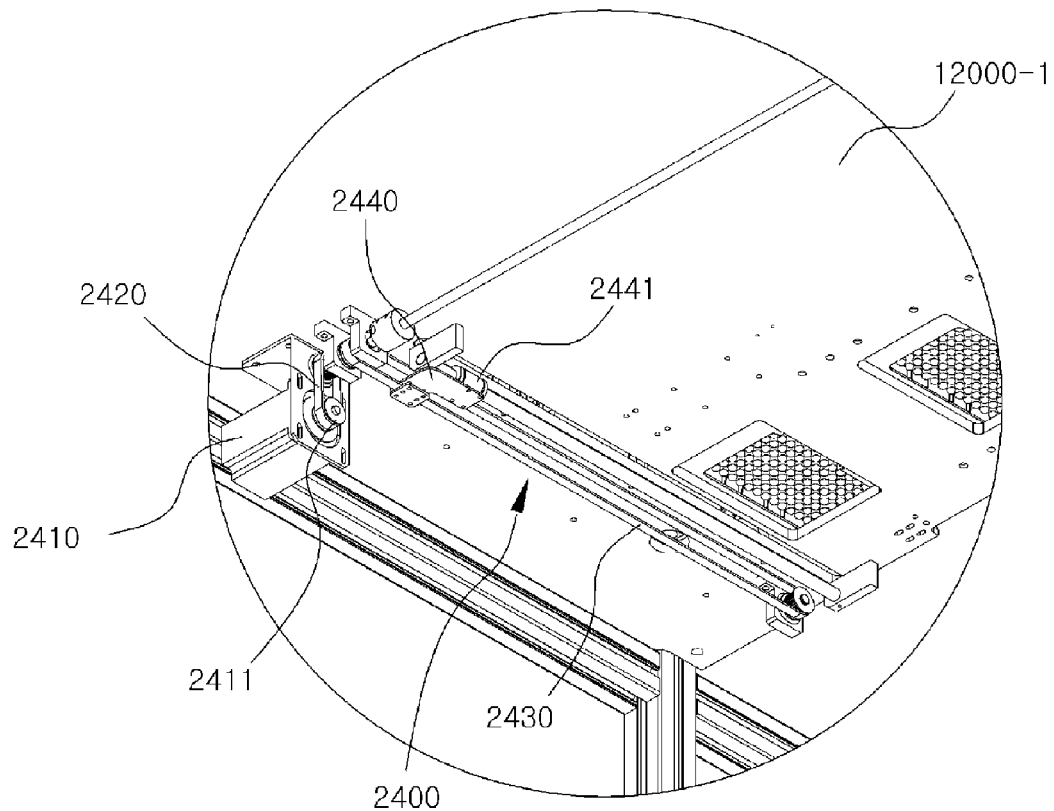
[Fig. 13]
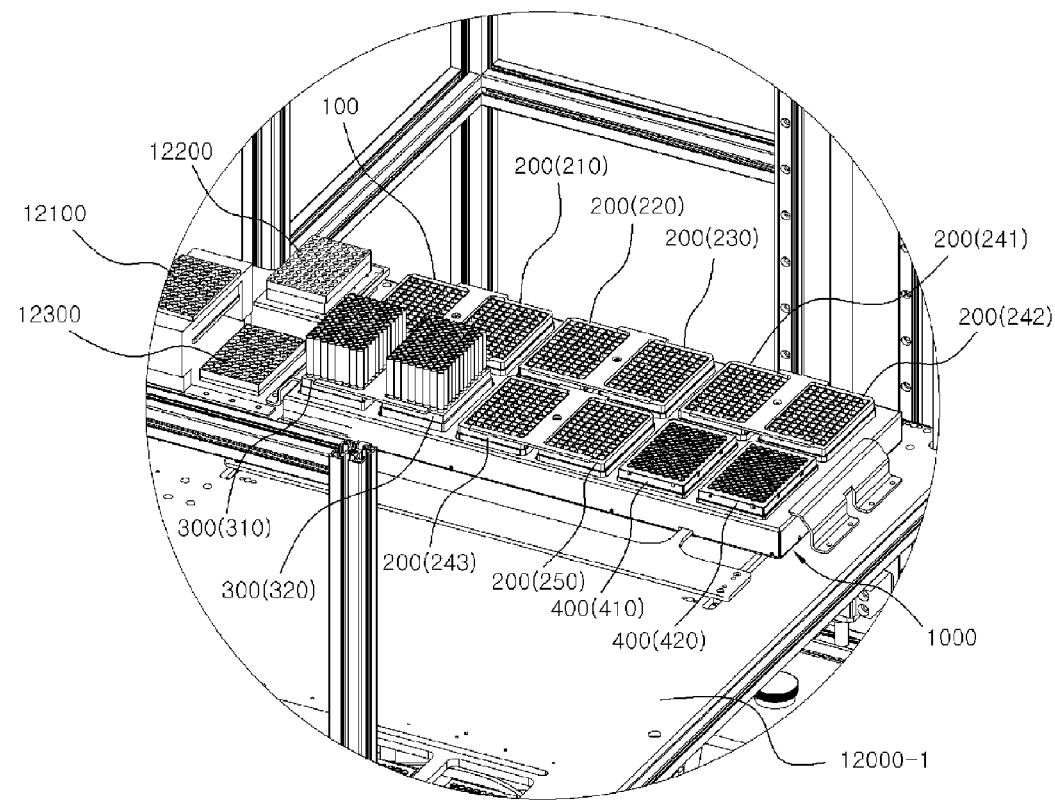

[Fig. 14]
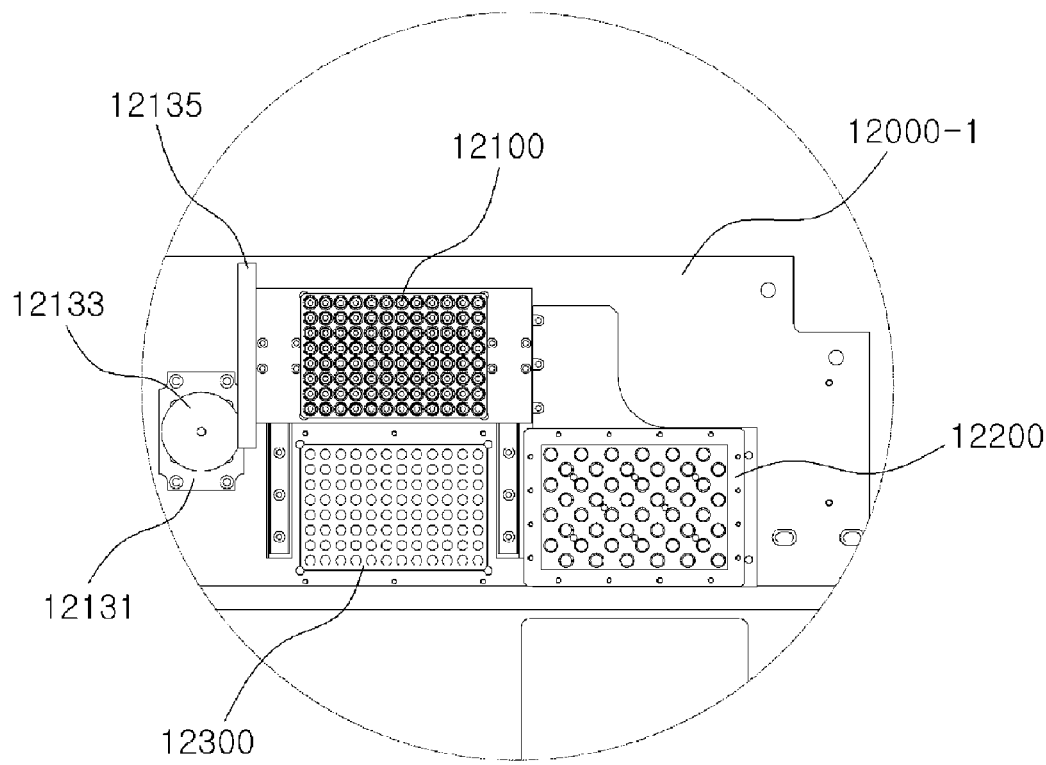
[Fig. 15]
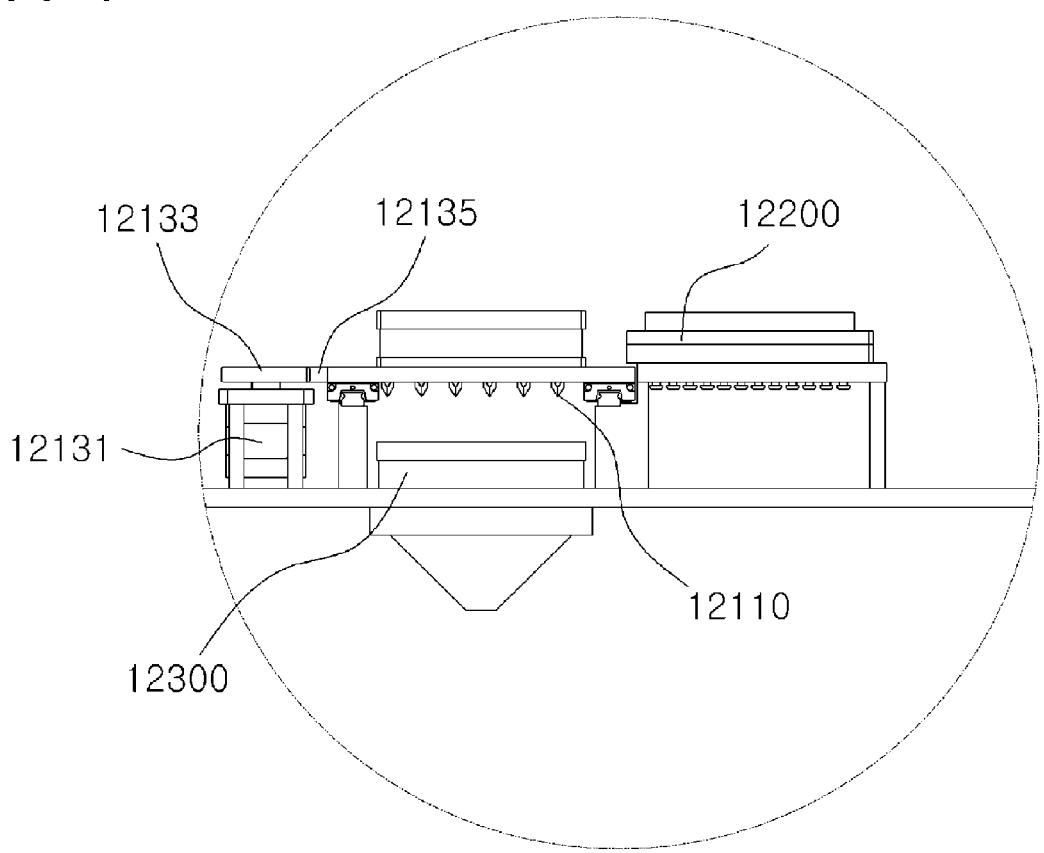

[Fig. 16]
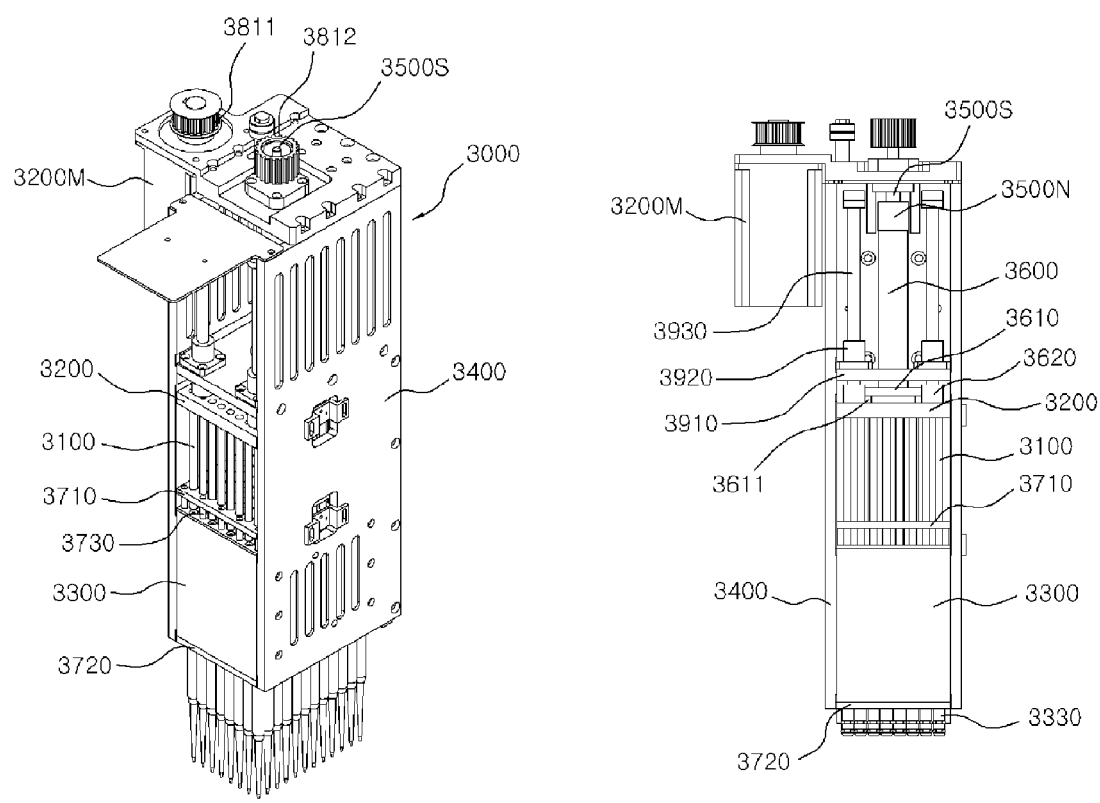

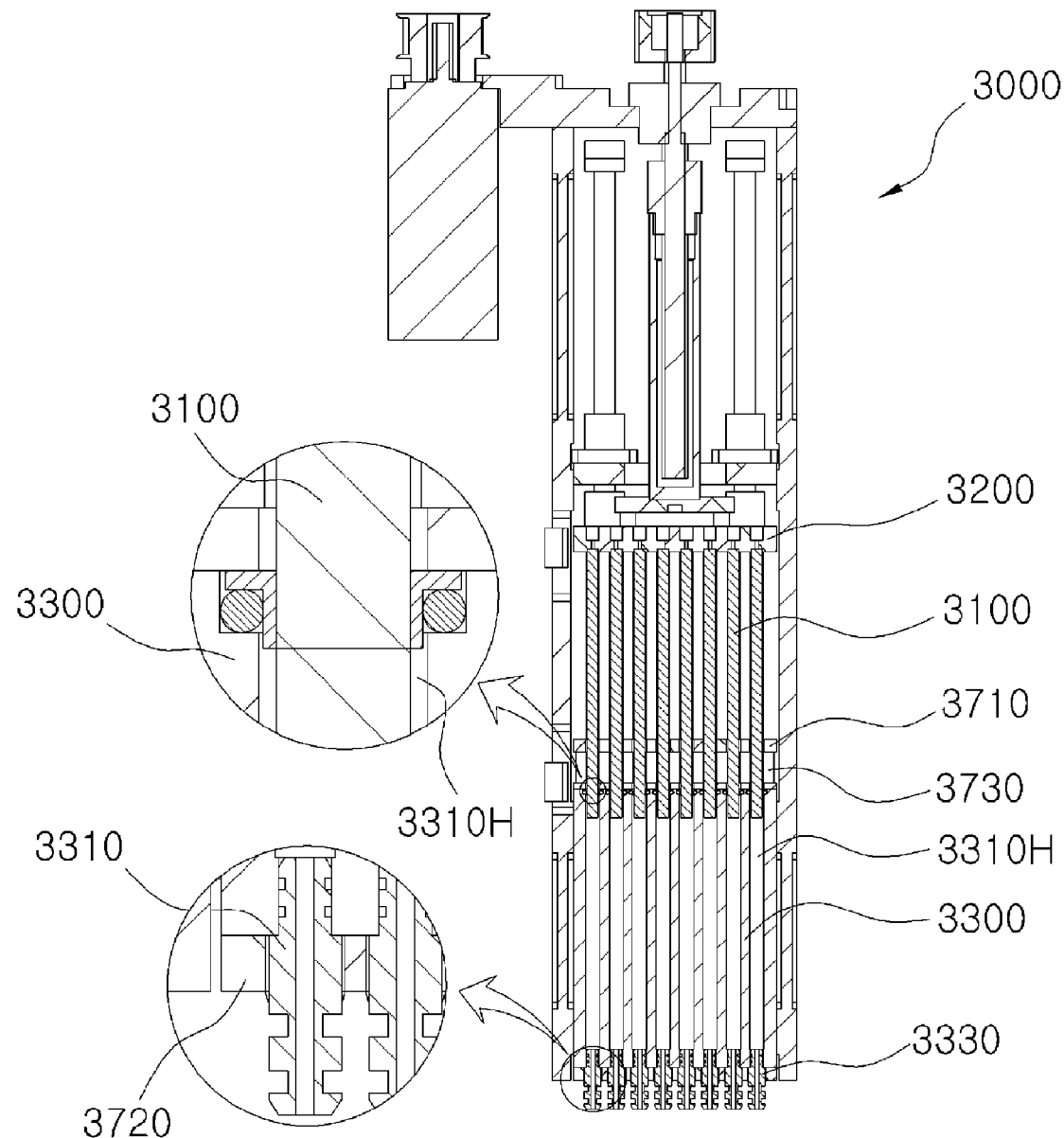
[Fig. 17]

[Fig. 18]
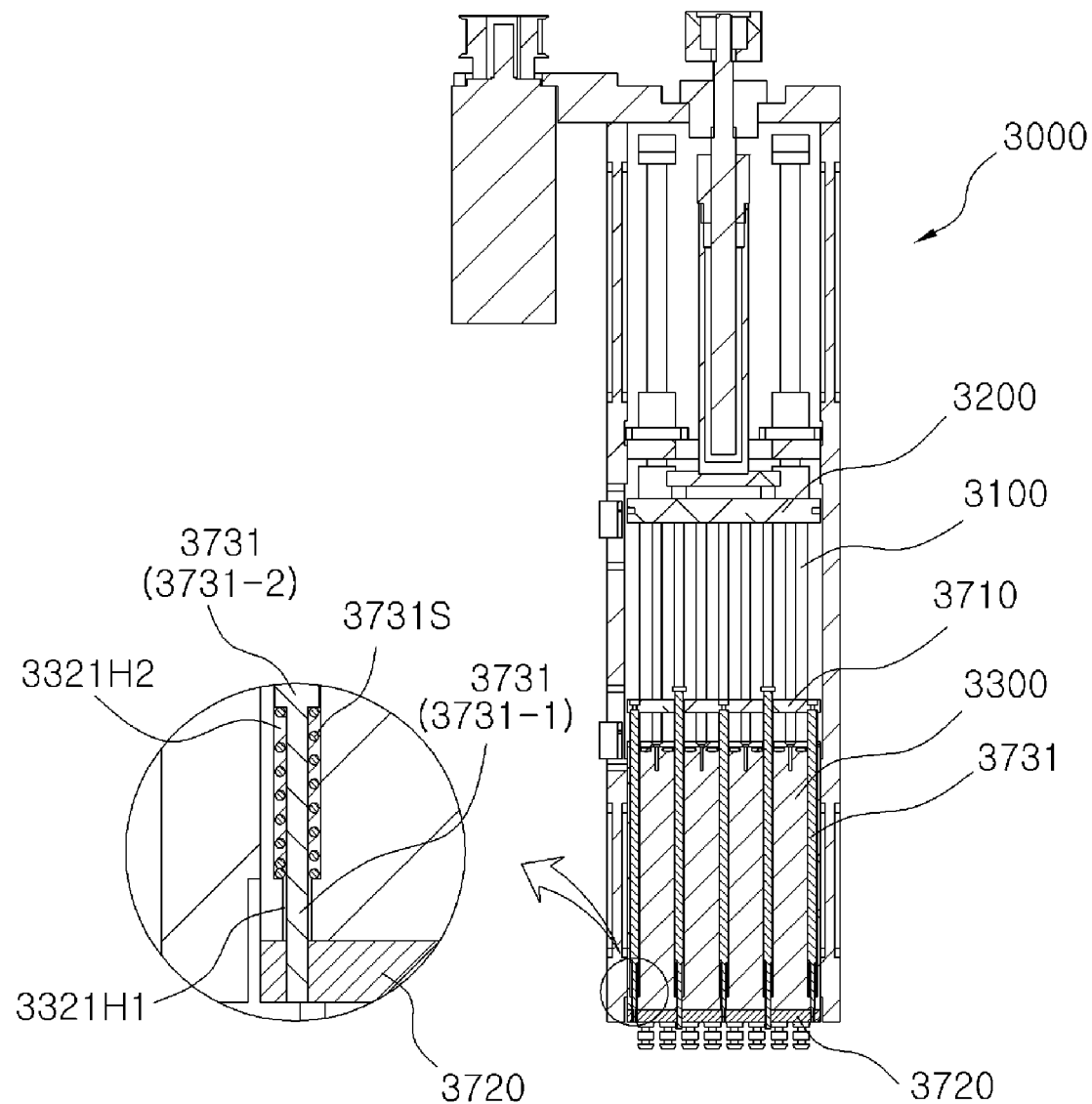

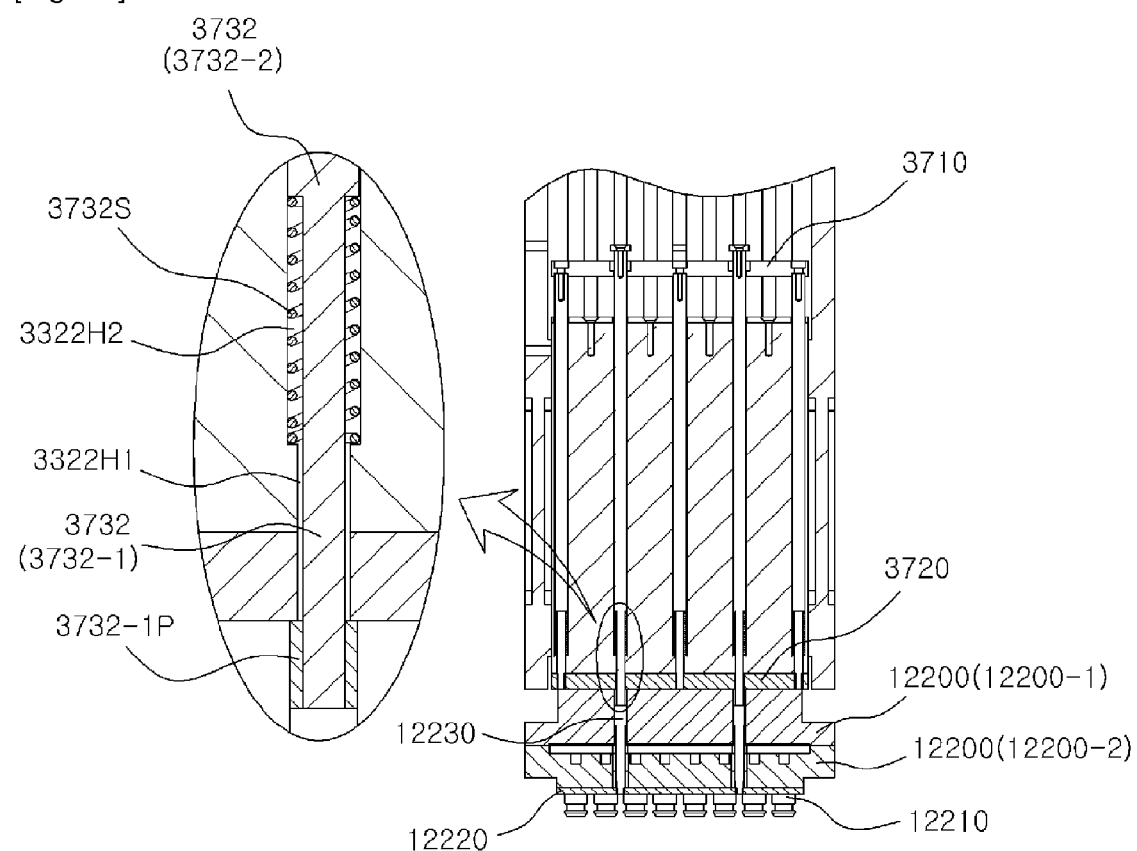
[Fig. 19]

[Fig. 20]
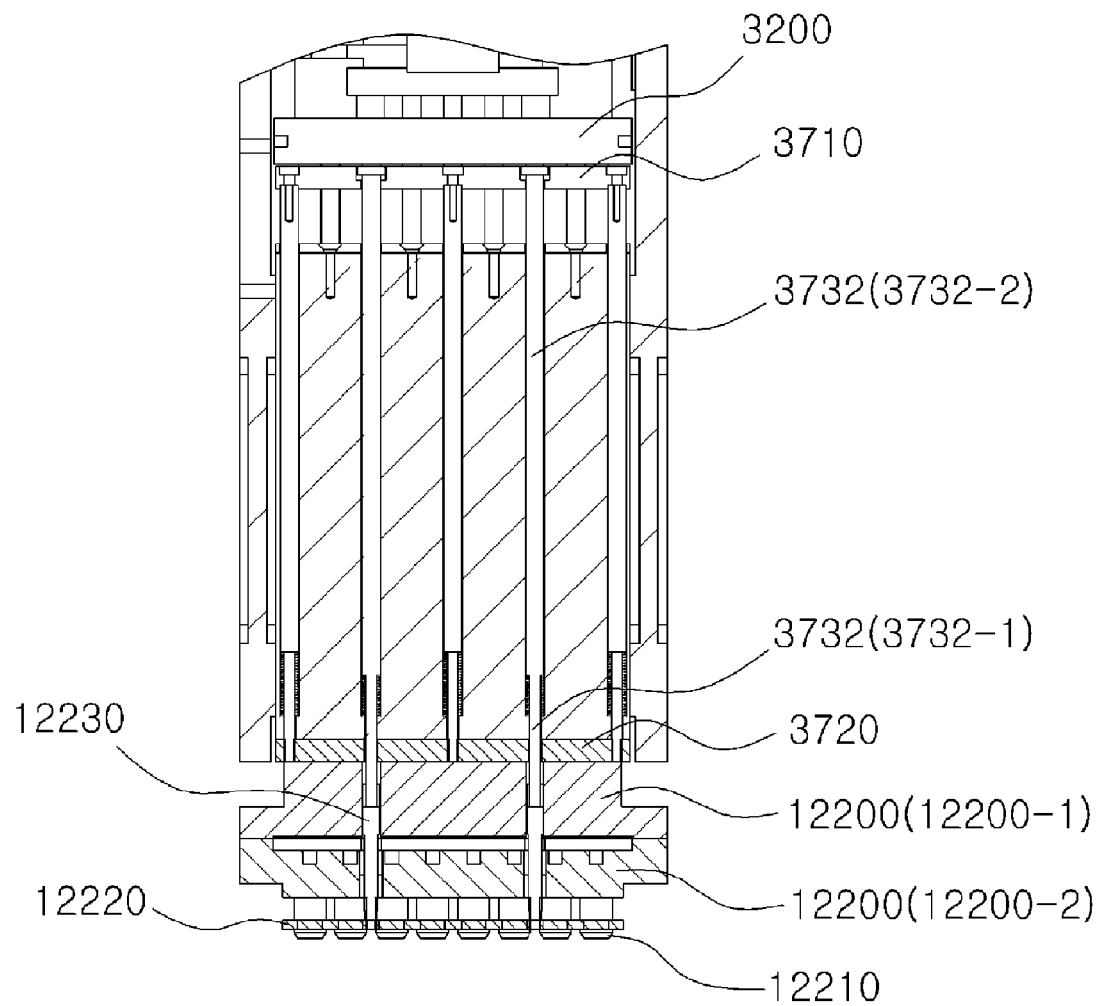

[Fig. 21]
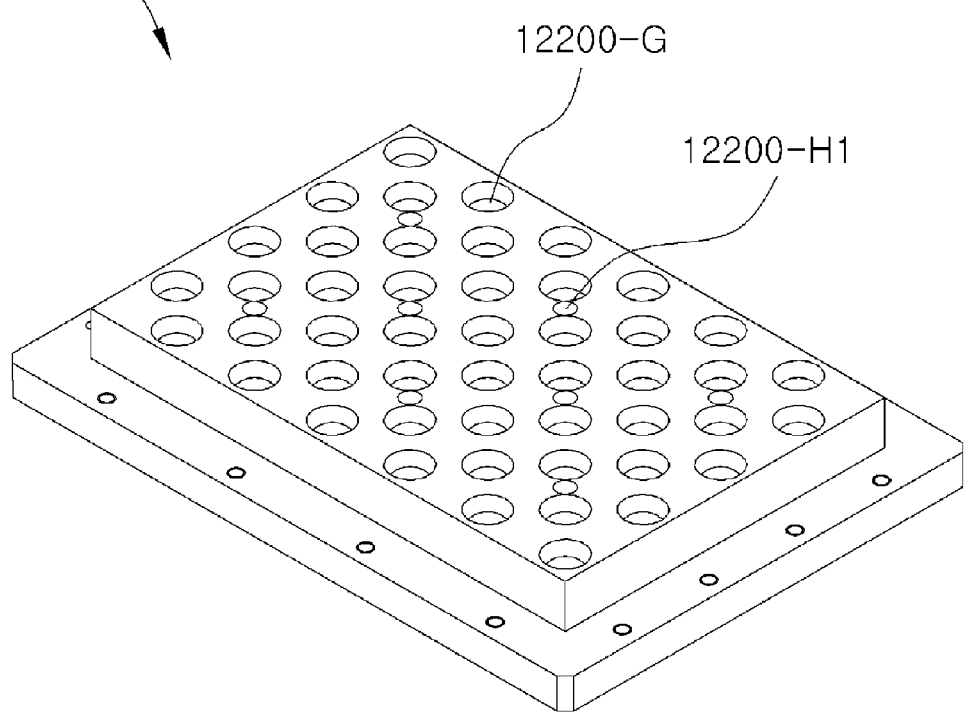
[Fig. 22]
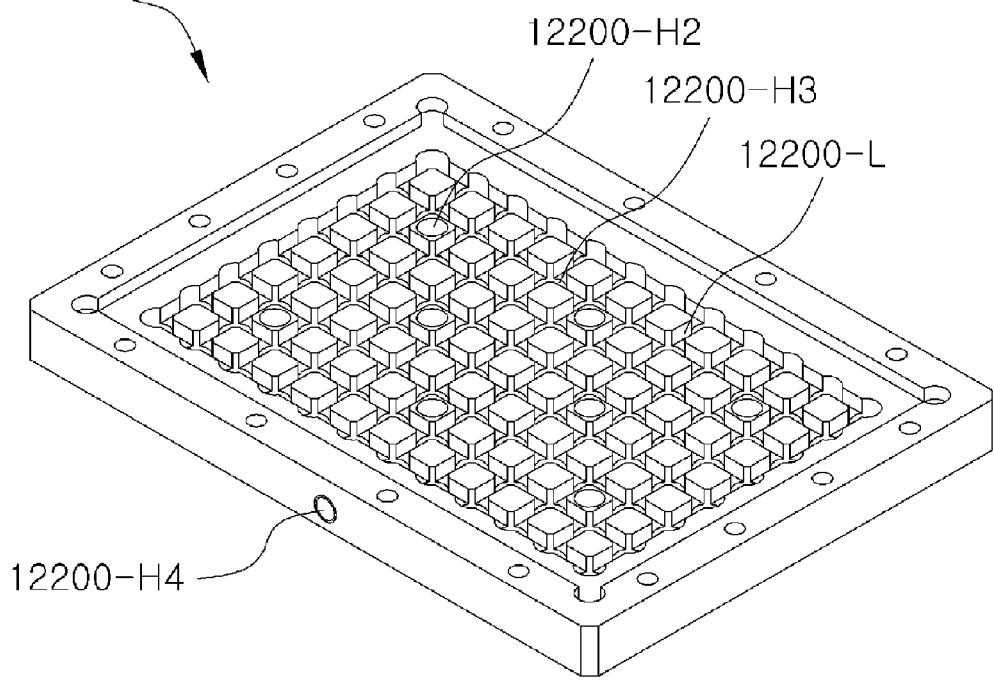

[Fig. 23]
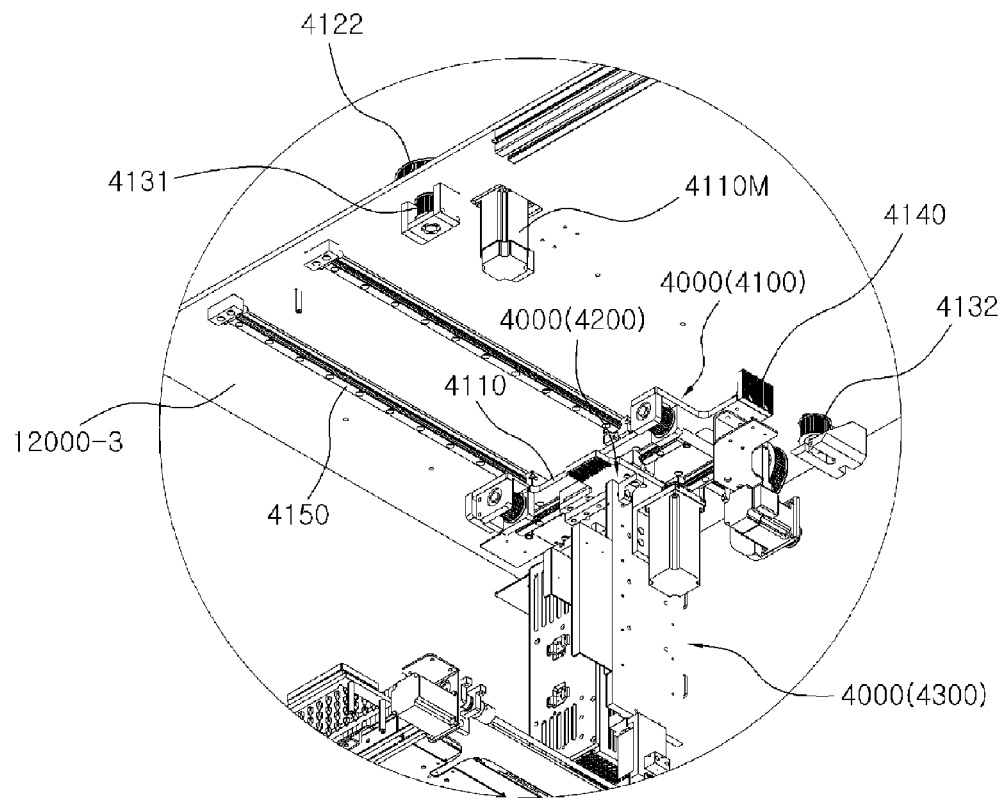
[Fig. 24]
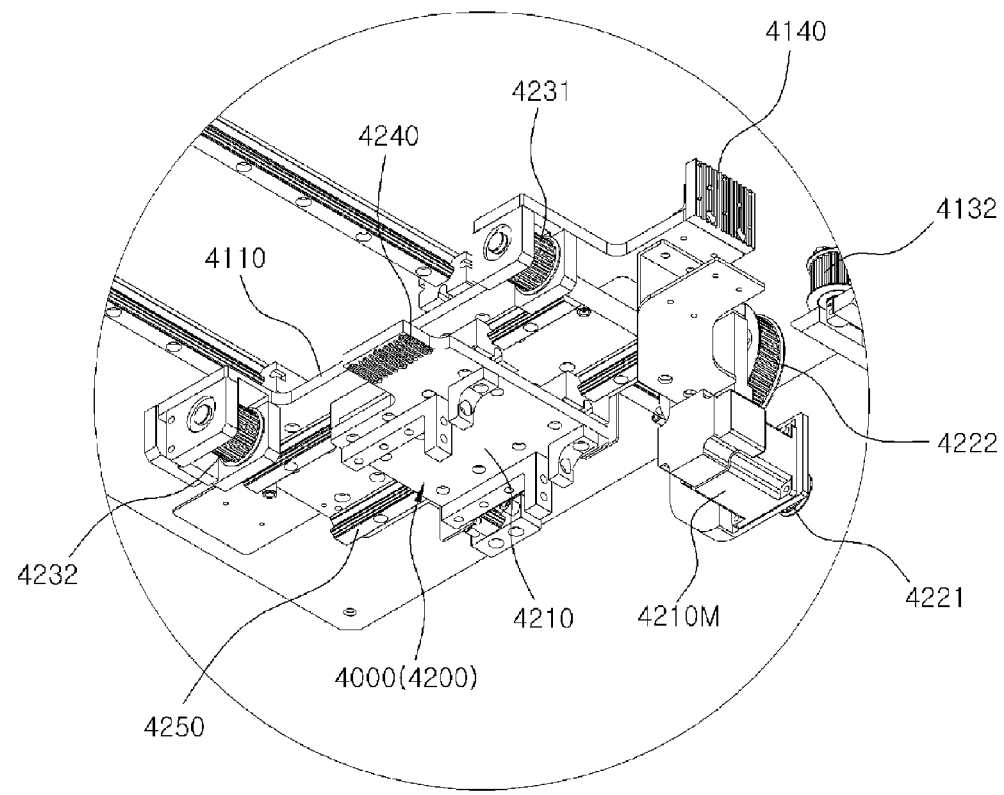

[Fig. 25]
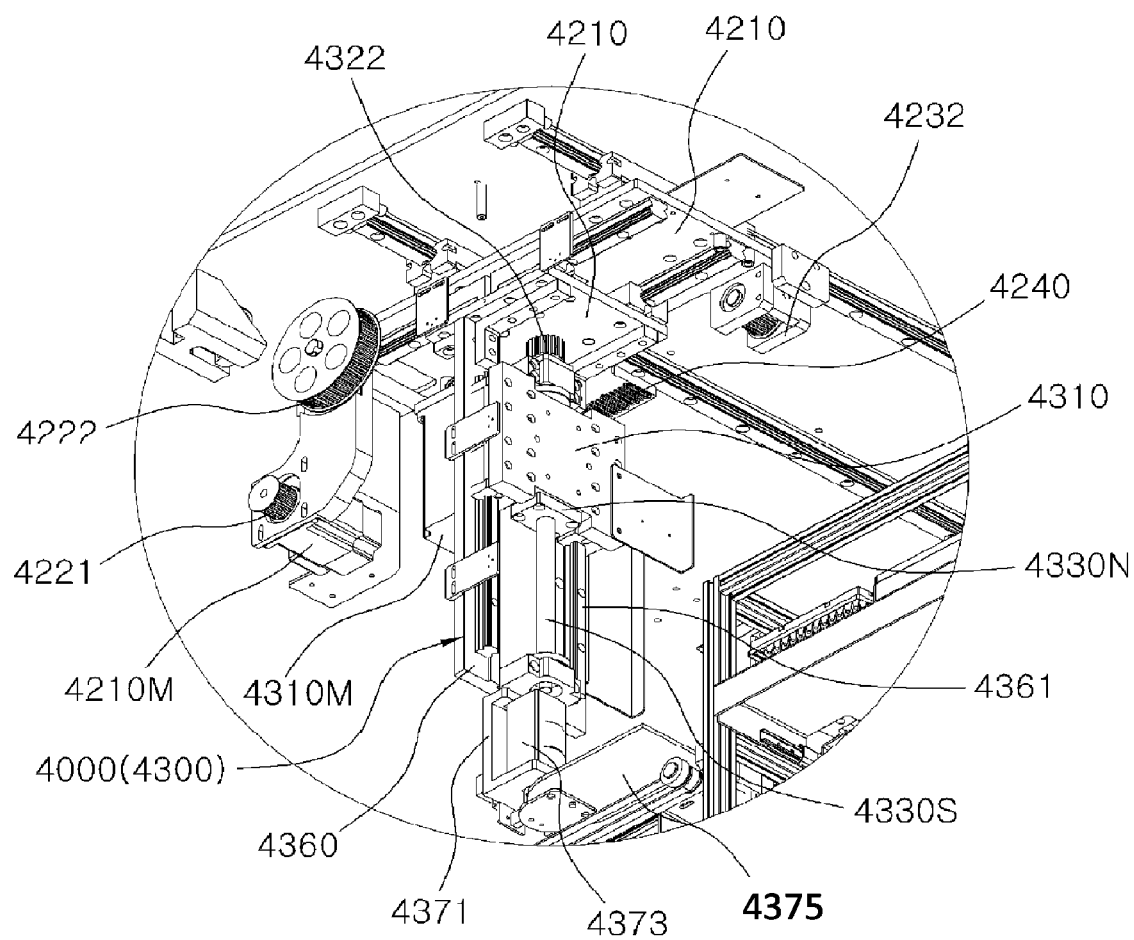

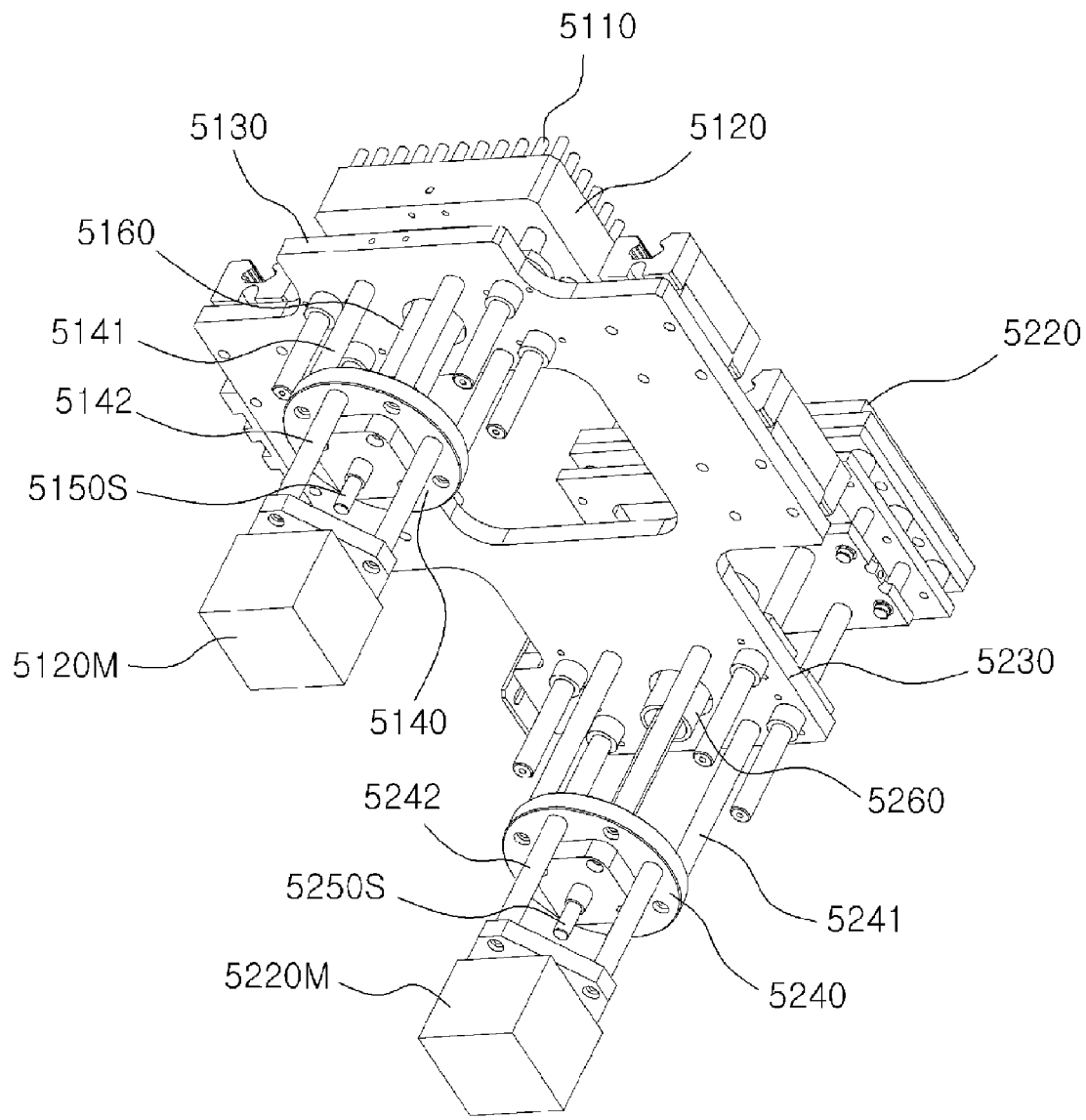
[Fig. 26]

[Fig. 27]
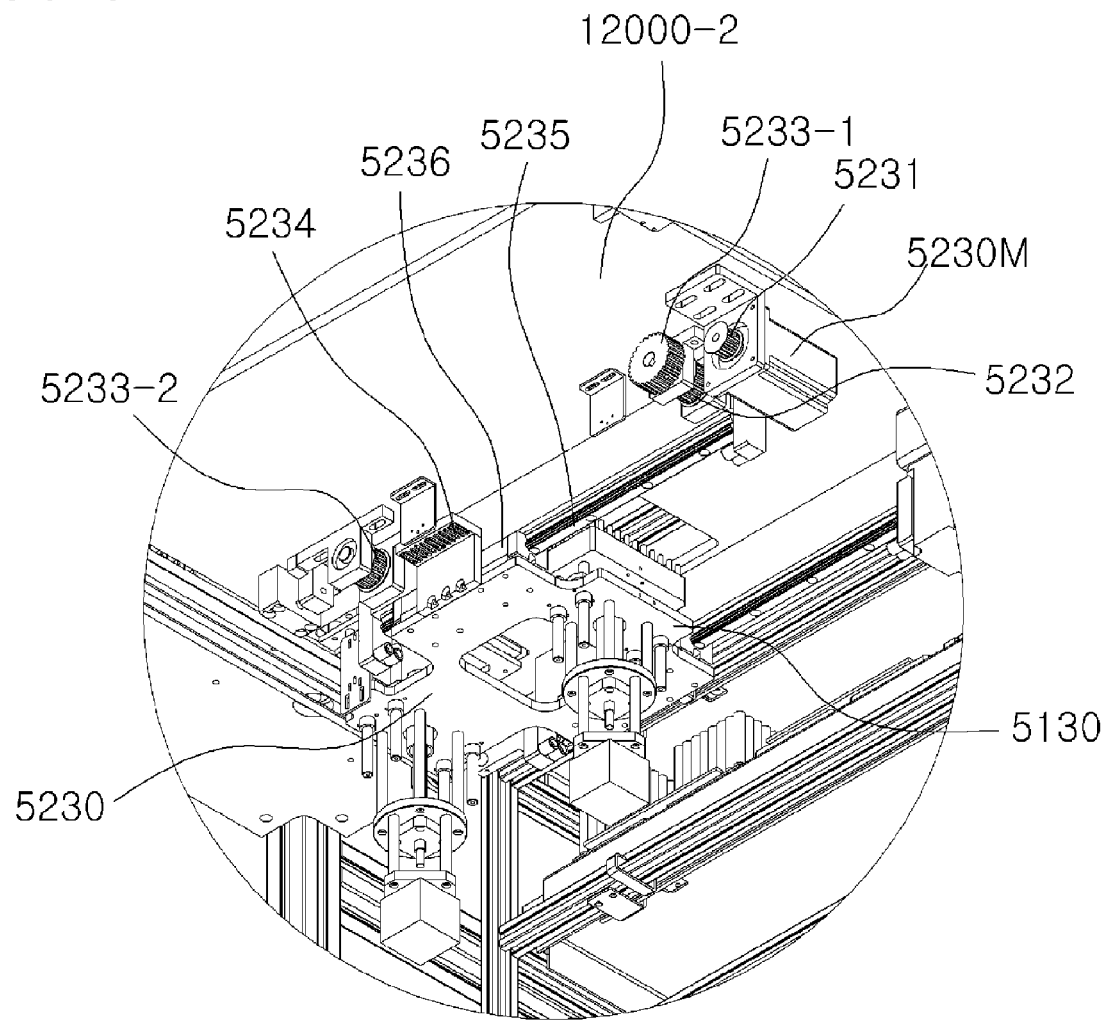

[Fig. 28]
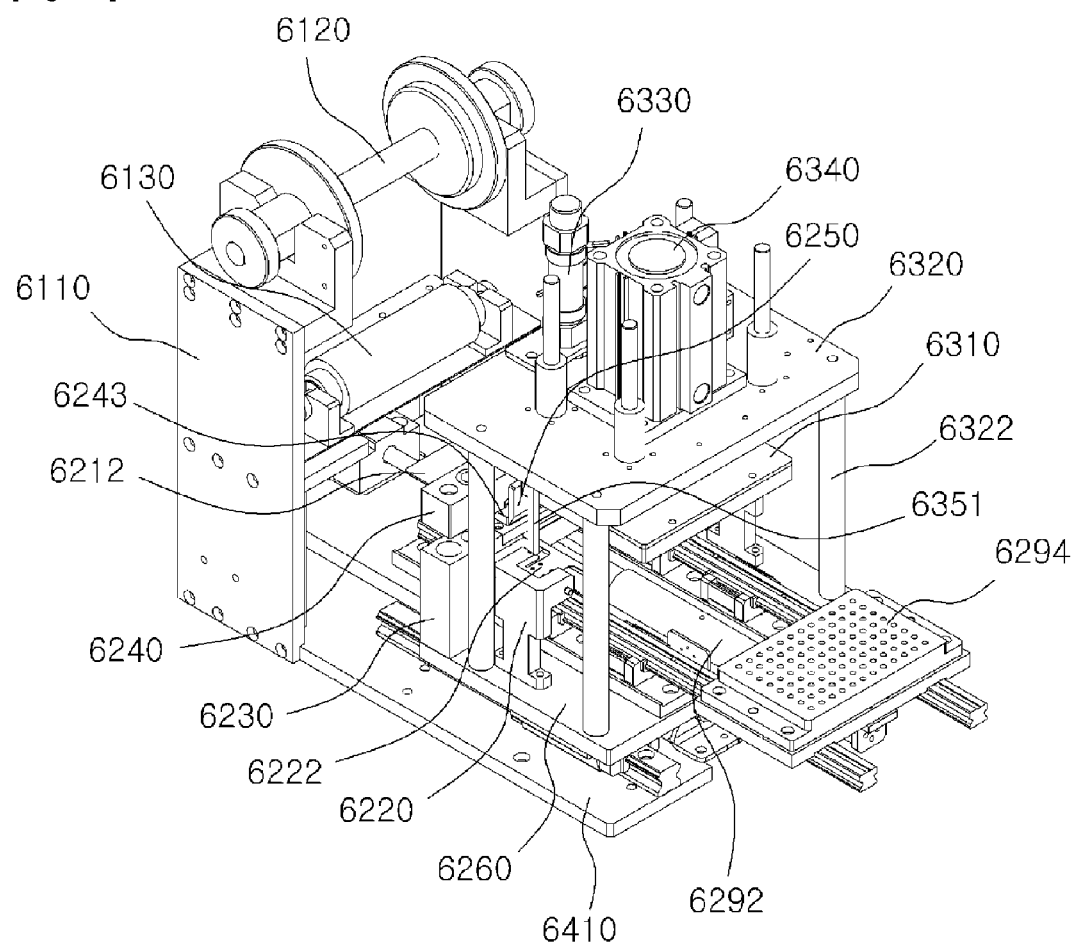

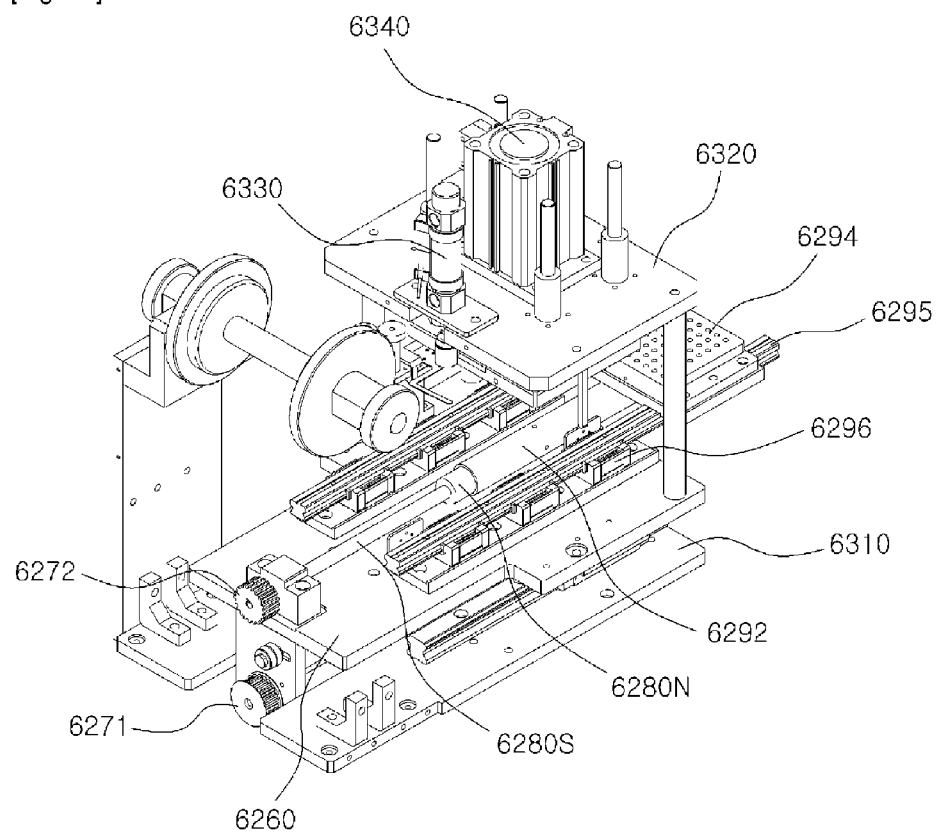
[Fig. 29]

[Fig. 30]
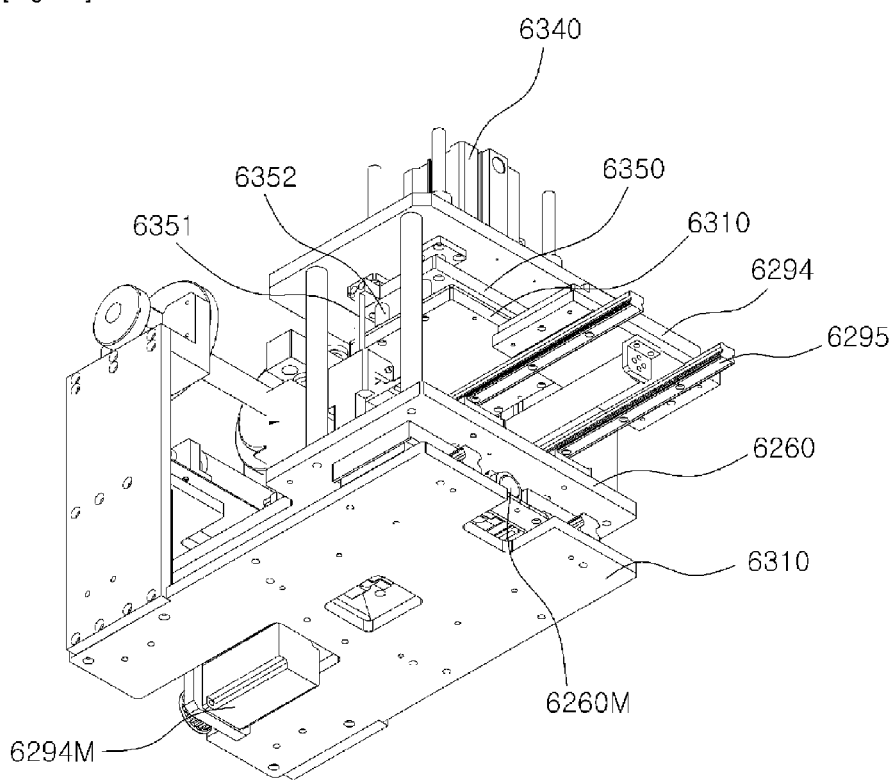

[Fig. 31]
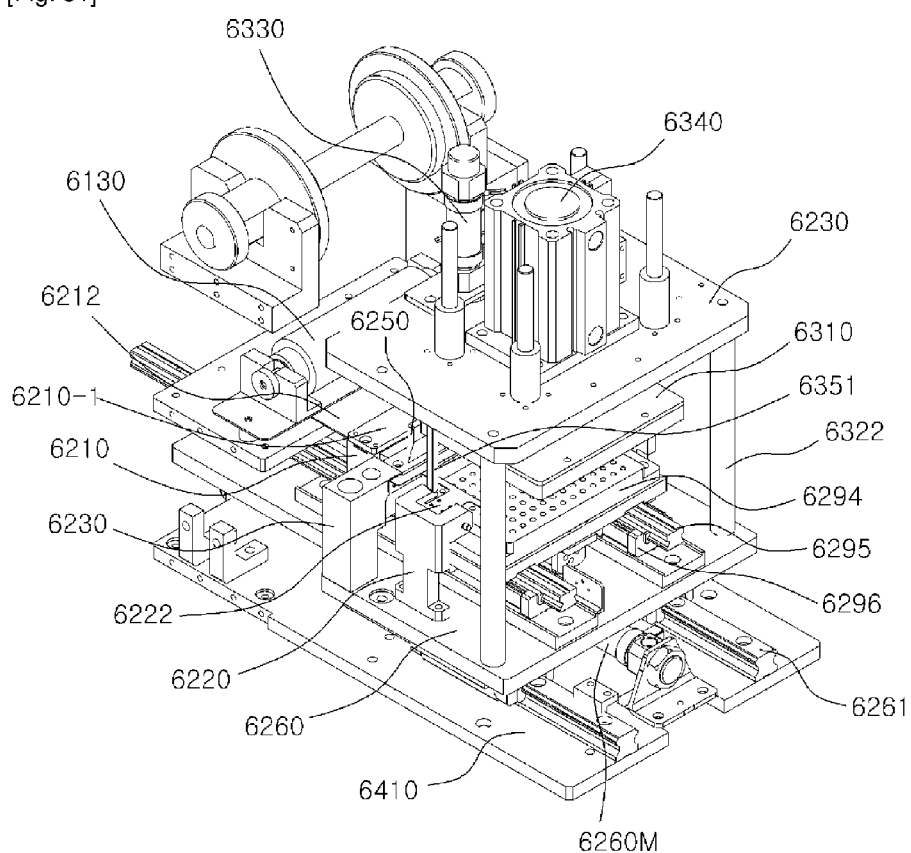

[Fig. 32]
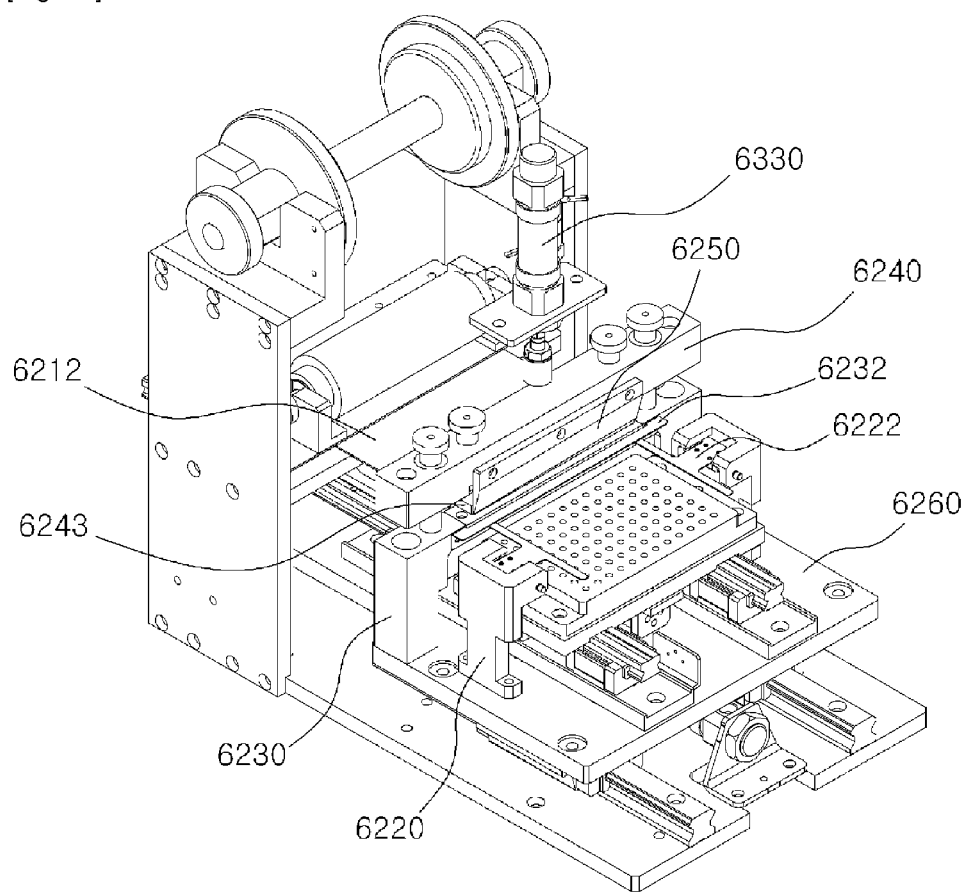

[Fig. 33]
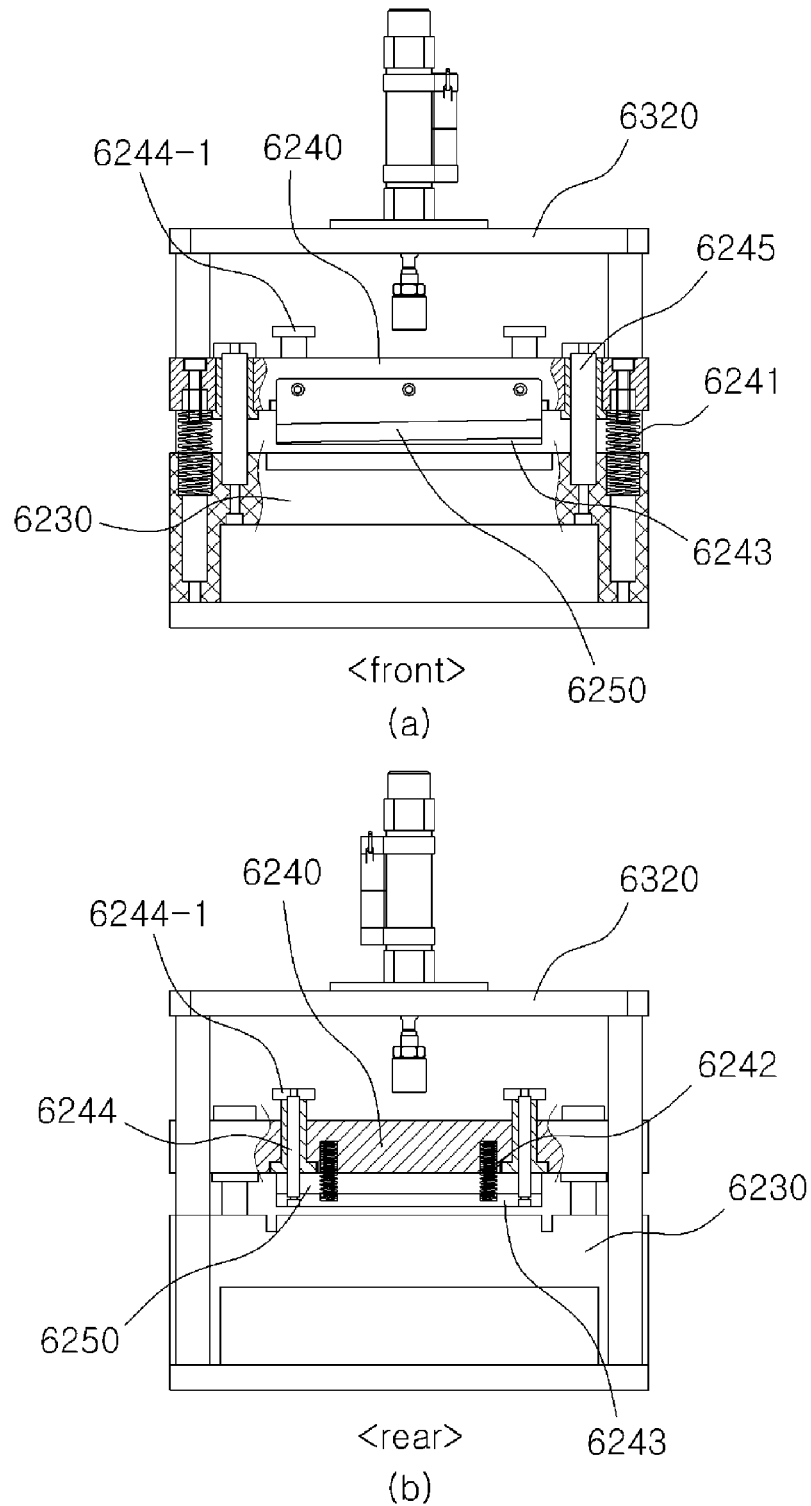

[Fig. 34]
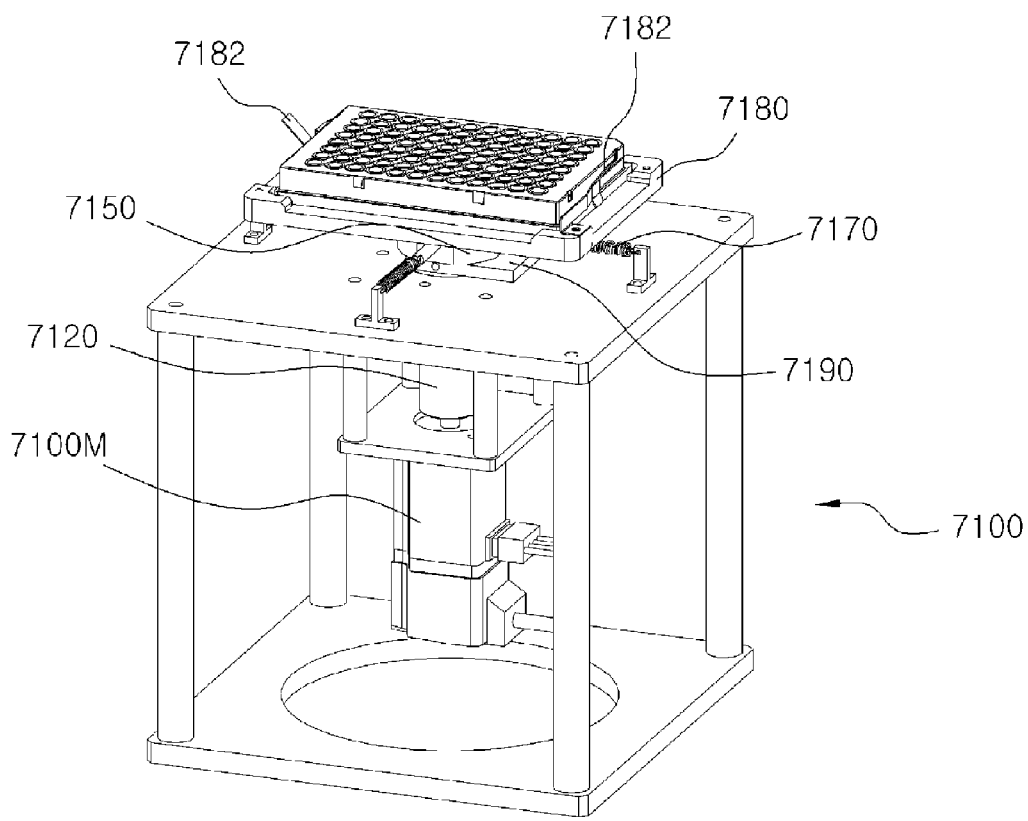
[Fig. 35]
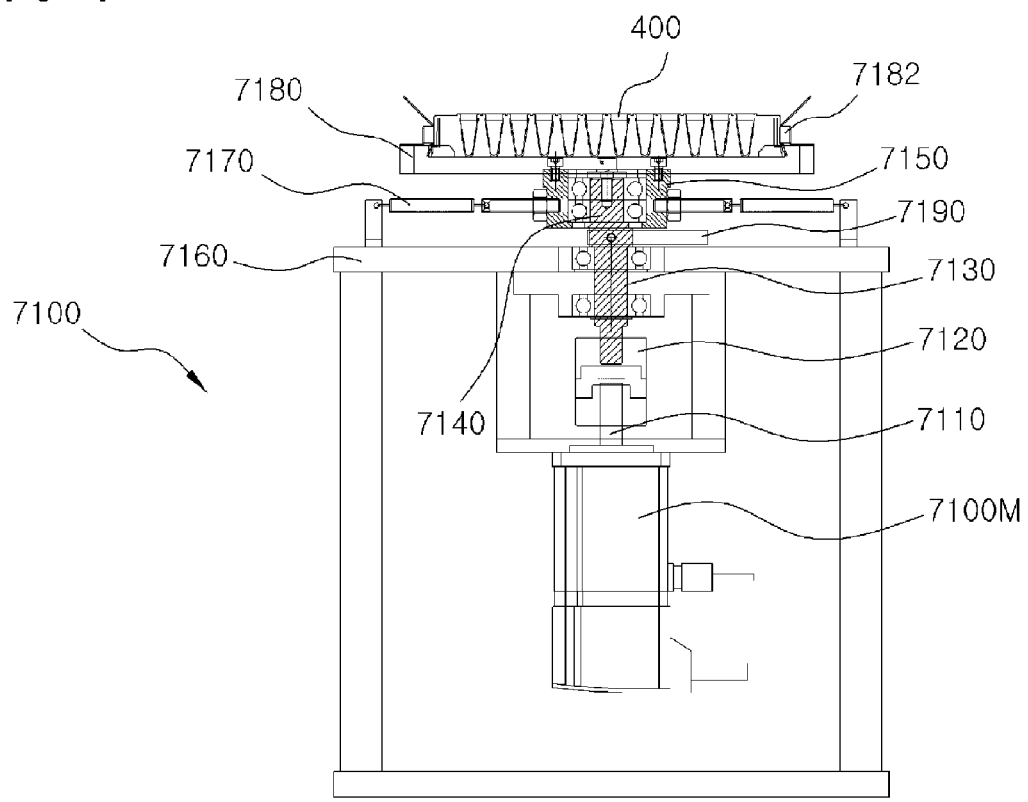

[Fig. 36]
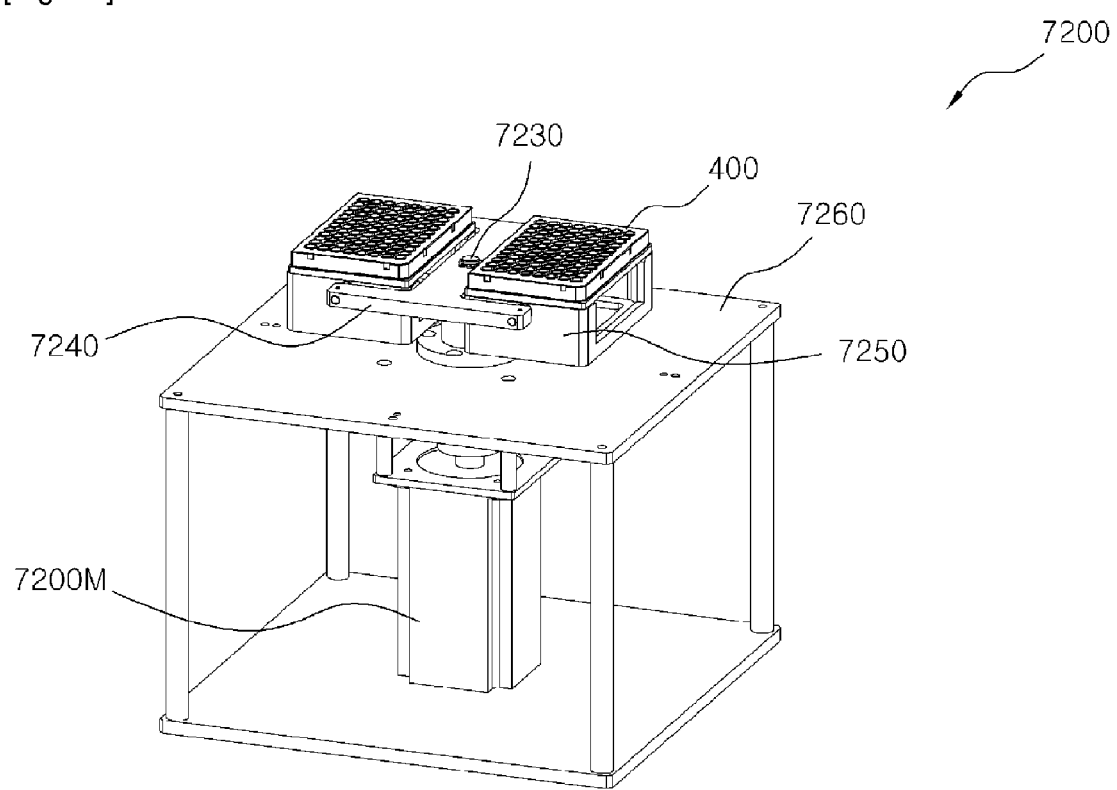

[Fig. 37]
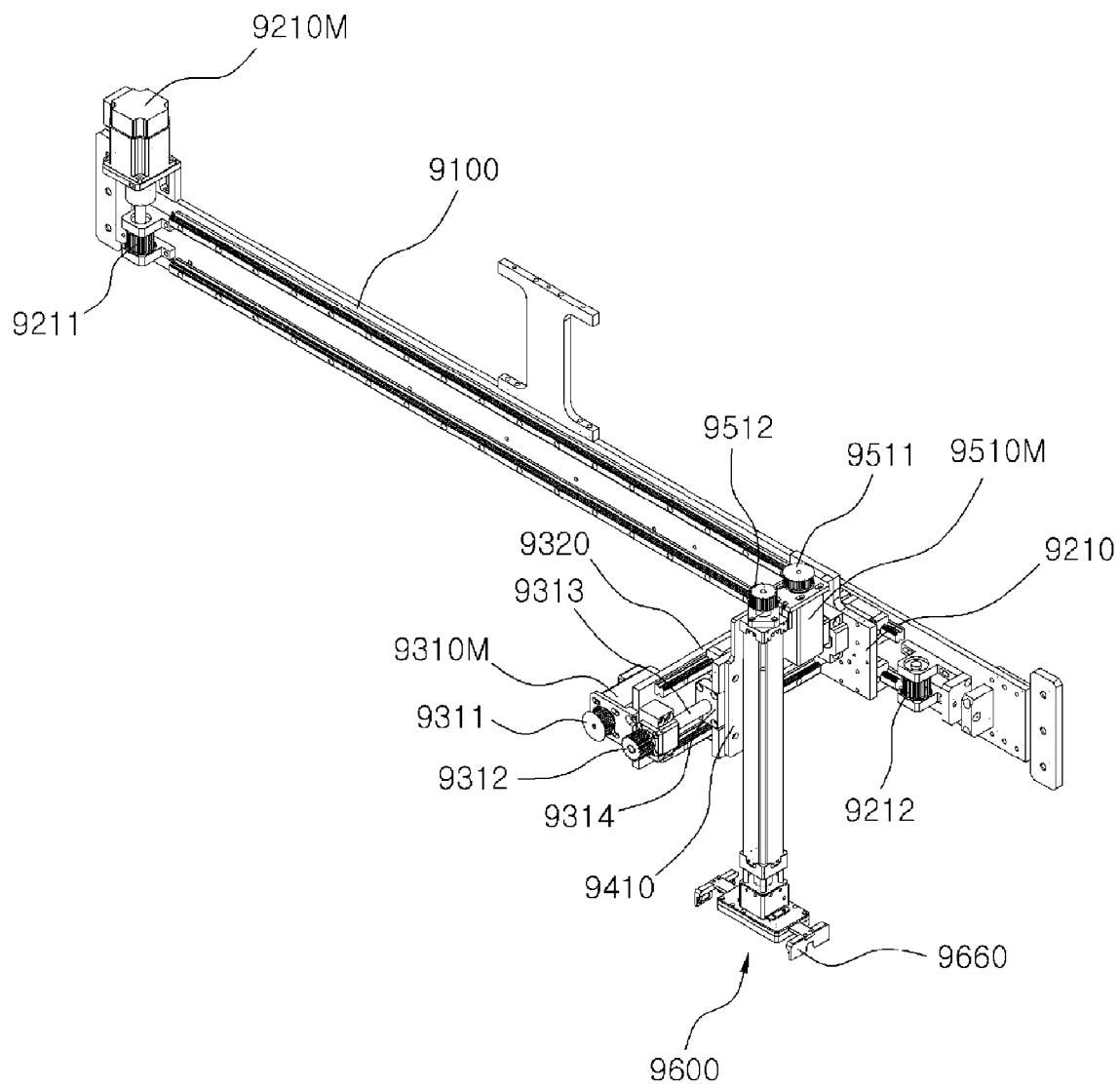

[Fig. 38]
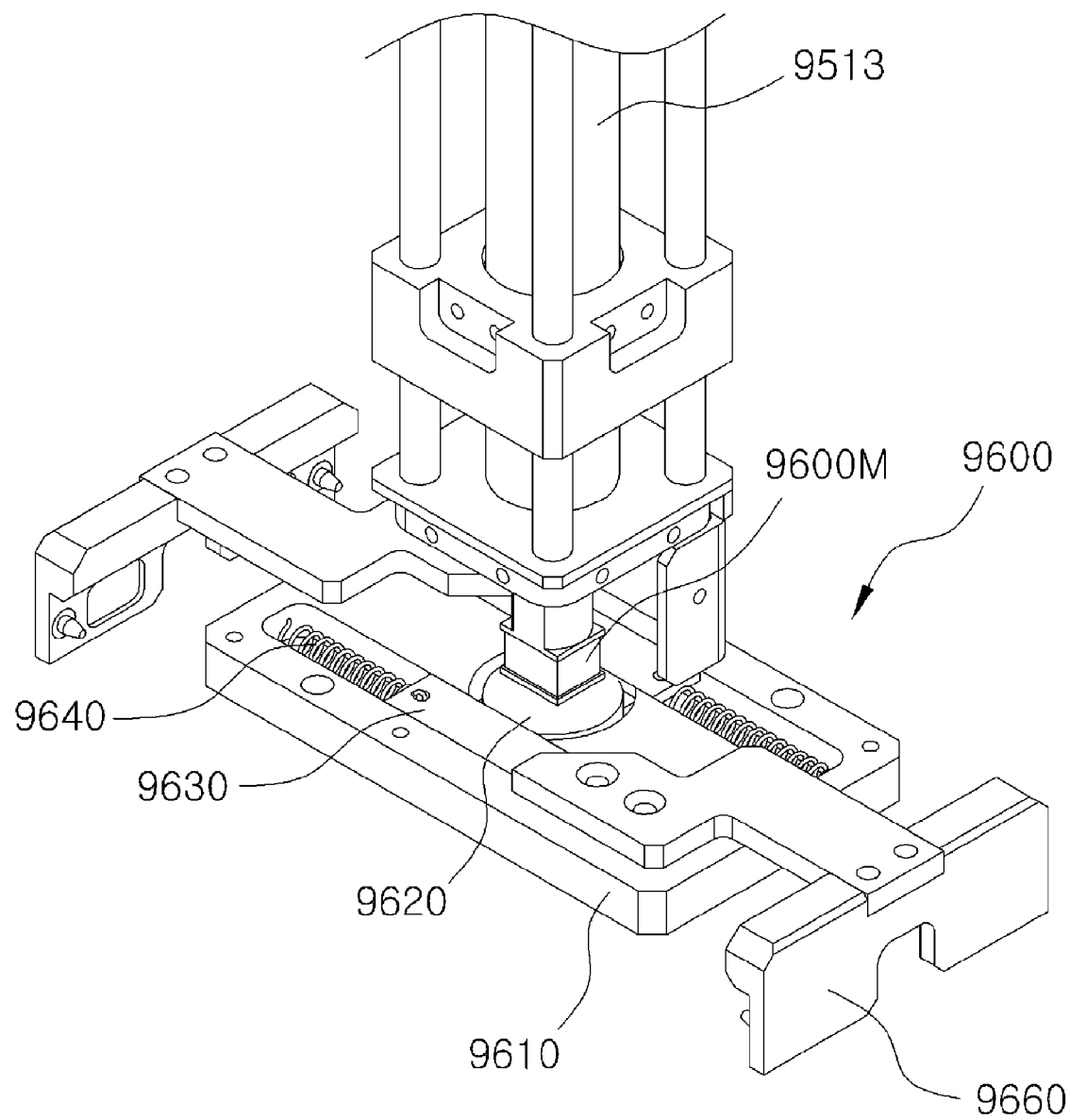

[Fig. 39]
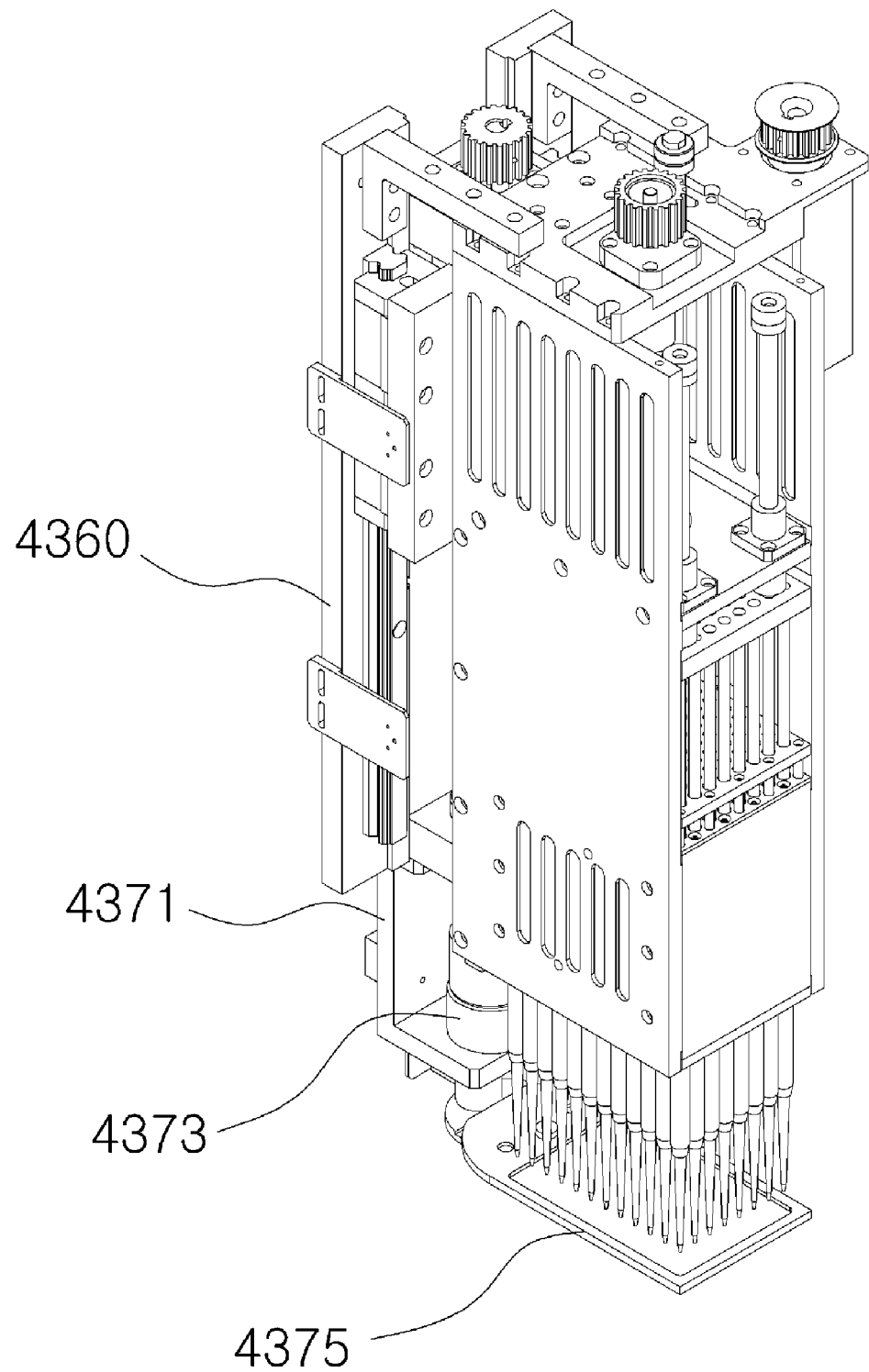

[Fig. 40]
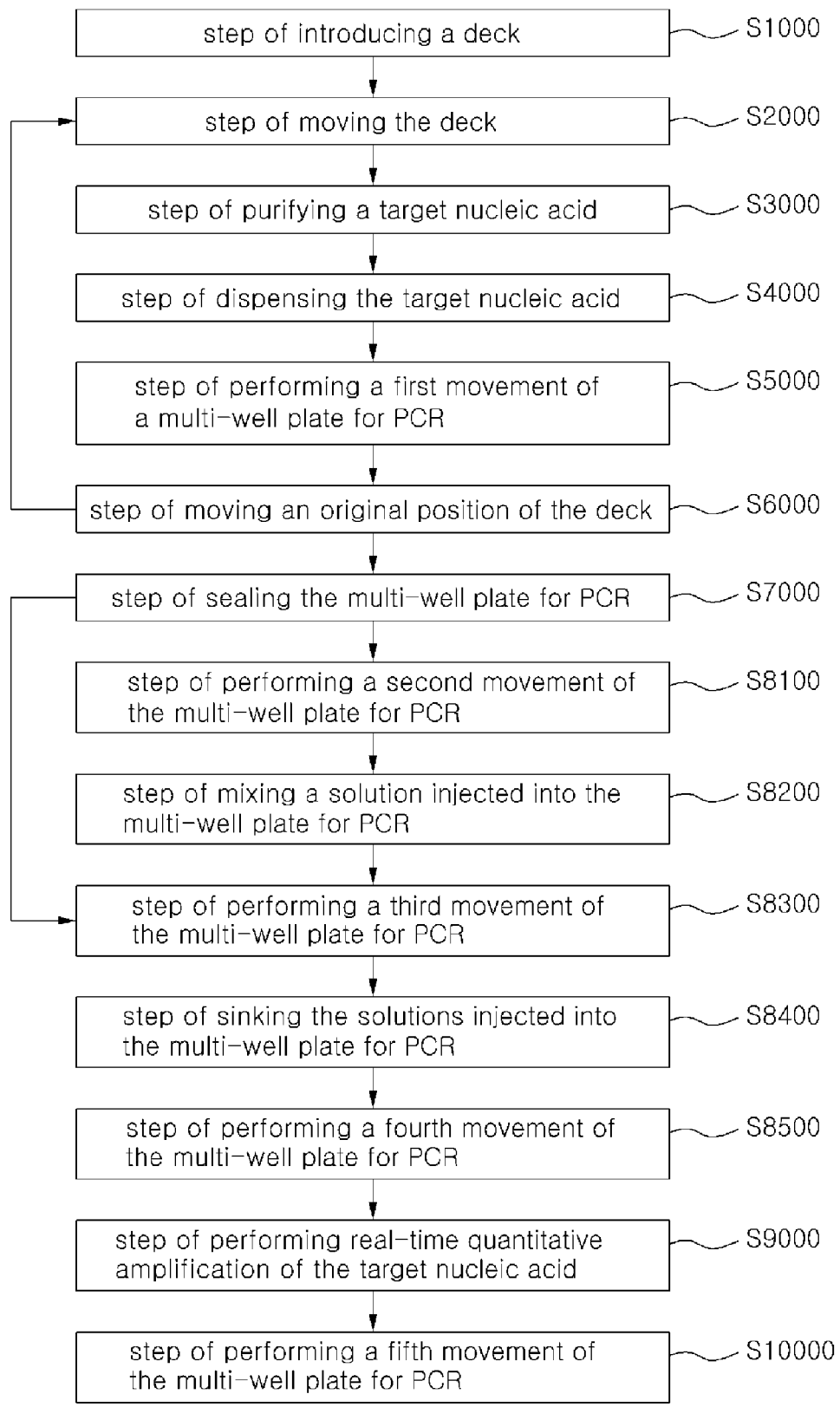

[Fig. 41]
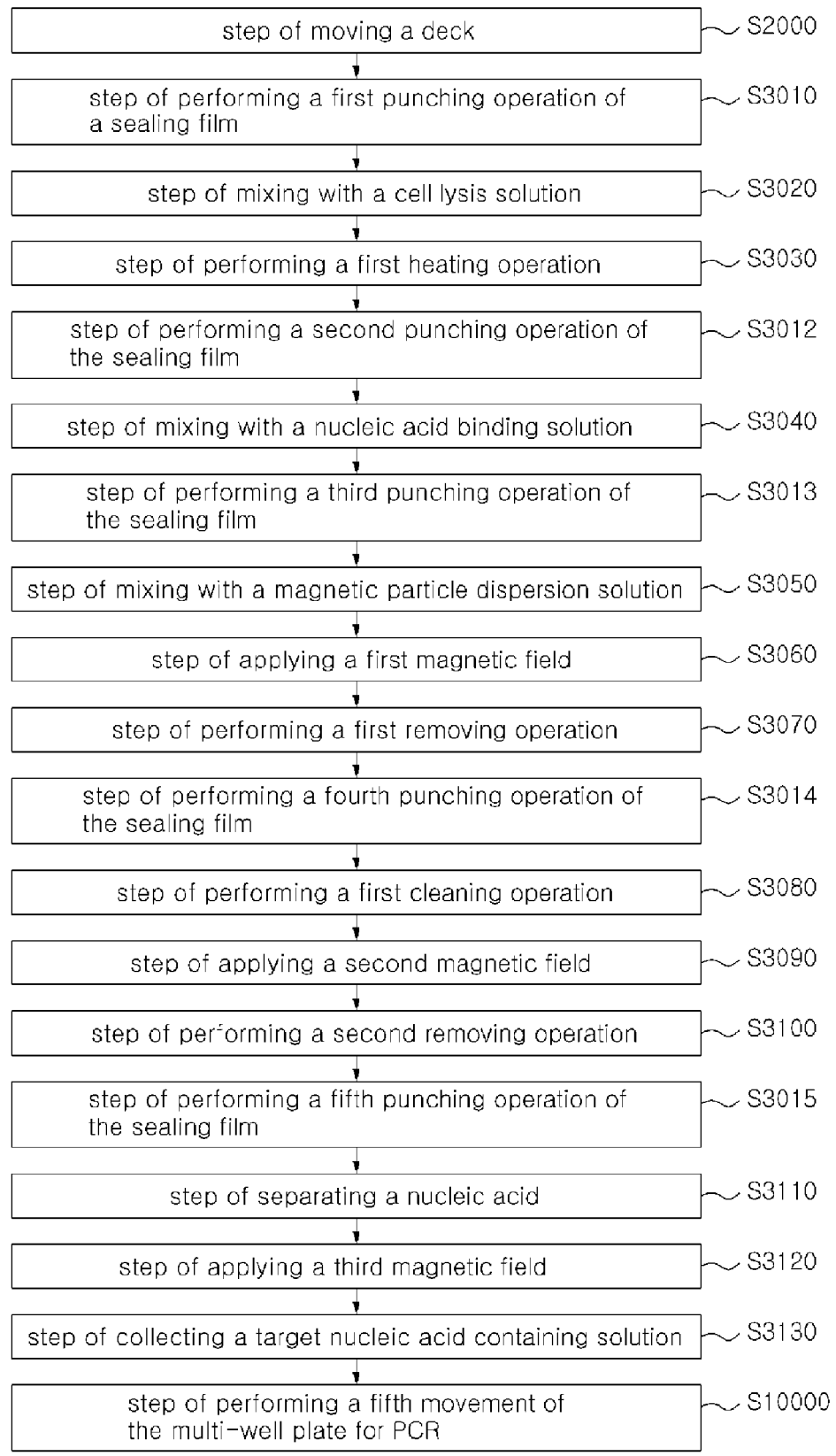

[Fig. 42]
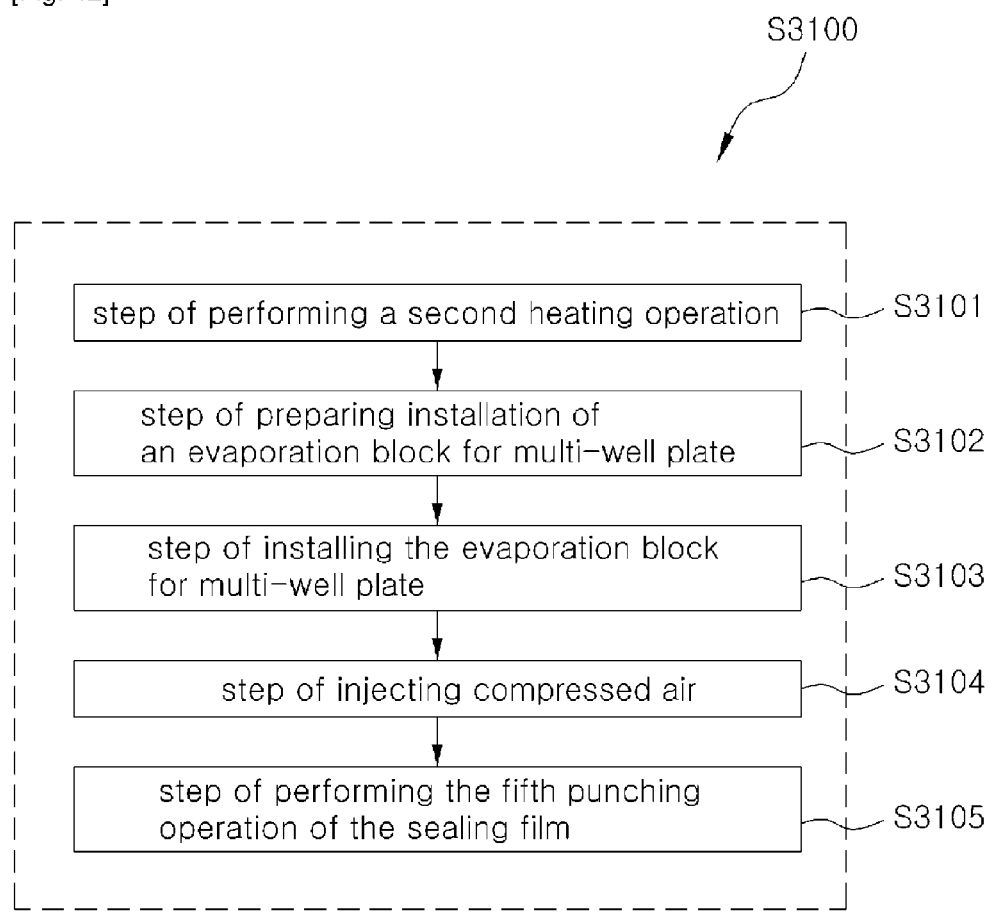

[Fig. 43]
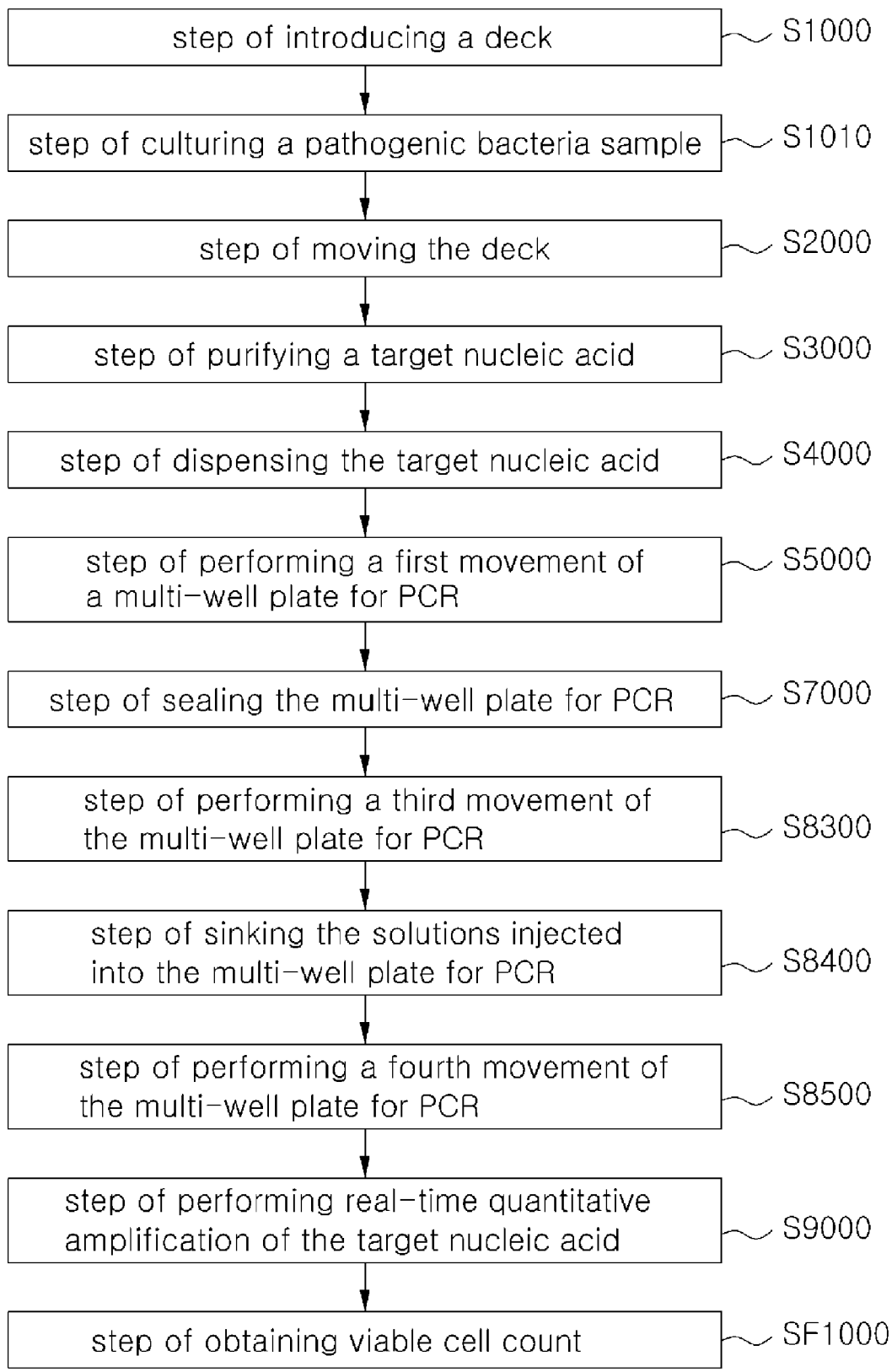

[Fig. 44]
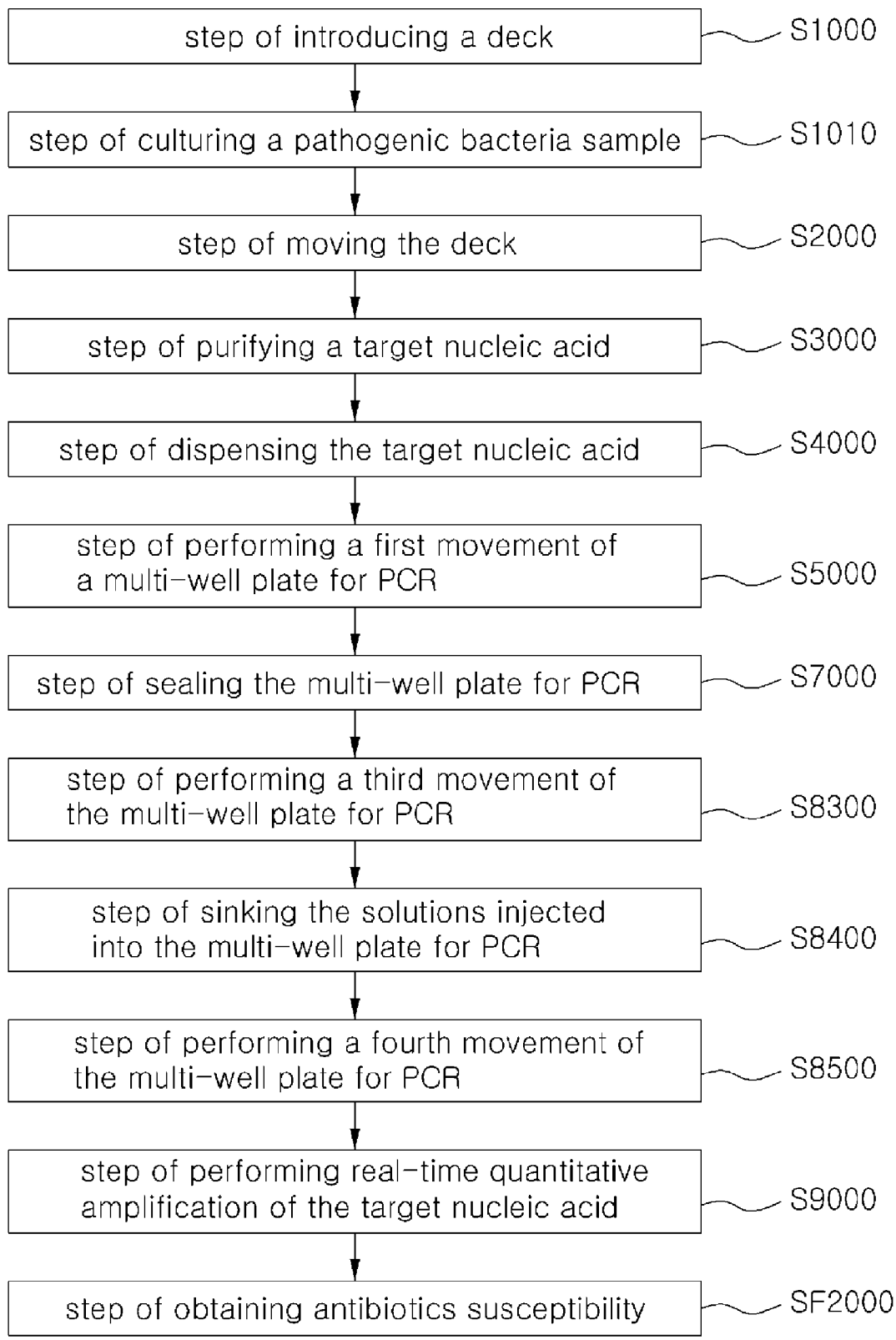

[Fig. 45]
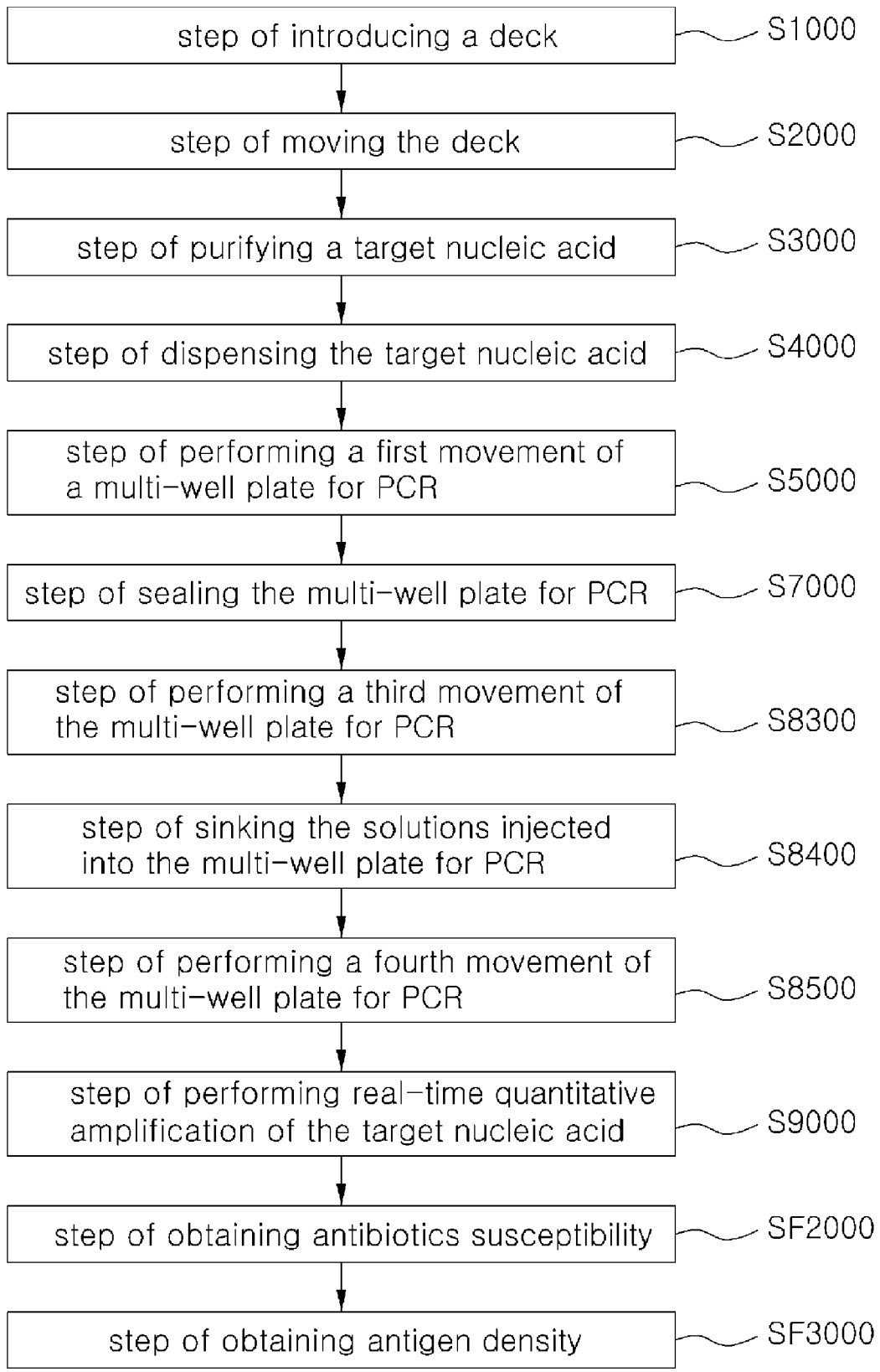

[Fig. 46]
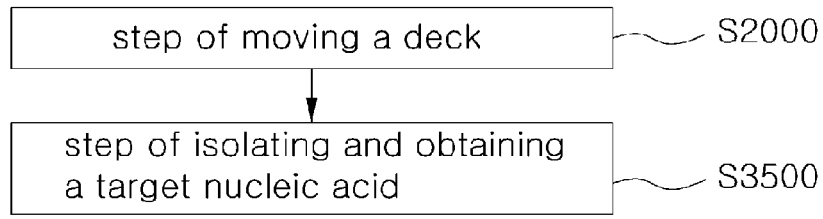
[Fig. 47]
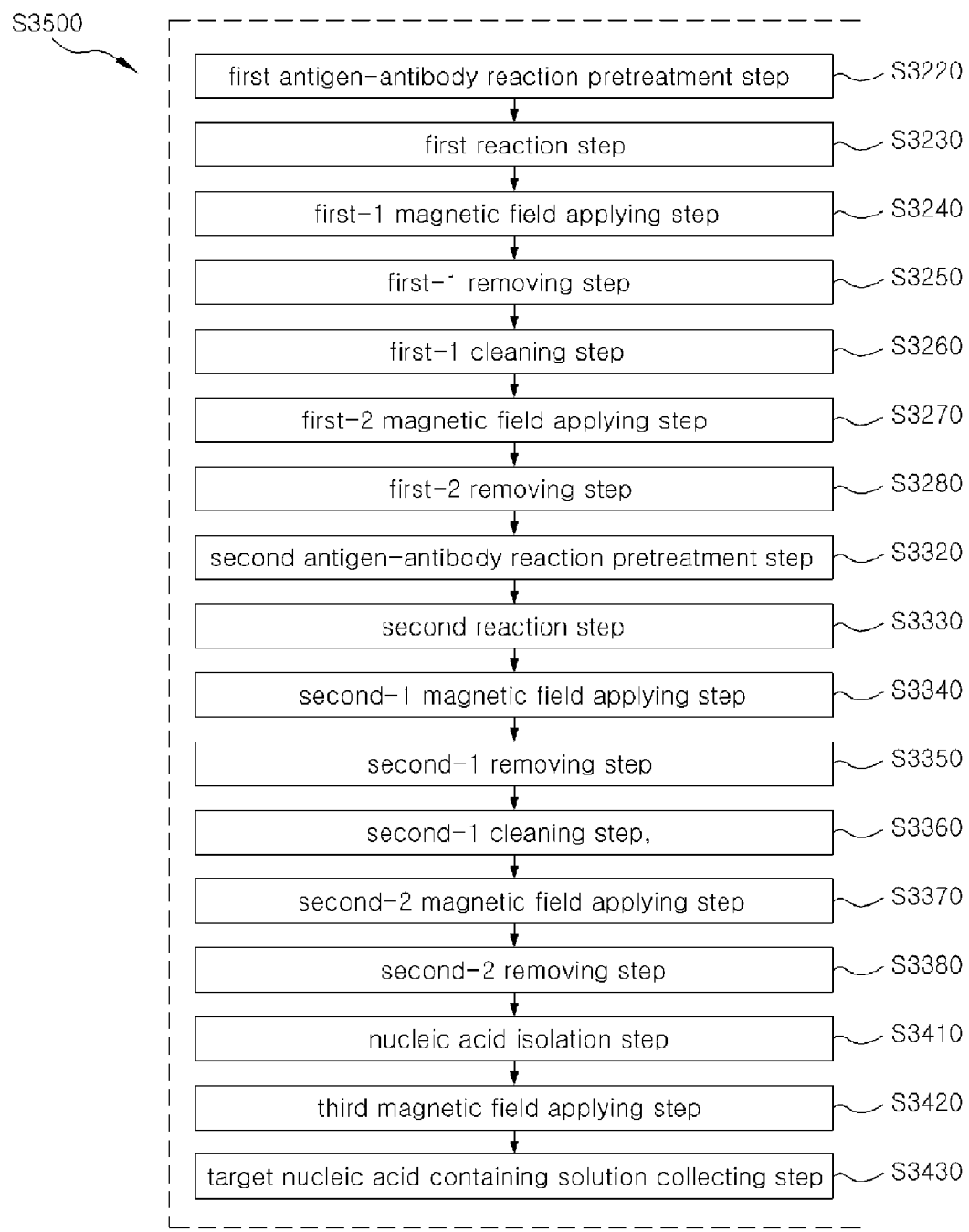

[Fig. 48]
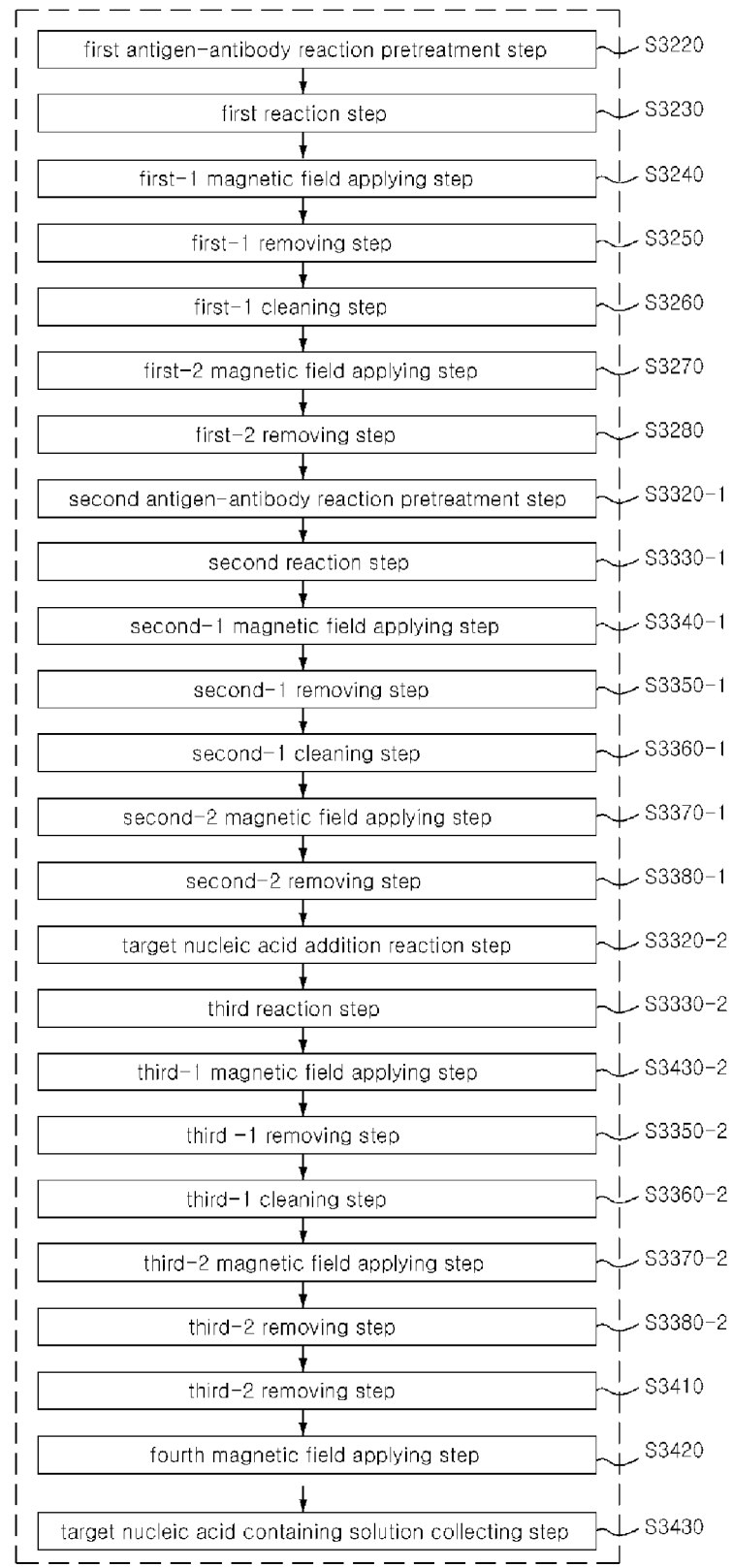

AUTOMATIC REAL-TIME PCR SYSTEM FOR THE VARIOUS ANALYSIS OF BIOLOGICAL SAMPLE

CROSS REFERENCE TO PRIOR APPLICATION

This application is a National Stage Patent Application of PCT International Patent Application No. PCT/KR2011/008100 (filed on Oct. 27, 2011) under 35 U.S.C. §371, which claims priority to Korean Patent Application No. 10-2010-0105630 (filed on Oct. 27, 2010) which are all hereby incorporated by reference in their entirety.

TECHNICAL FIELD

The present invention relates to an automatic real-time quantitative amplification system which can perform analysis of various biological samples, and more particularly to an automatic real-time quantitative amplification system in which a plurality of decks for respectively accommodating biological samples are put in a deck storing/transferring device, whereby it is possible to automatically analyze an amount or existence of a target substance containing a target nucleic acid in the biologic sample, such as a particular gene, a particular, a particular pathogenic bacterium and a particular protein, by amplifying the target nucleic acid purified by some processes of purification, purification after culture, or purification after reaction of the target substance contained in the biological sample and then checking an amount of the amplified target nucleic acid.

The present invention relates to an automatic real-time quantitative amplification system which can automatically perform various analyses of microorganisms contained in a biological sample, that is, which cultures the microorganisms contained in the multiple biological samples in an automatic deck, purifies nucleic acids from each microorganism, dispenses the purified nucleic acids to a multi-well plate for real-time quantitative PCR reaction, and then performs quantitative amplification and comparative analysis, thereby performing quantitative/qualitative analysis of the microorganism contained in the biological sample. The present invention relates to a system in which, in order to carry out antibiotics susceptibility tests, a constant amount of biological sample is injected into each well of the multi-well plate that various antibiotics are accommodated therein, and automatically cultured for a desired period of time, and then comparative analysis is performed by using a relative quantitative method for growth in a culture medium containing the antibiotics through automatic nucleic acid purification and real-time quantitative PCR, thereby rapidly obtaining results of the antibiotics susceptibility tests.

Further, the present invention relates to an automatic real-time quantitative amplification system which can carry out quantitative analysis of protein and antigen contained in a biological sample, that is, in which a plurality of biological samples are dispensed to a multi-well plate, in which a first antibody bound with a target antigen contained in the biological samples is fixed to an inner surface of each well or magnetic particles, so that an antigen in the biological sample is bound to the first antibody, and a second antibody solution containing a second antibody is applied thereto so that the second antibody is bound to the target antigen, and after a cleaning process, a quantitative amplification reagent mixture for amplifying a probe nucleic acid is applied to a probe nucleic acid obtained by using a nucleic acid elution solution, thereby performing quantitative analysis through the gene quantitative amplification, wherein all of the above-mentioned processes are carried out automatically, and thus the system of the present invention may be used in quantitative analysis of protein.

BACKGROUND ART

Real-time quantitative PCR that is the most widely used method for molecular diagnostic testing or nucleic acid testing (NAT) can rapidly perform quantitative and qualitative analysis of gene, and it is the fastest growing area in the world in-vitro diagnostic market, averaging about 20 percent a year.

This method can be applied to various fields such as: of a blood screening test for preventing infections caused by a blood transfusion, a viral load test for checking the effectiveness of a new treatment for viral diseases, a confirmatory test for independently confirming results of diagnostic testing, a pharmacogenomic test for determination of a treatment, selection of medication and estimation of medicinal effect, and a process of checking a genetic predisposition, or detecting or monitoring an abnormal gene in order to prevent disease.

However, since the real-time quantitative PCT is very complicated to operate, it is not yet used as widely as immunohistochemistry regardless of its various advantages. This method performs the testing with a pure nucleic acid in which substances interfering with gene amplification are removed, and thus it is necessary to isolate the pure nucleic from the biological sample. Accordingly, in order to carry out real-time quantification of gene amplification, it is required to perform nucleic acid purification. The nucleic acid purification has been traditionally carried out manually. But as the number of testing times is increased and the necessity of quality control also becomes higher, various automation equipments are propagated rapidly. However, even when using automatic nucleic acid purification equipment, a process of mixing the purified nucleic acid and various reagents and then analyzing the mixture is performed manually in order to perform the real-time quantitative analysis, and thus it is difficult to completely exclude operator s mistake. To solve the problem, there has been developed various equipments for automatically carrying out, in turn, a chain of steps from the nucleic acid purification to the real-time quantification of gene amplification.

By Cepheid, Inc., there have been developed cartridges (U.S. Pat. Nos. 6,818,185, 6,783,736, 9,970,434 and 11,977,697) which can extract a nucleic acid in a sealed structure, cartridges (U.S. Pat. Nos. 6,660,228 and 7,101,509) which can perform real-time quantitative PCR, and cartridge type automation equipments (U.S. Pat. Nos. 6,660,228, 7,101,509 and 11,742,028) which can independently perform the nucleic acid extraction and real-time quantitative PCR, wherein GeneXpert instruments as infinity systems use one, four or sixteen cartridges (by the cartridge unit), and cartridge installation and testing are automatically performed.

By IQuum, Inc., there have been developed equipments (U.S. Pat. Nos. 7,718,421, 7,785,535 and 12,782,354) which can automatically and rapidly perform the nucleic acid extraction and real-time quantitative PCR in a semi-fixed and divided tube based on Liat (Lab-in-a-tube) technology.

By Idaho technology, Inc., there has been developed a method based on Lab-in-a-film technology (U.S. Pat. Nos. 10,512,255 and 7,670,832), which can automatically and rapidly perform the real-time quantitative PCT by extracting a nucleic acid in a sealing film and moving between two different temperature blocks.

In these technologies, a module for treating a single sample is used as a standard unit, and thus a large number of equipments or a large scale system is needed to perform the real-time quantitative PCR on multiple samples required in clinical experiments, and also since the biological samples are treated one by one, it takes a lot of time and money to prepare the clinical samples. To solve the problem, there had been developed various equipments for treating multiple samples at the same time By Handy lab, Inc., there have been new equipments which extracts nucleic acids from multiple biological samples at the same time using a nucleic acid extractor having an XYZ-Cartesian robot with a cylinder, injects the extracted nucleic acids into a microfluidic cartridge for PCR reaction and then performs real-time quantitative PCR (U.S. Pat. Nos. 12,515,003, 200090719, 20090130745 and 20080714).

Roche diagnostic, Inc. releases a cobas s201 system which can automatically perform the nucleic purification and real-time quantitative PCR.

In these technologies, the number of samples which can be treated at a time is 32 or less, and the number of samples which can be installed at a time is 72 or less. Accordingly, there is inconvenience in that an operator has to install again the biological samples and the consumed reagents for a next analysis operation. Further, it takes too much time to treat hundreds of samples like in a blood bank screening test and also the operator has to check them often.

Furthermore, these equipments can be used only for the real-time quantitative PCR. Therefore, it is impossible to automatically perform various tests using real-time quantitative genetic analysis, such as microorganism culture testing, rapid antibiotics susceptibility testing and immune gene quantitative amplification testing.

Experiments of culturing and analyzing microorganism using a real-time genetic quantitative analysis are very important to obtain various useful information. However, since these experiments have several steps of culture, nucleic acid extraction and real-time quantitative PCR, and each step is performed manually, it requires much effort and artificial mistakes may occur. Therefore, it is required to develop new equipment for automatically performing the steps. The present invention relates to a multipurpose automatic real-time quantitative amplification system which can automatically such various experiments and thus can perform the analysis of biological samples.

Immuno real-time qPCR that is a protein detection method using high sensitivity of the real-time quantitative PCR is an immunodiagnostic method having the highest sensitivity. However, the immune real-time qPCR also have multiple steps of antigen antibody reaction, cleaning and real-time quantitative PCR, and each step has a significant influence on genetic sensitivity, specificity and excompression. Therefore, it is required to develop new equipment for automatically and uniformly performing the steps.

DISCLOSURE OF INVENTION

Technical Problem

An object of the present invention is to provide a system which can automatically perform nucleic acid purification and real-time quantitative PCR by the multi-well unit in order to treat a large amount of samples in a short period of time with minimum manual labor, thereby obtaining analysis results of various biological samples.

Further, another object of the present invention is to provide a system which can perform real-time quantitative PCR analysis after culturing microorganism and thus can automatically perform microorganism test in the biological samples and antibiotics susceptibility test. The system of the present invention can perform microorganism analysis. In case that the initial number of microorganisms is less than detection limit, the microorganism is amplified through the culture step and then analyzed by real-time quantitative PCR, and thus it is possible to precisely perform the test of microorganism.

Moreover, testing of only viable cells is significance to the actual microorganism test. For example, in case of infectious bacteria, both of dead cells and viable cells are contained in a biological sample isolated from a patient who is treated with antibiotics, and it is very important to measure a viable cell count in treatment. In case of food or agricultural and stockbreeding products, the measurement of viable cell count after sterilization is very important. Even though the real-time quantitative PCR is faster and more precise than the culturing method, the culturing method which is time consuming is used widely. This is caused by that it is impossible to distinguish the viable cells from the dead cells, because all of DNA is amplified regardless of life and death thereof. To solve the problem, in the present invention, the culturing is performed only for a short period time that is less than five generations, and then each amount of DNA in the samples before and after the culturing is compared with each other by relative quantification in real-time quantitative PCR, and thus it is possible to precisely and rapidly analyze the viable cell count. On the same principle, the system of the present invention can be used in automatically performing the antibiotics susceptibility test. There had been reported a method of rapidly performing the antibiotics susceptibility test, in which microorganisms are cultured for 2~4 hours in a culture medium which contains antibiotics and other culture medium which does not contain the antibiotics, respectively, and then 16S rRNA or rpoB gene of each microorganism is analyzed by real-time quantitative PCR. (Journal of Antimicrobial Chemotherapy (2004) 53, 538-541). There has been also proposed another method of rapidly performing the antibiotics susceptibility test within 4 to 6 hours, in which Gram-positive strains are cultured for 4 hours and Gram-negative strains are cultured for 2 hours at a temperature of 35 in each culture medium containing different antibiotics from each other, respectively, and then real-time quantitative PCR is performed, but an automatic system for performing the method has not been developed yet. The present invention is to provide a means in which a biological sample containing microorganisms is equally dispensed to a multi-well including different antibiotics from each other and cultured for a predetermined period of time, and then real-time quantitative PCR analysis is performed so as to compare the number of nucleic acids using a relative quantitative method, and thus it is possible to rapidly analyze antibiotics susceptibility of the microorganism, thereby allowing effective antibiotics to be selected within a short time period.

Yet another object of the present invention is to provide a system which can automatically perform quantitative Immuno-PCR in order to precisely perform a quantitative test for a small amount of proteins and antigens. The quantitative Immuno-PCR uses high sensitive features of real-time quantitative PCR which can detect even a few nucleic acids. In the principle of quantitative Immuno-PCR, an antigen is bound to a capture antibody immobilized on a solid, and a second antibody labeled with a target nucleic acid is bound thereto, and then the real-time quantitative PCR is performed. Herein, the used second antibody includes an antibody that is covalent-bonded with the target nucleic acid, and an antibody in which the second antibody bound with streptavidin is bound again with the target nucleic acid labeled with biotin (Nature Protocols 1918-1930 8, (2007)). In this method, various attachment reactions and cleaning processes are performed according to a method of attaching the target nucleic acid to the second antibody, and then the quantitative analysis of the target nucleic acid is performed through the real-time quantitative PCR. Therefore, in the quantitative Immuno-PCR, each step has a significant influence on genetic sensitivity, specificity and excompression. Nevertheless, an automatic system for automatically performing the method has not been developed yet.

Solution to Problem

To achieve the object of the present invention, the present invention provides an automatic real-time quantitative amplification system which can perform analysis of various biological samples, including a deck 1000 loading a multi-well plate for treating the biological sample, which purifies a target nucleic acid in a target substance contained in the biological sample, cultures the target substance contained in the biological sample and then purifies the target nucleic acid, or purifies a binding target nucleic acid bound with a target antigen contained in the biological sample by an antigen-antibody reaction, and a multi-well plate 400 for PCR, in which a reaction mixture for real-time quantitative PCR is injected; an automatic purification and reaction preparing device which automatically purifies the target nucleic acid or the cultured target nucleic acid from the biological sample and dispenses the purified target nucleic acid or the cultured and purified target nucleic acid to the multi-well plate 400 for PCR, and then mixes the dispensed target nucleic acid with a reagent for real-time quantitative PCR, or which automatically purifies the binding target nucleic acid bound with the target antigen contained in the biological sample by the antigen antibody reaction, and dispenses the purified binding target nucleic acid to the multi-well plate 400 for PCR, and then mixes the dispensed binding target nucleic acid with the reagent for real-time quantitative PCR; an automatic deck storing and moving device 2000 provided with a storing case 2000C which has a door 2000C-1 for taking in or out the deck 1000 and of which an internal portion can be maintained at predetermined temperature, and a deck transferring unit 2400 for transferring the deck 1000 to the automatic purification and reaction preparing device; a sealing device 6000 for sealing an upper surface of the multi-well plate 400 for PCR, in which the purified target nucleic acid, the cultured and purified target nucleic acid or the purified binding target nucleic acid is dispensed; a centrifugal separator 7200 which applies centripetal force to the multi-well plate 400 for PCR so that a substance remained on a side wall of each well formed in the multi-well plate 400 for PCR is separated and then moved to a bottom surface of the each well; a real-time quantitative amplification device 8000 which amplifies the target substance in the multi-well plate 400 for PCR; and a moving device 9000 for multi-well plate for PCR, which moves the multi-well plate 400 for PCR, in which the purified target nucleic acid, the cultured and purified target nucleic acid or the purified binding target nucleic acid is dispensed, to the sealing device 6000, and moves the multi-well plate 400 for PCR sealed by the sealing device 6000 to the centrifugal separator 7200, and also moves the multi-well plate 400 for PCR, to which the centripetal force is applied by the centrifugal separator 72000, to the real-time quantitative amplification device 8000.

Preferably, the automatic purification and reaction preparing device includes a syringe block 3000 formed with a plurality of first mounting portions 3330 in which a plurality of pipettes P for sucking and discharging a fluid substance is removably installed a syringe block moving unit 4000 which moves the syringe block 3000 so that the plurality of pipettes P mounted in the plurality of first mounting portions 3330 is located just above each of the multi-well plate for treating the biological sample and the multi-well plate 400 for PCR; a solution drip tray 4375 which is movable to a lower side of the plurality of pipettes P mounted in the plurality of first mounting portion 3330 by a solution drip tray moving unit installed to the syringe block moving unit 4000; a magnetic field applying unit 5100 which moves a magnet 5110 to a lower side of a first certain multi-well plate out of the multi-well plates for treating the biological sample so as to apply magnetic field to the first certain multi-well plate; a heating unit 5200 which moves a heating block 5229 to a lower side of a second certain multi-well plate out of the multi-well plates for treating the biological sample so as to heat the second certain multi-well plate; a puncher 12100 in which a plurality of awl-shaped puncher pins 12110 are protrusively formed so as to pierce holes in a sealing film for sealing an upper surface of the multi-well plate for treating the biological sample, and which is disposed at a lower side of the syringe block 3000 so as to be removably mounted in the plurality of first mounting portions 3330 at different time point as compared with the time point, when the plurality of pipettes P is mounted in the plurality of first mounting portions 3330 and a waste liquor discharging part 12300 which is disposed at a lower side of the syringe block so as to discharge waste liquor abandoned from the plurality of pipettes P mounted in the plurality of first mounting portions 3330.

Preferably, the solution drip tray moving unit includes a solution drip tray supporting plate 4371 which is installed to the syringe block moving unit 4000; and a solution drip tray moving motor 4373 which is installed at the solution drip tray supporting plate 4371 and which is connected to the solution drip tray 4375 so as to horizontally rotate the solution drip tray 4373.

Preferably, the automatic purification and reaction preparing device includes a syringe block 3000 formed with a plurality of first mounting portions 3330 which removably mounts the plurality of pipettes P for sucking and discharging the fluid substance; a syringe block moving unit 4000 which moves the syringe block 3000 so that the plurality of pipettes P mounted in the plurality of first mounting portions 3330 is located just above each of the multi-well plate for treating the biological sample and the multi-well plate 400 for PCR; a magnetic field applying unit 5100 which moves a magnet 5110 to a lower side of a first certain multi-well plate out of the multi-well plates for treating the biological sample so as to apply magnetic field to the first certain multi-well plate; a heating unit 5200 which moves a heating block 5229 to a lower side of a second certain multi-well plate out of the multi-well plates for treating the biological sample so as to heat the second certain multi-well plate; a puncher 12100 in which a plurality of awl-shaped puncher pins 12110 are protrusively formed so as to pierce holes in a sealing film for sealing an upper surface of the multi-well plate for treating the biological sample, and which is dis-posed at a lower side of the syringe block 3000 so as to be removably mounted in the plurality of first mounting portions 3330 at different time point as compared with the time point, when the plurality of pipettes P is mounted in the plurality of first mounting portions 3330 and an evaporation block 12200 for multi-well plate, which is connected with a compressed air supplying tube, and which is formed with a plurality of second mounting portions 12210 for shooting compressed air supplied through the compressed air supplying tube and removably mounting the plurality of pipettes P, and which is disposed at a lower side of the syringe block 3000 so as to be removably mounted in the plurality of first mounting portions 3330 at different time point as compared with the time points, when the plurality of pipettes P and the puncher 12100 are respectively mounted in the plurality of first mounting portions 3330 and a waste liquor discharging part 12300 which is disposed at a lower side of the syringe block 3000 so as to discharge waste liquor abandoned from the plurality of pipettes P mounted in the plurality of first mounting portions 3330.

Preferably, the multi-well plate 400 for PCR in which a reaction mixture for real-time quantitative PCR is injected is an amplification kit plate having a plurality tubes in which a reagent for real-time quantitative PCR is injected, and the first certain multi-well plate is a multi-well plate 220 for magnetic particle dispersion solution, in which a magnetic particle suspension including magnetic particles is injected when being loaded on the deck 1000, among the multi-well plates for treating the biological sample, and the second certain multi-well plate is a multi-well plate 100 for biological sample, in which the biological sample is injected when being loaded on the deck 1000, among the multi-well plates for treating the biological sample.

Preferably, the multi-well plates for treating the biological sample include the multi-well plate 100 for biological sample; a multi-well plate 210 for cell lysis solution, in which a cell lysis solution is injected when being loaded on the deck 1000; the multi-well plate 220 for magnetic particle dispersion solution; a multi-well plate 230 for nucleic acid binding solution, in which a nucleic acid binding solution is injected when being loaded on the deck 1000; a multi-well plate 241, 242, 243 for cleaning solution, in which a cleaning solution is injected when being loaded on the deck 1000; and a multi-well plate 250 for nucleic acid elution solution, in which a nucleic acid elution solution is injected when being loaded on the deck 1000.

Preferably, the plurality pipettes P are a plurality of purification pipettes P1, or a plurality of dispensation pipettes P2 having smaller a capacity than the plurality of purification pipettes P1, and a purification pipette rack 310 in which the plurality of purification pipettes P1 are received, and a dispensation pipette rack 320 in which the plurality of dispensation pipettes P2 are received are loaded on the deck 1000, and the multi-well plate 400 for PCR comprises a first multi-well plate 410 for PCR and a second multi-well plate 420 for PCR.

Preferably, the magnetic field applying unit 5100 includes a magnet mounting block 5120 in which the magnet 5110 is installed; and a magnet mounting block lifting part for lifting up and down the magnet mounting block 5120.

Preferably, the magnet 5110 is a plurality of rod-shaped magnets which are disposed so as to be spaced apart from each other so that an upper portion of the magnet 5110 encloses each well formed in the multi-well plate 220 for magnetic particle dispersion solution when the magnet mounting block 5120 is lifted up.

Preferably, the magnet mounting block lifting part includes a supporting plate 5130 for magnetic field applying unit, which is located at a lower side of the magnet mounting block 5120; and a magnet mounting block lifting motor 5120M which is connected to the supporting plate 5130 for magnetic field applying unit, and also connected to the magnet mounting block 5120 so as to lift up and down the magnet mounting block 5120.

Preferably, the automatic real-time quantitative amplification system further includes a ball screw shaft 51505 for magnet mounting block lifting, which is connected to the magnet mounting block lifting motor 5120M; a ball nut for magnet mounting block lifting, which is inserted onto the ball screw shaft 51505 for magnet mounting block lifting so as to be moved up and down when the ball screw shaft 51505 for magnet mounting block lifting is rotated; and a magnet mounting block moving rod 5160 which connects the ball nut for magnet mounting block lifting and the magnet mounting block 5120 with each other so as to move up and down the magnet mounting block 5120.

Preferably, the heating unit 5200 includes a heating block lifting part for lifting up and down the heating block 5220.

Preferably, the heating block lifting part includes a supporting plate 5230 for heating unit, which is located at a lower side of the heating block 5220; and a heating block lifting motor 5220M which is connected to the supporting plate 5230 for heating unit, and also connected to the heating block 5220 so as to lift up and down the heating block 5220.

Preferably, the automatic real-time quantitative amplification system further includes a ball screw shaft 5250S for heating block lifting, which is connected to the heating block lifting motor 5220M; a ball nut for heating block lifting which is inserted onto the ball screw shaft 5250S for heating block lifting so as to be moved up and down when the ball screw shaft 5250S for heating block lifting is rotated; and a heating block moving rod 5260 which connects the ball nut for heating block lifting and the heating block 5220 with each other so as to move up and down the heating block 5220.

Preferably, the magnetic field applying unit 5100 includes a supporting plate 5130 for magnetic field applying unit, which is located at a lower side of the magnet mounting block 5120; and a magnet mounting block lifting motor 5120M which is installed to the supporting plate 5130 for magnetic field applying unit, and also connected to the magnet mounting block 5120 so as to lift up and down the magnet mounting block 5120, and the heating unit 5200 comprises a front and rear moving part for heating block, which moves the heating block 5220 in a front and rear direction of the deck 1000, and the supporting plate 5130 for magnetic field applying unit and the supporting plate 5230 for heating unit are adjacent to each other in the front and rear direction of the deck 1000 and connected to each other.

Preferably, the front and rear moving part for heating block comprises a front and rear moving motor 5230M for heating block, which is disposed to be spaced apart from the supporting plate 5230 for heating unit, and which is connected to one or both of the supporting plate 5230 for heating unit and the supporting plate 5130 for magnetic field applying unit so as to move the supporting plate 5230 for heating unit in the front and rear direction of the deck 1000.

Preferably, the automatic real-time quantitative amplification system further includes a front and rear moving belt for heating block, which is moved in the front and rear direction of the deck 1000 by an operation of the front and rear moving motor 5230M for heating block; and a heating block connecting member 5234 of which one end is fixedly connected to the front and rear moving belt for heating block and the other end is fixedly connected to one or both of the supporting plate 5230 for heating unit and the supporting plate 5130 for magnetic field applying unit.

Preferably, the syringe block 3000 includes a syringe pin holder 3200 which is movable up and down and to which a plurality of rod-shaped syringe pins 3100 are attached; a syringe pin guide block 3300 which is formed with a plurality of syringe pin guide holes 3310H for guiding up/down movement of the plurality of syringe pins 3100; a first separation portion which is moved down, while being contacted with the syringe pin holder 3200, so as to separate at least the plurality of pipettes P and the evaporation block 12200 for multi-well plate among the plurality of pipettes P, the puncher 12100 and the evaporation block 12200 for multi-well plate from the first mounting portion 3330, which are respectively mounted in the first mounting portion 3330 at different time points; and a second-1 separation portion which is moved down, while being contacted with the syringe pin holder 3200, so as to be interlocked with a second-2 separation portion provided at the evaporation block 12200 for multi-well plate and thus to separate the plurality of pipettes P mounted in the second mounting portion 12210.

Preferably, the first separation portion includes a first separation rod 3731 which is inserted into a first separation rod guide hole formed in the syringe pin guide block 3300 so as to be moved down by compressing force of the syringe pin holder 3200; and a first lower separation plate 3720 which is inserted onto the plurality of first mounting portions 3330 protruded from a lower end of the syringe pin guide block 3300 so as to be moved up and down, and which is moved down by the first separation rod 3731 so as to compress and separate the plurality of pipettes P, the puncher 12100 and the evaporation block 12200 for multi-well plate which are respectively mounted in the plurality of mounting portions 3330 at different time points.

Preferably, the first separation portion comprises a first separation rod spring 3731S which exerts an upper portion of the first separation rod 3731 beyond the syringe pin guide block 3300 by elastic force thereof when the compressing force of the syringe pin holder 3200 is released.

Preferably, the first separation portion comprises a first upper separation plate 3710 which is attached to an upper portion of the first separation rod 3731 so as to be located between the syringe pin holder 3200 and the syringe pin guide block 3300, and through which the plurality of syringe pins 3100 are passed.

Preferably, the first separation rod 3731 comprises a first small-diameter separation rod 3731-1 which is formed at a lower portion of the first separation rod 3731, and a first large-diameter separation rod 3731-2 which is formed at an upper side of the first small-diameter separation rod 3731-1 so as to have a larger diameter than the first small-diameter separation rod 3731-1, and the first separation rod guide hole comprises a first small-diameter separation rod guide hole 3321H1 which is formed at a lower portion of the first separation rod guide hole so as to guide the first small-diameter separation rod 3731-1, and a first large-diameter separation rod guide hole 3321H2 which is formed at an upper side of the first small-diameter separation rod guide hole 3321H1 so as to guide the first large-diameter separation rod 3731-2, and the first separation rod spring 3731S which is inserted onto the first small-diameter separation rod 3731-1 and thus of which an upper end is elastically supported by a lower end of the first large-diameter separation rod 3731-2 and a lower end is elastically supported by a lower end of the first large-diameter separation rod guide hole 3321H2.

Preferably, the second-1 separation portion comprises a second separation rod 3732 which is inserted into a second separation rod guide hole formed in the syringe block guide 3300 so as to be moved down by the compressing force of the syringe pin holder 3200, and the second-2 separation portion comprises a second separation plate 12220 which is inserted onto the plurality of second mounting portions 12210 protruded from a lower end of the evaporation block 12200 for multi-well plate so as to be movable up and down, and which is moved down by the second separation rod 3732 so as to compress and separate the plurality of pipettes P mounted in the plurality of second mounting portions 12210.

Preferably, the second-2 separation portion comprises a second separation pin 12230 which is installed at the evaporation block 12200 for multi-well plate so as to be movable up and down, and which is moved down by the second separation rod 3732 so as to compress the second separation plate 12220.

Preferably, the second-1 separation portion comprises a second separation rod spring 3732S which exerts an upper portion of the second separation rod 3732 beyond an upper end of the first separation rod 3731 by elastic force thereof when the compressing force of the syringe pin holder 3200 is released.

Preferably, the second separation rod 3732 comprises a lower stopper 3732-1P which catches beneath a lower surface of the first lower separation plate 3720 by elastic force of the second separation rod spring 3732S when the compressing force of the syringe pin holder 3200 is released.

Preferably, the second separation rod 3732 comprises a second small-diameter separation rod 3732-1 which is formed at a lower portion of the second separation rod 3732, and a second large-diameter separation rod 3732-2 which is formed at an upper side of the second small-diameter separation rod 3732-1 so as to have a larger diameter than the second small-diameter separation rod 3732-1, and the second separation rod guide hole comprises a second small-diameter separation rod guide hole 3322H1 which is formed at the lower portion of the second separation rod guide hole so as to guide the second small-diameter separation rod 3732-1, and a second large-diameter separation rod guide hole 3322H2 which is formed at an upper side of the second small-diameter separation rod guide hole 3322H1 so as to guide the second large diameter separation rod 3732-2, and the second separation rod spring 3732S is inserted onto the second small-diameter separation rod 3732-1 so that an upper end thereof is elastically supported by a lower end of the second large-diameter separation rod 3732-2 and a lower end thereof is elastically supported by a lower end of the second large-diameter separation rod guide hole 3322H2.

Preferably, the syringe block moving unit 4000 comprises a front and rear moving part 4100 for syringe block, which moves the syringe block 3000 in a front and rear direction of the deck 1000, a left and right moving part 4200 for syringe block, which moves the syringe block 3000 in a left and right direction of the deck 1000, and an up and down moving part 4300 for syringe block, which moves up and down the syringe block 3000, and the front and rear moving part 4100 for syringe block comprises a front and rear moving body 4110 for syringe block; and a front and rear moving motor 4110M for syringe block which is disposed to be spaced apart from the front and rear moving body 4110 for syringe block, and which is connected to the front and rear moving body 4110 for syringe block so as to move the front and rear moving body 4110 for syringe block in the front and rear direction of the deck 1000, and the left and right moving part 4200 for syringe block comprises a left and right moving motor 4210M for syringe block, which is fixed to the front and rear moving body 4110 for syringe block; and a left and right moving body 4210 for syringe block, which is installed at the front and rear moving body 4110 for syringe block so as to be moved in the left and right direction of the deck 1000, and which is connected to the left and right moving motor 4210M for syringe block, and the up and down moving part 4300 for syringe block comprises a supporting plate 4360 for up and down movement of the syringe block, which is fixed to the left and right moving body 4210 for syringe block; and a front and rear moving motor 4110M for syringe block, which is installed at the supporting plate 4360 for up and down movement of the syringe block, and which is connected to the syringe block 3000 so as to move up and down the syringe block 3000.

Preferably, the front and rear moving part 4100 for syringe block comprises a front and a rear moving belt for syringe block, which is moved in the front and rear direction of the deck 1000 by the front and rear moving motor 4110M for syringe block; and a syringe block connecting member 4140, of which one end is fixed to the front and a rear moving belt for syringe block and the other end is fixed to the front and rear moving body 4110 for syringe block, and the left and right moving part 4200 for syringe block comprises a left and right moving belt for syringe block, which is moved in the left and right direction of the deck 1000 by the left and right moving motor 4210M for syringe block; and a syringe block connecting member 4240, of which one end is fixed to the left and right moving belt for syringe block and the other end is fixed to the left and right moving body 4210 for syringe block, and the up and down moving part 4300 for syringe block comprises a ball screw shaft 4330S for up and down movement of the syringe block, which is connected to the up and down lifting motor 4310M for syringe block; a ball nut 4330N for up and down movement of the syringe block, which is moved up and down when the ball screw shaft 4330S for up and down movement of the syringe block is rotated; and an up and down moving body 4310 for syringe block, in which the syringe block 3000 is installed, and which is fixed to the ball nut 4330N for up and down movement of the syringe block.

Preferably, wherein the automatic deck storing and moving device 2000 includes a stacking rack 2100 in which a plurality of racks 2110 are stacked; and a stacking rack lifting unit which moves up and down the stacking rack 2100 so that the plurality of decks 1000 can be taken in or out of the plurality of racks 2110 through the door 2000C-1.

Preferably, the automatic deck storing and moving device 2000 includes a pallet 2130 which is slidably installed at a pallet guider 2112 provided at the rack 2110, and which a pallet moving dog 2131 and a pallet withdrawal groove 2130H are formed at one side thereof; and a pallet moving unit 2300 which is contacted with the pallet moving dog 2131 so as to slide and withdraw the pallet 2130 to an outside of the storing case 2000C, so that the deck 1000 can be mounted on an upper surface of the pallet 2130.

Preferably, the pallet moving unit 2300 comprises a front and rear moving block 2330 for pallet which is connected to the pallet moving motor 2310 so as to be moved in the front and rear direction of the deck 1000, and which is formed into a "U" shape so that an inner side of an opened end is contacted with the pallet moving dog 2131.

Preferably, the automatic real-time quantitative amplification system further includes a front and rear moving belt 2320 for pallet, which is moved in the front and rear direction of the deck 1000 by pallet moving motor 2310, and to which a closed end of the front and rear moving block 2330 for pallet is fixedly connected.

Preferably, the stacking rack lifting unit includes a stacking rack lifting ball screw shaft 2240S which is connected to a stacking rack lifting motor 2210M; a stacking rack lifting ball nut 2240N which is moved up and down when the stacking rack lifting ball screw shaft 2240S is rotated; and a stacking rack connecting member 2250 of which one side surface is fixedly connected to the stacking rack lifting ball nut 2240N and the other side surface is fixedly connected to the stacking rack 2100.

Preferably, the deck transferring unit 2400 comprises a deck withdrawal slider 2450 in which a deck withdrawal protrusion 2451 put into the pallet withdrawal groove 2130H is formed at one side thereof, and in which an insertion pin 2451-1 inserted into a grasping hold 1110H formed at the deck 1000 is formed on an upper surface of the deck withdrawal protrusion 2451, and which is movable in the left and right direction of the deck 1000.

Preferably, the automatic real-time quantitative amplification system further includes a left and right moving belt 2430 for deck which is moved in the left and right direction of the deck 1000 by a deck moving motor 2410; and a deck withdrawal slider connecting member 2440 of which one end is fixedly connected to the left and right moving belt 2430 for deck and the other end is fixedly connected to the deck withdrawal slider 2450.

Preferably, the sealing device 6000 includes a sealed loading plate 6294 on which the multi-well plate 400 for PCR is mounted and which is disposed to be moved in the front and rear direction of the deck 1000; a lower compressing portion 6230 which supports a sealing film; an upper compressing portion 6243 which is disposed at an upper side of the lower compressing portion 6230 so as to be moved down and compress the sealing film; a film cutter 6250 which is located at a front or rear side of the upper compressing portion 6243 so as to be moved down and cut the sealing film compressed between the lower and upper compressing portions 6230 and 6243; and a film heating block 6310 which is disposed at an upper side of an intermediate plate 6260 for sealing device to be movable down and thermally compress the sealing film mounted on an upper surface of the multi-well plate 400 for PCR to the multi-well plate 400 for PCR.

Preferably, the automatic real-time quantitative amplification system further includes a first supporting spring 6241 which is elastically contacted with the lower compressing portion 6230; an upper compressing portion supporting block 6240 which is elastically supported by the first supporting spring 6241 and disposed at an upper side of the upper compressing portion 6243, and in which the film cutter 6250 is provided; a second supporting spring 6242 which is disposed to be elastically contacted between the upper and lower compressing portions 6243 and 6240; and an upper compressing portion supporting rod 6244 which is connected to the upper compressing portion 6243 so as to be extended to an upper side of the upper compressing portion 6243, and which is inserted onto the upper compressing portion 6240 so as to be slid up and down, and which is formed with a stopper 6244-1 for preventing separation from the upper compressing portion 6240.

Preferably, the automatic real-time quantitative amplification system further includes a film side guide plate 6222 which is disposed at a front side of the lower compressing portion 6230 so as to support an edge lower surface of the sealing film located at a front side of the lower compressing portion 6230; and a film side guide plate mounting portion 6220 to which the film side guide plate 6222 is installed so as to be rotated to an outside of an edge portion of the sealing film supported on an upper surface of the film side guide plate 6222 and thus to be separated from the sealing film supported on an upper surface of the film side guide plate 6222.

Preferably, the automatic real-time quantitative amplification system further includes a film roller 6120 which is rotatably disposed at a film roller supporter 6110 and on which the sealing film is wound; a film guide plate mounting portion 6210 which is located at a rear side of the lower compressing portion 6230 and to which a film guide plate 6212 for supporting a lower surface of the sealing film unwound from the film roller 6120 is fixed; an intermediate plate 6260 for sealing device, on which the film guide plate mounting portion 6210, the sealed loading plate 6294, the sealed loading plate moving motor 6294M for moving the sealed loading plate 6294 in the front and rear direction of the deck 1000, and the lower compressing portion 6230 are mounted; and an intermediate plate moving unit 6260M which moves the intermediate plate 6260 for sealing device in the front and rear direction of the deck 1000 so that the sealing film is unwound from the film roller 6120 or the sealing film supported by the film guide plate 6212 is located at an upper side of the multi-well plate 400 for PCR.

Preferably, the automatic real-time quantitative amplification system further includes an upper plate 6320 for sealing device which is fixedly installed at an upper side of the intermediate plate 6260 for sealing device by the upper plate supporting rod 6322; a compressing portion moving-down part which is installed at the upper plate 6320 for sealing device so as to move down the upper compressing portion supporting block 6240; and a film heating block lifting part which is installed at the upper plate 6320 for sealing device so as to move up and down the film heating block 6310.

Preferably, the intermediate plate moving unit 6260M is an intermediate plate moving pneumatic cylinder which is fixed to a lower plate 6410 for sealing device, in which the intermediate plate 6260 for sealing device is slidably installed, and the compressing portion moving-down part is a pneumatic cylinder 6330 for compressing portion, of which a piston rod is moved down and contacted with the upper compressing portion supporting block 6240, and the film heating block lifting part is a pneumatic cylinder 6340 for film heating block, of which a piston rod moving up and down is connected to the film heating block 6310.

Preferably, the automatic real-time quantitative amplification system further includes a ball screw shaft 6280S for sealed loading plate movement, which is connected to the sealed loading plate moving motor 6294M; and a ball nut 6280N for sealed loading plate movement, which is fitted to the ball screw shaft 6280S for sealed loading plate movement so as to be moved in the front and rear direction of the deck 1000 when the ball screw shaft 6280S for sealed loading plate movement is rotated, and which is connected to the sealed loading plate 6294.

Preferably, the automatic real-time quantitative amplification system further includes a vortex mixer 7100 which applies vibration to the multi-well plate 400 for PCR moved from the sealing device 6000 by the moving device 9000 for multi-well plate for PCR before being transferred to the centrifugal separator 7200, in order to mix a substance injected into the multi-well plate 400 for PCR.

Preferably, the vortex mixer 7100 includes a driven shaft 7130 for vortex mixer which is disposed in an up and down direction so as to be rotated by a motor 7100M for vortex mixer; an eccentric driven shaft 7140 for vortex mixer, which is integrally and eccentrically connected to the driven shaft 7130 for vortex mixer; an eccentric driven shaft bearing 7150 which is coupled to the eccentric driven shaft 7140 for vortex mixer; a plurality of separation preventing springs 7170 of which one ends are fixed to an outer surface of the eccentric driven shaft bearing 7150 and the other ends are fixed to an upper plate 7160 for vortex mixer; and a mounting plate 7180 for vortex mixer, which is fixedly installed at an upper end of the eccentric driven shaft bearing 7150, and on which the multi-well plate 400 for PCR is mounted.

Preferably, a barycenter block 7190 is fixedly disposed at the eccentric driven shaft 7140 for vortex mixer so as to be protruded in an opposite direction to an eccentric direction of the eccentric driven shaft 7140 for vortex mixer with respect to the driven shaft 7130 for vortex mixer.

Preferably, the centrifugal separator 7200 includes a driven shaft 7230 for centrifugal separator, which is disposed in an up and down direction so as to be rotated by a motor 7200M for centrifugal separator; a rotational plate 7240 for centrifugal separator, which is formed into an "I" shape so that an opening portion is formed at both side ends thereof, and which is integrally formed with the driven shaft 7230 for centrifugal separator; and a mounting block 7250 for centrifugal separator, on which the multi-well plate 400 for PCR is mounted, and which is rotatably disposed at an opening portion of both side ends of the rotational plate 7240 for centrifugal separator, such that an upper surface of the multi-well plate 400 for PCR looks in an inside direction and a lower surface thereof looks in an outside direction when the rotational plate 7240 for centrifugal separator is rotated.

Preferably, the moving device 9000 for multi-well plate for PCR includes a movement guide block 9100 for multi-well plate for PCR which is disposed in the left and right direction at a front upper side of the deck 1000 transferred by the deck transferring unit 2400; a left and right moving block 9210 for multi-well plate for PCR, which is connected to a left and right moving motor 9210M, and disposed at a movement guide block 9100 for multi-well plate for PCR so as to be moved in the left and right direction of the deck 1000; a front and rear moving guide block 9320 for multi-well plate for PCR, which is disposed at the left and right moving block 9210 for multi-well plate for PCR so as to be protruded in the front and rear direction of the deck 1000; a front and rear moving block 9314 for multi-well plate for PCR, which is connected to a front and rear moving motor 9310M for multi-well plate for PCR fixed to the front and rear moving guide block 9320 for multi-well plate for PCR, and disposed at the front and rear moving guide block 9320 for multi-well plate for PCR so as to be movable in the front and rear direction of the deck 1000; an up and down moving guide block 9410 for multi-well plate for PCR, which is fixed to the front and rear moving block 9314 for multi-well plate for PCR; and a grasping means 9600 for grasping the multi-well plate for PCR, which is connected to an up and down moving motor 9510M for multi-well plate for PCR fixed to up and down moving guide block 9410 for multi-well plate for PCR, so as to be moved up and down.

Preferably, the grasping means 9600 for grasping the multi-well plate for PCR comprises a grasping portion 9660 which is moved inwardly by a grasping motor 9600M for multi-well plate for PCR so as to grasp both side ends of the multi-well plate 400 for PCR.

Preferably, automatic real-time quantitative amplification system further includes a grasping portion pinion 9620 which is rotated by the grasping motor 9600M for multi-well plate for PCR; a grasping portion rack 9630 which is engaged with the grasping portion pinion 9620 so as to be moved, and connected to the grasping portion 9660; and a grasping portion spring 9640 which is connected to the grasping portion rack 9630 so as to maintain a state that the grasping portion 9660 continuously grasps the both side ends of the multi-well plate 400 for PCR, even when the grasping motor 9600M for multi-well plate for PCR is turned off.

Further, the present invention provides an automatic purification and reaction preparing device for biological sample analysis including a syringe block 3000 which is formed with a plurality of first mounting portions 3330 so as to removably mount a plurality of pipettes P for sucking and discharging a fluid substance; a syringe block moving unit 4000 which moves the syringe block 3000 so that the plurality of pipettes P mounted in the plurality of first mounting portions 3330 are located just above each of a multi-well plate 100 for biological sample, a plurality of multi-well plates for purification and a multi-well plate 400 for PCR, which are located in a lower side of the syringe block 3000 and a solution drip tray 4375 which is moved to a lower side of the plurality of pipettes P mounted in the plurality of first mounting portions 3330 by a solution drip tray moving unit installed to the syringe block moving unit 4000.

Preferably, the automatic purification and reaction preparing device further includes a puncher 12100 which is provided with a plurality of awl-shaped puncher pins so as to pierce holes in a sealing film for sealing an upper surface of the multi-well plate 100 for biological sample and the plurality of multi-well plates 200 for multiple biological samples, and which is disposed at a lower side of the syringe block 3000 so as to be removably mounted in the plurality of first mounting portions 3330 at different time point as compared with the time point, when the plurality of pipettes P is mounted in the plurality of first mounting portions 3330.

Preferably, the solution drip tray moving unit includes a solution drip tray supporting plate 4371 which is connected to the syringe block moving unit 4000; and a solution drip tray moving motor 4373 which is installed at the solution drip tray supporting plate 4371 and which is connected to the solution drip tray 4375 so as to horizontally rotate the solution drip tray 4373.

Further, the present invention provides an automatic purification and reaction preparing device which can perform analysis of various biological samples, including a syringe block 3000 formed with a plurality of first mounting portions 3330 which removably mounts the plurality of pipettes P for sucking and discharging the fluid substance; a syringe block moving unit 4000 which moves the syringe block 3000 so that the plurality of pipettes P mounted in the plurality of first mounting portions 3330 are located just above each of a multi-well plate 100 for biological sample, a plurality of multi-well plates 200 for purification and a multi-well plate 400 for PCR, which are disposed at a lower side of the syringe block 3000; and an evaporation block 12200 for multi-well plate, which is connected with a compressed air supplying tube, and of which a lower surface is formed with a plurality of second mounting portions 12210 for shooting compressed air supplied through the compressed air supplying tube and removably mounting the plurality of pipettes P, and which is disposed at a lower side of the syringe block 3000 so as to be removably mounted in the plurality of first mounting portions 3330 at different time point as compared with the time points, when the plurality of pipettes P and the puncher 12100 are respectively mounted in the plurality of first mounting portions 3330.

Preferably, the automatic purification and reaction preparing device further includes a solution drip tray 4375 which is connected to the syringe block moving unit 4000, and which is moved to a lower side of the plurality of pipettes P mounted in the plurality of first mounting portions 3330 by a solution drip tray moving unit.

Preferably, the automatic purification and reaction preparing device further includes a puncher 12100 which is provided with a plurality of awl-shaped puncher pins so as to pierce holes in a sealing film for sealing an upper surface of the multi-well plate 100 for biological sample and the plurality of multi-well plates 200 for multiple biological samples, and which is disposed at a lower side of the syringe block 3000 so as to be removably mounted in the plurality of first mounting portions 3330 at different time point as compared with the time points, when the plurality of pipettes P and the evaporation block 12200 for multi-well plate are respectively mounted in the plurality of first mounting portions 3330.

Preferably, the syringe block 3000 includes a syringe pin holder 3200 which is movable up and down and to which a plurality of rod-shaped syringe pins 3100 are attached; a syringe pin guide block 3300 which is formed with a guide hole 3310H for guiding up/down movement of the plurality of syringe pins 3100; a first separation portion which is moved down, while being contacted with the syringe pin holder 3200, so as to separate the plurality of pipettes P, the puncher 12100 and the evaporation block 12200 for multi-well plate from the first mounting portion 3330, which are respectively mounted in the first mounting portion 3330 at different time points; a second-1 separation portion which is moved down, while being contacted with the syringe pin holder 3200, so as to be interlocked with a second-2 separation portion provided at the evaporation block 12200 for multi-well plate and thus to separate the plurality of pipettes P mounted in the second mounting portion 12210.

Preferably, the first separation portion includes a first separation rod 3731 which is inserted into a first separation rod guide hole formed in the syringe pin guide block 3300 so as to be moved down by compressing force of the syringe pin holder 3200; and a first lower separation plate 3720 which is inserted onto the plurality of first mounting portions 3330 protruded from the syringe pin guide block 3300 so as to be moved up and down, and which is moved down by the first separation rod 3731 so as to compress and separate the plurality of pipettes P, the puncher 12100 and the evaporation block 12200 for multi-well plate which are respectively mounted in the plurality of mounting portions 3330 at different time points.

Preferably, the first separation portion comprises a first separation rod spring 37315 which exerts an upper portion of the first separation rod 3731 beyond the syringe pin guide block 3300 by elastic force thereof when the compressing force of the syringe pin holder 3200 is released.

Preferably, the first separation portion comprises a first upper separation plate 3710 which is attached to an upper portion of the first separation rod 3731 so as to be located between the syringe pin holder 3200 and the syringe pin guide block 3300, and through which the plurality of syringe pins 3100 are passed.

Preferably, the first separation rod 3731 comprises a first small-diameter separation rod 3731-1 which is formed at a lower portion of the first separation rod 3731, and a first large-diameter separation rod 3731-2 which is formed at an upper side of the first small-diameter separation rod 3731-1 so as to have a larger diameter than the first small-diameter separation rod 3731-1, and the first separation rod guide hole comprises a first small-diameter separation rod guide hole 3321H1 which is formed at a lower portion of the first separation rod guide hole so as to guide the first small-diameter separation rod 3731-1, and a first large-diameter separation rod guide hole 3321H2 which is formed at an upper side of the first small-diameter separation rod guide hole 3321H1 so as to guide the first large-diameter separation rod 3731-2, and the first separation rod spring 3731S which is inserted onto the first small-diameter separation rod 3731-1 and of which an upper end is elastically supported by a lower end of the first large-diameter separation rod 3731-2 and a lower end is elastically supported by a lower end of the first large-diameter separation rod guide hole 3321H2.

Preferably, the second-1 separation portion comprises a second separation rod 3732 which is inserted into a second separation rod guide hole formed in the syringe block guide 3300 so as to be moved down by the compressing force of the syringe pin holder 3200, and the second-2 separation portion comprises a second separation plate 12220 which is inserted onto the plurality of second mounting portions 12210 protruded from a lower end of the evaporation block 12200 for multi-well plate so as to be movable up and down, and which is moved down by the second separation rod 3732 so as to compress and separate the plurality of pipettes P mounted in the plurality of second mounting portions 12210.

Preferably, the second-2 separation portion comprises a second separation pin 12230 which is installed at the evaporation block 12200 for multi-well plate so as to be movable up and down, and which is moved down by the second separation rod 3732 so as to compress the second separation plate 12220.

Preferably, the second-1 separation portion comprises a second separation rod spring 3732S which exerts an upper portion of the second separation rod 3732 beyond an upper end of the first separation rod 3731 by elastic force thereof when the compressing force of the syringe pin holder 3200 is released.

Preferably, the second separation rod 3732 comprises a lower stopper 3732-1P which catches beneath a lower surface of the first lower separation plate 3720 by elastic force of the second separation rod spring 3732S when the compressing force of the syringe pin holder 3200 is released.

Preferably, the second separation rod 3732 includes a second small-diameter separation rod 3732-1 which is formed at a lower portion of the second separation rod 3732, and a second large-diameter separation rod 3732-2 which is formed at an upper side of the second small-diameter separation rod 3732-1 so as to have a larger diameter than the second small-diameter separation rod 3732-1, and the second separation rod guide hole includes a second small-diameter separation rod guide hole 3322H1 which is formed at the lower portion of the second separation rod guide hole so as to guide the second small-diameter separation rod 3732-1, and a second large-diameter separation rod guide hole 3322H2 which is formed at an upper side of the second small-diameter separation rod guide hole 3322H1 so as to guide the second large-diameter separation rod 3732-2, and the second separation rod spring 3732S is inserted onto the second small-diameter separation rod 3732-1 so that an upper end thereof is elastically supported by a lower end of the second large-diameter separation rod 3732-2 and a lower end thereof is elastically supported by a lower end of the second large-diameter separation rod guide hole 3322H2.

Furthermore, the present invention provides a method for automatic nucleic acid purification and real-time quantification of gene amplification using the automatic real-time quantitative amplification system for biological sample analysis, including introducing the deck 1000, on which the multi-well plate 100 for biological sample, in which the biological sample containing a target substance is injected, the plurality of multi-well plates 200 for purification, which purify a target nucleic acid in the target substance, and the multi-well plate 400 for PCR, in which the reaction mixture for real-time PCR is injected are mounted, in the storing case 2000C; moving the deck 1000 to a lower side of a syringe block 3000 having a plurality of first mounting portions 3330 in which a plurality of pipettes P for sucking and discharging a fluid substance are removably mounted, using the deck transferring unit 2400; purifying the target nucleic acid using the syringe block 3000 in which the plurality of pipettes P are removably mounted, the multi-well plate 100 for biological sample and the plurality of multi-well plates 200 for purification; dispensing the purified target nucleic acid to the multi-well plate 400 for PCR using the syringe block 3000 in which the plurality of pipettes P are removably mounted moving the multi-well plate 400 for PCR, in which the target nucleic acid is dispensed, to the sealing device 6000 using the moving device 9000 for multi-well plate for PCR; sealing an upper surface of the multi-well plate 400 for PCR, in which the target nucleic acid is dispensed, using the sealing device 6000; moving the multi-well plate 400 for PCR, of which the upper surface is sealed, to the centrifugal separator 7200 using the moving device 9000 for multi-well plate for PCR; applying centripetal force to the multi-well plate 400 for PCR using the centrifugal separator 7200 so as to separate substances remained on a side wall of each well formed in the multi-well plate 400 for PCR and thus to move the substances to a bottom surface of each well formed in the multi-well plate 400 for PCR; moving the multi-well plate 400 for PCR to the real-time quantitative amplification device 8000 using the moving device 9000 for multi-well plate for PCR after the applying of the centripetal force to the multi-well plate 400 for PCR using the centrifugal separator 7200; and performing real-time amplification of the target nucleic acid in the multi-well plate 400 for PCR using the real-time quantitative amplification device 8000.

Preferably, the performing of real-time amplification of the target nucleic acid in the multi-well plate 400 for PCR obtains real-time quantitative amplification data of the nucleic acid, which shows an amplified amount of the target nucleic acid over time, using the real-time quantitative amplification device 8000, and then displays the obtained real-time quantitative amplification data or transfers the data to the outside.

Preferably, in the introducing of the deck 1000, the plurality of decks 1000 are introduced into the storing case 2000C, and the method further includes moving the deck 1000 to the storing case 2000C using the deck transferring unit after the moving of the multi-well plate 400 for PCR to the sealing device 6000, and moving the multi-well plate 400 for PCR, in which the real-time amplification is performed, to a multi-well plate collecting container using the moving device 9000 for multi-well plate for PCR, and in order to perform the target nucleic acid purification and the purified target nucleic acid amplification with respect to each biological sample loaded in the plurality of decks 1000, the processes from the moving of the deck 1000 to the lower side of the syringe block 3000 to the moving of the multi-well plate 400 for PCR to the multi-well plate collecting container are repeatedly carried out corresponding to the number of decks 1000 introduced into the storing case 2000C.

Preferably, if one of the plurality of decks 1000 is moved to the storing case 2000C through the moving of the deck 1000 to the storing case 2000C after the moving of the multi-well plate 400 for PCR to the sealing device 6000, another one of the decks 1000 is moved to the lower side of the syringe block 3000 through the introducing of the deck 1000 in the storing case 2000C, and the processes from the sealing of the upper surface of the multi-well plate 400 for PCR to the moving of the multi-well plate 400 for PCR to the multi-well plate collecting container out of whole processes which are carried out in order to perform the target nucleic acid purification and the purified target nucleic acid amplification with respect to the biological sample mounted in the one of the decks 1000 are simultaneously carried out together with the processes from the moving of the deck 1000 to the lower side of the syringe block 3000 to the moving of the deck 1000 to the storing case 2000C after the moving of the multi-well plate 400 for PCR to the sealing device 6000 out of another whole processes which are carried out in order to perform the target nucleic acid purification and the purified target nucleic acid amplification with respect to the biological sample mounted in the other one of the decks 1000.

Preferably, method further includes moving the multi-well plate 400 for PCR, of which the upper surface is sealed, to a vortex mixer 7100 using the moving device 9000 for multi-well plate for PCR after the sealing of the upper surface of the multi-well plate 400 for PCR; and applying vibration to the multi-well plate 400 for PCR, of which the upper surface is sealed, using the vortex mixer 7100 so as to mix the substances injected into the multi-well plate 400 for PCR after the moving of the multi-well plate 400 for PCR to a vortex mixer 7100 and before the moving of the multi-well plate 400 for PCR to the centrifugal separator 7200.

Further, the present invention provides a method for automatic nucleic acid purification using the automatic purification and reaction preparing device for biological sample analysis, including moving the deck 1000, on which the multi-well plate 100 for biological sample, in which the biological sample containing a target substance is injected, the plurality of multi-well plates 200 for purification, which purify a target nucleic acid in the target substance, and the plurality of pipettes P for sucking and discharging a fluid substance are mounted, to a lower side of the syringe block 3000; moving the syringe block 3000 so as to mount the plurality of pipettes P in the first mounting portion 3310 and to inject a cell lysis solution in a multi-well plate 210 for cell lysis solution out of the plurality of multi-well plates 200 for purification into the multi-well plate 100 for biological sample and thus to obtain a biological sample mixing solution; sucking the biological sample mixing solution using the syringe block 3000 having the plurality of pipettes P and then mixing with a nucleic acid binding solution injected into a multi-well plate 230 for nucleic acid binding solution out of the plurality of multi-well plates 200 for purification; sucking a mixture of the nucleic acid binding solution and the biological sample mixing solution using the syringe block 3000 having the plurality of pipettes P and then mixing with a magnetic particle suspension injected into a multi-well plate 220 for magnetic particle dispersion solution out of the plurality of multi-well plates 200 for purification; applying magnetic field to a lower portion of the multi-well plate 220 for magnetic particle dispersion solution and thus to a mixture mixed with the magnetic particle suspension; removing a mixture except magnetic particles and attached matters to the magnetic particles using the syringe block 3000 having the plurality of pipettes P in a state that the magnetic particles and the attached matters to the magnetic particles in the mixture mixed with the magnetic particle suspension are adhered to an inner wall of the multi-well plate 220 for magnetic particle dispersion solution by the magnetic field applied to the lower portion of the multi-well plate 220 for magnetic particle dispersion solution; injecting a cleaning solution in a multi-well plate 241, 242, 243 for cleaning solution out of the plurality of multi-well plates 200 for purification into the multi-well plate 220 for magnetic particle dispersion solution using the syringe block 3000 having the plurality of pipettes P in a state that the magnetic field applied to the lower side of the multi-well plate 220 for magnetic particle dispersion solution is removed, and thus isolating impurities except the target nucleic acid from the magnetic particles; applying the magnetic field to the lower portion of the multi-well plate 220 for magnetic particle dispersion solution and thus to a mixture mixed with the cleaning solution; removing a mixture except the magnetic particles, on which the target nucleic acid is attached, using the syringe block 3000 having the plurality of pipettes P in a state that the magnetic particles, on which the target nucleic acid is attached, in the mixture mixed with the cleaning solution are adhered to the inner wall of the multi-well plate 220 for magnetic particle dispersion solution by the magnetic field applied to the lower portion of the multi-well plate 220 for magnetic particle dispersion solution; injecting a nucleic acid elution solution in a multi-well plate 250 for nucleic acid elution solution out of the plurality of multi-well plates 200 for purification into the multi-well plate 220 for magnetic particle dispersion solution using the syringe block 3000 having the plurality of pipettes P in a state that the magnetic field applied to the lower side of the multi-well plate 220 for magnetic particle dispersion solution is removed, and thus isolating the target nucleic acid from the magnetic particles; applying the magnetic field to the lower portion of the multi-well plate 220 for magnetic particle dispersion solution using the magnetic field applying unit 5100 and thus to a mixture mixed with nucleic acid elution solution; and collecting a mixture except the magnetic particles, i.e., a target nucleic acid containing solution in the mixture mixed with the nucleic acid elution solution using the syringe block 3000 having the plurality of pipettes P in a state that the magnetic particles in the mixture mixed with the nucleic acid elution solution are adhered to the inner wall of the multi-well plate 220 for magnetic particle dispersion solution by the magnetic field applied to the lower portion of the multi-well plate 220 for magnetic particle dispersion solution, wherein, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

Preferably, the method further includes mounting the puncher 12100, in which a plurality of awl-shaped puncher pins 12110 are protrusively formed, in the first mounting portion 3310 after the moving of the deck 1000 to the lower side of the syringe block 3000, piercing holes in a sealing film for sealing an upper surface of the multi-well plate 210 for cell lysis solution, and then moving the puncher 12100 to its original position and separating it; mounting the puncher 12100 in the first mounting portion 3310 after the moving of the syringe block 3000 so as to obtain the biological sample mixing solution, piercing holes in a sealing film for sealing an upper surface of the multi-well plate 230 for nucleic acid binding solution, and then moving the puncher 12100 to its original position and separating it; mounting the puncher 12100 in the first mounting portion 3310 after the sucking of the biological sample mixing solution and the mixing with the nucleic acid binding solution, piercing holes in a sealing film for sealing an upper surface of the multi-well plate 220 for magnetic particle dispersion solution, and then moving the puncher 12100 to its original position and separating it; mounting the puncher 12100 in the first mounting portion 3310 after the removing of the mixture except the magnetic particles and the attached matters to the magnetic particles in the mixture mixed with the magnetic particle suspension, piercing holes in a sealing film for sealing an upper surface of the multi-well plate 241, 242, 243 for cleaning solution, and then moving the puncher 12100 to its original position and separating it; and mounting the puncher 12100 in the first mounting portion 3310 after the removing of the mixture except the magnetic particles, on which the target nucleic acid is attached, in the mixture mixed with the cleaning solution, piercing holes in a sealing film for sealing an upper surface of the multi-well plate 250 for nucleic acid elution solution, and then moving the puncher 12100 to its original position and separating it.

Preferably, the method further includes heating a lower portion of the multi-well plate 100 for biological sample using the heating unit and thus heating the biological sample mixing solution before the sucking of the biological sample mixing solution and then the mixing with the nucleic acid binding solution.

Preferably, the cleaning solution includes alcohol, and the removing of the mixture except the magnetic particles, on which the target nucleic acid is attached, in the mixture mixed with the cleaning solution comprises heating a lower portion of the multi-well plate 220 for magnetic particle dispersion solution and thus removing alcohol contained in the cleaning solution remained on the magnetic particles.

Preferably, the removing of the mixture except the magnetic particles, on which the target nucleic acid is attached, in the mixture mixed with the cleaning solution includes moving the plurality of pipettes P mounted in the first mounting portion 3310 to its original and separating them; mounting the evaporation block 12200 for multi-well plate, in which compressed air supplied through a compressed air supplying tube is shot and the plurality of mounting portions 12210 for removably mounting the plurality of pipettes P are formed, in the first mounting portion 3310; mounting the plurality of pipettes P in the second mounting portion 12210, and shooting the compressed air into the multi-well plate 220 for magnetic particle dispersion solution using the plurality of pipettes P mounted in the evaporation block 12200 for multi-well plate, and thus removing the alcohol contained in the cleaning solution remained on the magnetic particles; moving the plurality of pipettes P mounted in the second mounting portion 12210 to its original position and removing them, and moving the evaporation block 12200 for multi-well plate, which is mounted in the first mounting portion 3310, to its original position and separating it.

Preferably, the plurality of pipettes P, which are removably mounted in the plurality of first mounting portions 3330, used in the moving of the syringe block 3000 so as to obtain the biological sample mixing solution, the sucking of the biological sample mixing solution and the mixing with the nucleic acid binding solution, the sucking of the mixture of the acid binding solution and the biological sample mixing and the mixing with a magnetic particle suspension, the removing of the mixture except the magnetic particles and the attached matters to the magnetic particles in the mixture mixed with the magnetic particle suspension, the injecting of the cleaning solution into the multi-well plate 220 for magnetic particle dispersion solution and the isolating of the impurities except the target nucleic acid from the magnetic particles, and the removing of the mixture except the magnetic particles, on which the target nucleic acid is attached, in the mixture mixed with the cleaning solution are a plurality of nucleic acid purification pipettes P1, and the plurality of pipettes P, which are removably mounted in the plurality of first mounting portions 3330, used in the injecting of the nucleic acid elution solution into the multi-well plate 220 for magnetic particle dispersion solution and the collecting of the target nucleic acid containing solution are a plurality of nucleic acid dispensation pipettes P2 having smaller a capacity than the plurality of purification pipettes P1, and a nucleic acid purification pipette rack 310 in which the plurality of nucleic acid purification pipettes P1 are received, and a nucleic acid dispensation pipette rack 320 in which the plurality of nucleic acid dispensation pipette P2 are received are loaded on the deck 1000, and the multi-well plate 400 for PCR includes a first multi-well plate 410 for PCR and a second multi-well plate 420 for PCR.

Preferably, in the applying of the magnetic field to the mixture mixed with the magnetic particle suspension, and the applying of the magnetic field to the mixture mixed with the cleaning solution, and the applying of the magnetic field to the mixture mixed with nucleic acid elution solution, the plurality of rod-shaped magnet 5110 which are disposed to be spaced apart from each other are lifted up so that upper ends of the magnets 5110 enclose each well formed in the multi-well plate 220 for magnetic particle dispersion solution.

Further, the present invention provides a method for automatically measuring viable cell count of pathogenic bacteria using real-time quantitative PCR, which can culture the pathogenic bacteria contained in a biological sample, and then can measure the viable cell count of the pathogenic bacteria by performing the real-time quantitative PCR using the automatic real-time quantitative amplification system, including introducing the deck 1000, in which the multi-well plate 100 for biological sample, in which the same biological sample mixed with a culture medium is injected into two wells forming a unit well, and another biological samples mixed with the culture medium are injected into another unit wells, and a sterilization substance is injected in one well out of the unit well, the plurality of multi-well plates for purification, which purify a target nucleic acid contained in the pathogenic bacteria, and the multi-well plate 400 for PCR, in which the reaction mixture for real-time quantitative PCR is injected, are loaded, into the storing case 2000C; culturing the pathogenic bacteria in the multi-well plate 100 for biological sample under predetermined conditions in the storing case 2000C; moving the deck 1000 to a lower portion of a syringe block 3000 formed with a plurality of first mounting portions 3330 which can removably mount a plurality of pipettes P for sucking and discharging a fluid substance; purifying the target nucleic acid using the syringe block 3000 in which the plurality of pipettes P are removably mounted, the multi-well plate 100 for biological sample, and the plurality of multi-well plates 200 for purification; dispensing the purified nucleic acid to the multi-well plate 400 for PCR using the syringe block 3000 in which the plurality of pipettes P are removably mounted; moving the multi-well plate 400 for PCR, in which the target nucleic acid is dispensed, to the sealing device 6000 using the moving device 9000 for multi-well plate for PCR; sealing an upper surface of the multi-well plate 400 for PCR, in which the target nucleic acid is dispensed, using the sealing device 6000; moving the multi-well plate 400 for PCR, of which the upper surface is sealed, to the centrifugal separator 7200 using the moving device 9000 for multi-well plate for PCR; applying centripetal force to the multi-well plate 400 for PCR using the centrifugal separator 7200 so as to separate substances remained on a side wall of each well formed in the multi-well plate 400 for PCR and thus to move the substances to a bottom surface of each well formed in the multi-well plate 400 for PCR; moving the multi-well plate 400 for PCR to the real-time quantitative amplification device 8000 using the moving device 9000 for multi-well plate for PCR after the applying of the centripetal force to the multi-well plate 400 for PCR using the centrifugal separator 7200; performing real-time amplification of the target nucleic acid in the multi-well plate 400 for PCR using the real-time quantitative amplification device 8000; and obtaining real-time quantitative amplification data of the nucleic acid, which shows an amplified amount of the target nucleic acid over time, using the real-time quantitative amplification device 8000, and then obtaining the viable cell count in the well out of the unit cell, in which the sterilization substance is injected, through relative quantification in real-time quantitative PCR using the real-time quantitative amplification data of the nucleic acid in the well in which the sterilization substance is injected and the real-time quantitative amplification data of the nucleic acid in the well in which the sterilization substance is not injected.

Further, the present invention provides a method for automatically getting antigen density using quantitative immunity PCR, which can perform a quantitative test for antigen density contained in the biological sample by performing the quantitative immunity PCR using the automatic real-time quantitative amplification system, including introducing the deck 1000, in which the multi-well plate 100 for PCR, in which a biological sample containing a target antigen is injected, the multi-well plate for trapped antibody magnetic particle suspension, in which a magnetic particle suspension including magnetic particles coated with a first antibody for antigen binding, which is bound with the target antigen, is injected, the multi-well plate for target nucleic acid labeling, in which a second antibody containing solution containing a second antibody labeled with a binding target nucleic acid, which is bound with the target antigen trapped by the first antibody for antigen binding, is injected, the multi-well plate 241, 242, 243 for cleaning solution, in which a cleaning solution is injected, the multi-well plate 250 for nucleic acid elution solution, in which a nucleic acid elution solution is injected, and the multi-well plate 400 for PCR, in which a reaction mixture for real-time quantitative PCR is injected, are loaded, into the storing case 2000C; moving the deck 1000 to a lower portion of a syringe block 3000 formed with a plurality of first mounting portions 3330 which can removably mount a plurality of pipettes P for sucking and discharging a fluid substance; performing an antigen-antibody reaction using the syringe block 3000 in which the plurality of pipettes P are removably mounted, the multi-well plate 100 for biological sample, the multi-well plate for trapped antibody magnetic particle suspension, the multi-well plate for target nucleic acid labeling, the multi-well plate 241, 242, 243 for cleaning solution, and the multi-well plate 250 for nucleic acid elution solution, and purifying the binding target nucleic acid labeled to the second antibody; dispensing the purified binding nucleic acid to the multi-well plate 400 for PCR using the syringe block 3000 in which the plurality of pipettes P are removably mounted; moving the multi-well plate 400 for PCR, in which the binding target nucleic acid is dispensed, to the sealing device 6000 using the moving device 9000 for multi-well plate for PCR; sealing an upper surface of the multi-well plate 400 for PCR, in which the binding target nucleic acid is dispensed, using the sealing device 6000; moving the multi-well plate 400 for PCR, of which the upper surface is sealed, to the centrifugal separator 7200 using the moving device 9000 for multi-well plate for PCR; applying centripetal force to the multi-well plate 400 for PCR using the centrifugal separator 7200 so as to separate substances remained on a side wall of each well formed in the multi-well plate 400 for PCR and thus to move the substances to a bottom surface of each well formed in the multi-well plate 400 for PCR; moving the multi-well plate 400 for PCR to the real-time quantitative amplification device 8000 using the moving device 9000 for multi-well plate for PCR after the applying of the centripetal force to the multi-well plate 400 for PCR using the centrifugal separator 7200; performing real-time amplification of the binding target nucleic acid in the multi-well plate 400 for PCR using the real-time quantitative amplification device 8000; and obtaining real-time quantitative amplification data of the nucleic acid, which shows an amplified amount of the binding target nucleic acid over time, using the real-time quantitative amplification device 8000, and then obtaining the antigen density in the biological sample using the real-time quantitative amplification data of the nucleic acid.

Further, the present invention provides a method for purification of a binding target nucleic acid labeled to a target antigen, in which a binding target nucleic acid is labeled to a target antigen contained in a biological sample, and the binding target nucleic acid labeled to the target antigen is purified using the automatic purification and reaction preparing device, including a deck moving step S2000 of moving the deck 1000, in which the multi-well plate 100 for biological sample, in which the biological sample containing the target antigen is injected, the multi-well plate for target nucleic acid binding, in which a target nucleic acid binding solution is injected to perform an antigen-antibody reaction for labeling the binding target nucleic acid to the target antigen, the multi-well plate 241, 242, 243 for cleaning solution, in which a cleaning solution is injected, the multi-well plate 250 for nucleic acid elution solution, in which a nucleic acid elution solution is injected, and a plurality of pipettes P for sucking and discharging a fluid substance are loaded, to a lower side of the syringe block 3000; and a target nucleic acid isolation and obtaining step S3500 of moving the syringe block 3000 so as to mount the plurality of pipettes P in the first mounting portion 3310, and performing the antigen-antibody reaction for labeling the binding target nucleic acid to the target antigen using the multi-well plate 100 for biological sample, the multi-well plate for target nucleic acid binding, the multi-well plate 241, 242, 243 for cleaning solution and the multi-well plate 250 for nucleic acid elution solution, and isolating and obtaining the binding target nucleic acid from the target antigen labeled with the binding target nucleic acid.

Preferably, the multi-well plate for target nucleic acid binding, in which a target nucleic acid binding solution is injected, comprises the multi-well plate for trapped antibody magnetic particle suspension, in which a magnetic particle suspension including magnetic particles coated with a first antibody for antigen binding, which is bound with the target antigen, is injected, and the multi-well plate for target nucleic acid labeling, in which a second antibody containing solution containing a second antibody labeled with a binding target nucleic acid, which is bound with the target antigen trapped by the first antibody for antigen binding, is injected, and the target nucleic acid isolation and obtaining step S3500 comprises: a first antigen-antibody reaction pretreatment step S3220 of moving the syringe block 3000 so that the plurality of pipettes P are mounted in the first mounting portion 3310, and injecting and mixing the biological sample in the multi-well plate 100 for biological sample into the multi-well plate for trapped antibody magnetic particle suspension; a first reaction step S3230 of adapting the target antigen contained in a mixture formed in the first antigen-antibody reaction pretreatment step S3220 to be trapped by the first antibody through the antigen-antibody reaction a first-1 magnetic field applying step S3240 of applying magnetic field to a lower side of the multi-well plate for trapped antibody magnetic particle suspension and thus applying the magnetic field to the mixture passing through the first reaction step S3230 a first-1 removing step S3250 of removing the mixture except complexes of the magnet particles, the first antibody and the target antigen using the syringe block 3000, in which the plurality of pipettes P are mounted, in a state that the magnetic particles and the first antibody trapping the target antigen in the mixture passing through the first reaction step S3230 are adhered to an inner wall of the multi-well plate for trapped antibody magnetic particle suspension by the magnetic field applied to the lower side of the multi-well plate for trapped antibody magnetic particle suspension; a first-1 cleaning step S3260 of injecting the cleaning solution of the multi-well plate 241, 242, 243 for cleaning solution into the multi-well plate for trapped antibody magnetic particle suspension using the syringe block 3000 having the plurality of pipettes P, and thus isolating the impurities adhered to the complexes of the magnetic particles, the first antibody and the target antigen, in a state that the magnetic field applied to the lower side of the multi-well plate for trapped antibody magnetic particle suspension is removed; a first-2 magnetic field applying step S3270 of applying the magnetic field to the lower portion of the multi-well plate for trapped antibody magnetic particle suspension and thus applying the magnetic field to the mixture mixed with the cleaning solution; a first-2 removing step S3280 of removing the mixture except the complexes of the magnet particles, the first antibody and the target antigen in the mixture mixed with the cleaning solution using the syringe block 3000, in which the plurality of pipettes P are mounted, in a state that the complexes of the magnet particles, the first antibody and the target antigen in the mixture mixed with the cleaning solution are adhered to the inner wall of the multi-well plate for trapped antibody magnetic particle suspension by the magnetic field applied to the lower side of the multi-well plate for trapped antibody magnetic particle suspension; a second antigen-antibody reaction pretreatment step S3320 of injecting and mixing the second antibody containing solution of the multi-well plate for target nucleic acid labeling into the multi-well plate for trapped antibody magnetic particle suspension using the syringe block 3000 having the plurality of pipettes P, in a state that the magnetic field applied to the lower portion of the multi-well plate for trapped antibody magnetic particle suspension is removed; a second reaction step S3330 of adapting the second antibody contained in the mixture passing through the second antigen-antibody reaction pretreatment step S3320 to be bound to the target antigen through the antigen-antibody reaction a second-1 magnetic field applying step S3340 of applying the magnetic field to the lower portion of the multi-well plate for trapped antibody magnetic particle suspension and thus applying the magnetic field to the mixture passing through the second reaction step S3330; a second-1 removing step S3350 of removing the mixture except the complexes of the magnet particles, the first antibody, the target antigen, the second antibody and the binding target nucleic acid using the syringe block 3000, in which the plurality of pipettes P are mounted, in a state that the complexes of the magnet particles, the first antibody, the target antigen, the second antibody and the binding target nucleic acid in the mixture passing through the second reaction step S3330 are adhered to the inner wall of the multi-well plate for trapped antibody magnetic particle suspension by the magnetic field applied to the lower side of the multi-well plate for trapped antibody magnetic particle suspension; a second-1 cleaning step S3360 of injecting the cleaning solution in the multi-well plate 241, 242, 243 for cleaning solution into the multi-well plate for trapped antibody magnetic particle suspension using the syringe block 3000 having the plurality of pipettes P, and thus isolating the impurities adhered to the complexes of the magnetic particles, the first antibody, the target antigen, the second antibody and the binding target nucleic acid in a state that the magnetic field applied to the lower portion of the multi-well plate for trapped antibody magnetic particle suspension is removed; a second-2 magnetic field applying step S3370 of applying the magnetic field to the lower portion of the multi-well plate for trapped antibody magnetic particle suspension and thus applying the magnetic field to the mixture mixed with the cleaning solution a second-2 removing step S3380 of removing the mixture except the complexes of the magnet particles, the first antibody, the target antigen, the second antibody and the binding target nucleic acid in the mixture mixed with the cleaning solution using the syringe block 3000, in which the plurality of pipettes P are mounted, in a state that the complexes of the magnet particles, the first antibody, the target antigen, the second antibody and the binding target nucleic acid in the mixture mixed with the cleaning solution are adhered to the inner wall of the multi-well plate for trapped antibody magnetic particle suspension by the magnetic field applied to the lower side of the multi-well plate for trapped antibody magnetic particle suspension; a nucleic acid isolation step S3410 of injecting and mixing the nucleic acid elution solution in the multi-well plate 250 for nucleic acid elution solution into the multi-well plate for trapped antibody magnetic particle suspension using the syringe block 3000 having the plurality of pipettes P, and thus isolating the impurities adhered to the complexes of the magnetic particles, the first antibody, the target antigen, the second antibody and the binding target nucleic acid, in a state that the magnetic field applied to the lower portion of the multi-well plate for trapped antibody magnetic particle suspension is removed; a third magnetic field applying step S3420 of applying the magnetic field to the lower portion of the multi-well plate for trapped antibody magnetic particle suspension and thus applying the magnetic field to the mixture mixed with the nucleic acid elution solution; a target nucleic acid containing solution collecting step S3430 of collecting a target nucleic acid containing solution, i.e., the mixture except the complexes of the magnetic particles, the first antibody, the target antigen and the second antibody in the mixture mixed with the nucleic acid elution solution using the syringe block 3000, in which the plurality of pipettes P are mounted, in a state that the complexes of the magnet particles, the first antibody, the target antigen and the second antibody in the mixture mixed with the nucleic acid elution solution are adhered to the inner wall of the multi-well plate for trapped antibody magnetic particle suspension by the magnetic field applied to the lower portion of the multi-well plate for trapped antibody magnetic particle suspension, and wherein, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

Preferably, the multi-well plate for target nucleic acid binding, in which a target nucleic acid binding solution is injected, comprises the multi-well plate for trapped antibody magnetic particle suspension, in which a magnetic particle suspension including magnetic particles coated with a first antibody for antigen binding, which is bound with the target antigen, is injected, and the multi-well plate for second antibody containing solution, in which a second antibody containing solution containing the second antibody for binding with the target antigen trapped by the first antibody for antigen binding is injected, and the multi-well plate for target nucleic acid containing solution, in which a target nucleic acid containing solution containing the binding target nucleic acid labeled to the second antibody bound with the target antigen is injected, and the target nucleic acid isolation and obtaining step S3500 comprises: a first antigen-antibody reaction pretreatment step S3220 of moving the syringe block 3000 so that the plurality of pipettes P are mounted in the first mounting portion 3310, and injecting and mixing the biological sample in the multi-well plate 100 for biological sample into the multi-well plate for trapped antibody magnetic particle suspension; a first reaction step S3230 of adapting the target antigen contained in a mixture formed in the first antigen-antibody reaction pretreatment step S3220 to be trapped by the first antibody through the antigen-antibody reaction a first-1 magnetic field applying step S3240 of applying magnetic field to a lower side of the multi-well plate for trapped antibody magnetic particle suspension and thus applying the magnetic field to the mixture passing through the first antigen-antibody reaction pretreatment step S3220; a first-1 removing step S3250 of removing the mixture except complexes of the magnet particles, the first antibody and the target antigen using the syringe block 3000, in which the plurality of pipettes P are mounted, in a state that the magnetic particles and the first antibody tripping the target antigen in the mixture passing through the first reaction step S3230 are adhered to an inner wall of the multi-well plate for trapped antibody magnetic particle suspension by the magnetic field applied to the lower side of the multi-well plate for trapped antibody magnetic particle suspension; a first-1 cleaning step S3260 of injecting the cleaning solution in the multi-well plate 241, 242, 243 for cleaning solution into the multi-well plate for trapped antibody magnetic particle suspension using the syringe block 3000 having the plurality of pipettes P, and thus isolating the impurities adhered to the complexes of the magnetic particles, the first antigen and the target antigen, in a state that the magnetic field applied to the lower portion of the multi-well plate for trapped antibody magnetic particle suspension is removed; a first-2 magnetic field applying step S3270 of applying the magnetic field to the lower portion of the multi-well plate for trapped antibody magnetic particle suspension and thus applying the magnetic field to the mixture mixed with the cleaning solution; a first-2 removing step S3280 of removing the mixture except the complexes of the magnet particles, the first antibody and the target antigen in the mixture mixed with the cleaning solution using the syringe block 3000, in which the plurality of pipettes P are mounted, in a state that complexes of the magnet particles, the first antibody and the target antigen in the mixture mixed with the cleaning solution are adhered to an inner wall of the multi-well plate for trapped antibody magnetic particle suspension by the magnetic field applied to the lower side of the multi-well plate for trapped antibody magnetic particle suspension; a second antigen-antibody reaction pretreatment step S3320-1 of injecting and mixing the second antibody containing solution in the multi-well plate for second antibody containing solution into the multi-well plate for trapped antibody magnetic particle suspension using the syringe block 3000 having the plurality of pipettes P, in a state that the magnetic field applied to the lower portion of the multi-well plate for trapped antibody magnetic particle suspension is removed; a second reaction step S3330-1 of adapting the second antibody contained in the mixture formed in the second antigen-antibody reaction pretreatment step S3320-1 to be bound to the target antigen through the antigen-antibody reaction a second-1 magnetic field applying step S3340-1 of applying the magnetic field to the lower portion of the multi-well plate for trapped antibody magnetic particle suspension and thus applying the magnetic field to the mixture passing through the second reaction step S3330-1; a second-1 removing step S3350-1 of removing the mixture except complexes of the magnet particles, the first antibody, the target antigen and the second antibody using the syringe block 3000, in which the plurality of pipettes P are mounted, in a state that the complexes of the magnet particles, the first antibody, the target antigen and the second antibody in the mixture passing through second reaction step S3330-1 are adhered to the inner wall of the multi-well plate for trapped antibody magnetic particle suspension by the magnetic field applied to the lower side of the multi-well plate for trapped antibody magnetic particle suspension; a second-1 cleaning step S3360-1 of injecting the cleaning solution of the multi-well plate 241, 242, 243 for cleaning solution into the multi-well plate for trapped antibody magnetic particle suspension using the syringe block 3000 having the plurality of pipettes P, and thus isolating the impurities adhered to the complexes of the magnetic particles, the first antibody, the target antigen and the second antibody in a state that the magnetic field applied to the lower portion of the multi-well plate for trapped antibody magnetic particle suspension is removed; a second-2 magnetic field applying step S3370-1 of applying the magnetic field to the lower portion of the multi-well plate for trapped antibody magnetic particle suspension and thus applying the magnetic field to the mixture mixed with the cleaning solution; a second-2 removing step S3380-1 of removing the mixture except the complexes of the magnet particles, the first antibody, the target antigen and the second antibody using the syringe block 3000, in which the plurality of pipettes P are mounted, in a state that the complexes of the magnet particles, the first antibody, the target antigen and the second antibody in the mixture mixed with the cleaning solution are adhered to the inner wall of the multi-well plate for trapped antibody magnetic particle suspension by the magnetic field applied to the lower side of the multi-well plate for trapped antibody magnetic particle suspension; a target nucleic acid addition reaction step S3320-2 of injecting and mixing the target nucleic acid containing solution in the multi-well plate for target nucleic acid containing solution into the multi-well plate for trapped antibody magnetic particle suspension using the syringe block 3000 having the plurality of pipettes P, in a state that the magnetic field applied to the lower portion of the multi-well plate for trapped antibody magnetic particle suspension is removed; a third reaction step S3330-2 of adapting the binding target nucleic acid contained in the mixture passing through the target nucleic acid addition reaction step S3320-2 to be bound to the second antibody a third-1 magnetic field applying step S3340-2 of applying the magnetic field to the lower portion of the multi-well plate for trapped antibody magnetic particle suspension and thus applying the magnetic field to the mixture passing through the third reaction step S3330-2 a third-1 removing step S3350-2 of removing the mixture except the complexes of the magnet particles, the first antibody, the target antigen, the second antibody and the binding target nucleic acid using the syringe block 3000, in which the plurality of pipettes P are mounted, in a state that the complexes of the magnet particles, the first antibody, the target antigen, the second antibody and the binding target nucleic acid in the mixture passing through the third reaction step S3330-2 are adhered to the inner wall of the multi-well plate for trapped antibody magnetic particle suspension by the magnetic field applied to the lower side of the multi-well plate for trapped antibody magnetic particle suspension; a third-1 cleaning step S3360-2 of injecting the cleaning solution in the multi-well plate 241, 242, 243 for cleaning solution into the multi-well plate for trapped antibody magnetic particle suspension using the syringe block 3000 having the plurality of pipettes P, and thus isolating the impurities adhered to the complexes of the magnetic particles, the first antibody, the target antigen, the second antibody and the binding target nucleic acid in a state that the magnetic field applied to the lower portion of the multi-well plate for trapped antibody magnetic particle suspension is removed; a third-2 magnetic field applying step S3370-2 of applying the magnetic field to the lower portion of the multi-well plate for trapped antibody magnetic particle suspension using the magnetic field applying unit 5100 and thus applying the magnetic field to the mixture mixed with the cleaning solution; a third-2 removing step S3380-2 of removing the mixture except the complexes of the magnet particles, the first antibody, the target antigen, the second antibody and the binding target nucleic acid using the syringe block 3000, in which the plurality of pipettes P are mounted, in a state that the complexes of the magnet particles, the first antibody, the target antigen, the second antibody and the binding target nucleic acid in the mixture mixed with the cleaning solution are adhered to the inner wall of the multi-well plate for trapped antibody magnetic particle suspension by the magnetic field applied to the lower side of the multi-well plate for trapped antibody magnetic particle suspension; a nucleic acid isolation step S3410 of injecting the nucleic acid elution solution in the multi-well plate 250 for nucleic acid elution solution into the multi-well plate for trapped antibody magnetic particle suspension using the syringe block 3000 having the plurality of pipettes P, and isolating the target nucleic acid from the complexes of the magnetic particles, the first antibody, the target antigen, the second antibody and the binding target nucleic acid in a state that the magnetic field applied to the lower portion of the multi-well plate for trapped antibody magnetic particle suspension is removed; a fourth magnetic field applying step S3420 of applying the magnetic field to the lower portion of the multi-well plate for trapped antibody magnetic particle suspension and thus applying the magnetic field to the mixture mixed with the nucleic acid elution solution; a target nucleic acid containing solution collecting step S3430 of collecting a target nucleic acid containing solution, i.e., the mixture except complexes of the magnetic particles, the first antibody, the target antigen and the second antibody in the mixture mixed with the nucleic acid elution solution using the syringe block 3000, in which the plurality of pipettes P are mounted, in a state that complexes of the magnet particles, the first antibody, the target antigen and the second antibody in the mixture mixed with the nucleic acid elution solution are adhered to the inner wall of the multi-well plate for trapped antibody magnetic particle suspension by the magnetic field applied to the lower portion of the multi-well plate for trapped antibody magnetic particle suspension, and wherein, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

Advantageous Effects of Invention

According to the present invention as described above, since it is possible to automatically carry out a series of processes from the nucleic acid purification to the real-time quantification of gene amplification, there is an advantage that it is possible to treat a large amount of samples in a short period of time with minimum manual labor, thereby obtaining analysis results of various biological samples.

Further, the present invention has another advantage that the real-time quantitative PCR analysis can be performed after the culturing of microorganism, and thus it is possible to automatically perform the microorganism test and the microorganism test in the biological samples and the antibiotics susceptibility test.

Further, the present invention has yet another advantage that it is possible to perform the very useful microorganism analysis using both of the microorganism culture and the real-time quantitative amplification. When the initial number of microorganisms contained in the biological sample is less than detection limit, the microorganism is amplified through the culture step and then analyzed by real-time quantitative PCR, and thus it is possible to precisely perform the test of microorganism.

Further, According to the present invention, the culturing is performed only for a short period time that is less than five generations, and then each amount of DNA in the samples before and after the culturing is compared with each other by relative quantification in real-time quantitative PCR, and thus it is possible to precisely and rapidly analyze the viable cell count. On the same principle, the system of the present invention can be used in automatically performing the antibiotics susceptibility test. In other words, the present invention has yet another advantage that the biological sample containing microorganisms is equally dispensed to the multi-well including different antibiotics from each other and cultured for a predetermined period of time, and then real-time quantitative PCR analysis is performed so as to compare the number of nucleic acids using a relative quantitative method, and thus it is possible to rapidly analyze antibiotics susceptibility of the microorganism, thereby allowing effective antibiotics to be selected within a short time period.

Further, the present invention can automatically perform the quantitative Immuno-PCR so as to precisely perform a quantitative test for a small amount of proteins and antigens.

BRIEF DESCRIPTION OF DRAWINGS

The above and other objects, features and advantages of the present invention will become apparent from the following description of preferred embodiments given in conjunction with the accompanying drawings, in which:

FIGS. 1 and 2 are schematic perspective views showing a first embodiment of the present invention.

FIG. 3 is a schematic front view of the first embodiment.

FIG. 4 is a perspective view of a deck having a plurality of multi-well plates and loaded in a pallet.

FIG. 5 is a perspective view showing the deck of FIG. 4, of which side and upper plates are removed.

FIG. 6 is a perspective view showing an appearance of the first embodiment.

FIG. 7 is a schematic perspective view of an automatic deck storing and transferring device in the first embodiment.

FIG. 8 is a schematic perspective view of a stacking rack and a stacking rack lifting unit in FIG. 7.

FIG. 9 is a schematic perspective view of the stacking rack lifting unit in FIG. 8.

FIG. 10 is a schematic view of a pallet moving unit and a deck transferring unit in FIG. 7.

FIG. 11 is a detailed view of the pallet moving unit in FIG. 10.

FIGS. 12 and 13 are detailed views of the deck transferring unit in FIG. 10.

FIGS. 14 and 15 are plane and front views of a puncher, an evaporation block for multi-well plate, and a waste liquor discharging part in the first embodiment.

FIG. 16 is a perspective view and a side view of a syringe block in the first embodiment.

FIG. 17 is a cross-sectional view of the syringe block passing through a syringe pin in FIG. 16.

FIG. 18 is a cross-sectional view of the syringe block passing through a first separation rod in FIG. 16.

FIGS. 19 and 20 are cross-sectional views of the syringe block passing through a second separation rod in FIG. 16.

FIG. 21 is a perspective view of an upper evaporation block for multi-well plate in the first embodiment.

FIG. 22 is a perspective view of a lower evaporation block for multi-well plate in the first embodiment.

FIG. 23 is a schematic perspective view of a front and rear moving part for syringe block in the first embodiment.

FIG. 24 is a schematic perspective view of a left and right moving part for syringe block in the first embodiment.

FIG. 25 is a schematic perspective view of an up and down moving part for syringe block in the first embodiment.

FIG. 26 is a perspective view of main parts of a magnetic field applying unit and a heating unit in the first embodiment.

FIG. 27 is a schematic perspective view of the main parts of the magnetic field applying unit and the heating unit in the first embodiment.

FIGS. 28 to 32 perspective views of main parts of a sealing device in the first embodiment.

FIG. 33 is a cross-sectional view of the main parts of the sealing unit in the first embodiment.

FIG. 34 is a perspective view of a vortex mixer in the first embodiment.

FIG. 35 is a cross-sectional view of the vortex mixer of FIG. 34.

FIG. 36 is a perspective view of a centrifugal separator in the first embodiment.

FIG. 37 is a perspective view of a moving unit of a multi-well plate for PCR in the first embodiment.

FIG. 38 is a schematic perspective view of a grasping means of a multi-well plate for PCR in the first embodiment.

FIG. 39 is an installation view of a solution drip tray in the first embodiment.

FIG. 40 is a flow chart of a third embodiment of the present invention.

FIG. 41 is a flow chart of a fourth embodiment of the present invention.

FIG. 42 is a block diagram of a second removing step of FIG. 41.

FIG. 43 is a flow chart of a fifth embodiment of the present invention.

FIG. 44 is a flow chart of a sixth embodiment of the present invention.

FIG. 45 is a flow chart of a seventh embodiment of the present invention.

FIGS. 46 and 47 are flow charts of an eighth embodiment of the present invention.

FIGS. 46 and 48 are flow charts of a ninth embodiment of the present invention.

DETAILED DESCRIPTION OF MAIN ELEMENTS

100: multi-well plate for biological 200: multi-well plate for purification
210: multi-well plate for cell lysis solution
220: multi-well plate for magnetic particle dispersion solution
230: multi-well plate for nucleic acid binding solution
241, 242, 243: multi-well plate for cleaning solution
250: multi-well plate for nucleic acid elution solution
310: purification pipette 320: dispensation pipette
400: multi-well plate for PCR 410: first multi-well plate for PCR
420: second multi-well plate for PCR
1000: deck 1110H: grasping hole
2000: automatic deck storing and moving device
2000C: storing case 2000C-1: door
2100: stacking rack 2110: rack
2112: pallet guider 2130: pallet
2130H: pallet withdrawal groove 2131: pallet moving dog
2210M: stacking rack lifting motor 2240S: stacking rack lifting ball screw shaft
2240N: stacking rack lifting ball nut 2250: stacking rack connecting member
2300: pallet moving unit 2310: pallet moving motor
2320: front and rear moving belt for pallet
2330: front and rear moving block for pallet
2400: deck transferring unit 2410: deck transferring motor
2430: left and right moving belt for deck
2440: deck withdrawal slider connecting member
2450: deck withdrawal slider 2451: deck withdrawal protrusion
2451-1: insertion pin
3000: syringe block 3100: syringe pin

MODE FOR THE INVENTION

Hereinafter, the embodiments of the present invention will be described in detail with reference to accompanying drawings.

First Embodiment

A first embodiment of the present invention relates to a multi-purpose automatic real-time quantitative amplification system for analyzing a biological sample.

FIGS. 1 and 2 are schematic perspective views showing a first embodiment of the present invention, FIG. 3 is a schematic front view of the first embodiment, FIG. 4 is a perspective view of a deck having a plurality of multi-well plates and loaded in a pallet, FIG. 5 is a perspective view showing the deck of FIG. 4, of which side and upper plates are removed, FIG. 6 is a perspective view showing an appearance of the first embodiment, FIG. 7 is a schematic perspective view of an automatic deck storing and transferring device in the first embodiment, FIG. 8 is a schematic perspective view of a stacking rack and a stacking rack lifting unit in FIG. 7, FIG. 9 is a schematic perspective view of the stacking rack lifting unit in FIG. 8, FIG. 10 is a schematic view of a pallet moving unit and a deck transferring unit in FIG. 7, FIG. 11 is a detailed view of the pallet moving unit in FIG. 10, FIGS. 12 and 13 are detailed views of the deck transferring unit in FIG. 10, FIGS. 14 and 15 are plane and front views of a puncher, an evaporation block for multi-well plate, and a waste liquor discharging part in the first embodiment, FIG. 16 is a perspective view and a side view of a syringe block in the first embodiment, FIG. 17 is a cross-sectional view of the syringe block passing through a syringe pin in FIG. 16, FIG. 18 is a cross-sectional view of the syringe block passing through a first separation rod in FIG. 16, FIGS. 19 and 20 are cross-sectional views of the syringe block passing through a second separation rod in FIG. 16, FIG. 21 is a perspective view of an upper evaporation block for multi-well plate in the first embodiment, FIG. 22 is a perspective view of a lower evaporation block for multi-well plate in the first embodiment, FIG. 23 is a schematic perspective view of a front and rear moving part for syringe block in the first embodiment, FIG. 24 is a schematic perspective view of a left and right moving part for syringe block in the first embodiment, FIG. 25 is a schematic perspective view of an up and down moving part for syringe block in the first embodiment, FIG. 26 is a perspective view of main parts of a magnetic field applying unit and a heating unit in the first embodiment, FIG. 27 is a schematic perspective view of the magnetic field applying unit and the heating unit in the first embodiment, FIGS. 28 to 32 perspective views of main parts of a sealing device in the first embodiment, FIG. 33 is a cross-sectional view of the main parts of the sealing unit in the first embodiment, FIG. 34 is a perspective view of a vortex mixer in the first embodiment, FIG. 35 is a cross-sectional view of the vortex mixer of FIG. 34, FIG. 36 is a perspective view of a centrifugal separator in the first embodiment, FIG. 37 is a perspective view of a moving unit of a multi-well plate for PCR in the first embodiment, FIG. 38 is a schematic perspective view of a grasping means of a multi-well plate for PCR in the first embodiment, and FIG. 39 is an installation view of a solution drip tray in the first embodiment.

Referring to FIGS. 1 to 3, the multi-purpose automatic real-time quantitative amplification system according to the present invention includes a deck 1000, an automatic deck storing and moving device 2000, an automatic purification and reaction preparing device (which is not designated by a reference numeral), a sealing device 6000, a vortex mixer 7100, a centrifugal separator 7200, a real-time quantitative amplification device 8000, and a moving device for multi-well plate for PCR. The automatic purification and reaction preparing device includes a syringe block 3000, a syringe block moving unit 4000, a magnetic field applying unit 5100, a heating unit 5200, a puncher 12100 (referring to FIG. 13), an evaporation block 12200 for multi-well plate (referring to FIG. 13) and a waste liquor discharging part 12300 (referring to FIG. 13).

Referring to FIGS. 4 and 5, the deck 1000 includes a lower plate 1100, a side plate 1200 and an upper plate 1300. A plurality of mounting boxes 1400 are disposed on the lower plate 1100 so that upper portions thereof are protruded to an upper side of the upper plate 1300. The mounting boxes 1400 are arranged in two rows. Meanwhile, an upper end of each mounting box 1400 is opened.

Referring to FIG. 5, the lower plate 1100 is formed with a deck withdrawal groove 1100H. The deck withdrawal groove 1100H is formed to pass through upper and lower surfaces the lower plate 1100 from a side surface thereof to a desired inner portion. A T-shaped grasping hole body 1110 formed with a grasping hole 1110H is disposed on the lower plate 1100. The grasping hole 1110H is formed to pass through upper and lower surfaces of the T-shaped grasping hole body 1110.(주기) The grasping hole body 1110 is disposed on the deck withdrawal groove 1100H so that the grasping hole 1110H is corresponded to the deck withdrawal groove 1100H.

Referring to FIGS. 4 and 5, a multi-well plate for treating a biological sample, which purifies a target nucleic acid of a target substance contained in the biological sample, cultures the target substance contained in the biological sample and then purifies the target nucleic acid of the target substance contained in the biological sample, or purifies the binding target nucleic acid bound by an antigen-antibody reaction with a target antigen contained in the biological sample, a plurality of pipette racks 300 and a plurality of multi-well plates 400 for PCR are mounted in the certain order in the plurality of mounting boxes 1400 of which the upper ends are opened. In case of purifying the target nucleic acid of the target substance contained in the biological sample, the multi-well plate for treating the biological sample includes a multi-well plate 100 for biological sample and a plurality of multi-well plates 200 for purification. In this case, the multi-well plate 100 for biological sample is a multi-well plate in which the biological sample containing the target substance is injected, and the plurality of multi-well plates 200 for purification are a plurality of multi-well plates for purifying the target nucleic acid of the target substance injected into the multi-well plate 100 for biological sample, and the plurality of multi-well plates 400 for PCR are a plurality of multi-well plates in which a reaction mixture for real-time quantitative PCR is injected. Herein, the reaction mixture for real-time quantitative PCR is a reagent for real-time quantitative PCR, and the multi-well plate 400 for PCR may be an amplification kit plate having a plurality of tubes.

Referring to FIGS. 4 and 5, the plurality of multi-well plates 200 for purification includes a multi-well plate 210 for cell lysis solution in which the cell lysis solution is injected, a multi-well plate 220 for magnetic particle dispersion solution in which magnetic particle suspension including magnetic particles is injected, a multi-well plate 230 for nucleic acid binding solution in which the acid binding solution is injected, a multi-well plate 241 for first cleaning solution in which the first cleaning solution is injected, a multi-well plate 242 for second cleaning solution in which the second cleaning solution is injected, a multi-well plate 243 for third cleaning solution in which the third cleaning solution is injected, and a multi-well plate 250 for nucleic acid elution solution in which the nucleic acid elution solution is injected, when being mounted in the deck 1000. However, the present invention is not limited to this. In the present invention, the plurality of multi-well plates 200 for purification may include a multi-well plate for mixing. The multi-well plate for mixing, of which each well is empty when it is mounted in the deck 1000, may function to mix certain-substances injected into other multi-well plates.

Referring to FIGS. 4 and 5, the plurality of pipette racks 300 include a purification pipette rack 310 and a dispensation pipette rack 320. The purification pipette rack 310 is to install a plurality of purification pipettes P1, and the dispensation pipette rack 320 is to install a plurality of dispensation pipettes P2 having smaller a capacity than the plurality of purification pipettes P1. The plurality of purification pipettes P1 function to suck and discharge the substances injected into the multi-well plate 100 for biological sample and the plurality of multi-well plates 200 for purification and then to purify them, and the plurality of dispensation pipettes P2 function to suck the purified target nucleic acid and to dispense it to the multi-well plate 400 for PCR.

Referring to FIGS. 4 and 5, the plurality of multi-well plates 400 for PCR are a first multi-well plate 410 for PCR and a second multi-well plate 420 for PCR. As described above, the multi-well plate 400 for PCR has the plurality of tubes, and also multi-well plate 400 for PCR may be an amplification kit plate in which a reagent for real-time quantitative PCR is injected into each tube.

Referring to FIGS. 4 and 5, the plurality of multi-well plates 100 and 200 are paired with each other and also disposed so as to be prevented from being separated in an upper direction of the deck 1000 for extracting a nucleic acid by a compressing plate 500. The compressing plate 500 is formed with a mounting hole through which a snap cap (not shown) is passed. The mounting hole is formed to pass through upper and lower surfaces of the pressing plate 500. Meanwhile, a mount (not shown) in which the snap cap passing through the mounting hole is inserted is formed to be protruded from the deck 1000. A fitting hole (not shown) in which a lower end of the snap cap (not shown) is inserted is formed in an upper surface of the mount (not shown). In the same way, two pipette racks 300 are also disposed so as to be prevented from being separated in an upper direction of the deck 1000 for extracting a nucleic acid by a compressing plate 500.

Referring to FIGS. 6 to 13, the automatic deck storing and moving device 2000 includes a storing case 2000C, a stacking rack 2100, a stacking rack lifting unit (not designated by a reference numeral), a pallet moving unit 2300 and a deck transferring unit 2400.

Referring to FIG. 6, the storing case 2000C is formed into a sealed box shape which can maintain its internal portion at certain temperature or within a certain range of temperature. Therefore, the storing case 2000C may be provided with a cooling unit for lowering the internal temperature. Meanwhile, a door 2000C-1 through which the deck 1000 is taken in and out is formed at a front surface of the storing case 2000C. Referring to FIG. 11, a moving groove (not designated by a reference numeral) through which the deck 1000 is moved to the automatic purification and reaction preparing device is formed at one side of the storing case 2000C. FIG. 11 also shows a sliding groove (not designated by a reference numeral) formed at the one side of the storing case 2000C so that a pallet 2130 (referring to FIG. 4) grasped by the pallet moving unit 2300 can be slid therethrough.

Referring to FIG. 7, a plurality of racks 2100 are arranged up and down at the stacking rack 2100. The pallet 2130 for loading the deck 1000 is put on an upper surface of the rack 2110. A pallet moving dog 2131 (referring to FIG. 5) and a pallet withdrawal groove 2130H (referring to FIG. 5) are formed at a side surface of the pallet 2130. The pallet withdrawal groove 2130H is formed so as to communicate with the deck withdrawal groove 1100H of the deck 1000 loaded on the upper surface of the pallet 2130.

Referring to FIG. 8, the rack 2110 is provided with a pallet guider 2112. The pallet 2130 is slidably disposed at the pallet guider 2112.

Referring to FIGS. 8 and 9, the stacking rack lifting unit (not designated by a reference numeral) includes a stacking rack lifting motor 2210, a lifting motor fixing plate 2230, a stacking rack lifting ball screw shaft 2240S, a stacking rack lifting ball nut 2240N, a stacking rack connecting member 2250 and a slider 2251.

Referring to FIG. 8, a supporting frame 2010 is disposed in the storing case 2000C (referring to FIG. 6), and the lifting motor fixing plate 2230 is fixed to the supporting frame 2010. Meanwhile, the stacking rack lifting motor 2210 (referring to FIG. 9) is fixedly installed on the lifting motor fixing plate 2230.

Referring to FIGS. 8 and 9, an upper end of the stacking rack lifting ball screw shaft 2240S is connected with the stacking rack lifting motor 2210. The stacking rack lifting ball screw shaft 2240S is also rotatably supported by bearings 2240B 1 and 2240B2. The upper bearing 2240B 1 is fixedly installed to the lifting motor fixing plate 2230, and the lower bearing 2240B2 is fixedly installed to an auxiliary fixing plate 2270. The auxiliary fixing plate 2270 is fixedly installed to the supporting frame 2010. Meanwhile, a male thread is formed on the stacking rack lifting ball screw shaft 2240S.

Referring to FIGS. 8 and 9, the stacking rack lifting ball nut 2240N is inserted onto the stacking rack lifting ball screw shaft 2240S so as to be moved up and down by rotation of the stacking rack lifting ball screw shaft 2240S. Therefore, a female thread corresponding to the male thread of the stacking rack lifting ball screw shaft 2240S is formed at the stacking rack lifting ball nut 2240N.

Referring to FIG. 8, two rails 2231 are disposed at the supporting frame 2010. The slider 2251 is disposed at the rails 2231 so as to be slid up and down.

Referring to FIGS. 8 and 9, the stacking rack 2100 is fixedly connected to one side surface of the stacking rack connecting member 2250. Meanwhile, the slider 2251 and the stacking rack lifting ball nut 2240N are fixed connected to the other side surface of the stacking rack connecting member 2250. Therefore, as the stacking rack lifting ball screw shaft 2240S is rotated, the stacking rack lifting ball nut 2240S is moved up and down, and thus the stacking rack 2100 is also moved up and down.

Referring to FIGS. 8 and 9, one side surface of a stacking rack auxiliary connecting member 2260 is fixed to the stacking rack 2100 to so as to be spaced apart from the stacking rack connecting member 2250, and an auxiliary slider 2251 is fixed to the other side surface of the auxiliary connecting member 2260. The auxiliary slider 2251 is disposed at the rail 2231 so as to be slid up and down.

Referring to FIG. 11, the pallet moving unit 2300 includes a pallet moving motor 2310, a front and rear moving belt 2320 for pallet and a front and rear moving block 2330 for pallet.

Referring to FIG. 10, the pallet moving motor 2310 is fixed to a lower surface of a main intermediate plate 12000-1.

Referring to FIG. 11, the front and rear moving belt 2320 for pallet is wound on two pulleys which are spaced apart from each other so as to be moved in a front and rear direction of the deck 1000 by the pallet moving motor 2310. In other words, a driving shaft for pallet movement is connected to the pallet moving motor 2310, and a driving pulley for pallet movement is inserted onto the driving shaft for pallet movement. Meanwhile, a first driven shaft for pallet movement is disposed to be spaced apart from the driving shaft for pallet movement, and a first-1 driven pulley for pallet movement is inserted onto one end of the first driven shaft for pallet movement, and a first-2 driven pulley for pallet movement is inserted onto the other end of the first driven shaft for pallet movement. Further, a second driven shaft for pallet movement is disposed to be spaced apart from the first driven shaft for pallet movement in the front and rear direction of the deck 1000. A second driven pulley for pallet movement is inserted onto the second driven shaft for pallet movement. The driving pulley for pallet movement and the first-1 driven pulley for pallet movement are wound with a driving belt for pallet movement, and the first-2 driven pulley for pallet movement and the second driven pulley for pallet movement are wound with the front and rear moving belt 2320 for pallet. Therefore, the driving pulley for pallet movement is rotated by the pallet moving motor 2310, and first-1 driven pulley for pallet movement and the first-2 driven pulley for pallet movement are rotated by rotation of the driving pulley for pallet movement, and thus the front and rear moving belt 2320 for pallet is moved in the front and rear direction of the deck 1000 by rotation of the first-2 driven pulley for pallet movement.

Referring to FIG. 11, the front and rear moving block 2330 for pallet is fixedly connected to the front and rear moving belt 2320 for pallet. The front and rear moving block 2330 is formed into a U-shape, and a closed end thereof is fixedly connected to the front and rear moving belt 2320 for pallet. An opened end of the front and rear moving block 2330 for pallet is formed so that the pallet moving dog 2131 (referring to FIG. 5) is located therein. Therefore, if the stacking rack 2100 is moved down and thus the pallet moving dog 2131 (referring to FIG. 5) is located in the opened end of the front and rear moving block 2330 for pallet, the front and rear moving belt 2320 for pallet is moved in a front and rear direction of the pallet 2130 so as to move the pallet moving dog 2131 and the pallet 2130. Thus, the pallet 2130 is taken in or out through the automatic door 2000C-1. When the pallet 2130 is taken out through the automatic door 2000C-1, the deck 1000 may be mounted on or removed from the pallet 2130.

Referring to FIGS. 7, 10 and 12, the deck transferring unit 2400 includes a deck moving motor 2410, a left and right moving belt 2430 for deck, a deck withdrawal slider connecting member 2440 and a deck withdrawal slider 2450.

Referring to FIG. 12, the deck moving motor 2410 is fixed to a lower surface of a main intermediate plate 12000-1.

Referring to FIG. 12, the left and right moving belt 2430 for deck is wound on two pulleys which are spaced apart from each other so as to be moved in a left and right direction of the deck 1000 by the deck moving motor 2410. In other words, a driving shaft for deck movement is connected to the deck moving motor 2410, and a driving pulley 2411 for deck movement is inserted onto the driving shaft for deck movement. Meanwhile, a first driven shaft for deck movement is disposed to be spaced apart from the driving shaft for deck movement, and a first-1 driven pulley for deck movement is inserted onto one end of the first driven shaft for deck movement, and a first-2 driven pulley for deck movement is inserted onto the other end of the first driven shaft for deck movement. Further, a second driven shaft for deck movement is disposed to be spaced apart from the first driven shaft for deck movement in the left and right direction of the deck 1000. A second driven pulley for deck movement is inserted onto the second driven shaft for deck movement. The driving pulley for deck movement and the first-1 driven pulley for deck movement are wound with a driving belt 2420 for deck movement, and the first-2 driven pulley for deck movement and the second driven pulley for deck movement are wound with the left and right moving belt 2430 for pallet. Therefore, the driving pulley for deck movement is rotated by the deck moving motor 2410, and first-1 driven pulley for deck movement and the first-2 driven pulley for deck movement are rotated by rotation of the driving pulley for deck movement, and thus the left and right moving belt 2430 for pallet is moved in the left and right direction of the deck 1000 by rotation of the first-2 driven pulley for deck movement.

Referring to FIG. 12, the deck withdrawal slider connecting member 2440 is fixedly connected to the left and right moving belt 2430 for deck. The deck withdrawal slider connecting member 2440 is provided with a connecting member guider 2441, and the connecting member guider 2441 is slidably inserted onto a guider rod.

Referring to FIGS. 12 and 7, the deck withdrawal slider connecting member 2440 is connected to the deck withdrawal slider 2450 via a guide groove formed at the main intermediate plate 12000-1. The deck withdrawal slider 2450 is disposed to be slid in the left and right direction of the deck 1000 along the guide groove formed in the upper surface of the main intermediate plate 12000-1.

FIGS. 7 and 13, a deck withdrawal protrusion 2451 which is inserted into the pallet withdrawal groove 2130H (referring to FIG. 5) is formed at a side end of the deck withdrawal slider 2450. An insertion pin 2451-1 which is inserted into the grasping hole 1110H (referring to FIG. 5) formed at the deck 1000 is formed on an upper surface of the deck withdrawal protrusion 2451. Therefore, if the stacking rack 2100 is moved down while the deck withdrawal protrusion 2451 is inserted into the pallet withdrawal groove 2130H (referring to FIG. 5), the insertion pin 2451-1 formed on the upper surface of the deck withdrawal protrusion 2451 is inserted into the grasping hole 1110H (referring to FIG. 5). If the insertion pin 2451-1 is inserted into the grasping hole 1110H (referring to FIG. 5), the deck withdrawal slider 2450 is slid, and the deck 1000 is moved to the upper surface of the main intermediate plate 12000-1. Thus, the deck 1000 is located at a lower side of the syringe block 3000.

As described above, the automatic purification and reaction preparing device (which is not designated by a reference numeral) includes the syringe block 3000, the syringe block moving unit 4000, the magnetic field applying unit 5100, the heating unit 5200, the puncher 12100 (referring to FIG. 13), the evaporation block 12200 for multi-well plate (referring to FIG. 13) and the waste liquor discharging part 12300 (referring to FIG. 13). The automatic purification and reaction preparing device (which is not designated by a reference numeral) functions to automatically purify the target nucleic acid from the biological sample and also to dispense the purified target nucleic acid to the multi-well plate 400 (referring to FIG. 13) for PCR.

Referring to FIG. 13, the puncher 12100, the evaporation block 12200 for multi-well plate and the waste liquor discharging part 12300 are installed on the main intermediate plate 12000-1 so as to be disposed at a rear side of the deck 1000 transferred by the deck transferring unit 2400.

Referring to FIGS. 14 and 15, a plurality of awl-shaped puncher pins 12110 are formed to be protruded from a lower surface of the puncher 12100. The plurality of puncher pins 12110 function to pierce holes in a sealing film for sealing an upper surface of the multi-well plate 100 for biological sample and the plurality of multi-well plates 200 for purification. Meanwhile, multiple puncher inserting grooves are formed in the upper surface of the puncher 12100.

Referring to FIGS. 14 and 15, the puncher 12100 is disposed at a rear side of the evaporation block 12200 for multi-well plate, but as it is moved to the front side, it is located at an upper side of the waste liquor discharging part 12300. Therefore, on the upper surface of the main intermediate plate 12000-1, there are disposed a puncher moving motor 12133 for moving the puncher 12100, a pinion gear 12133 for puncher movement and a rack gear 12135 for puncher movement.

Referring to FIGS. 19 and 20, the evaporation block 12200 for multi-well plate includes an upper evaporation block 12200-1 and a lower evaporation block 12200-2.

Referring to FIG. 21, a plurality of evaporation block inserting grooves 12200-G are formed in an upper surface of the upper evaporation block 12200-1. The plurality of evaporation block inserting grooves 12200-G are closely contacted with a plurality of first mounting portion 3330 (referring to FIG. 16) and inserted therein. Further, the upper evaporation block 12200-1 is formed with a first evaporation block guide hole 12200-H1 for guiding a lower end of a second separation rod 3732 (referring to FIG. 19) and an upper end of a second separation pin 12230 (referring to FIG. 19) up and down. The second separation rod 3732 (referring to FIG. 19) and the second separation pin 12230 (referring to FIG. 19) will be described later.

Referring to FIG. 22, the lower evaporation block 12200-2 is formed with a second evaporation guide hole 12200-H2 for guiding a lower end of the second separation pin 12230 (referring to FIG. 19) up and down. The second evaporation guide hole 12200-H2 is formed communicate with the first evaporation block guide hole 12200-H1. Further, lower evaporation block 12200-2 is formed with a second mounting portion installing hole 12200-H3. The second mounting portion installing hole 12200-H3 is formed to pass through upper and lower surfaces of the lower evaporation block 12200-2. A second mounting portion 12210 (referring to FIG. 19) having a second mounting portion communicating hole is inserted into a lower end of the second mounting portion installing hole 12200-H3. The second mounting portion communicating hole is formed to pass through upper and lower surfaces of the second mounting portion 12210 (referring to FIG. 19). The second mounting portion 12210 (referring to FIG. 19) functions to removably receive the plurality of pipettes P. Further, a compressed air passage 12200-L for connecting upper portions of the multiple second mounting portion installing holes 12200-H3 with each other is formed in an upper surface of the lower evaporation block 12200-2. Meanwhile, an compressed air introduction hole 12200-H4 connected with a compressed air supplying tube is formed at a side surface of the lower evaporation block 12200-2. The compressed air introduction hole 12200-H4 is communicated with the compressed air passage 12200-L or an upper portion of the second mounting portion installing hole 12200-H3. Meanwhile, a plate-shaped gasket is disposed between the upper surface of the lower evaporation block 12200-2 and the upper surface of the upper evaporation block 12200-1. Therefore, the compressed air introduced through the compressed air supplying tube is discharged to the outside through compressed air passage 12200-L and the plurality of pipettes P mounted in the second mounting portion 12210 (referring to FIG. 19).

Meanwhile, the cleaning solution includes alcohol. The evaporation block 12200 for multi-well plate is located just above a certain multi-well plate among the plurality of multi-well plates 200 for purification, which is filled with magnetic particles that alcohol is remained thereon, so as to remove the alcohol remained on the surfaces of the magnetic particles by shooting the compressed air.

Referring to FIGS. 14 and 15, the waste liquor discharging part 12300 is located at a front side of the puncher 12100. The waste liquor discharging part 12300 functions to discharge waste liquor abandoned from the plurality of pipettes P mounted in the plurality of first mounting portions 3330 (referring to FIG. 16). The waste liquor discharging part 12300 is formed with a plurality of through-holes corresponding to the plurality of pipettes P installed in the plurality of first mounting portions 3330 (referring to FIG. 16). The waste liquor discharging part 12300 is connected to a waste liquor discharging container. The waste liquor discharging container is mounted on an upper surface of a main lower plate 12000-2 which is located at a lower side of the main intermediate plate 12000-1.

Referring to FIG. 16, the syringe block 3000 includes a syringe block body 3400, a syringe pin holder lifting motor 3200M and a syringe pin guide block 3300. The pin holder lifting motor 3200M and the syringe pin guide block 3300 are fixed to the syringe block body 3400.

Referring to FIG. 16, a syringe pin holder 3200 is disposed at the syringe block body 3400 so as to be movable up and down. That is, a driving shaft for syringe pin holder lifting is connected to the syringe pin holder lifting motor 3200M, and a driving pulley 3811 for syringe pin holder lifting is inserted onto the driving shaft for syringe pin holder lifting. Meanwhile, a ball screw shaft 3500S for syringe pin holder lifting is disposed so as to be spaced apart from the driving shaft for syringe pin holder lifting, and a driven pulley 3812 for syringe pin holder lifting is inserted onto an upper end of the ball screw shaft 3500S for syringe pin holder lifting. A male thread is formed on the ball screw shaft 3500S for syringe pin holder lifting. Meanwhile, the driving pulley 3811 for syringe pin holder lifting and the driven pulley 3812 for syringe pin holder lifting are wound with a driving belt (not shown) for syringe pin holder lifting. A ball nut 3500N for syringe pin holder lifting is inserted onto the ball screw shaft 3500S for syringe pin holder lifting. A female thread corresponding to the male thread of the ball screw shaft 3500S for syringe pin holder lifting is formed at the ball nut 3500N for syringe pin holder lifting so that the ball nut 3500N for syringe pin holder lifting is moved up and down by rotation of the ball screw shaft 3500S for syringe pin holder lifting. An upper end of a syringe pin holder moving rod 3600 is fixedly connected to the ball nut 3500N for syringe pin holder lifting, and a lower end of the syringe pin holder moving rod 3600 is fixedly connected to the moving rod connecting member 3610. The moving rod connecting member 3610 is fixedly connected to the syringe pin holder 3200 through a connecting member supporter 3610. Therefore, the ball nut 3500N for syringe pin holder lifting is moved up and down by the syringe pin holder lifting motor 3200M, and thus the syringe pin holder 3200 is moved up and down.

Referring to FIG. 16, a guide rod fixing bush 3620 is fixed to an upper surface of the syringe pin holder 3200. Meanwhile, a lower end of a holder guide rod 3930 is fixed to the guide rod fixing bush 3620.

Referring to FIG. 16, a guide rod guiding block 3910 is fixedly disposed in the syringe block body 3400. The holder guide rod 3930 is inserted into the guide rod guiding block 3910 so as to be slid up and down. Meanwhile, a guide rod bush 3920 into which the holder guide rod 3930 is slidably inserted is fixed to an upper surface of the guide rod guiding block 3910. At an upper end of the holder guide rod 3930, there is formed a stopper which is caught by the guide rod bush 3920.

Referring to FIG. 16, a plurality of syringe pins 3100 are attached to a lower surface of the syringe pin holder 3200.

Referring to FIG. 16, the syringe pin guide block 3300 is disposed at a lower side of the syringe pin holder 3200. Referring to FIG. 17, the syringe pin guide block 3300 is formed with a plurality of syringe pin guide holes 3310H for guiding up/down movement of the plurality of syringe pins 3100.

Referring to FIG. 17, a plurality of first mounting portions 3330 are formed at a lower end of the syringe pin guide block 3300 so as to respectively mount the plurality of purification pipettes P1, the plurality of dispensation pipettes P2, the puncher 12100 (referring to FIG. 14) and the evaporation block 12200 for multi-well plate (referring to FIG. 14) at different time points. That is, the plurality of first mounting portions 3330 are inserted into upper ends of the plurality of purification pipettes P1, upper ends of the plurality of dispensation pipettes P2, upper ends of puncher inserting grooves formed in the upper surface of the puncher 12100 (referring to FIG. 14) and upper ends of the evaporation block inserting grooves 12200-G formed in the upper surface of the evaporation block 12200 for multi-well plate (referring to FIG. 14) at different time points. The first mounting portion 3330 is formed with a first mounting portion communicating hole communicated with the syringe pin guide hole 3310H. Therefore, when the plurality of syringe pins 3100 are moved up and down along the syringe pin guide hole 3310H, a fluid substance is sucked or discharged through the plurality of pipettes P mounted in the plurality of first mounting portions 3330.

Referring to FIG. 18, at the syringe block 3000, there is formed a first separation portion which is moved down, while being contacted with a lower surface of the syringe pin holder 3200, so as to separate at least the plurality of pipettes P and the evaporation block 12200 for multi-well plate among the plurality of pipettes P, the puncher 12100 and the evaporation block 12200 for multi-well plate from the first mounting portion 3330, which are respectively mounted in the plurality of mounting portions 3330 at different time points.

Referring to FIG. 18, the first separation portion includes a first upper separation plate 3710, a first lower separation plate 3720, a first separation rod 3731 and a first separation rod spring 37315.

Referring to FIG. 17, the first upper separation plate 3710 is located between the syringe pin holder 3200 and the syringe pin guide block 3300. The first upper separation plate 3710 is formed with syringe pin through-holes through in the plurality of syringe pins 3100 are inserted.

Referring to FIG. 17, the first lower separation plate 3720 is located at a lower side of the syringe pin guide block 3300. The first lower separation plate 3720 is formed with a plurality of first mounting portion through-holes in which the first mounting portions 3330 are inserted. The first mounting portion through-holes are formed so that the first mounting portions 3330 can be passed therethrough but the plurality of pipettes P mounted in the first mounting portion 3330 cannot be passed therethrough. Therefore, when the first lower separation plate 3720 is moved down, the upper portions of the pipettes P and the upper surface of evaporation block 12200 for multi-well plate are compressed down and then the pipettes P and evaporation block 12200 for multi-well plate, which are respectively mounted in the plurality of mounting portions 3330 at different time points, are separated therefrom.

Referring to FIG. 18, an upper end of the first separation rod 3731 is fixedly connected to the first upper separation plate 3710, and a lower end thereof is fixedly connected to the first lower separation plate 3720. A first small-diameter separation rod 3731-1 is formed at a lower portion of the first separation rod 3731, and a first large-diameter separation rod 3731-2 having a larger diameter than the first small-diameter separation rod 3731-1 is formed at an upper side of the first small-diameter separation rod 3731-1.

Referring to FIG. 18, a first small-diameter separation rod guide hole 3321H1 is formed at a lower portion of the syringe block 3000, and a first large-diameter separation rod guide hole 3321H2 is formed at an upper side of the first small-diameter separation rod guide hole 3321H1. The first small-diameter separation rod guide hole 3321H1 functions to guide the first small-diameter separation 3731-1, and the first large-diameter separation rod guide hole 3321H2 functions to guide the first large-diameter separation rod guide 3731-2.

Referring to FIG. 18, the first separation rod spring 37315 is inserted onto the first small-diameter separation 3731-1. An upper end of the first separation rod spring 37315 is elastically supported by a lower end of the first large-diameter separation rod guide 3731-2, and a lower end thereof is elastically supported by a lower end of the first large-diameter separation rod guide hole 3321H2. Therefore, if the syringe pin holder 3200 is moved up and thus is not contacted with the first upper separation plate 3710, the first lower separation plate 3720 is contacted with a lower end of the syringe pin guide block 3300 by elastic force of the first separation rod spring 37315.

Referring to FIGS. 19 and 20, at the syringe block 3000 and the evaporation block 12200 for multi-well plate, there is formed a second separation portion which is moved down, while being contacted with the lower surface of the syringe pin holder 3200, so as to separate the plurality of pipettes P mounted in the second mounting portion 12210. The second separation portion includes a second-1 separation portion which is disposed at the syringe block 3000, and a second-2 separation portion which is disposed at the evaporation block 12200 for multi-well plate. The second-1 separation portion includes a second separation rod 3732 and the second separation rod spring 3732S, and the second-2 separation portion includes a second separation plate 12220 and a second separation pin 12230.

Referring to FIGS. 19 and 20, the second separation rod 3732 is disposed so as to pass through the first upper separation plate 3710 and the first lower separation plate 3720. The second separation rod 3732 includes a second small-diameter separation rod 3732-1 and a second large-diameter separation rod 3732-2 having a larger diameter than the second small-diameter separation rod 3732-1. The second small-diameter separation rod 3732-1 is formed at a lower portion of the second separation rod 3732, and the second large-diameter separation rod 3732-2 is formed at an upper side of the second small-diameter separation rod 3732-1. Meanwhile, at a lower end of the second small-diameter separation rod 3732-1, there is formed a lower stopper 3732-1P which is caught by a lower surface of the first lower separation plate 3720.

Referring to FIGS. 19 and 20, a second small-diameter separation rod guide hole 3322H1 is formed at the lower end of the syringe block 3000, and a second large-diameter separation rod guide hole 3322H2 is formed at an upper side of the second small-diameter separation rod guide hole 3322H1. The second small-diameter separation rod guide hole 3322H1 functions to guide the second small-diameter separation rod 3732-1, and the second large-diameter separation rod guide hole 3322H2 functions to guide the second large-diameter separation rod 3732-2.

Referring to FIGS. 19 and 20, the second separation rod spring 3732S is inserted onto the second small-diameter separation 3732-1. An upper end of the second separation rod spring 3732S is elastically supported by a lower end of the second large-diameter separation rod guide 3732-2, and a lower end thereof is elastically supported by a lower end of the second large-diameter separation rod guide hole 3322H2. Therefore, if the syringe pin holder 3200 is moved up and thus is not contacted with the second separation rod 3732, the lower stopper 3732-1P of the second separation rod 3732 is caught with a lower surface of the first lower separation plate 3720 by elastic force of the second separation rod spring 3732S, and an upper end of the second separation rod 3732 is protruded to an upper side of the first upper separation plate 3710.

Referring to FIGS. 19 and 20, a plurality of second mounting portions 12210 are formed to be protruded at a lower end of the evaporation block 12200 for multi-well plate. The second separation plate 12220 is located at a lower side of the evaporation block 12200 for multi-well plate. The second separation plate 12220 is formed with a plurality of second mounting portion through-holes in which the second mounting portions 12210 are inserted. The second mounting portion through-holes are formed so that the second mounting portions 12210 can be passed therethrough but the plurality of pipettes P mounted in the second mounting portion 12210 cannot be passed therethrough. Therefore, when the second lower separation plate 12220 is moved down, the upper portions of the pipettes P mounted in the plurality of second mounting portions 12210 are compressed down and then separated therefrom.

Referring to FIGS. 19 and 20, the second separation pin 12230 is disposed to be moved up and down at the evaporation block 12200 for multi-well plate. Since an upper end of the second separation pin 12230 is contacted with a lower end of the second small-diameter separation rod 3732-1 which is moved down, and a lower end thereof is contacted with an upper surface of the second separation plate 12220, the second separation plate 12220 can be moved down by the second separation pin 12230. In other words, if the syringe pin holder 3200 is moved down, and thus the second separation rod 3732 is compressed by force that is larger than the elastic force of the second separation rod spring 3732S, the second separation rod 3732 is moved down. If the second separation rod 3732 is moved down, the second separation pin 12230 is contacted with the second separation rod 3732 and then moved down. As the second separation rod 3732 is moved down, the second separation plate 12220 is also moved down, and thus the plurality of pipettes P mounted in the second mounting portion 12210 can be separated.

Meanwhile, in case that a puncher guide hole (not shown) in which the lower end of the second small-diameter separation rod 3732-1 (referring to FIG. 20) is inserted is formed to have a sufficient depth in the upper surface of the puncher 12100 so that the lower end of the second small-diameter separation rod 3732-1 (referring to FIG. 20) is not compressed to the puncher 12100 until the first lower separation plate 3720 is moved down by the syringe pin holder 3200 and contacted with the upper surface of the puncher 12100, the puncher 12100 is separated from the first mounting portion 3330 by the first separation portion. However, in case that the puncher guide hole (not shown) is not formed to have the sufficient depth in the upper surface of the puncher 12100 and thus the lower end of the second small-diameter separation rod 3732-1 (referring to FIG. 20) is compressed to the puncher 12100 before the first lower separation plate 3720 is moved down by the syringe pin holder 3200 and contacted with the upper surface of the puncher 12100, the puncher 12100 is separated from the first mounting portion 3330 by the second-1 separation portion.

Referring to FIGS. 23 to 25, the first embodiment includes the syringe block moving unit 4000 for moving the syringe block 3000. The syringe block moving unit 4000 includes a front and rear moving part 4100 for syringe block, a left and right moving part 4200 for syringe block, and an up and down moving part 4300 for syringe block. The front and rear moving part 4100 for syringe block functions to move the syringe block 3000 in a front and rear direction of the deck 1000 transferred to the main intermediate plate 12000-1. The left and right moving part 4200 for syringe block functions to move the syringe block 3000 in a left and right direction of the deck 1000 transferred to the main intermediate plate 12000-1. The up and down moving part 4300 for syringe block functions to move the syringe block 3000 in an up and down direction of the deck 1000 transferred to the main intermediate plate 12000-1. By the syringe block moving unit 4000, the plurality of pipettes P mounted in the plurality of first mounting potions 3330 is located just above the multi-well plate 100 for biological sample, the plurality of multi-well plates 200 for purification and the multi-well plate 400 for PCR, respectively.

Referring to FIG. 23, the front and rear moving part 4100 for syringe block includes a front and rear moving motor 4110M for syringe block, a front and rear moving belt (not shown) for syringe block, a front and rear moving body 4110 for syringe block, and a syringe block connecting member 4140.

Referring to FIG. 23, the front and rear moving motor 4110M for syringe block is mounted on a main upper plate 12000-3. The main upper plate 12000-3 is disposed at an upper side of the main intermediate plate 12000-1.

Referring to FIG. 23, the front and rear moving belt (not shown) for syringe block is wound on two pulleys 4131 and 4132 which are spaced apart from each other so as to be moved in a front and rear direction of the deck 1000 by the front and rear moving motor 4110M for syringe block. In other words, a driving shaft for front and rear movement of the syringe block is connected to the front and rear moving motor 4110M for syringe block, and a driving pulley 4121 (referring to FIG. 1) for front and rear movement of the syringe block is inserted onto the driving shaft for front and rear movement of the syringe block. Meanwhile, a first driven shaft for front and rear movement of the syringe block is disposed to be spaced apart from the driving shaft for front and rear movement of the syringe block, and a first-1 driven pulley 4122 for front and rear movement of the syringe block is inserted onto an upper end of the first driven shaft for front and rear movement of the syringe block, and a first-2 driven pulley 4131 for front and rear movement of the syringe block is inserted onto a lower end of the first driven shaft for front and rear movement of the syringe block. Further, a second driven shaft for front and rear movement of the syringe block is disposed to be spaced apart from the first driven shaft for front and rear movement of the syringe block in the front and rear direction of the deck 1000. A second driven pulley 4132 for front and rear movement of the syringe block is inserted onto the second driven shaft for front and rear movement of the syringe block. The driving pulley 4121 (referring to FIG. 1) for front and rear movement of the syringe block and the first-1 driven pulley 4122 for front and rear movement of the syringe block are wound with the driving belt (not shown) for front and rear movement of the syringe block, and the first-2 driven pulley 4131 for front and rear movement of the syringe block and the second driven pulley 4132 for front and rear movement of the syringe block are wound with the front and rear moving belt (not shown) for syringe block. Therefore, the driving pulley 4121 (referring to FIG. 1) for front and rear movement of the syringe block is rotated by the front and rear moving motor 4110M for syringe block, and the first-1 driven pulley 4122 for front and rear movement of the syringe block and the first-2 driven pulley 4131 for front and rear movement of the syringe block are rotated by rotation of the driving pulley 4121 (referring to FIG. 1) for front and rear movement of the syringe block, and thus the front and rear moving belt (not shown) for syringe block is moved in the front and rear direction of the deck 1000 by rotation of the first-2 driven pulley 4131 for front and rear movement of the syringe block.

Referring to FIG. 23, one end of the syringe block connecting member 4140 is fixedly connected to the front and rear moving belt (not shown) for syringe block.

Referring to FIG. 23, a front and rear moving rail 4150 for syringe block is disposed at the main upper plate 12000-3 in the front and rear direction of the deck 1000.

Referring to FIG. 23, the front and rear moving body 4110 for syringe block is slidably disposed at the front and rear moving rail 4150 for syringe block. Meanwhile, the other end of the syringe block connecting member 4140 is fixedly connected to the front and rear moving body 4110 for syringe block. Therefore, as the front and rear moving belt (not shown) for syringe block is moved in the front and rear direction of the deck 1000, the front and rear moving body 4110 for syringe block is also moved in the front and rear direction of the deck 1000.

Referring to FIG. 24, the left and right moving part 4200 for syringe block includes a left and right moving motor 4210M for syringe block, a left and right moving belt (not shown) for syringe block, a left and right moving body 4210 for syringe block, and a syringe block connecting member 4240.

Referring to FIG. 24, the left and right moving motor 4210M for syringe block is fixedly connected to the front and rear moving body 4110 for syringe block.

Referring to FIG. 24, the left and right moving belt (not shown) for syringe block is wound on two pulleys 4231 and 4232 which are spaced apart from each other so as to be moved in a left and right direction of the deck 1000 by the left and right moving motor 4210M for syringe block. In other words, a driving shaft for left and right movement of the syringe block is connected to the left and right moving motor 4210M for syringe block, and a driving pulley 4221 for left and right movement of the syringe block is inserted onto the driving shaft for left and right movement of the syringe block. Meanwhile, a first driven shaft for left and right movement of the syringe block is disposed to be spaced apart from the driving shaft for left and right movement of the syringe block, and a first-1 driven pulley 4222 for left and right movement of the syringe block is inserted onto one end of the first driven shaft for left and right movement of the syringe block, and a first-2 driven pulley 4231 for left and right movement of the syringe block is inserted onto the other end of the first driven shaft for left and right movement of the syringe block. Further, a second driven shaft for left and right movement of the syringe block is disposed to be spaced apart from the first driven shaft for left and right movement of the syringe block in the left and right direction of the deck 1000. A second driven pulley 4232 for left and right movement of the syringe block is inserted onto the second driven shaft for left and right movement of the syringe block. The driving pulley 4221 for left and right movement of the syringe block and the first-1 driven pulley 4222 for left and right movement of the syringe block are wound with the driving belt (not shown) for left and right movement of the syringe block, and the first-2 driven pulley 4231 for left and right movement of the syringe block and the second driven pulley 4232 for left and right movement of the syringe block are wound with the left and right moving belt (not shown) for syringe block. Therefore, the driving pulley 4221 for left and right movement of the syringe block is rotated by the left and right moving motor 4210M for syringe block, and first-1 driven pulley 4222 for left and right movement of the syringe block and the first-2 driven pulley 4231 for left and right movement of the syringe block are rotated by rotation of the driving pulley 4221 for left and right movement of the syringe block, and thus the left and right moving belt (not shown) for syringe block is moved in the left and right direction of the deck 1000 by rotation of the first-2 driven pulley 4231 for left and right movement of the syringe block.

Referring to FIG. 24, one end of the syringe block connecting member 4240 is fixedly connected to the left and right moving belt (not shown) for syringe block.

Referring to FIG. 24, a left and right moving rail 4250 for syringe block is disposed at the front and rear moving body 4110 for syringe block in the left and right direction of the deck 1000.

Referring to FIG. 24, a left and right moving body 4210 for syringe block is slidably disposed at the left and right moving rail 4250 for syringe block. Meanwhile, the other end of the syringe block connecting member 4240 is fixedly connected to the left and right moving body 4210 for syringe block. Therefore, as the left and right moving belt (not shown) for syringe block is moved in the left and right direction of the deck 1000, the left and right moving body 4210 for syringe block is also moved in the left and right direction of the deck 1000.

Referring to FIG. 25, the up and down moving part 4300 for syringe block includes a up and down lifting motor 4310M for syringe block, an up and down moving body 4310 for syringe block, a ball screw shaft 4330S for up and down movement of the syringe block, a ball nut 4330N for up and down movement of the syringe block, and a supporting plate 4360 for up and down movement of the syringe block.

Referring to FIG. 25, the supporting plate 4360 for up and down movement of the syringe block is fixedly connected to the left and right moving motor 4210M for syringe block.

Referring to FIG. 25, the up and down lifting motor 4310M for syringe block is fixed to one side of the supporting plate 4360 for up and down movement of the syringe block. A driving shaft for up and down movement of the syringe block is connected to the up and down lifting motor 4310M for syringe block, and a driving pulley for up and down movement of the syringe block is inserted onto the driving shaft for up and down movement of the syringe block.

Referring to FIG. 25, the ball screw shaft 4330S for up and down movement of the syringe block is spaced apart from the driving shaft for up and down movement of the syringe block, and also disposed to be opposite to the up and down lifting motor 4310M for syringe block with the supporting plate 4360 for up and down movement of the syringe block as the center. A male thread is formed on the ball screw shaft 4330S for up and down movement of the syringe block. Meanwhile, a driven pulley 4322 for up and down movement of the syringe block is inserted onto the ball screw shaft 4330S for up and down movement of the syringe block. Although not shown in the drawings, the driving pulley for up and down movement of the syringe block and the driven pulley 4322 for up and down movement of the syringe block are wound with a driving belt (not shown) for up and down movement of the syringe block.

Referring to FIG. 25, the ball nut 4330N for up and down movement of the syringe block is inserted onto the ball screw shaft 4330S for up and down movement of the syringe block so as to be moved up and down by rotation of the ball screw shaft 4330S for up and down movement of the syringe. Therefore, a female thread corresponding to the male thread of the ball screw shaft 4330S for up and down movement of the syringe block is formed at the ball nut 4330N for up and down movement of the syringe block.

Referring to FIG. 25, the an up and down moving body 4310 for syringe block is fixedly connected to the up and down moving body 4310 for syringe block so as to be moved up and down together with the ball nut 4330N for up and down movement of the syringe block. The syringe block 3000(referring to FIG. 2) is fixedly installed to the up and down moving body 4310 for syringe block. Therefore, when the driven pulley 4322 for up and down movement of the syringe block is rotated, the ball screw shaft 4330S for up and down movement of the syringe is also rotated, and thus the ball nut 4330N for up and down movement of the syringe block and the up and down moving body 4310 for syringe block are moved in an up and down direction of the deck 1000. The syringe block 3000(referring to FIG. 2) are moved in an up and down direction of the deck 1000 as the up and down moving body 4310 for syringe block are moved in an up and down direction of the deck 1000.

Referring to FIG. 25, a rail 1361 for guiding movement of the up and down moving body 4310 for syringe block is formed at the supporting plate 4360 for up and down movement of the syringe block.

Referring to FIGS. 25 and 39, a solution drip tray supporting plate 4371 is fixed to the supporting plate 4360 for up and down movement of the syringe block in the up and down direction. A solution drip tray moving motor 4373 is fixed to the solution drip tray supporting plate 4371. A solution drip tray driving shaft is connected to the solution drip tray moving motor 4373 in the up and down direction.

Referring to FIGS. 25 and 39, a solution drip tray 4375 is coupled to the solution drip tray driving shaft. The solution drip tray 4375 is horizontally rotated by rotation of the solution drip tray driving shaft so as to be located at a lower side of the pipettes P mounted in the first mounting portions 3330 or to be separated from the lower side of the pipettes P mounted in the first mounting portions 3330. Therefore, when the syringe block 3000 is moved in the front/rear and left/right direction of the deck 1000, the solution drip dray 4375 is located at the lower side of the pipettes P so as to prevent a solution sucked in the pipettes P from being undesirably dripped and introduced into the certain multi-well plate.

Referring to FIGS. 26 and 27, the magnetic field applying unit 5100 includes a magnet mounting block 5120 and a magnet mounting block lifting part for lifting up and down the magnet mounting block 5120. The magnetic field applying unit 5100 functions to move a magnet 5110 to a lower side of a first certain multi-well plate out of the plurality of multi-well plates 200 for purification and then to apply a magnet field to the lower side of the first certain multi-well plate. The first certain multi-well plate is the multi-well plate 220 for magnetic particle dispersion solution.

Referring to FIG. 26, the magnet 5110 is protruded to an upper surface of the magnet mounting block 5120. The magnet 5110 is formed so as to enclose each well formed in the first certain multi-well plate when the magnet mounting block 5120 is lifted up. Therefore, referring to FIG. 7, a through-opening is formed at a portion of the main intermediate plate 12000-1, on which the multi-well plate 220 for magnetic particle dispersion solution is located. Meanwhile, the magnet 5110 may a plurality of bar magnets which are spaced apart from each other so as to enclose each well formed in the first certain multi-well plate.

Referring to FIG. 26, the magnet mounting block lifting part includes a supporting plate 5130 for magnetic field applying unit, a magnet mounting block lifting motor 5120M, a ball screw shaft 51505 for magnet mounting block lifting, a ball nut for magnet mounting block lifting and a magnet mounting block moving rod 5160.

Referring to FIG. 26, the supporting plate 5130 for magnetic field applying unit is located at a lower side of the magnet mounting block 5120.

Referring to FIG. 26, a supporting plate 5140 for magnet mounting block lifting motor is disposed at a lower side of the supporting plate 5130 for magnetic field applying unit. The supporting plate 5140 for magnet mounting block lifting motor is fixedly connected to a lower end of an upper connecting rod 5141 for magnet mounting block lifting motor. Meanwhile, an upper end of the upper connecting rod 5141 for magnet mounting block lifting motor is fixed to the supporting plate 5130 for magnetic field applying unit.(추가)

Referring to FIG. 26, the magnet mounting block lifting motor 5120M is fixed at a lower side of the supporting plate 5140 for magnet mounting block lifting motor. An upper end of the magnet mounting block lifting motor 5120M is fixedly connected to a lower end of a lower connecting rod 5142 for magnet mounting block lifting motor, which is fixed to the supporting plate 5140 for magnet mounting block lifting motor. Meanwhile, an upper end of the lower connecting rod 5142 for magnet mounting block lifting motor is fixed to the supporting plate 5140 for magnet mounting block lifting motor. Therefore, the magnet mounting block lifting motor 5120M is spaced apart from the supporting plate 5130 for magnetic field applying unit via the connecting rod 5141, 5142 for magnet mounting block lifting motor and thus fixed at the lower side of the supporting plate 5130 for magnetic field applying unit.

Referring to FIG. 26, the ball screw shaft 51505 for magnet mounting block lifting is connected to the magnet mounting block lifting motor 5120M through a shaft coupling (not shown). The ball screw shaft 51505 for magnet mounting block lifting is disposed to pass through the supporting plate 5140 for magnet mounting block lifting motor. A male thread is formed on the ball screw shaft 5150S for magnet mounting block lifting. Although not shown in the drawings, a ball nut (not shown) for magnet mounting block lifting is inserted onto the ball screw shaft 51505 for magnet mounting block lifting so as to be moved up and down by rotation of the ball screw shaft 51505 for magnet mounting block lifting. Accordingly, a female thread corresponding to the male thread of the ball screw shaft 51505 for magnet mounting block lifting is formed at the ball nut (not shown) for magnet mounting block lifting.

Referring to FIG. 26, the magnet mounting block moving rod 5160 is disposed to pass through the supporting plate 5130 for magnetic field applying unit. An upper end of the magnet mounting block moving rod 5160 is fixed to the magnet mounting block 5120, and a lower end thereof is fixed to the ball nut (not shown) for magnet mounting block lifting. Therefore, the ball nut (not shown) for magnet mounting block lifting and the magnet mounting block moving rod 5160 are moved up and down, as the ball screw shaft 5150S for magnet mounting block lifting is rotated. If the magnet mounting block moving rod 5160 is moved up and down, the magnet mounting block 5120 is moved up and down with respect to the supporting plate 5130 for magnetic field applying unit.

Referring to FIGS. 26 and 27, the heating unit 5200 includes a heating block 5220, a heating block lifting part which lifts up and down the heating block 5220, and a front and rear moving part for heating block, which moves the heating block 5220 in the front and rear direction of the deck 1000. The heat unit 5200 functions to move the heating block 5220 to a lower side of a second certain multi-well plate out of the multi-well plate 100 for biological sample and the plurality of multi-well plates 200 for purification and then to heat the second certain multi-well plate. The second certain multi-well plate is the multi-well plate 100 for biological sample.

Although not shown in FIG. 26, a plurality of mounting grooves (not shown) is formed in an upper surface of the heating block 5220. The mounting grooves (not shown) are formed so as to enclose each well formed in the second certain multi-well plate when the heating block 5220 is lifted up. Therefore, heat transfer is facilely performed from the heating block 5220 to a lower end of each well inserted into the mounting groove (not shown). Therefore, referring to FIG. 7, a through-opening is formed at a portion of the main intermediate plate 12000-1, on which the multi-well plate 100 for biological sample is located.

Referring to FIG. 26, the heating block lifting part includes a supporting plate 5230 for heating unit, a heating block lifting motor 5220M, a ball screw shaft 5250S for heating block lifting, a ball nut for heating block lifting and a heating block moving rod 5260.

Referring to FIG. 26, the supporting plate 5230 for heating unit is located at a lower side of the heating block 5220. Meanwhile, the supporting plate 5230 for heating unit is adjacent to the supporting plate 5130 for magnetic field applying unit in the front and rear direction of the deck 1000, and formed integrally with the supporting plate 5130 for magnetic field applying unit. Therefore, as the supporting plate 5230 for heating unit is moved in the front and rear direction of the deck 1000, the unit supporting plate 5130 for magnetic field applying is also moved in the front and rear direction of the deck 1000.

Referring to FIG. 26, a supporting plate 5240 for heating block lifting motor is disposed at a lower side of the supporting plate 5230 for heating unit. The supporting plate 5240 for heating block lifting motor is fixedly connected to a lower end of an upper connecting rod 5241 for heating block lifting motor. Meanwhile, an upper end of the upper connecting rod 5241 for heating block lifting motor is fixed to the supporting plate 5230 for heating unit.

Referring to FIG. 26, the heating block lifting motor 5220M is fixed at a lower side of the supporting plate 5240 for heating block lifting motor. An upper end of the heating block lifting motor 5220M is fixedly connected to a lower end of a lower connecting rod 5242 for heating block lifting motor. Meanwhile, an upper end of the lower connecting rod 5242 for heating block lifting motor is fixed to the supporting plate 5240 for heating block lifting motor. Therefore, the heating block lifting motor 5220M is spaced apart from the supporting plate 5230 for heating unit via the connecting rod 5241, 5242 for heating block lifting motor, and fixed at the lower side of the supporting plate 5230 for heating unit.

Referring to FIG. 26, the ball screw shaft 5250S for heating block lifting is connected to the heating block lifting motor 5220M through a shaft coupling (not shown). The ball screw shaft 5250S for heating block lifting is disposed to pass through the supporting plate 5240 for heating block lifting motor. A male thread is formed on the ball screw shaft 5250S for heating block lifting. Although not shown in the drawings, a ball nut (not shown) for heating block lifting is inserted onto the ball screw shaft 5250S for heating block lifting so as to be moved up and down by rotation of the ball screw shaft 5250S for heating block lifting. Accordingly, a female thread corresponding to the male thread of the ball screw shaft 5250S for heating block lifting is formed at the ball nut (not shown) for heating block lifting.

Referring to FIG. 26, the heating block moving rod 5260 is disposed to pass through the supporting plate 5230 for heating unit. An upper end of the heating block moving rod 5260 is fixed to heating block 5220, and a lower end thereof is fixed to the ball nut (not shown) for heating block lifting. Therefore, the ball nut (not shown) for heating block lifting and the heating block moving rod 5260 are moved up and down, as the ball screw shaft 5250S for heating block lifting is rotated. If the heating block moving rod 5260 is moved up and down, the heating block 5220 is moved up and down with respect to the supporting plate 5230 for heating unit.

Referring to FIG. 27, the front and rear moving part for heating block includes a front and rear moving motor 5230M for heating block, a front and rear moving belt (not shown) for heating block, and a heating block connecting member 5234.

Referring to FIG. 27, the front and rear moving motor 5230M for heating block is mounted on the main lower plate 12000-2.

Referring to FIG. 27, the front and rear moving belt (not shown) for heating block is wound on two pulleys 5233-1 and 5233-2 which are spaced apart from each other so as to be moved in a front and rear direction of the deck 1000 by the front and rear moving motor 5230M for heating block. In other words, a driving shaft for front and rear movement of the heating block is connected to the front and rear moving motor 5230M for heating block, and a driving pulley 5231 for front and rear movement of the heating block is inserted onto the driving shaft for front and rear movement of the heating block. Meanwhile, a first driven shaft for front and rear movement of the heating block is disposed to be spaced apart from the driving shaft for front and rear movement of the heating block, and a first-1 driven pulley 5232 for front and rear movement of the heating block is inserted onto one end of the first driven shaft for front and rear movement of the heating block, and a first-2 driven pulley 5233-1 for front and rear movement of the heating block is inserted onto the other end of the first driven shaft for front and rear movement of the heating block. Further, a second driven shaft for front and rear movement of the heating block is disposed to be spaced apart from the first driven shaft for front and rear movement of the heating block in the front and rear direction of the deck 1000. A second driven pulley 5233-2 for front and rear movement of the heating block is inserted onto the second driven shaft for front and rear movement of the heating block. The driving pulley 5231 for front and rear movement of the heating block and the first-1 driven pulley 5232 for front and rear movement of the heating block are wound with the driving belt (not shown) for front and rear movement of the heating block, and the first-2 driven pulley 5233-1 for front and rear movement of the heating block and the second driven pulley 5233-2 for front and rear movement of the heating block are wound with the front and rear moving belt (not shown) for heating block. Therefore, the driving pulley 5231 for front and rear movement of the heating block is rotated by the front and rear moving motor 5230M for heating block, and the first-1 driven pulley 5232 for front and rear movement of the heating block and the first-2 driven pulley 5233-1 for front and rear movement of the heating block are rotated by rotation of the driving pulley 5231 for front and rear movement of the heating block, and thus the front and rear moving belt (not shown) for heating block is moved in the front and rear direction of the deck 1000 by rotation of the first-2 driven pulley 5233-1 for front and rear movement of the heating block.

Referring to FIG. 27, one end of the heating block connecting member 5234 is fixedly connected to the front and rear moving belt (not shown) for heating block.

Referring to FIG. 27, a front and rear moving rail 5235 for heating block is disposed at the main upper plate 12000-3 in the front and rear direction of the deck 1000.

Referring to FIG. 27, the supporting plate 5130 for magnetic field applying unit and the supporting plate 5230 for heating unit are slidably disposed at the front and rear moving rail 5235 for heating block. Meanwhile, the other end of the heating block connecting member 5234 is fixedly connected to one of the supporting plate 5130 for magnetic field applying unit and the supporting plate 5230 for heating unit. Therefore, as the front and rear moving belt (not shown) for heating block is moved in the front and rear direction of the deck 1000, the heating block 5220 and the magnet mounting block 5120 are also moved in the front and rear direction of the deck 1000. Meanwhile, the heating block 5220 is located just below a certain multi-well plate out of the plurality of multi-well plates 200 for purification, which is filled with magnetic particles that alcohol is remained thereon, so as to remove the alcohol remained on the surfaces of the magnetic particles. That is, the heating block can be used in removing the alcohol remained on the surfaces of the magnetic particles together with the evaporation block 12200 for multi-well plate.

Referring to FIGS. 28 to 32, the sealing device 6000 includes a film roller supporter 6110, a film roller 6120, a film guide plate mounting portion 6210, a intermediate plate 6260 for sealing device, a ball nut 6280N for sealed loading plate movement, a sealed loading plate 6294, a lower compressing portion 6230, an upper compressing portion 6243, a film cutter 6250, a film heating block 6310 and an intermediate plate moving unit 6260M. The sealing device 6000 is to seal an upper surface of the multi-well plate 400 for PCR in which the target nucleic acid is dispensed.

Referring to FIG. 28, the film roller 6120 is rotatably disposed at the film roller supporter 6110. The film roller 6120 is wound with a sealing film for sealing the upper surface of the multi-well plate 400 for PCR.

Referring to FIG. 28, the film guide roller 6130 is disposed at the film roller supporter 6110. The film guide roller 6130 functions to guide the sealing film unwound from the film roller 6120.

Referring to FIG. 31, the film guide plate 6212 is disposed at a front side of the film guide roller 6130. A fore-end of the film guide plate 6212 is fixed to an upper surface of the film guide plate mounting portion 6210. Meanwhile, an auxiliary film guide plate 6210-1 is provided at an upper surface of the film guide plate mounting portion 6210 so that a gap through which the sealing film is passed is formed between the auxiliary film guide plate 6210-1 and the upper surface of the film guide plate mounting portion 6210.

Referring to FIG. 31, a lower end of the film guide plate mounting portion 6210 is fixed to the intermediate plate 6260 for sealing device. The film guide plate 6212 functions to support a lower surface of the sealing film guided by the film guide roller 6130.

Referring to FIG. 30, a sealed loading plate moving motor 6294M is fixedly disposed at a lower surface of the intermediate plate 6260 for sealing device.

Referring to FIG. 29, a driving shaft for sealed loading plate movement is connected to the sealed loading plate moving motor 6294M, and a driving pulley 6271 for sealed loading plate movement is inserted onto the driving shaft for sealed loading plate movement.

Referring to FIG. 29, a ball screw shaft 6280S for sealed loading plate movement is rotatably disposed at an upper surface of the intermediate plate 6260 for sealing device, and a male thread is formed on the ball screw shaft 6280S for sealed loading plate movement. A driven pulley 6272 for sealed loading plate movement is inserted onto an end of the screw shaft 6280S for sealed loading plate movement. Although not shown in the drawings, the driving pulley 6271 for sealed loading plate movement and the driven pulley 6272 for sealed loading plate movement are wound with a driving belt (not shown) for sealed loading plate movement.

Referring to FIG. 29, the ball nut 6280N for sealed loading plate movement is inserted onto the ball screw shaft 6280S for sealed loading plate movement so as to be moved in the front and rear direction of the deck 1000 by rotation of the ball screw shaft 6280S for sealed loading plate movement. Therefore, a female thread corresponding to the male thread of the ball screw shaft 6280S for sealed loading plate movement is formed at the ball nut 6280N for sealed loading plate movement.

Referring to FIGS. 28 and 29, an end of a sealed loading plate moving rod 6292 is connected to ball nut 6280N for sealed loading plate movement.

Referring to FIGS. 28 and 29, the other end of the sealed loading plate moving rod 6292 is fixedly connected to the sealed loading plate 6294. The sealed loading plate 6294 functions to safely mount the multi-well plate 400 for PCR.

Referring to FIGS. 29 and 31, a rail-shape slider 6295 is fixedly mounted on a lower surface of the sealed loading plate 6294. The slider 6295 is disposed at a guide 6296 fixed to the intermediate plate 6260 for sealing device so as to be slid forward and backward.

Referring to FIG. 31, the lower compressing portion 6230 is fixed to the intermediate plate 6260 for sealing device. The lower compressing portion 6230 is disposed at a front side of the fore-end of the film guide plate 6212, i.e., a front side of the film guide plate mounting portion 6210.

Referring to FIGS. 28 and 32, an upper compressing portion supporting block 6240 is disposed at an upper side of the lower compressing portion 6230.

Referring to FIG. 33A, the upper compressing portion supporting block 6240 is elastically supported by a first supporting spring 6241 so as to be located at the upper side of the lower compressing portion 6230. In other words, a lower end of the first supporting spring 6241 is elastically contacted with the lower compressing portion 6230, and an upper end thereof is elastically contacted with the upper compressing portion 6243. Meanwhile, the upper compressing portion supporting block 6240 is coupled to a guide rod 6245 for upper compressing portion supporting block so as to be slid up and down. A lower end of the guide rod 6245 for upper compressing portion supporting block is fixed to the lower compressing portion 6230.

Referring to FIGS. 28 and 32, the upper compressing portion 6243 is disposed between the upper compressing portion supporting block 6240 and the lower compressing portion 6230. The upper compressing portion 6243 is moved down so as to compress the sealing film located on the upper surface of the lower compressing portion 6230 together with the lower compressing portion 6230.

Referring to FIG. 33B, an upper compressing portion supporting rod 6244 is coupled to the upper compressing portion supporting block 6240 so as to be slid up and down. A stopper 6244-1 is formed at an upper end of the upper compressing portion supporting rod 6244 so as to restrict upper movement of the upper compressing portion supporting block 6240 with respect to the upper compressing portion supporting rod 6244. A lower end of the upper compressing portion supporting rod 6244 is fixedly connected to the upper compressing portion 6243.

Referring to FIG. 33B, a second supporting spring 6242 is disposed between the upper compressing portion 6243 and the upper compressing portion supporting block 6240. A lower end of the second supporting spring 6242 is elastically contacted with the upper compressing portion 6243, and an upper end thereof is elastically contacted with the upper compressing portion supporting block 6240.

Referring to FIG. 32, the film cutter 6250 is disposed at a front side of the upper compressing portion 6243. The film cutter 6250 is moved down so as to cut the sealing film compressed between the lower compressing portion 6230 and the upper compressing portion 6243.

Referring to FIG. 32, an upper end of the film cutter 6250 is fixed to the upper compressing portion supporting block 6240. Referring to FIGS. 32 and 33, the film cutter 6250 is disposed so that a lower end thereof having a cutting blade is located at an upper side of the lower surface of the upper compressing portion 6243. Thus, the film cutter 6250 can cut the sealing film after the upper compressing portion 6243 compresses the sealing film.

Referring to FIG. 32, an auxiliary cutting plate 6232 is coupled to a fore-end of the lower compressing portion 6230 so that a cutting blade passing groove is formed between the auxiliary cutting plate 6232 and the fore-end of the lower compressing portion 6230. When cutting the sealing film, the cutting blade of the film cutter 6250 is passed through the cutting blade passing groove. Since a front lower end of a cut portion of the sealing film is supported by the auxiliary cutting plate 6232, the cutting of the sealing film can be carried out facilely.

Referring to FIGS. 28 and 29, an upper plate 6320 for sealing device is disposed at an upper side of the intermediate plate 6260 for sealing device. The upper plate 6320 for sealing device is supported by an upper plate supporting rod 6322 and also fixed to the intermediate plate 6260 for sealing device.

Referring to FIGS. 28 and 29, a pneumatic cylinder 6330 for compressing portion is fixed to the upper plate 6320 for sealing device. The pneumatic cylinder 6330 for compressing portion is disposed so that a piston rod of the pneumatic cylinder 6330 for compressing portion is moved to a lower side of the upper plate 6320 for sealing device and contacted with the upper compressing portion supporting block 6240. If the piston rod of the pneumatic cylinder 6330 for compressing portion is moved down so as to compress the upper compressing portion supporting block 6240, the upper compressing portion supporting block 6240 is also moved down. That is, the pneumatic cylinder 6330 for compressing portion is a compressing portion moving-down part for moving down the upper compressing portion supporting block 6240.

Referring to FIG. 32, it will be described of a process of cutting the sealing film compressed between the lower and upper compressing portions 6230 and 6243.

Referring to FIG. 33, if the piston rod of the pneumatic cylinder 6330 for compressing portion is moved down, the upper compressing portion supporting block 6240 is contacted with the piston rod of the pneumatic cylinder 6330 for compressing portion and also moved down. If the upper compressing portion supporting block 6240 is moved down, the upper compressing portion 6243 is also moved down and then contacted with an upper surface of the sealing film supported on the upper surface of the lower compressing portion 6230. Then, if the upper compressing portion supporting block 6240 is further moved down, the upper compressing portion 6243 compresses the sealing film supported on the upper surface of the lower compressing portion 6230 by elastic force of the second supporting spring 6242 of which downward movement is stopped. In this case, the film cutter 6250 is further moved down together with the upper compressing portion supporting block 6240 and then cuts the sealing film. Meanwhile, if the piston rod of the pneumatic cylinder 6330 for compressing portion is moved upward, the upper compressing portion supporting block 6240 is also moved up by elastic force of the first and second supporting springs 6241 and 6242. If the second supporting spring 6242 is returned to its original position, the upper compressing portion 6243 is moved up together with the upper compressing portion supporting block 6240 by the elastic force of the first supporting spring 6241.

Referring to FIGS. 28 and 32, a film side guide plate mounting portion 6220 is fixedly installed to the intermediate plate 6260 for sealing device. The film side guide plate mounting portion 6220 is disposed at a front side of the lower compressing portion 6230.

Referring to FIGS. 28 and 32, a film side guide plate 6222 is disposed at a film side guide plate mounting portion 6220. The film side guide plate 6222 functions to support an edge lower surface of the sealing film located at a front side of the fore-end of the lower compressing portion 6230. Meanwhile, the film side guide plate 6222 is disposed to be rotated to an edge portion of the sealing film supported on a surface of the film side guide plate 6222. Therefore, the film side guide plate 6222 is rotated to an outside of the edge portion of the sealing film supported on an upper surface of the film side guide plate 6222, and thus separated from the sealing film supported on the upper surface of the film side guide plate 6222. The film side guide plate 6222 is contacted with a film side guide plate operating rod 6351 and thus rotated to the outside of the edge portion of the sealing film supported on an upper surface of the film side guide plate 6222.

Referring to FIGS. 28 and 30, a pneumatic cylinder 6340 for film heating block is fixed to the upper plate 6320 for sealing device. The pneumatic cylinder 6340 for film heating block is a film heating block lifting part for moving up and down a film heating block 6310.

Referring to FIG. 30, a film heating block supporting plate 6350 is disposed at a lower side of the upper plate 6320 for sealing device. The film heating block supporting plate 6350 is fixedly connected to a piston rod of the pneumatic cylinder 6340 for film heating block. Therefore, as the piston rod of the pneumatic cylinder 6340 for film heating block is moved up and down, the film heating block supporting plate 6350 is also moved up and down.

Referring to FIG. 30, the film heating block 6310 is disposed at a lower side of the film heating block supporting plate 6350. The film heating block 6310 is fixed connected to the film heating block supporting plate 6350 through a film heating block supporting rod 6352. The film heating block 6310 functions to thermally compress the sealing film put on the upper surface of the multi-well plate 400 for PCR to the of the multi-well plate 400 for PCR.

Referring to FIG. 30, the film side guide plate operating rod 6351 is fixed to the film heating block supporting plate 6350. A lower end of the film side guide plate operating rod 6351 is located at a lower side of a lower surface of the film heating block 6310. Thus, before the film heating block 6310 is contacted with the sealing film supported by the film side guide plate 6222, the film side guide plate 6222 is rotated by the film side guide plate operating rod 6351 so as to put the sealing film on the multi-well plate 400 for PCR (referring to FIG. 31).

Referring to FIG. 31, the intermediate plate 6260 for sealing device is slidably disposed at a lower plate for sealing device. Therefore, a rail-shaped guider 6261 is formed in the front and rear direction of the deck 1000 at an upper surface of the lower plate 6410 for sealing device, and a slider is disposed at the lower surface of the intermediate plate 6260 for sealing device so as to be slid along the guider 6261.

Referring to FIG. 31, an intermediate plate moving unit 6260M is fixedly disposed at the lower plate 6410 for sealing device so as to move the intermediate plate 6260 for sealing device in the front and rear direction of the deck 1000. The intermediate plate moving unit 6260M may be an intermediate plate moving pneumatic cylinder. In this case, a piston rod of the intermediate plate moving pneumatic cylinder is fixed to the intermediate plate 6260 for sealing device. Therefore, when the intermediate plate moving unit 6260M is operated, the intermediate plate 6260 for sealing device is moved so as to get near or go away from the film roller supporter 6110.

Hereinafter, the sealing device 6000 will be described.

Referring to FIG. 28, while the sealed loading plate 6294 is protruded to a front side of the intermediate plate 6260 for sealing device, the multi-well plate 400 for PCR is mounted on the upper surface of the sealed loading plate 6294. In this case, a fore-end of the sealing film unwound from the film roller 6120 is located at a fore-end of the lower compressing portion 6230. Then, the sealed loading plate 6294 is moved to a rear side of the intermediate plate 6260 for sealing device, and thus the multi-well plate 400 for PCR is located at a lower side of the film side guide plate 6222.

Referring to FIGS. 31 and 32, if the multi-well plate 400 for PCR is located at the lower side of the film side guide plate 6222, the intermediate plate 6260 for sealing device is moved to the rear side of the lower plate 6410 for sealing device. Therefore, the film guide plate 6212, the lower compressing portion 6230, the film side guide plate 6222, the upper compressing portion supporting block 6240, the upper plate 6320 for sealing device and the sealed loading plate 6294 are moved together with the intermediate plate 6260 for sealing device.

Referring to FIGS. 31 and 32, when the intermediate plate 6260 for sealing device is moved to the rear side of the lower plate 6410 for sealing device while the sealing film is stopped, the sealing film unwound from the film roller 6120 is supported by the film side guide plate 6222, and the fore-end of the sealing film is located at the fore-end of the film side guide plate 6222.

Referring to FIGS. 31 to 33, if the fore-end of the sealing film is located at the fore-end of the film side guide plate 6222, the piston rod of the pneumatic cylinder 6330 for compressing portion is moved down, and thus the film cutter 6250 cuts the sealing film compressed between the lower and upper compressing portions 6230 and 6243. The description thereof is the same as the above-mentioned. Meanwhile, even after the sealing film is cut, the lower and upper compressing portions 6230 and 6243 continuously compress the sealing film.

Referring to FIG. 31, if the sealing film is cut, the film side guide plate operating rod 6351 and the film heating block 6310 are moved down by operation of the pneumatic cylinder 6340 for film heating block. Meanwhile, because a lower end of the film side guide plate operating rod 6351 is located at a lower side of the lower surface of the film heating block 6310, the film side guide plate 6222 is rotated to the outside of the edge portion of the sealing film by the film side guide plate operating rod 6351 so that the sealing film is mounted on the upper surface of the multi-well plate 400 for PCR. If the sealing film is mounted on the upper surface of the multi-well plate 400 for PCR, the film heating block 6310 is further moved downward so as to thermally compress the sealing film to the upper surface of the multi-well plate 400 for PCR.

Referring to FIG. 28, if the film heating block 6310 thermally compresses the sealing film to the upper surface of the multi-well plate 400 for PCR, the intermediate plate 6260 for sealing device is moved to the front side of the lower plate 6410 for sealing device. Thus, the film guide plate 6212, the lower compressing portion 6230, the film side guide plate 6222, the upper compressing portion supporting block 6240, the upper plate 6320 for sealing device and the sealed loading plate 6294 are moved together with the intermediate plate 6260 for sealing device. Meanwhile, since the sealing film is still compressed by the lower and upper compressing portions 6230 and 6243, the sealing film is unwound from the film roller 6120 and moved to the front side of the lower plate 6410 for sealing device.

Referring to FIG. 28, if the sealing film is unwound from the film roller 6120 and moved to the front side of the lower plate 6410 for sealing device, the upper compressing portion supporting block 6240 and the film heating block 6310 are moved upward. If the film heating block 6310 is moved upward, the sealed loading plate 6294 is protruded to the front side of the intermediate plate 6260 for sealing device.

Referring to FIGS. 34 and 35, the first embodiment includes the vortex mixer 7100. The vortex mixer 7100 functions to apply vibration to the multi-well plate 400 for PCR, which is moved from the sealing device 6000, and uniformly mix substances injected into the multi-well plate 400 for PCR. Meanwhile, the vortex mixer 7100 includes a motor 7100M for vortex mixer.

Referring to FIG. 35, a driving shaft 7110 for vortex mixer is connected to the motor 7100M for vortex mixer. The driving shaft 7110 for vortex mixer is disposed up and down.

Referring to FIG. 35, a driven shaft 7130 for vortex mixer is connected to an upper side of the driving shaft 7110 for vortex mixer. The driving shaft 7110 for vortex mixer and the driven shaft 7130 for vortex mixer are connected to each other through a coupler 7120.

Referring to FIG. 35, an eccentric driven shaft 7140 for vortex mixer is integrally formed with an upper portion of the driven shaft 7130 for vortex mixer. The eccentric driven shaft 7140 for vortex mixer is eccentrically connected to the driven shaft 7130 for vortex mixer so that a longitudinal center line thereof is not coincided with that of the driven shaft 7130 for vortex mixer. The eccentric driven shaft 7140 for vortex mixer is disposed to be protruded to an upper side of an upper plate 7160 for vortex mixer.

Referring to FIG. 35, an eccentric driven shaft bearing 7150 is installed at an upper portion of the eccentric driven shaft 7140 for vortex mixer.

Referring to FIGS. 34 and 35, one end of a separation preventing spring 7170 is fixedly connected to an outer surface of the eccentric driven shaft bearing 7150, and the other end thereof is fixedly connected to a spring supporter protruded from an upper surface of the upper plate 7160 for vortex mixer. The separation preventing spring 7170 is provided in plural so as to be arranged along the outer surface of the eccentric driven shaft bearing 7150 at regular intervals. The separation preventing spring 7170 functions to apply centripetal force to the eccentric driven shaft bearing 7150 and thus to allow the eccentric driven shaft bearing 7150 to facilely carry out its circular movement.

FIGS. 34 and 35, a barycenter block 7190 is fixed to a lower end of the eccentric driven shaft 7140 for vortex mixer. The barycenter block 7190 is fixedly disposed at the eccentric driven shaft 7140 for vortex mixer so as to be protruded in an opposite direction to an eccentric direction of the eccentric driven shaft 7140 for vortex mixer with respect to the driven shaft 7130 for vortex mixer. In this case, the barycenter block 7190 is fixedly inserted onto the eccentric driven shaft 7140 for vortex mixer.

FIGS. 34 and 35, a mounting plate 7180 for vortex mixer is fixedly installed at an upper end of the eccentric driven shaft bearing 7150, and the multi-well plate 400 for PCR is mounted on an upper surface of the mounting plate 7180 for vortex mixer.

Referring to FIG. 34, a plate spring 7182 is provided at the mounting plate 7180 for vortex mixer so as to firmly mount the multi-well plate 400 for PCR. The plate spring 7182 is provided in plural. Since the plurality of plate springs 7182 are elastically contacted with side surfaces of the multi-well plate 400 for PCR so that the multi-well plate 400 for PCR is firmly mounted on the upper surface of the mounting plate 7180 for vortex mixer.

Due to the circular movement of the eccentric driven shaft bearing 7150, vibration is applied to the multi-well plate 400 for PCR in all directions, and thus the substance injected into the multi-well plate 400 for PCR are mixed. Meanwhile, the mixing operation using the vortex mixer 7100 is carried out by vibrating the multi-well plate 400 for PCR in all directions. Therefore, after the mixing operation using the vortex mixer 7100, part of the substance injected into the multi-well plate 400 for PCR is attached to a side wall of each well of the multi-well plate 400 for PCR and thus remained thereon.

Referring to FIG. 36, the first embodiment includes the centrifugal separator 7200. The centrifugal separator 7200 functions to exert centripetal force to the multi-well plate 400 for PCR so that the substance remained on the side wall of each well of the multi-well plate 400 for PCR is separated and then moved to a bottom surface of each well. Meanwhile, the centrifugal separator 7200 is provided with a motor 7200M for centrifugal separator. A driven shaft 7230 for centrifugal separator is connected to the motor 7200M for centrifugal separator so as to be rotated by the motor 7200M for centrifugal separator. The structure for connecting the driven shaft 7230 for centrifugal separator and the motor 7200M for centrifugal separator is the same as that for connecting the motor 7100M for vortex mixer and the driven shaft 7130 for vortex mixer.

Referring to FIG. 36, a rotational plate 7240 for centrifugal separator is integrally formed with the driven shaft 7230 for centrifugal separator. A center portion of the rotational plate 7240 for centrifugal separator is coupled to the driven shaft 7230 for centrifugal separator. The rotational plate 7240 for centrifugal separator is formed into an "I" shape so that an opening portion is formed at both side ends thereof.

Referring to FIG. 36, a mounting block 7250 for centrifugal separator is rotatably disposed at the opening portion formed at both side ends. The mounting block 7250 for centrifugal separator is disposed so as to be rotated by centripetal force when the rotational plate 7240 for centrifugal separator is rotated, such that an upper surface thereof is inclined to an inside portion and a lower surface thereof is inclined to an outside thereof. The multi-well plate 400 for PCR is mounted on the rotational plate 7240 for centrifugal separator. Therefore, if the rotational plate 7240 for centrifugal separator is rotated, the multi-well plate 400 for PCR is inclined together with the block 7250 for centrifugal separator so that the bottom surface of each well of the multi-well plate 400 for PCR is inclined to the outside. Therefore, after the mixing operation using the vortex mixer 7100, the substance remained at the side wall of each well of the multi-well plate 400 for PCR is separated by centripetal force and then moved to the bottom surface of each well.

Referring to FIG. 1, the real-time quantitative amplification device 8000 is mounted on the main intermediate plate 12000-1. The real-time quantitative amplification device 8000 functions to amplify the nucleic acid in the multi-well plate 400 for PCR to which the centripetal force is applied by the centrifugal separator 7200 and then to measure an amount of the amplified nucleic acid in real time.

The real-time quantitative amplification device 8000 stores information of a target nucleic acid which is dispensed to each well of the multi-well plate 400 for PCR and a biological sample containing the target nucleic acid dispensed to each well. The information of the biological sample includes various contents for distinguishing or classifying the biological sample, such as kind, sex and age of an object from which the biological sample is obtained. Further, the real-time quantitative amplification device 8000 is provided with a display unit for displaying an amount of the amplified target nucleic acid dispensed to each well of the multi-well plate 400 for PCR in real time. Furthermore, the real-time quantitative amplification device 8000 stores the amount of the amplified target nucleic acid dispensed to each well of the multi-well plate 400 for PCR. Meanwhile, the real-time quantitative amplification device 8000 can transfer the amount of the amplified target nucleic acid to an external device such as analysis instrument.

Referring to FIG. 37, the moving device 9000 for multi-well plate for PCR is provided with a movement guide block 9100 for multi-well plate for PCR. Referring to FIG. 1, the movement guide block 9100 for multi-well plate for PCR is disposed at an upper side of a fore-end of the main intermediate plate 12000-1 in a left and right direction. That is, the movement guide block 9100 for multi-well plate for PCR is disposed in the left and right direction at a front upper side of the deck 1000 transferred by the deck transferring unit 2400.

Referring to FIG. 37, a left and right moving motor 9210M for multi-well plate for PCR is fixed to one side of the movement guide block 9100 for multi-well plate for PCR.

Referring to FIG. 37, a driving shaft for left and right movement of the multi-well plate for PCR is connected to the left and right moving motor 9210M for multi-well plate for PCR, and a driving pulley 9211 for left and right movement of the multi-well plate for PCR is inserted onto the driving shaft for left and right movement of the multi-well plate for PCR.

Referring to FIG. 37, a driven shaft for left and right movement of the multi-well plate for PCR is connected to one side of the movement guide block 9100 for multi-well plate for PCR, and a driven pulley 9212 for left and right movement of the multi-well plate for PCR is inserted onto the driven shaft for left and right movement of the multi-well plate for PCR. Although not shown in the drawings, the driving pulley 9211 for left and right movement of the multi-well plate for PCR and the driven pulley 9212 for left and right movement of the multi-well plate for PCR are wound with a left and right moving belt (not shown) for multi-well plate for PCR. Meanwhile, one side of a left and right moving block 9210 for multi-well plate for PCR is coupled to the left and right moving belt (not shown) for multi-well plate for PCR. Therefore, when the left and right moving motor 9210M for multi-well plate for PCR is operated, the left and right moving belt (not shown) for multi-well plate for PCR and the left and right moving block 9210 for multi-well plate for PCR are moved in the left and right direction of the deck 1000.

Referring to FIG. 37, a front and rear moving guide block 9320 for multi-well plate for PCR is fixed to the other side of the left and right moving block 9210 for multi-well plate for PCR. The front and rear moving guide block 9320 for multi-well plate for PCR is arranged in the front and rear direction of the deck 1000.

Referring to FIG. 37, a front and rear moving motor 9310M for multi-well plate for PCR is fixed to the front and rear moving guide block 9320 for multi-well plate for PCR.

Referring to FIG. 37, a front and rear moving block 9310 for multi-well plate for PCR is disposed at the front and rear moving guide block 9320 for multi-well plate for PCR. The front and rear moving block 9310 for multi-well plate for PCR is disposed to be moved in the front and rear direction of the deck 1000 when the front and rear moving motor 9310M for multi-well plate for PCR is operated. In other words, a driving shaft for front and rear movement for the multi-well plate for PCR is connected to the front and rear moving motor 9310M for multi-well plate for PCR, and a driving pulley 9311 for front and rear movement of the multi-well plate for PCR is inserted onto the driving shaft for front and rear movement for the multi-well plate for PCR. Meanwhile, a ball screw shaft 9313 for front and rear movement of the multi-well plate for PCR is rotatably disposed at the front and rear moving guide block 9320 for multi-well plate for PCR. A front and rear moving block 9314 for multi-well plate for PCR is inserted onto the ball screw shaft 9313 for front and rear movement of the multi-well plate for PCR so as to be moved in the front and rear direction of the deck 1000 when the ball screw shaft 9313 for front and rear movement of the multi-well plate for PCR is rotated. Therefore, the front and rear moving block 9314 for multi-well plate for PCR is a ball screw nut for front and rear movement of the multi-well plate for PCR, in which a female thread corresponding to a male thread formed on the ball screw shaft 9313 for front and rear movement of the multi-well plate for PCR is formed. A driven pulley 9312 for front and rear movement of the multi-well plate for PCR is inserted onto one end of the ball screw shaft 9313 for front and rear movement of the multi-well plate for PCR. Meanwhile, the driving pulley 9311 for front and rear movement of the multi-well plate for PCR and the driven pulley 9312 for front and rear movement of the multi-well plate for PCR are wound with a moving belt (not shown) for front and rear movement of the multi-well plate for PCR.

Referring to FIG. 37, an up and down moving guide block 9410 for multi-well plate for PCR is fixed to the front and rear moving block 9314 for multi-well plate for PCR. Meanwhile, an up and down moving motor 9510M for multi-well plate for PCR is also fixed to the up and down moving guide block 9410 for multi-well plate for PCR.

Referring to FIG. 37, a driving shaft for up and down movement of the multi-well plate for PCR is connected to the up and down moving motor 9510M for multi-well plate for PCR, and a driving pulley 9511 up and down movement of the multi-well plate for PCR is inserted onto the driving shaft for up and down movement of the multi-well plate for PCR.

Referring to FIG. 37, a ball screw shaft for up and down movement of the multi-well plate for PCR is rotatably disposed at the front and rear moving block 9314 for multi-well plate for PCR so as to be spaced apart from the driving shaft for up and down movement of the multi-well plate for PCR. A driven pulley 9512 for up and down movement of the multi-well plate for PCR is inserted onto an upper end of the ball screw shaft for up and down movement of the multi-well plate for PCR. Although not shown in the drawings, a ball nut (not shown) for up and down movement of the multi-well plate for PCR is inserted onto the ball screw shaft for up and down movement of the multi-well plate for PCR so as to be moved up and down when the ball screw shaft for up and down movement of the multi-well plate for PCR is rotated. Therefore, a female thread corresponding to a male thread formed on the ball screw shaft for up and down movement of the multi-well plate for PCR is formed at the ball nut (not shown) for up and down movement of the multi-well plate for PCR.

Referring to FIG. 37, an upper end of an up and down moving rod 9515 for multi-well plate for PCR is fixedly connected to the ball nut (not shown) for up and down movement of the multi-well plate for PCR, and a lower end thereof is fixedly connected to a grasping means 9600 for grasping the multi-well plate for PCR. Therefore, the grasping means 9600 for grasping the multi-well plate for PCR is moved up and down by the up and down moving motor 9510M for multi-well plate for PCR.

Referring to FIG. 38, the grasping means 9600 for grasping the multi-well plate for PCR is provided with a grasping portion case 7610. An upper surface of the grasping portion case 7610 is fixed to the lower end of the up and down moving rod 9515 for multi-well plate for PCR.

Referring to FIG. 38, a grasping motor 9600M for multi-well plate for PCR, a grasping portion pinion 9620, a grasping portion rack 9630 and a grasping portion spring 9640 are mounted in the grasping portion case 7610.

Referring to FIG. 38, the grasping portion pinion 9620 is connected to the grasping motor 9600M for multi-well plate for PCR so as to be rotated when the grasping motor 9600M for multi-well plate for PCR is operated.

Referring to FIG. 38, the grasping portion rack 9630 is engaged with the grasping portion pinion 9620 so as to be moved linearly when the pinion 9620 for grasping portion is rotated. The grasping portion rack 9630 is connected to a grasping portion. Therefore, when the up and down moving motor 9510M for multi-well plate for PCR is operated, two grasping portions 9660 are moved inwardly so as to grasp the both side ends of the multi-well plate 400 for PCR.

Therefore, the moving device 9000 for multi-well plate for PCR moves the multi-well plate 400 for PCR, in which the target nucleic acid is dispensed, to the sealing device 6000, and moves the multi-well plate 400 for PCR, which is sealed by the sealing device 6000, to the vortex mixer 7100, and moves the multi-well plate 400 for PCR, to which vibration is applied by the vortex mixer 7100, to the centrifugal separator 7200, and then moves the multi-well plate 400 for PCR, to which centripetal force is applied by the centrifugal separator 7200, to the real-time quantitative amplification device 8000.

Referring to FIG. 38, one end of the grasping portion spring 9640 is fixed to the grasping portion case 7610, and the other end thereof is fixed to the grasping portion rack 9630. The grasping spring 9640 functions to provide inwardly directed elastic force to the grasping portion and thus to maintain the state that the grasping portion 9660 continuously grasps the both side ends of the multi-well plate 400 for PCR, even when the grasping motor 9600M for multi-well plate for PCR is turned off. Therefore, it is prevented that the multi-well plate 400 for PCR is separated from the grasping portion 9660 in the event of a power outage.

Referring to FIG. 1, a through-opening 12000-1H is formed in the main intermediate plate 12000-1. A multi-well plate collecting container is disposed at a lower side of the through-opening 12000-1H. The multi-well plate collecting container is disposed at the main lower plate 12000-2. The multi-well plate 400 for PCR, which passes through the amplifying process in the real-time quantitative amplification device 8000, is transferred by the moving device 9000 for multi-well plate for PCR and then collected in the multi-well plate collecting container through the through-opening 12000-1H.

Second Embodiment

A second embodiment relates to an automatic purification and reaction preparing device for biological sample analysis according to the present invention.

The automatic purification and reaction preparing device according to the second embodiment of the present invention includes a syringe block 3000, a syringe block moving unit 4000, a solution drip tray 4375, a solution drip tray moving unit, a puncher 12100, an evaporation block 12200 for multi-well plate, a magnetic field applying unit 5100, a heating unit 5200 and a waste liquor discharging part 12300. The description thereof is the same as that in the first embodiment.

Third Embodiment

A third embodiment relates to a method for automatic nucleic acid purification and real-time quantification of gene amplification.

FIG. 40 is a flow chart of a third embodiment of the present invention.

Referring to FIG. 40, the third embodiment includes a step S 1000 of introducing a deck, a step S2000 of moving the deck, a step S3000 of purifying a target nucleic acid, a step S4000 of dispensing the target nucleic acid, a step S5000 of performing a first movement of a multi-well plate for PCR, a step S6000 of moving an original position of the deck, a step S7000 of sealing the multi-well plate for PCR, a step S8100 of performing a second movement of the multi-well plate for PCR, a step S8200 of mixing a solution injected into the multi-well plate for PCR, a step S8300 of performing a third movement of the multi-well plate for PCR, a step S8400 of sinking the solutions injected into the multi-well plate for PCR, a step S8500 of performing a fourth movement of the multi-well plate for PCR, a step S9000 of performing real-time quantitative amplification of the target nucleic acid, and a step S 10000 of performing a fifth movement of the multi-well plate for PCR.

Referring to FIGS. 3, 6 and 7, in the step S 1000 of introducing the deck, a plurality of decks 1000 are introduced through the door 2000C-1 into the storing case 2000C. The plurality of decks 1000 are stacked in the stacking rack 2100 of the storing case 2000C.

Referring to FIGS. 4 and 5, the multi-well plate 100 for biological sample, the plurality of multi-well plate 200 for purification, the plurality of pipette racks 300 and the plurality of multi-well plate 400 for PCR are loaded in the certain order in each deck 1000 introduced into the storing case 2000C. The plurality of multi-well plate 200 for purification include a multi-well plate 210 for cell lysis solution, a multi-well plate 220 for magnetic particle dispersion solution, a multi-well plate 230 for nucleic acid binding solution, a multi-well plate 241 for first cleaning solution, a multi-well plate 242 for second cleaning solution, a multi-well plate 243 for third cleaning, and a multi-well plate 250 for nucleic acid elution solution. The plurality of pipette racks 300 include the purification pipette rack 310 and the dispensation pipette rack 320. The plurality of multi-well plate 400 for PCR includes the first multi-well plate 410 for PCR and the second multi-well plate 420 for PCR. A biological sample containing a target substance is injected into the multi-well plate 100 for biological sample, and a cell lysis solution is injected into the multi-well plate 210 for cell lysis solution, and a magnetic particle suspension including magnetic particles is injected into the multi-well plate 220 for magnetic particle dispersion solution, and an acid binding solution is injected into the multi-well plate 230 for nucleic acid binding solution, and a first cleaning solution is injected into the multi-well plate 241 for first cleaning solution, and a second cleaning solution is injected into the multi-well plate 242 for second cleaning solution, and a third cleaning solution is injected into the multi-well plate 243 for third cleaning solution, and a nucleic acid elution solution is injected into the multi-well plate 250 for nucleic acid elution solution. In other words, a plurality of solutions for purifying the target nucleic acid in the target substance injected into the multi-well plate 100 for biological sample are injected into the plurality of multi-well plates 200 for purification. A plurality of purification pipettes P1 are mounted in the purification pipette rack 310, and a plurality of dispensation pipettes P2 having smaller a capacity than the plurality of purification pipettes P1 are mounted in the dispensation pipette rack 320. A reaction mixture for real-time quantitative PCR is injected into the first multi-well plate 410 for PCR and the second multi-well plate 420 for PCR.

Referring to FIGS. 1 and 3, in the step S2000 of moving the deck, the deck 1000 introduced in the step S 1000 of introducing the deck is moved to the lower side of the syringe block 3000 having the plurality of mounting portions 3330 (referring to FIG. 16). Referring to FIGS. 7 and 13, the step S1000 of introducing the deck is carried out by the deck withdrawal slider 2450 of the deck transferring unit 2400 (referring to FIG. 12).

In the step S3000 of purifying the target nucleic acid, the target nucleic acid is purified using the syringe block 3000 (referring to FIG. 16) in which the plurality of pipettes P (referring to FIG. 4) for sucking and discharging a fluid substance are removably installed, the multi-well plate 100 (referring to FIG. 4) for biological sample, and the plurality of multi-well plates 200 (referring to FIG. 4) for purification. This will be described fully in a fourth embodiment of the present invention.

In the step S4000 of dispensing the target nucleic acid, the target nucleic acid purified in the step S3000 of purifying the target nucleic acid is dispensed to each multi-well plate 410, 420 (referring to FIG. 4) for PCR using the syringe block 3000 (referring to FIG. 16) in which the plurality of pipettes P (referring to FIG. 4) for sucking and discharging a fluid substance are removably installed. In this case, the plurality of pipettes P (referring to FIG. 4) installed in the syringe block 3000 (referring to FIG. 16) are the plurality of dispensation pipettes P2 (referring to FIG. 4).

Referring to FIG. 3, in the step S5000 of performing the first movement of the multi-well plate for PCR, the multi-well plate 410, 420 (referring to FIG. 4) for PCR, in which the target nucleic acid is dispensed, is moved to the sealing device 6000. The step S5000 of performing the first movement of the multi-well plate for PCR is carried out by the moving device 9000 for multi-well plate for PCR.

Referring to FIGS. 7 and 13, in the step S6000 of moving the original position of the deck, the deck 1000 (referring to FIG. 4) is moved to the storing case 2000C (referring to FIG. 6) by the deck withdrawal slider 2450 of the deck transferring unit 2400 (referring to FIG. 12) and then stacked in the stacking rack 2100 (referring to FIG. 7). The step S6000 of moving the original position of the deck is carried out after the step S5000 of performing the first movement of the multi-well plate for PCR.

Referring to FIGS. 28 to 32, in the step S7000 of sealing the multi-well plate for PCR, the upper surface of the multi-well plate 400 (referring to FIG. 4) for PCR, in which the target nucleic acid is dispensed, is sealed by using the sealing device 6000.

Referring to FIG. 3, in the step S8100 of performing the second movement of the multi-well plate for PCR, the multi-well plate 400 (referring to FIG. 4) for PCR, of which the upper surface is sealed by using the sealing device 6000, is moved to the vortex mixer 7100. The step S8100 of performing the second movement of the multi-well plate for PCR is carried out after the step S7000 of sealing the multi-well plate for PCR.

Referring to FIGS. 34 and 35, in the step S8200 of mixing the solution injected into the multi-well plate for PCR, vibration is applied to the multi-well plate 400 (referring to FIG. 4) for PCR, of which the upper surface is sealed, by using the vortex mixer 7100, and thus the solution injected into the multi-well plate 400 for PCR is mixed.

Referring to FIG. 3, in the step S8300 of performing the third movement of the multi-well plate for PCR, the multi-well plate 400 for PCR, of which the upper surface is sealed, is moved to the centrifugal separator 7200 by using the moving device 9000 for multi-well plate for PCR. The step S8300 of performing the third movement of the multi-well plate for PCR is carried out after the step S8200 of mixing the solution injected into the multi-well plate for PCR.

Referring to FIG. 36, in the step S8400 of sinking the solutions injected into the multi-well plate for PCR, centripetal force is applied to the multi-well plate 400 for PCR using the centrifugal separator 7200. In the step S8400 of sinking the solutions injected into the multi-well plate 400 for PCR, the substance remained on the side wall of each well of the multi-well plate 400 for PCR is separated by the centripetal force and then moved to the bottom surface of each well.

Referring to FIG. 3, the step S8500 of performing the fourth movement of the multi-well plate for PCR, the multi-well plate 400 for PCR is moved to the real-time quantitative amplification device 8000 by using the moving device 9000 for multi-well plate for PCR. The step S8500 of performing the fourth movement of the multi-well plate for PCR is carried out after the step S8400 of sinking the solutions injected into the multi-well plate for PCR.

In the step S9000 of performing real-time quantitative amplification of the target nucleic acid, the target nucleic acid in the multi-well plate 400 for PCR is amplified in real time using the real-time quantitative amplification device 8000. Meanwhile, the real-time quantitative amplification device 8000 obtains real-time quantitative amplification data of the nucleic acid, which shows an amplified amount of the target nucleic acid over time, and then displays the obtained data on a screen or analyzes the obtained data. Further, the real-time quantitative amplification device 8000 may transfer the real-time quantitative amplification data of the nucleic acid to an external device such as analysis instrument.

Referring to FIG. 1, in the step S10000 of performing the fifth movement of the multi-well plate for PCR, the multi-well plate 400 for PCR, in which the real-time amplification is performed, is moved to the multi-well plate collecting container through the through-opening 12000-1H using the moving device 9000 for multi-well plate for PCR.

In the third embodiment, in order to perform the target nucleic acid purification and the purified target nucleic acid amplification with respect to each biological sample loaded in the plurality of decks 1000, the steps from S2000 to S10000 are repeatedly carried out corresponding to the number of decks 1000 introduced into the storing case 2000C. That is, referring to FIG. 40, if one of the plurality of decks 1000 is moved to the storing case 2000C through the step S6000 of moving the original position of the deck, another one of the decks 1000 is moved to the lower side of the syringe block 3000 through the step S10000 of performing the fifth movement of the multi-well plate for PCR.

Meanwhile, referring to FIG. 40, the steps from S7000 to S10000 out of whole steps which are carried out in order to perform the target nucleic acid purification and the purified target nucleic acid amplification with respect to the biological sample injected in the one of the decks 1000 are simultaneously carried out together with the steps from S2000 to S6000 out of another whole steps which are carried out in order to perform the target nucleic acid purification and the purified target nucleic acid amplification with respect to the biological sample injected in the other one of the decks 1000.

Fourth Embodiment

A fourth embodiment relates to a method for automatic nucleic acid purification using the second embodiment.

FIG. 41 is a flow chart of the fourth embodiment of the present invention, and FIG. 42 is a block diagram of a second removing step of FIG. 41.

Referring to FIG. 41, the fourth embodiment includes a step S2000 of moving a deck, a step S3011 of performing a first punching operation of a sealing film, a step S3020 of mixing with a cell lysis solution, a step S3030 of performing a first heating operation, a step S3012 of performing a second punching operation of the sealing film, a step S3040 of mixing with a nucleic acid binding solution, a step S3013 of performing a third punching operation of the sealing film, a step S3050 of mixing with a magnetic particle dispersion solution, a step S3060 of applying a first magnetic field, a step S3070 of performing a first removing operation, a step S3014 of performing a fourth punching operation of the sealing film, a step S3080 of performing a first cleaning operation, a step S3090 of applying a second magnetic field, a step S3100 of performing a second removing operation, a step S3015 of performing a fifth punching operation of the sealing film, a step S3110 of separating a nucleic acid, a step S3120 of applying a third magnetic field and a step S3130 of collecting a target nucleic acid containing solution.

Referring to FIGS. 1 and 3, the multi-well plate 100 for biological sample, the plurality of multi-well plate 200 for purification, the plurality of pipettes P and the plurality of multi-well plate 400 for PCR are loaded in the deck 1000 moved through the in the step S2000 of moving the deck. The plurality of multi-well plate 200 for purification include a multi-well plate 210 for cell lysis solution, a multi-well plate 220 for magnetic particle dispersion solution, a multi-well plate 230 for nucleic acid binding solution, a multi-well plate 241 for first cleaning solution, a multi-well plate 242 for second cleaning solution, a multi-well plate 243 for third cleaning, and a multi-well plate 250 for nucleic acid elution solution. A biological sample containing a target substance is injected into the multi-well plate 100 for biological sample. A cell lysis solution is injected into the multi-well plate 210 for cell lysis solution, and a magnetic particle suspension including magnetic particles is injected into the multi-well plate 220 for magnetic particle dispersion solution, and an acid binding solution is injected into the multi-well plate 230 for nucleic acid binding solution, and a first cleaning solution is injected into the multi-well plate 241 for first cleaning solution, and a second cleaning solution is injected into the multi-well plate 242 for second cleaning solution, and a third cleaning solution is injected into the multi-well plate 243 for third cleaning solution, and a nucleic acid elution solution is injected into the multi-well plate 250 for nucleic acid elution solution. Meanwhile, the plurality of pipettes P includes a plurality of purification pipettes P1 and a plurality of dispensation pipettes P2 having smaller a capacity than the plurality of purification pipettes P1. The plurality of multi-well plate 400 for PCR includes the first multi-well plate 410 for PCR and the second multi-well plate 420 for PCR.

Referring to FIGS. 13 to 16, in the step S3011 of performing the first punching operation of the sealing film, first of all, the syringe block 3000 is moved so as to compress the upper surface of the puncher 12100, such that the plurality of first mounting portions 3310 are inserted into the plurality of puncher inserting grooves formed in the upper surface of the puncher 12100. If the puncher 12100 is mounted in the first mounting portions 3310, the syringe block 3000 is moved so as to pierce holes in the sealing film for sealing an upper surface of the multi-well plate 210 for cell lysis solution. Because the plurality of awl-shaped puncher pins 12110 are formed to be protruded from the lower surface of the puncher 12100, when the syringe block 3000 is moved down, the plurality of puncher pins 12110 can pierce holes in the sealing film for sealing the upper surface of the multi-well plate 210 for cell lysis solution. After the holes are formed in the sealing film for sealing the upper surface of the multi-well plate 210 for cell lysis solution, the syringe block 3000 is moved so that the puncher 12100 is returned to its original position and then separated from the first mounting portion 3310. In case that the puncher guide hole (not shown) in which the lower end of the second small-diameter separation rod 3732-1 (referring to FIG. 20) is inserted is formed to have a sufficient depth, the puncher 12100 is separated from the first mounting portion 3310 by compression of the first lower separation plate 3720 (referring to FIG. 18). Otherwise, the puncher 12100 is separated from the first mounting portion 3310 by compression of the second separation rod 3732.

Referring to FIGS. 13 and 16, in the step S3020 of mixing with the cell lysis solution, the syringe block 3000 is moved so that the plurality of first mounting portions 3310 are inserted onto the upper portions of the plurality of pipettes P and thus the plurality of pipettes P are mounted in the plurality of first mounting portions 3310. Then, the syringe block 3000 is moved so as to suck the cell lysis solution injected into the multi-well plate 210 for cell lysis solution through the plurality of pipettes P. And the syringe block 3000 is moved again so that the cell lysis solution sucked in the plurality of pipettes P is injected into the multi-well plate 100 for biological sample. Accordingly, a mixed solution of the biological sample and the cell lysis solution is formed in the multi-well plate 100 for biological sample. By repeatedly sucking and discharging the mixed solution using the plurality of pipettes P, it is possible to obtain the uniformly mixed solution.

Referring to FIGS. 7, 13 and 27, in the step S3030 of performing the first heating operation, the lower portion of the multi-well plate 100 for biological sample is heated by the heating unit 5200 (referring to FIG. 2) so as to heat the mixed solution. Therefore, the cell lysis in the biological sample contained in the mixed solution is rapidly and safely performed.

Referring to FIGS. 13 to 16, in the step S3012 of performing the second punching operation of the sealing film, the puncher 12100 is mounted in the first mounting portion 3310 so as to pierce holes in the sealing film for sealing an upper surface of the multi-well plate 230 for nucleic acid binding solution, and returned to its original position, and then separated from the first mounting portion 3310. The step S3012 of performing the second punching operation of the sealing film is carried out after the step S3020 of mixing with the cell lysis solution. Meanwhile, before the step S3012 of performing the second punching operation of the sealing film, the syringe block 3000 is moved so that the plurality of pipettes P are separated form the plurality of first mounting portions 3310, and then the syringe block 3000 is returned to its original position. Referring to FIG. 18, if the first separation rod 3731 is moved down, the first lower separation plate 3720 is also moved down, and thus the plurality of pipettes P are compressed by the first lower separation plate 3720. The plurality of pipettes P are separated from the first mounting portions 3310 by the compression of the first lower separation plate 3720.

Referring to FIGS. 13 and 16, in the step S3040 of mixing with the nucleic acid binding solution, the plurality of pipettes P are mounted in the plurality of first mounting portions 3310. And the syringe block 3000 is moved so as to suck the mixed solution filled in the multi-well plate 100 for biological sample and then to inject the mixed solution into the multi-well plate 230 for nucleic acid binding solution. Therefore, the mixed solution and the nucleic acid binding solution are mixed in the multi-well plate 230 for nucleic acid binding solution.

Referring to FIGS. 13 to 16, in the step S3013 of performing the third punching operation of the sealing film, the puncher 12100 is mounted in the first mounting portion 3310 so as to pierce holes in the sealing film for sealing an upper surface of the multi-well plate 220 for magnetic particle dispersion solution, and returned to its original position, and then separated from the first mounting portion 3310. The step S3013 of performing the third punching operation of the sealing film is carried out after the step S3040 of mixing with the nucleic acid binding solution. Meanwhile, before the step S3040 of mixing with the nucleic acid binding solution, the syringe block 3000 is moved so that the plurality of pipettes P mounted in the plurality of first mounting portions 3310 are separated and then returned to its original position.

Referring to FIGS. 13 and 16, in the step S3050 of mixing with the magnetic particle dispersion solution, first of all, the plurality of pipettes P are mounted in the plurality of first mounting portions 3310. And the syringe block 3000 is moved so as to suck the nucleic acid binding solution filled in the multi-well plate 230 for nucleic acid binding solution and the mixture of the biological sample and then to inject them into the multi-well plate 220 for magnetic particle dispersion solution. Therefore, the nucleic acid binding solution and the mixture of the biological sample are mixed in the multi-well plate 220 for magnetic particle dispersion solution.

Referring to FIGS. 7, 13 and 27, in the step S3060 of applying the first magnetic field, magnetic field is applied to the lower portion of the multi-well plate 220 for magnetic particle dispersion solution using the magnetic field applying unit 5100 (referring to FIG. 1), and thus applied to the mixture mixed with the magnetic particle suspension. Referring to FIG. 26, in the S3060 of applying the first magnetic field, the rod-shaped magnets 5110 which are disposed to be spaced apart form each other are moved upward. Therefore, the upper portions of the magnets 5110 enclose each well formed at the multi-well plate 220 for magnetic particle dispersion solution.

Referring to FIGS. 13 and 16, in the step S3070 of performing the first removing operation, sucking force is applied to the mixture mixed with the magnetic particle suspension filled in the multi-well plate 220 for magnetic particle dispersion solution by using the plurality of pipettes P mounted in the syringe block 3000. Therefore, in the step S3070 of performing the first removing operation, magnetic particles of the magnetic particle suspension and substance attached to the magnetic particles in the mixture mixed with the magnetic particle suspension are maintained in the state that they are attached to the side wall of the multi-well plate 220 for magnetic particle dispersion solution. Therefore, the mixture except the magnetic particles and the substance attached to the magnetic particles is sucked by the plurality of pipettes P mounted in the syringe block 3000. If the mixture except the magnetic particles and the substance attached to the magnetic particles is sucked, the syringe block 3000 is moved and the sucked mixture is discharged through the waste liquor discharging part 12300 (referring to FIG. 13).

Referring to FIGS. 13 to 16, in the step S3014 of performing the fourth punching operation of the sealing film, the puncher 12100 is mounted in the first mounting portion 3310 so as to pierce holes in the sealing film for sealing an upper surface of the multi-well plate 241, 242, 243 for cleaning solution, and returned to its original position, and then separated from the first mounting portion 3310. The step S3014 of performing the fourth punching operation of the sealing film is carried out after the step S3070 of performing the first removing operation. Meanwhile, before the step S3070 of performing the first removing operation, the syringe block 3000 is moved so that the plurality of pipettes P mounted in the plurality of first mounting portions 3310 are separated and then returned to its original position.

Referring to FIGS. 13 and 16, in the step S3080 of performing the first cleaning operation, the plurality of pipettes P are mounted in the plurality of first mounting portions 3310. And the syringe block 3000 is moved so as to suck the cleaning solution injected into the multi-well plate 241, 242, 243 for cleaning solution and then to inject the cleaning solution into the multi-well plate 220 for magnetic particle dispersion solution using the plurality of pipettes P. Meanwhile, the step S3080 of performing the first cleaning operation is performed in the state that the magnetic field applied to the lower portion of the multi-well plate 220 for magnetic particle dispersion solution is removed. Therefore, in the multi-well plate 220 for magnetic particle dispersion solution, impurities except the target nucleic acid in the substances attached to the magnetic particles are separated from the magnetic particles.

Referring to FIGS. 7, 13 and 27, in the step S3090 of applying the second magnetic field, magnetic field is applied to the lower portion of the multi-well plate 220 for magnetic particle dispersion solution using the magnetic field applying unit 5100 (referring to FIG. 1), and thus applied to the mixture mixed with the cleaning solution.

Referring to FIGS. 13 and 16, in the step S3100 of performing the second removing operation, sucking force is applied to the mixture mixed with the cleaning solution filled in the multi-well plate 220 for magnetic particle dispersion solution by using the plurality of pipettes P mounted in the syringe block 3000. Meanwhile, step S3100 of performing the second removing operation is carried out in the state that magnetic field is applied to the lower portion of the multi-well plate 220 for magnetic particle dispersion solution by the step S3090 of applying the second magnetic field. Therefore, in the step S3100 of performing the second removing operation, the magnetic particles, to which the target nucleic acid is attached, in the mixture mixed with the cleaning solution are maintained in the state that they are attached to the side wall of the multi-well plate 220 for magnetic particle dispersion solution. Therefore, the mixture except the magnetic particles to which the target nucleic acid is attached is sucked by the plurality of pipettes P mounted in the syringe block 3000. If the mixture except the magnetic particles to which the target nucleic acid is sucked, the syringe block 3000 is moved and the sucked mixture is discharged through the waste liquor discharging part 12300 (referring to FIG. 13).

Meanwhile, the cleaning solution injected into the multi-well plate 241, 242, 243 for cleaning solution includes alcohol. Therefore, referring to FIG. 42, in order to remove the alcohol contained in the cleaning solution remained on the magnetic particles, the step S3100 of performing the second removing operation includes a step S3101 of performing a second heating operation, a step S3102 of preparing installation of an evaporation block for multi-well plate, a step S3103 of installing the evaporation block for multi-well plate, and a step S3104 of injecting compressed air.

Referring to FIGS. 7, 13 and 27, in the step S3101 of performing the second heating operation, the lower portion of the multi-well plate 220 for magnetic particle dispersion solution is heated by the heating unit 5200 (referring to FIG. 2), and thus the alcohol contained in the cleaning solution remained on the magnetic particles is also heated. Therefore, the alcohol contained in the cleaning solution remained on the magnetic particles is rapidly evaporated and removed.

In the step S3102 of preparing installation of an evaporation block for multi-well plate, the plurality of pipettes P mounted in the first mounting portions 3310 is moved to its original position and then separated.

Referring to FIGS. 13 to 16, in the step S3103 of installing the evaporation block for multi-well plate, the syringe block 3000 is moved so as to compress the upper surface of the evaporation block 12200 for multi-well plate, and thus the plurality of first mounting portions 3310 are inserted into the plurality of evaporation block inserting grooves 12200-G (referring to FIG. 21).

Referring to FIG. 19, the second mounting portion 12210 is protruded from the evaporation block 12200 for multi-well plate. The second mounting portion 12210 functions to removably install the plurality of pipettes P. Referring to FIGS. 19 and 20, the second separation plate 12220 is disposed at the second mounting portion 12210. The second separation plate 12220 is moved down so as to compress the upper portions of the plurality of pipettes P mounted in the second mounting portion 12220 and thus to separate them. Referring to FIGS. 19 and 20, the second separation pin 12230 is disposed at the evaporation block 12200 for multi-well plate so as to be movable up and down. When the second separation pin 12230 is moved down by the second separation rod 3732, the second separation pin 12230 is contacted with the second separation plate 12220 so as to compress down the second separation plate 12220. Referring to FIG. 22, the second separation plate 12220 is formed with the compressed air introduction hole 12200-H4 connected with a compressed air supplying tube.

In the step S3104 of injecting compressed air, the syringe block 3000 is moved so that the plurality of pipettes P are mounted in the second mounting portion 12210. And the syringe block 3000 is moved again so as to inject the compressed air into the multi-well plate 220 for magnetic particle dispersion solution using the plurality of pipettes P mounted in the evaporation block 12200 for multi-well plate. Therefore, the alcohol contained in the cleaning solution remained on the magnetic particles is rapidly evaporated and removed.

In the step S3105 of performing the fifth punching operation of the sealing film, first of all, the plurality of pipettes P mounted in the second mounting portion 12210 is moved to its original position and then separated from the second mounting portion 12210. The separation of the pipettes P mounted in the second mounting portion 12210 is carried out by the compression of the second separation plate 12220. Then, the evaporation block 12200 for multi-well plate mounted in the first mounting portion 3310 is moved to its original position and then separated from the first mounting portion 3310. The separation of the evaporation block 12200 for multi-well plate is carried out by the compression of the first lower separation plate 3720.

Referring to FIGS. 13 and 16, in the step S3015 of performing the fifth punching operation of the sealing film, after the puncher 12100 is mounted in the first mounting portion 3310 so as to pierce holes in the sealing film for sealing an upper surface of the multi-well plate 250 for nucleic acid elution solution, the puncher 12100 is moved to its original position and then separated. The step S3015 of performing the fifth punching operation of the sealing film is carried out after the step S3100 of performing the second removing operation.

Referring to FIGS. 13 and 16, in the step S3110 of separating the nucleic acid, the plurality of pipettes P are mounted in the plurality of first mounting portions 3310. And the syringe block 3000 is moved so as to suck the nucleic acid elution solution injected into the multi-well plate 250 for nucleic acid elution solution using the plurality of pipettes P and then to inject the solution into the multi-well plate 220 for magnetic particle dispersion solution. The step S3110 of separating the nucleic acid is carried out in the state that the magnetic field applied to the lower portion of the multi-well plate 220 for magnetic particle dispersion solution is removed. Therefore, in the multi-well plate 220 for magnetic particle dispersion solution, the target nucleic acid is separated from the magnetic particles.

Referring to FIGS. 7, 13 and 27, in the step S3120 of applying the third magnetic field, the magnetic field is applied to the lower portion of the multi-well plate 220 for magnetic particle dispersion solution using the magnetic field applying unit 5100 (referring to FIG. 1), and thus applied to the mixture mixed with the nucleic acid elution solution.

Referring to FIGS. 13 and 16, in the step S3130 of collecting the target nucleic acid containing solution, sucking force is applied to the mixture mixed with the nucleic acid elution solution filled in the multi-well plate 220 for magnetic particle dispersion solution by using the plurality of pipettes P mounted in the syringe block 3000. Meanwhile, the step S3130 of collecting the target nucleic acid containing solution is carried out in the state that the magnetic field is applied to the lower portion of the multi-well plate 220 for magnetic particle dispersion solution through the step S3120 of applying the third magnetic field. Therefore, in the step S3130 of collecting the target nucleic acid containing solution, the magnetic particles in the mixture mixed with the nucleic acid elution solution, which are separated from the target nucleic acid, are maintained in the state that they are attached to the side wall of the multi-well plate 220 for magnetic particle dispersion solution. Therefore, the target nucleic acid containing solution except the magnetic particles in the mixture mixed with the nucleic acid elution solution is sucked by the plurality of pipettes P mounted in the syringe block 3000.

In the fourth embodiment, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

In the fourth embodiment, in the step S3020 of mixing with the cell lysis solution, the step S3040 of mixing with the nucleic acid binding solution, the step S3050 of mixing with the magnetic particle dispersion solution, the step S3070 of performing the first removing operation, the step S3080 of performing the first cleaning operation and the a step S3100 of performing the second removing operation, the plurality of pipettes P which are removably mounted in the plurality of first mounting portions 3330 are the plurality of purification pipettes P1.

In the fourth embodiment, in the step S3110 of separating the nucleic acid and the step S3130 of collecting the target nucleic acid containing solution, the plurality of pipettes P which are removably separated from the plurality of first mounting portions 3330 are the plurality of dispensation pipettes P2 having smaller a capacity than the plurality of purification pipettes P1.

Fifth Embodiment

A fifth embodiment relates to a method for automatic viable cell count of pathogenic bacteria using real-time quantitative PCR.

FIG. 43 is a flow chart of the fifth embodiment of the present invention.

Referring to FIG. 43, the fifth embodiment includes a step S 1000 of introducing a deck, a step S1010 of culturing a pathogenic bacteria sample, a step S2000 of moving the deck, a step S3000 of purifying a target nucleic acid, a step S4000 of dispensing the target nucleic acid, a step S5000 of performing a first movement of a multi-well plate for PCR, a step S7000 of sealing the multi-well plate for PCR, a step S8300 of performing a third movement of the multi-well plate for PCR, a step S8400 of sinking the solutions injected into the multi-well plate for PCR, a step S8500 of performing a fourth movement of the multi-well plate for PCR, a step S9000 of performing real-time quantitative amplification of the target nucleic acid, and a step SF1000 of obtaining viable cell count.

Referring to FIGS. 3, 6 and 7, in the step S 1000 of introducing the deck, a plurality of decks 1000 are introduced through the door 2000C-1 into the storing case 2000C. The plurality of decks 1000 are stacked in the stacking rack 2100 of the storing case 2000C.

Referring to FIGS. 4 and 5, the multi-well plate 100 for biological sample, the plurality of multi-well plate 200 for purification, the plurality of pipette racks 300 and the plurality of multi-well plate 400 for PCR are loaded in the certain order in each deck 1000 introduced into the storing case 2000C. In the multi-well plate 100 for biological sample, two wells are paired with each other so as to form the unit well. The same biological sample mixed with a culture medium is injected into two wells forming the unit well, and another biological samples mixed with the culture medium are injected into the other unit wells, and a sterilization substance is injected in one well out of the unit well. Meanwhile, the biological sample injected into the multi-well plate 100 for biological sample contains pathogenic bacteria. The plurality of multi-well plates 200 for purification are to purify the target nucleic acid contained in the pathogenic bacteria, and they are the same as those in the third embodiment. Like in the third embodiment, the plurality of pipette racks 300 are the plurality of purification pipettes P1 and the plurality of dispensation pipettes P2. And the multi-well plate 400 for PCR are the first multi-well plate 410 for PCR and the second multi-well plate 420 for PCR, which are the same as in the third embodiment. Like in the first embodiment, a reaction mixture for real-time quantitative PCR is injected into each of the first multi-well plate 410 for PCR and the second multi-well plate 420 for PCR.

In the step S 1010 of culturing the pathogenic bacteria sample, the pathogenic bacteria in the multi-well plate 100 for PCR stored in the storing case 2000C (referring to FIG. 6) is cultured for a desired time period under predetermined conditions.

In the step S2000 of moving the deck, the deck 1000 introduced through the step S1000 of introducing the deck is moved to the lower side of the syringe block 3000 having the plurality of first mounting portions 3330 in which the plurality of pipettes P for sucking and discharging a fluid substance are removably mounted. The step S2000 of moving the deck is carried out in the same manner as in the third embodiment.

In the step S3000 of purifying the target nucleic acid, the target nucleic acid in the pathogenic bacteria is purified using the syringe block 3000 in which the plurality of pipettes P are removably mounted, the multi-well plate 100 for biological sample and the plurality of multi-well plates 200 for purification. The step S3000 of purifying the target nucleic acid is carried out in the same manner as in the fourth embodiment.

The step S4000 of dispensing the target nucleic acid, the step S5000 of performing the first movement of the multi-well plate for PCR, the step S7000 of sealing the multi-well plate for PCR, the step S8300 of performing the third movement of the multi-well plate for PCR, the step S8400 of sinking the solutions injected into the multi-well plate for PCR, the step S8500 of performing the fourth movement of the multi-well plate for PCR, and the step S9000 of performing real-time quantitative amplification of the target nucleic acid are carried out in the same manner as in the third embodiment.

Meanwhile, although not shown in FIG. 43, a step (not shown) of performing a second movement of the multi-well plate for PCR and a step (not shown) of mixing a solution injected into the multi-well plate for PCR, like in the second embodiment, may be included between the step S7000 of sealing the multi-well plate for PCR and the step S8300 of performing the third movement of the multi-well plate for PCR.

In the step SF1000 of obtaining viable cell count, real-time quantitative amplification data of the nucleic acid, which shows an amplified amount of the target nucleic acid over time, is obtained by using the real-time quantitative amplification device 8000 (referring to FIG. 3), and the viable cell count in the well in which the sterilization substance is injected can be obtained by relative quantification in real-time quantitative PCR between the real-time quantitative amplification data of the nucleic acid in the well in which the sterilization substance is injected and the real-time quantitative amplification data of the nucleic acid in the well in which the sterilization substance is not injected.

Sixth Embodiment

A sixth embodiment relates to a method for automatic antibiotics susceptibility analysis of pathogenic bacteria using the real-time quantitative PCR using the first embodiment.

FIG. 44 is a flow chart of the sixth embodiment of the present invention.

Referring to FIG. 44, the sixth embodiment includes a step S 1000 of introducing a deck, a step S 1010 of culturing a pathogenic bacteria sample, a step S2000 of moving the deck, a step S3000 of purifying a target nucleic acid, a step S4000 of dispensing the target nucleic acid, a step S5000 of performing a first movement of a multi-well plate for PCR, a step S7000 of sealing the multi-well plate for PCR, a step S8300 of performing a third movement of the multi-well plate for PCR, a step S8400 of sinking the solutions injected into the multi-well plate for PCR, a step S8500 of performing a fourth movement of the multi-well plate for PCR, a step S9000 of performing real-time quantitative amplification of the target nucleic acid, and a step SF2000 of obtaining antibiotics susceptibility.

Referring to FIGS. 3, 6 and 7, in the step S 1000 of introducing the deck, a plurality of decks 1000 are introduced through the door 2000C-1 into the storing case 2000C. The plurality of decks 1000 are stacked in the stacking rack 2100 of the storing case 2000C.

Referring to FIGS. 4 and 5, the multi-well plate 100 for biological sample, the plurality of multi-well plate 200 for purification, the plurality of pipette racks 300 and the plurality of multi-well plate 400 for PCR are loaded in the certain order in each deck 1000 introduced into the storing case 2000C. In the multi-well plate 100 for biological sample, M wells form one unit well. The same biological sample mixed with a culture medium is injected into M wells forming the unit well in the multi-well plate 100 for biological sample, and another biological samples mixed with the culture medium are injected into the other unit wells, and different antibiotics are respectively injected in M-1 wells out of the unit well. Meanwhile, the biological sample injected into the multi-well plate 100 for biological sample contains pathogenic bacteria. The plurality of multi-well plates 200 for purification are to purify the target nucleic acid contained in the pathogenic bacteria, and they are the same as those in the third embodiment. Like in the third embodiment, the plurality of pipette racks 300 are the plurality of purification pipettes P1 and the plurality of dispensation pipettes P2. And the multi-well plate 400 for PCR are the first multi-well plate 410 for PCR and the second multi-well plate 420 for PCR, which are the same as in the third embodiment. Like in the first embodiment, a reaction mixture for real-time quantitative PCR is injected into each of the first multi-well plate 410 for PCR and the second multi-well plate 420 for PCR.

In the step S 1010 of culturing the pathogenic bacteria sample, the pathogenic bacteria in the multi-well plate 100 for PCR stored in the storing case 2000C (referring to FIG. 6) is cultured for a desired time period under predetermined conditions.

The step S2000 of moving the deck, the step S3000 of purifying the target nucleic acid, the step S4000 of dispensing the target nucleic acid, the step S5000 of performing the first movement of the multi-well plate for PCR, the step S7000 of sealing the multi-well plate for PCR, the step S8300 of performing the third movement of the multi-well plate for PCR, the step S8400 of sinking the solutions injected into the multi-well plate for PCR, the step S8500 of performing the fourth movement of the multi-well plate for PCR, and the step S9000 of performing real-time quantitative amplification of the target nucleic acid are carried out in the same manner as in the fifth embodiment.

Meanwhile, like in the fifth embodiment, a step (not shown) of performing a second movement of the multi-well plate for PCR and a step (not shown) of mixing a solution injected into the multi-well plate for PCR may be included between the step S7000 of sealing the multi-well plate for PCR and the step S8300 of performing the third movement of the multi-well plate for PCR.

In the step SF 2000 of obtaining antibiotics susceptibility, real-time quantitative amplification data of the nucleic acid, which shows an amplified amount of the target nucleic acid over time, is obtained by using the real-time quantitative amplification device 8000 (referring to FIG. 1), and the antibiotics susceptibility with respect to the different antibiotics injected in each unit can be obtained by relative quantification in real-time quantitative PCR between the real-time quantitative amplification data of the nucleic acid in the well in which the antibiotic is injected and the real-time quantitative amplification data of the nucleic acid in the well in which the antibiotic is not injected.

Seventh Embodiment

A seventh embodiment relates to a method for automatically getting antigen density using quantitative immunity PCR, which can perform a quantitative test for antigen density contained in the biological sample by performing the quantitative immunity PCR using the first embodiment.

FIG. 45 is a flow chart of a seventh embodiment of the present invention.

Referring to FIG. 45, the seventh embodiment includes a step S 1000 of introducing a deck, a step S 1010 of culturing a pathogenic bacteria sample, a step S2000 of moving the deck, a step S3000 of purifying a target nucleic acid, a step S4000 of dispensing the target nucleic acid, a step S5000 of performing a first movement of a multi-well plate for PCR, a step S7000 of sealing the multi-well plate for PCR, a step S8300 of performing a third movement of the multi-well plate for PCR, a step S8400 of sinking the solutions injected into the multi-well plate for PCR, a step S8500 of performing a fourth movement of the multi-well plate for PCR, a step S9000 of performing real-time quantitative amplification of the target nucleic acid, and a step SF3000 of obtaining antigen density.

Referring to FIGS. 3, 6 and 7, in the step S 1000 of introducing the deck, a plurality of decks 1000 are introduced through the door 2000C-1 into the storing case 2000C. The plurality of decks 1000 are stacked in the stacking rack 2100 of the storing case 2000C.

Referring to FIGS. 4 and 5, the multi-well plate 100 for biological sample, the multi-well plate (not shown) for trapped antibody magnetic particle suspension, the multi-well plate (not shown) for target nucleic acid labeling, the multi-well plate 241, 242, 243 for cleaning solution, the multi-well plate 250 for nucleic acid elution solution, the plurality of pipette racks 300 and the plurality of multi-well plate 400 for PCR are loaded in each deck 1000 introduced into the storing case 2000C. A biological sample containing a target antigen is injected into the multi-well plate 100 for biological sample. The magnetic particle suspension including magnetic particles is injected into the multi-well plate (not shown) for trapped antibody magnetic particle suspension, and a first antibody for antigen binding, which is bound with the target antigen, is coated on the magnetic particles. A second antibody containing solution containing a second antibody for binding with the target antigen trapped by the first antibody for antigen binding is injected into the multi-well plate (not shown) for target nucleic acid labeling, and the second antibody is labeled with the binding target nucleic acid. A cleaning solution is injected into the multi-well plate 241, 242, 243 for cleaning solution. A nucleic acid elution solution is injected into the multi-well plate 250 for nucleic acid elution solution. The plurality of purification pipettes P1 and the plurality of dispensation pipettes P2 having smaller a capacity than the plurality of purification pipettes P1 are mounted in the plurality of pipette racks 300. The plurality of multi-well plate 400 for PCR are the first multi-well plate 410 for PCR and the second multi-well plate 420 for PCR, and a reaction mixture for real-time quantitative PCR is injected into the first multi-well plate 410 for PCR and the second multi-well plate 420 for PCR.

Referring to FIGS. 1 and 3, in the step S1000 of introducing the deck, the deck 1000 introduced through the step S1000 of introducing the deck is moved to the lower side of the syringe block 3000 having the plurality of first mounting portions 3330 (referring to FIG. 16). Referring to FIGS. 7 and 13, the step S 1000 of introducing the deck is carried out by the deck withdrawal slider 2450 of the deck transferring unit 2400 (referring to FIG. 12).

In the step S3000 of purifying the target nucleic acid, an antigen-antibody reaction is performed using the syringe block 3000 in which the plurality of pipettes P are removably mounted, the multi-well plate 100 for PCR, the multi-well plate (not shown) for trapped antibody magnetic particle suspension, the multi-well plate (not shown) for target nucleic acid labeling, the multi-well plate 241, 242, 243 for cleaning solution, and the multi-well plate 250 for nucleic acid elution solution. And the binding nucleic acid labeled to the second antibody is purified. The step S3000 of purifying the target nucleic acid will be described in the eighth and ninth embodiments.

In the step S4000 of dispensing the target nucleic acid, the binding target nucleic acid purified in the step S3000 of purifying the target nucleic acid is disposed to the multi-well plate 400 for PCR using the syringe block 3000 in which the plurality of pipettes P are removably disposed.

The step S5000 of performing the first movement of the multi-well plate for PCR, the step S7000 of sealing the multi-well plate for PCR, the step S8300 of performing the third movement of the multi-well plate for PCR, the step S8400 of sinking the solutions injected into the multi-well plate for PCR, the step S8500 of performing the fourth movement of the multi-well plate for PCR, and the step S9000 of performing real-time quantitative amplification of the target nucleic acid are carried out in the same manner as in the fifth embodiment.

Meanwhile, like in the fifth embodiment, a step (not shown) of performing a second movement of the multi-well plate for PCR and a step (not shown) of mixing a solution injected into the multi-well plate for PCR may be included between the step S7000 of sealing the multi-well plate for PCR and the step S8300 of performing the third movement of the multi-well plate for PCR.

In the step SF3000 of obtaining antigen density, real-time quantitative amplification data of the nucleic acid, which shows an amplified amount of the target nucleic acid over time, is obtained by using the real-time quantitative amplification device 8000, and the antigen density contained in the biological sample can be obtained using the obtained real-time quantitative amplification data of the nucleic acid.

Eighth Embodiment

An eighth embodiment relates to a method for purification of a binding target nucleic acid labeled to a target antigen using the second embodiment.

FIGS. 46 and 47 are flow charts of an eighth embodiment of the present invention.

Referring to FIG. 46, the eighth embodiment includes a step S2000 of moving a deck and a step S3500 of isolating and obtaining a target nucleic acid.

Referring to FIGS. 1 and 3, in the step S2000 of moving the deck, the deck 1000 is moved to the lower side of the syringe block 3000 having the plurality of first mounting portions 3330 (referring to FIG. 16). Referring to FIG. 7, the step S2000 of moving the deck is carried out by taking out the deck 1000 stacked on the stacking rack 2100 using the deck withdrawal slider 2450.

Referring to FIGS. 4 and 13, the multi-well plate 100 for biological sample, the multi-well plate (not shown) for target nucleic acid binding, the multi-well plate 241, 242, 243 for cleaning solution, the multi-well plate 250 for nucleic acid elution solution, the plurality of pipette P and the plurality of multi-well plate 400 for PCR are loaded in each deck 1000 moved through the step S2000 of moving the deck. In case of the eighth embodiment, the multi-well plate (not shown) for target nucleic acid binding includes the multi-well plate (not shown) for trapped antibody magnetic particle suspension and the multi-well plate (not shown) for target nucleic acid labeling. A biological sample containing a target antigen is injected into the multi-well plate 100 for biological sample. A magnetic particle suspension including magnetic particles coated with a first antibody for antigen binding, which is bound with the target antigen, is injected into the multi-well plate (not shown) for trapped antibody magnetic particle suspension. A second antibody containing solution containing a second antibody for binding with the target antigen trapped by the first antibody for antigen binding is injected into the multi-well plate (not shown) for target nucleic acid labeling, and the second antigen is labeled with the binding target nucleic acid. A cleaning solution is injected into the multi-well plate 241, 242, 243 for cleaning solution. A nucleic acid elution solution is injected into the multi-well plate 250 for nucleic acid elution solution. The plurality of pipettes P includes the plurality of purification pipettes P1 and the plurality of dispensation pipettes P2 having smaller a capacity than the plurality of purification pipettes P1. The plurality of multi-well plate 400 for PCR are the first multi-well plate 410 for PCR and the second multi-well plate 420 for PCR, and a reaction mixture for real-time quantitative PCR is injected into the first multi-well plate 410 for PCR and the second multi-well plate 420 for PCR.

In the step S3500 of isolating and obtaining the target nucleic acid, the syringe block 3000 is moved so that the plurality of pipettes P are mounted in the first mounting portion 3310. Then, an antigen-antibody reaction for labeling the binding target nucleic acid to the target antigen is performed using the multi-well plate 100 for biological sample, the multi-well plate (not shown) for target nucleic acid binding, the multi-well plate 241, 242, 243 for cleaning solution and the multi-well plate 250 for nucleic acid elution solution. The binding target nucleic acid is isolated and obtained from the target antigen labeled with the binding target nucleic acid.

Hereinafter, the step S3500 of isolating and obtaining the target nucleic acid will be described fully with reference to FIG. 47.

Referring to FIG. 47, the step S3500 of isolating and obtaining the target nucleic acid includes a first antigen-antibody reaction pretreatment step S3220, a first reaction step S3230, a first-1 magnetic field applying step S3240, a first-1 removing step S3250, a first-1 cleaning step S3260, a first-2 magnetic field applying step S3270, a first-2 removing step S3280, a second antigen-antibody reaction pretreatment step S3320, a second reaction step S3330, a second-1 magnetic field applying step S3340, a second-1 removing step S3350, a second-1 cleaning step S3360, a second-2 magnetic field applying step S3370, a second-2 removing step S3380, a nucleic acid isolation step S3410, a third magnetic field applying step S3420, and a target nucleic acid containing solution collecting step S3430.

Referring to FIGS. 13 and 16, in the first antigen-antibody reaction pretreatment step S3220, the syringe block 3000 is moved so that the plurality of pipettes P are mounted in the first mounting portion 3310, and the biological sample injected into the multi-well plate 100 for biological sample is injected and mixed into the multi-well plate (not shown) for trapped antibody magnetic particle suspension.

In the first reaction step S3230, a target antigen contained in a mixture formed in the first antigen-antibody reaction pretreatment step S3220 is trapped by a first antigen. The first reaction step S3230 is carried out in the multi-well plate (not shown) for trapped antibody magnetic particle suspension. Referring to FIG. 13, the multi-well plate (not shown) for trapped antibody magnetic particle suspension is loaded on a position that the multi-well plate 220 for magnetic particle dispersion solution is loaded in the fourth embodiment. Therefore, in case that a heating operation is required in the first reaction step S3230, the multi-well plate (not shown) for trapped antibody magnetic particle suspension can be heated using the heating unit 5200 (referring to FIG. 2).

Referring to FIGS. 7, 13 and 27, in the first-1 magnetic field applying step S3240, magnetic field is applied to a lower portion of the multi-well plate (not shown) for trapped antibody magnetic particle suspension by using the magnetic field applying unit 5100 (referring to FIG. 2), and thus applied to the mixture passed through the first reaction step S3230.

Referring to FIGS. 13 and 16, in the a first-1 removing step S3250, sucking force is applied to the mixture, which is filled in the multi-well plate (not shown) for trapped antibody magnetic particle suspension and passed through the first reaction step S3230, by using the plurality of pipettes P mounted in the syringe block 3000. Meanwhile, the first-1 removing step S3250 is performed in the state that the magnetic field is applied to the lower portion of the multi-well plate (not shown) for trapped antibody magnetic particle suspension by using the magnetic field applying unit 5100. Therefore, the plurality of pipettes P mounted in the syringe block 3000 sucks the mixture except the magnetic particles, the first antibody, and the target antigen complex. If the mixture except the magnetic particles, the first antibody, and the target antigen complex is sucked, the syringe block 3000 is moved and the sucked mixture is discharged through the waste liquor discharging part 12300 (referring to FIG. 13).

Referring to FIGS. 13 and 16, in the first-1 cleaning step S3260, while the magnetic field applied to the lower portion of the multi-well plate (not shown) for trapped antibody magnetic particle suspension is removed, the cleaning solution injected into the multi-well plate 241, 242, 243 for cleaning solution is injected and mixed into the multi-well plate (not shown) for trapped antibody magnetic particle suspension by using the syringe block 3000 having the plurality of pipettes P. Therefore, impurities attached to complexes of the magnetic particles, the first antibody, and the target antigen filled in the multi-well plate (not shown) for trapped antibody magnetic particle suspension are isolated.

Referring to FIGS. 7, 13 and 27, in the first-2 magnetic field applying step S3270, the magnetic field is applied to the lower portion of the multi-well plate (not shown) for trapped antibody magnetic particle suspension by using the magnetic field applying unit 5100 (referring to FIG. 1), and thus applied to the mixture mixed with the cleaning solution.

Referring to FIGS. 13 and 16, in the first-2 removing step S3280, while the magnetic field is applied to the lower portion of the multi-well plate (not shown) for trapped antibody magnetic particle suspension, sucking force is applied to the mixture mixed with the cleaning solution by using the syringe block 3000 having the plurality of pipettes P so as to suck the mixture except complexes of the magnetic particles, the first antibody and the target antigen. If the mixture except complexes of the magnetic particles, the first antibody and the target antigen is sucked, the syringe block 3000 is moved and the sucked mixture is discharged through the waste liquor discharging part 12300 (referring to FIG. 13).

Referring to FIGS. 13 and 16, in the second antigen-antibody reaction pretreatment step S3320, while the magnetic field applied to the lower portion of the multi-well plate (not shown) for trapped antibody magnetic particle suspension is removed, the second antibody containing solution injected into the multi-well plate for target nucleic acid labeling is injected and mixed into the multi-well plate for trapped antibody magnetic particle suspension by using the syringe block 3000 having the plurality of pipettes P.

In the second reaction step S3330, the second antibody contained in the mixture mixed in the second antigen-antibody reaction pretreatment step S3320 is bound with the target antigen through the antigen-antibody reaction. The second reaction step S3330 is carried out in the multi-well plate (not shown) for trapped antibody magnetic particle suspension.

Referring to FIGS. 7, 13 and 27, in the second-1 magnetic field applying step S3340, the magnetic field is applied to the lower portion of the multi-well plate (not shown) for trapped antibody magnetic particle suspension using the magnetic field applying unit 5100, and thus applied to the mixture passed through the second reaction step S3330.

Referring to FIGS. 13 and 16, in the second-1 removing step S3350, while the magnetic field is applied to the lower portion of the multi-well plate (not shown) for trapped antibody magnetic particle suspension, sucking force is applied to the mixture passed through the second reaction step S3330 by using the syringe block 3000 having the plurality of pipettes P so as to suck the mixture except complexes of the magnetic particles, the first antibody the target antigen and the binding target nucleic acid. If the mixture except complexes of the magnetic particles, the first antibody, the target antigen and the binding target nucleic acid is sucked, the syringe block 3000 is moved and the sucked mixture is discharged through the waste liquor discharging part 12300 (referring to FIG. 13).

Referring to FIGS. 13 and 16, in the second-1 cleaning step S3360, while the magnetic field applied to the lower portion of the multi-well plate (not shown) for trapped antibody magnetic particle suspension is removed, the cleaning solution injected into the multi-well plate 241, 242, 243 for cleaning solution is injected and mixed into the multi-well plate (not shown) for trapped antibody magnetic particle suspension by using the syringe block 3000 having the plurality of pipettes P. Therefore, impurities attached to complexes of the magnetic particles, the first antibody, the target antigen, the second antigen and the binding target nucleic acid filled in the multi-well plate (not shown) for trapped antibody magnetic particle suspension are isolated.

Referring to FIGS. 7, 13 and 27, in the second-2 magnetic field applying step S3370, the magnetic field is applied to the multi-well plate for trapped antibody magnetic particle suspension by using the magnetic applying unit 5100 (referring to FIG. 1), and thus applied to the mixture mixed with the cleaning solution.

Referring to FIGS. 13 and 16, in the second-2 removing step S3380, while the magnetic field is applied to the lower portion of the multi-well plate (not shown) for trapped antibody magnetic particle suspension, sucking force is applied to the mixture mixed with the cleaning solution by using the syringe block 3000 having the plurality of pipettes P so as to suck the mixture except complexes of the magnetic particles, the first antibody, the target antigen, the second antibody and the binding target nucleic acid. If the mixture except complexes of the magnetic particles, the first antibody, the target antigen, the second antibody and the binding target nucleic acid is sucked, the syringe block 3000 is moved and the sucked mixture is discharged through the waste liquor discharging part 12300 (referring to FIG. 13).

Referring to FIGS. 13 and 16, in the nucleic acid isolation step S3410, while the magnetic field applied to the lower portion of the multi-well plate (not shown) for trapped antibody magnetic particle suspension is removed, the nucleic acid elution solution injected into the multi-well plate 250 for nucleic acid elution solution is injected into the multi-well plate for trapped antibody magnetic particle suspension by using the syringe block 3000 having the plurality of pipettes P, and thus the target nucleic acid is isolated from the complexes of the magnetic particles, the first antibody, the target antigen, the second antigen and the binding target nucleic acid.

Referring to FIGS. 7, 13 and 27, in the third magnetic field applying step S3420, the magnetic field is applied to the multi-well plate for trapped antibody magnetic particle suspension by using the magnetic applying unit 5100 (referring to FIG. 1), and thus applied to the mixture mixed with the nucleic acid elution solution.

Referring to FIGS. 13 and 16, in the second-2 removing step S3380, while the magnetic field is applied to the lower portion of the multi-well plate (not shown) for trapped antibody magnetic particle suspension, sucking force is applied to the mixture mixed with the nucleic acid elution solution by using the syringe block 3000 having the plurality of pipettes P so as to suck the target nucleic acid containing solution except complexes of the magnetic particles, the first antibody, the target antigen and the second antibody.

Meanwhile, in the eighth embodiment, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

Ninth Embodiment

A ninth embodiment relates another method for purification of a binding target nucleic acid labeled to a target antigen using the second embodiment.

FIGS. 46 and 48 are flow charts of a ninth embodiment of the present invention.

Referring to FIG. 46, the eighth embodiment includes a step S2000 of moving a deck and a step S3500 of isolating and obtaining a target nucleic acid.

Referring to FIGS. 1 and 3, in the step S2000 of moving the deck, the deck 1000 is moved to the lower side of the syringe block 3000 having the plurality of first mounting portions 3330 (referring to FIG. 16). Referring to FIG. 7, the step S2000 of moving the deck is carried out by taking out the deck 1000 stacked on the stacking rack 2100 using the deck withdrawal slider 2450.

Referring to FIGS. 4 and 13, the multi-well plate 100 for biological sample, the multi-well plate (not shown) for target nucleic acid binding, the multi-well plate 241, 242, 243 for cleaning solution, the multi-well plate 250 for nucleic acid elution solution, the plurality of pipette P and the plurality of multi-well plate 400 for PCR are loaded in each deck 1000 moved through the step S2000 of moving the deck. In case of the ninth embodiment, the multi-well plate (not shown) for target nucleic acid binding includes the multi-well plate (not shown) for trapped antibody magnetic particle suspension, the multi-well plate (not shown) for second antibody containing solution and the multi-well plate (not shown) for target nucleic acid containing solution. A biological sample containing a target antigen is injected into the multi-well plate 100 for biological sample. A magnetic particle suspension including magnetic particles coated with a first antibody for antigen binding, which is bound with the target antigen, is injected into the multi-well plate (not shown) for trapped antibody magnetic particle suspension. A second antibody containing solution containing a second antibody for binding with the target antigen trapped by the first antibody for antigen binding is injected into the multi-well plate (not shown) for second antibody containing solution. A binding target nucleic acid containing solution for labeling to the second antibody bound with the target antigen is injected into the multi-well plate (not shown) for target nucleic acid containing solution. A cleaning solution is injected into the multi-well plate 241, 242, 243 for cleaning solution. A nucleic acid elution solution is injected into the multi-well plate 250 for nucleic acid elution solution. The plurality of pipettes P includes the plurality of purification pipettes P1 and the plurality of dispensation pipettes P2 having smaller a capacity than the plurality of purification pipettes P1. The plurality of multi-well plate 400 for PCR are the first multi-well plate 410 for PCR and the second multi-well plate 420 for PCR, and a reaction mixture for real-time quantitative PCR is injected into the first multi-well plate 410 for PCR and the second multi-well plate 420 for PCR.

In the step S3500 of isolating and obtaining the target nucleic acid, the syringe block 3000 is moved so that the plurality of pipettes P are mounted in the first mounting portion 3310. Then, an antigen-antibody reaction for labeling the binding target nucleic acid to the target antigen is performed using the multi-well plate 100 for biological sample, the multi-well plate (not shown) for target nucleic acid binding, the multi-well plate 241, 242, 243 for cleaning solution, and the multi-well plate 250 for nucleic acid elution solution. The binding target nucleic acid is isolated and obtained from the target antigen labeled with the binding target nucleic acid.

Hereinafter, the step S3500 of isolating and obtaining the target nucleic acid will be described fully with reference to FIG. 48.

Referring to FIG. 48, the step S3500 of isolating and obtaining the target nucleic acid includes a first antigen-antibody reaction pretreatment step S3220, a first reaction step S3230, a first-1 magnetic field applying step S3240, a first-1 removing step S3250, a first-1 cleaning step S3260, a first-2 magnetic field applying step S3270, a first-2 removing step S3280, a second antigen-antibody reaction pretreatment step S3320-1, a second reaction step S3330-1, a second-1 magnetic field applying step S3340-1, a second-1 removing step S3350-1, a second-1 cleaning step S3360-1, a second-2 magnetic field applying step S3370-1, a second-2 removing step S3380-1, a target nucleic acid addition reaction step S3320-2, a third reaction step S3330-2, a third-1 magnetic field applying step S3340-2, a third-1 removing step S3350-2, a third-1 cleaning step S3360-2, a third-2 magnetic field applying step S3370-2, a third-2 removing step S3380-2, a nucleic acid isolation step S3410, a fourth magnetic field applying step S3420, and a target nucleic acid containing solution collecting step S3430.

The steps from S3220 to S3280 are the same as in the eighth embodiment.

Referring to FIGS. 13 and 16, in the second antigen-antibody reaction pretreatment step S3320-1, while the magnetic field applied to the lower portion of the multi-well plate (not shown) for trapped antibody magnetic particle suspension is removed, the second antibody containing solution injected into the multi-well plate for second antibody containing solution is injected and mixed into the multi-well plate for trapped antibody magnetic particle suspension by using the syringe block 3000 having the plurality of pipettes P.

In the second reaction step S3330-1, the second antibody contained in the mixture mixed in the second antigen-antibody reaction pretreatment step S3320-1 is bound with the target antigen through the antigen-antibody reaction. The second reaction step S3330-1 is carried out in the multi-well plate (not shown) for trapped antibody magnetic particle suspension.

Referring to FIGS. 7, 13 and 27, in the second-1 magnetic field applying step S3340-1, the magnetic field is applied to the lower portion of the multi-well plate (not shown) for trapped antibody magnetic particle suspension using the magnetic field applying unit 5100 (referring to FIG. 1), and thus applied to the mixture passed through the second reaction step S3330-1.

Referring to FIGS. 13 and 16, in the second-1 removing step S3350-1, while the magnetic field is applied to the lower portion of the multi-well plate (not shown) for trapped antibody magnetic particle suspension, sucking force is applied to the mixture passed through the second reaction step S3330-1 by using the syringe block 300 having the plurality of pipettes P so as to suck the mixture except complexes of the magnetic particles, the first antibody the target antigen and the second antibody. If the mixture except complexes of the magnetic particles, the first antibody, the target antigen and the second antibody is sucked, the syringe block 3000 is moved and the sucked mixture is discharged through the waste liquor discharging part 12300 (referring to FIG. 13).

Referring to FIGS. 13 and 16, in the second-1 cleaning step S3360-1, while the magnetic field applied to the lower portion of the multi-well plate (not shown) for trapped antibody magnetic particle suspension is removed, the cleaning solution injected into the multi-well plate 241, 242, 243 for cleaning solution is injected and mixed into the multi-well plate (not shown) for trapped antibody magnetic particle suspension by using the syringe block 3000 having the plurality of pipettes P. Therefore, impurities attached to complexes of the magnetic particles, the first antibody, the target antigen and the second antigen filled in the multi-well plate (not shown) for trapped antibody magnetic particle suspension are isolated.

Referring to FIGS. 7, 13 and 27, in the second-2 magnetic field applying step S3370-1, the magnetic field is applied to the multi-well plate for trapped antibody magnetic particle suspension by using the magnetic applying unit 5100 (referring to FIG. 1), and thus applied to the mixture mixed with the cleaning solution.

Referring to FIGS. 13 and 16, in the second-2 removing step S3380-1, while the magnetic field is applied to the lower portion of the multi-well plate (not shown) for trapped antibody magnetic particle suspension, sucking force is applied to the mixture mixed with the cleaning solution by using the syringe block 3000 having the plurality of pipettes P so as to suck the mixture except complexes of the magnetic particles, the first antibody, the target antigen and the second antibody. If the mixture except complexes of the magnetic particles, the first antibody, the target antigen and the second antibody is sucked, the syringe block 3000 is moved and the sucked mixture is discharged through the waste liquor discharging part 12300 (referring to FIG. 13).

Referring to FIGS. 13 and 16, in the third reaction step S3330-2, while the magnetic field applied to the lower portion of the multi-well plate (not shown) for trapped antibody magnetic particle suspension is removed, the target nucleic acid containing solution injected into the multi-well plate for target nucleic acid is injected and mixed into the multi-well plate for trapped antibody magnetic particle suspension by using the syringe block 3000 having the plurality of pipettes P.

In the third reaction step S3330-2, the binding target nucleic acid contained in the mixture mixed in the third reaction step S3330-2 is bound to the second antibody. The third reaction step S3330-2 is carried out in the multi-well plate for trapped antibody magnetic particle suspension.

Referring to FIGS. 7, 13 and 27, in the third-1 magnetic field applying step S3340-2, the magnetic field is applied to the lower portion of the multi-well plate (not shown) for trapped antibody magnetic particle suspension using the magnetic field applying unit 5100, and thus applied to the mixture passed through the third reaction step S3330-2.

Referring to FIGS. 13 and 16, in the third-1 removing step S3350-2, while the magnetic field is applied to the lower portion of the multi-well plate (not shown) for trapped antibody magnetic particle suspension, sucking force is applied to the mixture passed through the third reaction step S3330-2 by using the syringe block 3000 having the plurality of pipettes P so as to suck the mixture except complexes of the magnetic particles, the first antibody the target antigen, the second antibody and the binding target nucleic acid. If the mixture except complexes of the magnetic particles, the first antibody, the target antigen, the second antibody and the binding target nucleic acid is sucked, the syringe block 3000 is moved and the sucked mixture is discharged through the waste liquor discharging part 12300 (referring to FIG. 13).

Referring to FIGS. 13 and 16, in the third-1 cleaning step S3360-2, while the magnetic field applied to the lower portion of the multi-well plate (not shown) for trapped antibody magnetic particle suspension is removed, the cleaning solution injected into the multi-well plate 241, 242, 243 for cleaning solution is injected and mixed into the multi-well plate (not shown) for trapped antibody magnetic particle suspension by using the syringe block 3000 having the plurality of pipettes P. Therefore, impurities attached to complexes of the magnetic particles, the first antibody, the target antigen, the second antigen and the binding target nucleic acid filled in the multi-well plate (not shown) for trapped antibody magnetic particle suspension are isolated.

Referring to FIGS. 7, 13 and 27, in the third-2 magnetic field applying step S3370-2, the magnetic field is applied to the multi-well plate for trapped antibody magnetic particle suspension by using the magnetic applying unit 5100 (referring to FIG. 1), and thus applied to the mixture mixed with the cleaning solution.

Referring to FIGS. 13 and 16, in the third-2 removing step S3380-2, while the magnetic field is applied to the lower portion of the multi-well plate (not shown) for trapped antibody magnetic particle suspension, sucking force is applied to the mixture mixed with the cleaning solution by using the syringe block 3000 having the plurality of pipettes P so as to suck the mixture except complexes of the magnetic particles, the first antibody, the target antigen, the second antibody and the binding target nucleic acid. If the mixture except complexes of the magnetic particles, the first antibody, the target antigen, the second antibody and the binding target nucleic acid is sucked, the syringe block 3000 is moved and the sucked mixture is discharged through the waste liquor discharging part 12300 (referring to FIG. 13).

Referring to FIGS. 13 and 16, in the nucleic acid isolation step S3410, while the magnetic field applied to the lower portion of the multi-well plate (not shown) for trapped antibody magnetic particle suspension is removed, the nucleic acid elution solution injected into the multi-well plate 250 for nucleic acid elution solution is injected into the multi-well plate for trapped antibody magnetic particle suspension by using the syringe block 3000 having the plurality of pipettes P, and thus the target nucleic acid is isolated from the complexes of the magnetic particles, the first antibody, the target antigen, the second antigen and the binding target nucleic acid.

Referring to FIGS. 7, 13 and 27, in the fourth magnetic field applying step S3420, the magnetic field is applied to the multi-well plate for trapped antibody magnetic particle suspension by using the magnetic applying unit 5100 (referring to FIG. 1), and thus applied to the mixture mixed with the nucleic acid elution solution.

Referring to FIGS. 13 and 16, in the target nucleic acid containing solution collecting step S3430, while the magnetic field is applied to the lower portion of the multi-well plate (not shown) for trapped antibody magnetic particle suspension, sucking force is applied to the mixture mixed with the nucleic acid elution solution by using the syringe block 3000 having the plurality of pipettes P so as to suck the target nucleic acid containing solution except complexes of the magnetic particles, the first antibody, the target antigen and the second antibody.

Meanwhile, in the eighth embodiment, in order to collect the solution falling down from the pipettes P mounted in the first mounting portions 3330 in the solution drip tray 4375 when the syringe block 4000 is moved horizontally, the solution drip tray 4375 is located at the lower side of the pipettes P mounted in the first mounting portion 3330 when the syringe block 4000 is moved horizontally.

INDUSTRIAL APPLICABILITY

According to the present invention as described above, since it is possible to automatically carry out a series of processes from the nucleic acid purification to the real-time quantification of gene amplification, there is an advantage that it is possible to treat a large amount of samples in a short period of time with minimum manual labor, thereby obtaining analysis results of various biological samples.

Further, the present invention has another advantage that the real-time quantitative PCR analysis can be performed after the culturing of microorganism, and thus it is possible to automatically perform the microorganism test and the microorganism test in the biological samples and the antibiotics susceptibility test.

Further, the present invention has yet another advantage that it is possible to perform the very useful microorganism analysis using both of the microorganism culture and the real-time quantitative amplification. When the initial number of microorganisms contained in the biological sample is less than detection limit, the microorganism is amplified through the culture step and then analyzed by real-time quantitative PCR, and thus it is possible to precisely perform the test of microorganism.

Further, According to the present invention, the culturing is performed only for a short period time that is less than five generations, and then each amount of DNA in the samples before and after the culturing is compared with each other by relative quantification in real-time quantitative PCR, and thus it is possible to precisely and rapidly analyze the viable cell count. On the same principle, the system of the present invention can be used in automatically performing the antibiotics susceptibility test. In other words, the present invention has yet another advantage that the biological sample containing microorganisms is equally dispensed to the multi-well including different antibiotics from each other and cultured for a predetermined period of time, and then real-time quantitative PCR analysis is performed so as to compare the number of nucleic acids using a relative quantitative method, and thus it is possible to rapidly analyze antibiotics susceptibility of the microorganism, thereby allowing effective antibiotics to be selected within a short time period.

Further, the present invention can automatically perform the quantitative Immuno-PCR so as to precisely perform a quantitative test for a small amount of proteins and antigens.

While the present invention has been described with respect to the specific embodiments, it will be apparent to those skilled in the art that various changes and modifications may be made without departing from the spirit and scope of the invention as defined in the following claims.

The invention claimed is:

1. An automatic real-time quantitative amplification system which can perform analysis of various biological samples, comprising:
   a deck loading a multi-well plate for treating the biological sample, which purifies a target nucleic acid in a target substance contained in the biological sample, cultures the target substance contained in the biological sample and then purifies the target nucleic acid, or purifies a binding target nucleic acid bound with a target antigen contained in the biological sample by an antigen-antibody reaction, and a multi-well plate for PCR, in which a reaction mixture for real-time quantitative PCR is injected;
   an automatic purification and reaction preparing device which automatically purifies the target nucleic acid or the cultured target nucleic acid from the biological sample and dispenses the purified target nucleic acid or the cultured and purified target nucleic acid to the multi-well plate for PCR, and then mixes the dispensed target nucleic acid with a reagent for real-time quantitative PCR, or which automatically purifies the binding target nucleic acid bound with the target antigen contained in the biological sample by the antigen-antibody reaction, and dispenses the purified binding target nucleic acid to the multi-well plate for PCR, and then mixes the dispensed binding target nucleic acid with the reagent for real-time quantitative PCR;
   an automatic deck storing and moving device including:
      a storing case which has a door for taking in or out the deck and of which an internal portion can be maintained at predetermined temperature,
      a stacking rack lifting unit which moves a stacking unit in an up and down direction,
      a plurality of racks arranged in the up and down direction in the stacking unit so that the plurality of racks move in the up and down direction when the sacking unit moves in the up and down direction, each of the plurality of racks configured to receive the deck, and
      a deck transferring unit movable in a left and right direction of the deck and transferring the deck loaded in the stacking rack to the automatic purification and reaction preparing device,
   a sealing device which seals an upper surface of the multi-well plate for PCR, in which the purified target nucleic acid, the cultured and purified target nucleic acid or the purified binding target nucleic acid is dispensed;
   a centrifugal separator which applies centripetal force to the multi-well plate for PCR so that a substance remained on a side wall of each well formed in the multi-well plate for PCR is separated and then moved to a bottom surface of the each well;
   a real-time quantitative amplification device which amplifies the target substance in the multi-well plate for PCR; and
   a moving device for multi-well plate for PCR, which moves the multi-well plate for PCR, in which the purified target nucleic acid, the cultured and purified target nucleic acid or the purified binding target nucleic acid is dispensed, to the sealing device, and moves the multi-well plate for PCR sealed by the sealing device to the centrifugal separator, and also moves the multi-well plate for PCR, to which the centripetal force is applied by the centrifugal separator, to the real-time quantitative amplification device, wherein the automatic purification and reaction preparing device comprises:
- a syringe block formed with a plurality of first mounting portions to which a plurality of pipettes P for sucking and discharging a fluid substance is removably mounted; and
- a syringe block moving unit which moves the syringe block so that the plurality of pipettes P mounted in the plurality of first mounting portions is located just above each of the multi-well plate for treating the biological sample and the multi-well plate for PCR.

2. The automatic real-time quantitative amplification system according to claim 1, wherein the automatic purification and reaction preparing device further comprises:
- a solution drip tray which is rotatably disposed under the plurality of pipettes P mounted in the plurality of first mounting portion and above each of the multi-well plate for biological sample and the multi-well plate for PCR and movable by a solution drip tray moving unit installed to the syringe block moving unit;
- a magnetic field applying unit which moves a magnet to a lower side of a first certain multi-well plate out of the multi-well plates for treating the biological sample so as to apply magnetic field to the first certain multi-well plate;
- a heating unit which moves a heating block to a lower side of a second certain multi-well plate out of the multi-well plates for treating the biological sample so as to heat the second certain multi-well plate;
- a puncher in which a plurality of awl-shaped puncher pins are protrusively formed so as to pierce holes in a sealing film for sealing an upper surface of the multi-well plate for treating the biological sample, and which is disposed at a lower side of the syringe block so as to be removably mounted in the plurality of first mounting portions at different time point as compared with the time point, when the plurality of pipettes P is mounted in the plurality of first mounting portions; and
- a waste liquor discharging part which is disposed at a lower side of the syringe block so as to discharge waste liquor abandoned from the plurality of pipettes P mounted in the plurality of first mounting portions.

3. The automatic real-time quantitative amplification system according to claim 2, wherein the solution drip tray moving unit comprises:
- a solution drip tray supporting plate which is installed to the syringe block moving unit; and
- a solution drip tray moving motor which is installed at the solution drip tray supporting plate and which is connected to the solution drip tray so as to horizontally rotate the solution drip tray.

4. The automatic real-time quantitative amplification system according to claim 1, wherein the automatic purification and reaction preparing device further comprises:
- a magnetic field applying unit which moves a magnet to a lower side of a first certain multi-well plate out of the multi-well plates for treating the biological sample so as to apply magnetic field to the first certain multi-well plate;
- a heating unit which moves a heating block to a lower side of a second certain multi-well plate out of the multi-well plates for treating the biological sample so as to heat the second certain multi-well plate;
- a puncher in which a plurality of awl-shaped puncher pins are protrusively formed so as to pierce holes in a sealing film for sealing an upper surface of the multi-well plate for treating the biological sample, and which is disposed at a lower side of the syringe block so as to be removably mounted in the plurality of first mounting portions at different time point as compared with the time point, when the plurality of pipettes P is mounted in the plurality of first mounting portions;
- an evaporation block for multi-well plate, which is connected with a compressed air supplying tube, and which is formed with a plurality of second mounting portions for shooting compressed air supplied through the compressed air supplying tube and removably mounting the plurality of pipettes P, and which is disposed at a lower side of the syringe block so as to be removably mounted in the plurality of first mounting portions at different time point as compared with the time points, when the plurality of pipettes P and the puncher are respectively mounted in the plurality of first mounting portions; and
- a waste liquor discharging part which is disposed at a lower side of the syringe block so as to discharge waste liquor abandoned from the plurality of pipettes P mounted in the plurality of first mounting portions.

5. The automatic real-time quantitative amplification system according to claim 4, wherein the multi-well plate for PCR in which a reaction mixture for real-time quantitative PCR is injected is an amplification kit plate having a plurality tubes in which a reagent for real-time quantitative PCR is injected, and
- the first certain multi-well plate is a multi-well plate for magnetic particle dispersion solution, in which a magnetic particle suspension including magnetic particles is injected when being loaded on the deck, among the multi-well plates for treating the biological sample, and
- the second certain multi-well plate is a multi-well plate for biological sample, in which the biological sample is injected when being loaded on the deck, among the multi-well plates for treating the biological sample.

6. The automatic real-time quantitative amplification system according to claim 5, wherein the multi-well plates for treating the biological sample comprise:
- the multi-well plate for biological sample;
- a multi-well plate for cell lysis solution, in which a cell lysis solution is injected when being loaded on the deck;
- the multi-well plate for magnetic particle dispersion solution;
- a multi-well plate for nucleic acid binding solution, in which a nucleic acid binding solution is injected when being loaded on the deck;
- a multi-well plate for cleaning solution, in which a cleaning solution is injected when being loaded on the deck; and
- a multi-well plate for nucleic acid elution solution, in which a nucleic acid elution solution is injected when being loaded on the deck.

7. The automatic real-time quantitative amplification system according to claim 2, wherein the plurality pipettes P are a plurality of purification pipettes P1, or a plurality of dispensation pipettes P2 having smaller a capacity than the plurality of purification pipettes P1, and
- a purification pipette rack in which the plurality of purification pipettes P1 are received, and a dispensation pipette rack in which the plurality of dispensation pipettes P2 are received are loaded on the deck, and the multi-well plate for PCR comprises a first multi-well plate for PCR and a second multi-well plate for PCR.

8. The automatic real-time quantitative amplification system according to claim 2, wherein the magnetic field applying unit comprises;
 a magnet mounting block in which the magnet is installed; and
 a magnet mounting block lifting part for lifting up and down the magnet mounting block.

9. The automatic real-time quantitative amplification system according to claim 8, wherein the magnet is a plurality of rod-shaped magnets which are disposed so as to be spaced apart from each other so that an upper portion of the magnet encloses each well formed in the multi-well plate for magnetic particle dispersion solution when the magnet mounting block is lifted up.

10. The automatic real-time quantitative amplification system according to claim 8, wherein the magnet mounting block lifting part comprises:
 a supporting plate for magnetic field applying unit, which is located at a lower side of the magnet mounting block; and
 a magnet mounting block lifting motor which is connected to the supporting plate for magnetic field applying unit, and also connected to the magnet mounting block so as to lift up and down the magnet mounting block.

11. The automatic real-time quantitative amplification system according to claim 2, wherein the heating unit comprises a heating block lifting part for lifting up and down the heating block.

12. The automatic real-time quantitative amplification system according to claim 11, wherein the heating block lifting part comprises:
 a supporting plate for heating unit, which is located at a lower side of the heating block; and
 a heating block lifting motor which is connected to the supporting plate for heating unit, and also connected to the heating block so as to lift up and down the heating block.

13. The automatic real-time quantitative amplification system according to claim 12, wherein the magnetic field applying unit comprises;
 a supporting plate for magnetic field applying unit, which is located at a lower side of the magnet mounting block; and
 a magnet mounting block lifting motor which is installed to the supporting plate for magnetic field applying unit, and also connected to the magnet mounting block so as to lift up and down the magnet mounting block, and
 wherein the heating unit comprises a front and rear moving part for heating block, which moves the heating block in a front and rear direction of the deck, and the supporting plate for magnetic field applying unit and the supporting plate for heating unit are adjacent to each other in the front and rear direction of the deck and connected to each other.

14. The automatic real-time quantitative amplification system according to claim 13, wherein the front and rear moving part for heating block comprises a front and rear moving motor for heating block, which is disposed to be spaced apart from the supporting plate for heating unit, and which is connected to one or both of the supporting plate for heating unit and the supporting plate for magnetic field applying unit so as to move the supporting plate for heating unit in the front and rear direction of the deck.

15. The automatic real-time quantitative amplification system according to claim 4, wherein the syringe block comprises:
 a syringe pin holder which is movable up and down and to which a plurality of rod-shaped syringe pins are attached;
 a syringe pin guide block which is formed with a plurality of syringe pin guide holes for guiding up/down movement of the plurality of syringe pins;
 a first separation portion which is moved down, while being contacted with the syringe pin holder, so as to separate at least the plurality of pipettes P and the evaporation block for multi-well plate among the plurality of pipettes P, the puncher and the evaporation block for multi-well plate from the first mounting portion, which are respectively mounted in the first mounting portion at different time points; and
 a second-1 separation portion which is moved down, while being contacted with the syringe pin holder, so as to be interlocked with a second-2 separation portion provided at the evaporation block for multi-well plate and thus to separate the plurality of pipettes P mounted in the second mounting portion.

16. The automatic real-time quantitative amplification system according to claim 15, wherein the first separation portion comprises:
 a first separation rod which is inserted into a first separation rod guide hole formed in the syringe pin guide block so as to be moved down by compressing force of the syringe pin holder; and
 a first lower separation plate which is inserted onto the plurality of first mounting portions protruded from a lower end of the syringe pin guide block so as to be moved up and down, and which is moved down by the first separation rod so as to compress and separate the plurality of pipettes P, the puncher and the evaporation block for multi-well plate which are respectively mounted in the plurality of mounting portions at different time points.

17. The automatic real-time quantitative amplification system according to claim 16, wherein the second-1 separation portion comprises a second separation rod which is inserted into a second separation rod guide hole formed in the syringe block guide so as to be moved down by the compressing force of the syringe pin holder, and
 the second-2 separation portion comprises a second separation plate which is inserted onto the plurality of second mounting portions protruded from a lower end of the evaporation block for multi-well plate so as to be movable up and down, and which is moved down by the second separation rod so as to compress and separate the plurality of pipettes P mounted in the plurality of second mounting portions.

18. The automatic real-time quantitative amplification system according to claim 2, wherein the syringe block moving unit comprises a front and rear moving part for syringe block, which moves the syringe block in a front and rear direction of the deck, a left and right moving part for syringe block, which moves the syringe block in the left and right direction of the deck, and an up and down moving part for syringe block, which moves up and down the syringe block, and
 the front and rear moving part for syringe block comprises a front and rear moving body for syringe block; and a front and rear moving motor for syringe block which is disposed to be spaced apart from the front and rear moving body for syringe block, and which is connected to the front and rear moving body for syringe block so as to move the front and rear moving body for syringe block in the front and rear direction of the deck, and the left and right moving part for syringe block comprises a left and right moving motor for syringe block, which is fixed to the front and rear moving body for syringe block;

and a left and right moving body for syringe block, which is installed at the front and rear moving body for syringe block so as to be moved in the left and right direction of the deck, and which is connected to the left and right moving motor for syringe block, and the up and down moving part for syringe block comprises a supporting plate for up and down movement of the syringe block, which is fixed to the left and right moving body for syringe block; and a front and rear moving motor for syringe block, which is installed at the supporting plate for up and down movement of the syringe block, and which is connected to the syringe block so as to move up and down the syringe block.

19. The automatic real-time quantitative amplification system according to claim 1, wherein the automatic deck storing and moving device comprises:
a pallet which is slidably installed at a pallet guider provided at the rack, and which a pallet moving dog and a pallet withdrawal groove are formed at one side thereof; and
a pallet moving unit which is contacted with the pallet moving dog so as to slide and withdraw the pallet to an outside of the storing case, so that the deck can be mounted on an upper surface of the pallet.

20. The automatic real-time quantitative amplification system according to claim 1, wherein the stacking rack lifting unit comprises:
a stacking rack lifting ball screw shaft which is connected to a stacking rack lifting motor a stacking rack lifting ball nut which is moved up and down when the stacking rack lifting ball screw shaft is rotated; and
a stacking rack connecting member of which one side surface is fixedly connected to the stacking rack lifting ball nut and the other side surface is fixedly connected to the stacking unit.

21. The automatic real-time quantitative amplification system according to claim 1, wherein the deck transferring unit comprises a deck withdrawal slider in which a deck withdrawal protrusion put into the pallet withdrawal groove is formed at one side thereof, and in which an insertion pin inserted into a grasping hold formed at the deck is formed on an upper surface of the deck withdrawal protrusion.

22. The automatic real-time quantitative amplification system according to claim 1, wherein the sealing device comprises:
a sealed loading plate on which the multi-well plate for PCR is mounted and which is disposed to be moved in the front and rear direction of the deck;
a lower compressing portion which supports a sealing film;
an upper compressing portion which is disposed at an upper side of the lower compressing portion so as to be moved down and compress the sealing film;
a film cutter which is located at a front or rear side of the upper compressing portion so as to be moved down and cut the sealing film compressed between the lower and upper compressing portions; and
a film heating block which is disposed at an upper side of an intermediate plate for sealing device to be movable down and thermally compress the sealing film mounted on an upper surface of the multi-well plate for PCR to the multi-well plate for PCR.

23. The automatic real-time quantitative amplification system according to claim 22, further comprising:
a first supporting spring which is elastically contacted with the lower compressing portion;
an upper compressing portion supporting block which is elastically supported by the first supporting spring and disposed at an upper side of the upper compressing portion, and in which the film cutter is provided;
a second supporting spring which is disposed to be elastically contacted between the upper and lower compressing portions; and
an upper compressing portion supporting rod which is connected to the upper compressing portion so as to be extended to an upper side of the upper compressing portion, and which is inserted onto the upper compressing portion so as to be slid up and down, and which is formed with a stopper for preventing separation from the upper compressing portion.

24. The automatic real-time quantitative amplification system according to claim 22, further comprising:
a film side guide plate which is disposed at a front side of the lower compressing portion so as to support an edge lower surface of the sealing film located at a front side of the lower compressing portion; and
a film side guide plate mounting portion to which the film side guide plate is installed so as to be rotated to an outside of an edge portion of the sealing film supported on an upper surface of the film side guide plate and thus to be separated from the sealing film supported on an upper surface of the film side guide plate.

25. The automatic real-time quantitative amplification system according to claim 1, further comprising a vortex mixer which applies vibration to the multi-well plate for PCR moved from the sealing device by the moving device for multi-well plate for PCR before being transferred to the centrifugal separator, in order to mix a substance injected into the multi-well plate for PCR.

26. The automatic real-time quantitative amplification system according to claim 25, wherein the vortex mixer comprises:
a driven shaft for vortex mixer which is disposed in an up and down direction so as to be rotated by a motor for vortex mixer;
an eccentric driven shaft for vortex mixer, which is integrally and eccentrically connected to the driven shaft for vortex mixer;
an eccentric driven shaft bearing which is coupled to the eccentric driven shaft for vortex mixer;
a plurality of separation preventing springs of which one ends are fixed to an outer surface of the eccentric driven shaft bearing and the other ends are fixed to an upper plate for vortex mixer; and
a mounting plate for vortex mixer, which is fixedly installed at an upper end of the eccentric driven shaft bearing, and on which the multi-well plate for PCR is mounted.

27. The automatic real-time quantitative amplification system according to claim 1, wherein the centrifugal separator comprises:
a driven shaft for centrifugal separator, which is disposed in an up and down direction so as to be rotated by a motor for centrifugal separator;

a rotational plate for centrifugal separator, which has an I shape so that an opening portion is formed at both side ends thereof, and which is integrally formed with the driven shaft for centrifugal separator; and a mounting block for centrifugal separator, on which the multi-well plate for PCR is mounted, and which is rotatably disposed at an opening portion of both side ends of the rotational plate for centrifugal separator, such that an upper surface of the multi-well plate for PCR looks in an inside direction and a lower surface thereof looks in an outside direction when the rotational plate for centrifugal separator is rotated.

28. The automatic real-time quantitative amplification system according to claim 1, wherein the moving device for multi-well plate for PCR comprises:

a movement guide block for multi-well plate for PCR which is disposed in the left and right direction at a front upper side of the deck transferred by the deck transferring unit;

a left and right moving block for multi-well plate for PCR, which is connected to a left and right moving motor, and disposed at a movement guide block for multi-well plate for PCR so as to be moved in the left and right direction of the deck;

a front and rear moving guide block for multi-well plate for PCR, which is disposed at the left and right moving block for multi-well plate for PCR so as to be protruded in the front and rear direction of the deck;

a front and rear moving block for multi-well plate for PCR, which is connected to a front and rear moving motor for multi-well plate for PCR fixed to the front and rear moving guide block for multi-well plate for PCR, and disposed at the front and rear moving guide block for multi-well plate for PCR so as to be movable in the front and rear direction of the deck;

an up and down moving guide block for multi-well plate for PCR, which is fixed to the front and rear moving block for multi-well plate for PCR; and a grasping means for grasping the multi-well plate for PCR, which is connected to an up and down moving motor for multi-well plate for PCR fixed to up and down moving guide block for multi-well plate for PCR, so as to be moved up and down.

29. The automatic real-time quantitative amplification system according to claim 28, wherein the grasping means for grasping the multi-well plate for PCR comprises a grasping portion which is moved inwardly by a grasping motor for multi-well plate for PCR so as to grasp both side ends of the multi-well plate for PCR.

30. An automatic purification and reaction preparing device for biological sample analysis, comprising:

a syringe block which is formed with a plurality of first mounting portions so as to removably mount a plurality of pipettes P for sucking and discharging a fluid substance;

a syringe block moving unit which moves the syringe block so that the plurality of pipettes P mounted in the plurality of first mounting portions are located just above each of a multi-well plate for biological sample, a plurality of multi-well plates for purification and a multi-well plate for PCR, which are located in a lower side of the syringe block;

a solution drip tray which is rotatably disposed under the plurality of pipettes P mounted in the plurality of first mounting portions and above each of the multi-well plate for biological sample, the plurality of multi-well plates for purification and the multi-well plate for PCR; and a solution drip tray moving unit attached to the syringe block moving unit and the solution trip tray, and rotating the solution drip tray on a horizontal plane.

31. The automatic purification and reaction preparing device according to claim 30, further comprising a puncher which is provided with a plurality of awl-shaped puncher pins so as to pierce holes in a sealing film for sealing an upper surface of the multi-well plate for biological sample and the plurality of multi-well plates for multiple biological samples, and which is disposed at a lower side of the syringe block so as to be removably mounted in the plurality of first mounting portions at different time point as compared with the time point, when the plurality of pipettes P is mounted in the plurality of first mounting portions.

32. The automatic purification and reaction preparing device according to claim 30, wherein the solution drip tray moving unit comprises:

a solution drip tray supporting plate which is connected to the syringe block moving unit; and a solution drip tray moving motor which is installed at the solution drip tray supporting plate and which is connected to the solution drip tray so as to horizontally rotate the solution drip tray.

* * * * *